(12) United States Patent
Campbell et al.

(10) Patent No.: US 9,085,765 B2
(45) Date of Patent: *Jul. 21, 2015

(54) **REDUCED GENOME *E. COLI***

(75) Inventors: John W. Campbell, Oak Park, IL (US);
Frederick R. Blattner, Madison, WI (US); Guy Plunkett, Madison, WI (US);
Gyorgy Posfai, Szeged (HU)

(73) Assignee: SCARAB GENOMICS LLC, Madison, WI (US)

( * ) Notice: Subject to any disclaimer, the term of this patent is extended or adjusted under 35 U.S.C. 154(b) by 570 days.

This patent is subject to a terminal disclaimer.

(21) Appl. No.: 13/445,672

(22) Filed: Apr. 12, 2012

(65) Prior Publication Data
US 2013/0011874 A1 Jan. 10, 2013

Related U.S. Application Data

(63) Continuation of application No. 12/064,332, filed as application No. PCT/US2006/032525 on Aug. 18, 2006, now Pat. No. 8,178,339.

(60) Provisional application No. 60/709,960, filed on Aug. 20, 2005.

(51) Int. Cl.
*C12P 21/04* (2006.01)
*C12P 19/34* (2006.01)
*C12N 1/20* (2006.01)
*C12R 1/19* (2006.01)

(52) U.S. Cl.
CPC .... *C12N 1/20* (2013.01); *C12R 1/19* (2013.01)

(58) Field of Classification Search
None
See application file for complete search history.

(56) References Cited

U.S. PATENT DOCUMENTS

2003/0138937 A1 7/2003 Blattner et al.

OTHER PUBLICATIONS

International Search Report of PCT/US2006/032525 dated Feb. 20, 2007.
Kolisnychenko, V., et al., "Engineering a Reduced *Escherichia coli* Genome," Genome Research, vol. 12, No. 4, pp. 650-647 (2002 (SP002317216).
Posfai, G., et al., "Emergent Properties of Reduced-Genome *Escherichia coli*," Science, vol. 312, No. 5776, pp. 1044-1046 (2006)(XP 0024100684).
Science, (Online), vol. 312, No. 5776, pp. 1-36, May 2006 (XP 002410685).
Yu, B., et al., "Minimization of the *Escherichia coli* Genome Using a Tn5-Targeted CRE/10xP Excision System," Nature Biotechnology, vol. 20, No. 10, pp. 1018-1023 (2002) (XP-002327128).
U.S. Appl. No. 12/064,332—Restriction requirement dated Dec. 30, 2010.
U.S. Appl. No. 12/064,332—Non-final office action dated Jul. 15, 2011.
U.S. Appl. No. 12/064,332—Final office action dated Dec. 12, 2011.
U.S. Appl. No. 12/064,332—Advisory Action dated Jan. 5, 2012.
U.S. Appl. No. 12/064,332—Notice of Allowance dated Jan. 17, 2012.

*Primary Examiner* — Robert A Zeman
(74) *Attorney, Agent, or Firm* — Morgan, Lewis & Bockius LLP

(57) ABSTRACT

Reduced genome strains of *E. coli* MG1655 are described. In various embodiments, the strains have one or more of equal or improved growth rate, transformation efficiency, protein expression, DNA production, DNA yield and/or DNA quality compared to the parental strain and commercially available strains.

5 Claims, 6 Drawing Sheets

Figure 6

REDUCED GENOME E. COLI

CROSS REFERENCE TO RELATED APPLICATIONS

This application is a continuation of U.S. application Ser. No. 12/064,332, filed Jul. 16, 2008, which is a National Stage of International Application Number PCT/US2006/032525, filed Aug. 18, 2006, which claims the benefit of U.S. Provisional Application No. 60/709,960, filed Aug. 20, 2005.

SEQUENCE LISTING SUBMISSION VIA EFS-WEB

A computer readable text file, entitled "010447-5017-US01-Amended-Seq-Listing.txt" created on or about Sep. 14, 2012, with a file size of about 5,740 kb, contains the sequence listing for this application and is hereby incorporated by reference in its entirety.

FIELD OF THE INVENTION

The present invention relates to strains of microorganisms and processes involving these microorganisms. More specifically, the present invention relates to genetically modified strains of microorganisms and the use thereof for the production of commercial products, such as recombinant proteins, nucleic acids, such as DNA, and amino acids. The present invention also relates to methods of preparing strains of microorganisms for such uses.

BACKGROUND OF THE INVENTION

Bacteria have been used to produce a wide range of commercial products. For example, many *Streptomyces* strains and *Bacillus* strains have been used to produce antibiotics; *Pseudomonas denitrificans* and many *Propionibacterium* strains have been used to produce vitamin B12; some other bacteria have been used to produce vitamin Riboflavin; *Brevibacterium flavum* and *Corynebacterium glutamicum* have been used to produce lysine and glutamic acid, respectively, as food additives; other bacteria have been used to produce other amino acids used as food additives; *Alcaligenes eutrophas* has been used to produce biodegradable microbial plastics; and many *Acetobacter* and *Gluconobacter* strains have been used to produce vinegar. More recently, it has become common for bacteria, such as *Escherichia coli* (*E. coli*), to be genetically engineered and used as host cells for the production of biological reagents, such as proteins and nucleic acids, in laboratory as well as industrial settings. The pharmaceutical industry supports several examples of successful products which are human proteins which are manufactured in *E. coli* cultures cultivated in a fermenter.

It is not an uncommon occurrence for normal bacterial proteins to adversely affect the production or the purification of a desired protein product from an engineered bacteria. For example, when *E. coli* bacteria are used as host cells to generate a large quantity of a desired product encoded by a gene that is introduced into the host cells by a plasmid, certain normal *E. coli* gene products can interfere with the introduction and maintenance of plasmid DNA. More significantly, because of the economies of bacterial culture in making proteins in bacteria, often the cost of purification of a recombinant protein can be more than the cost of production, and some of the natural proteins produced by the bacterial host are sensitive to purification procedures. Further, many bacterial strains produce toxins that must be purified away from the target protein being produced and some strains can produce, by coincidence, native proteins that are close in size to the target protein, thereby making size separation ineffective for the purification process.

The genome of a bacteria used in a fermenter to produce a recombinant protein includes many unnecessary genes. A bacteria living in a natural environment has many condition responsive genes to provide mechanisms for surviving difficult environmental conditions of temperature, stress or lack of food source. Bacteria living in a fermentation tank do not have these problems and hence do not require these condition responsive genes. The bacterial host spends metabolic energy each multiplication cycle replicating these genes. Thus the unnecessary genes and the unneeded proteins, produced by a bacterial host used for production of recombinant protein, result in a lack of efficiencies in the system that could be improved upon.

It is not terribly difficult to make deletions in the genome of a microorganism. One can perform random deletion studies in organisms by simply deleting genomic regions to study what traits of the organism are lost by the deleted genes. It is more difficult, however, to make targeted deletions of specific regions of genomic DNA and more difficult still if one of the objectives of the method is to leave no inserted DNA or mutations, here termed a "scar," in the genome of the organism after the deletion. If regions of inserted DNA or mutations, i.e. scars, are left behind after a genomic deletion procedure, those regions can be the locations for unwanted recombination events that could excise from the genome regions that are desirable or engender genome rearrangements. In building a series of multiple deletions, scars left behind in previous steps could become artifactual targets for succeeding steps of deletion. This is especially so when the method is used repeatedly to generate a series of deletions from the genome. In other words, the organism becomes by the deletion process genetically unstable if inserted DNA or mutations are left behind.

BRIEF DESCRIPTION OF SEQUENCE LISTING, TABLES AND COMPUTER PROGRAM LISTING

A sequence listing is attached to the present application in a file named SEQ.txt (5740 KB, 19 May. 2005), and is hereby incorporated by reference herein.

SUMMARY OF THE INVENTION

In one embodiment of the invention, a reduced genome strain is provided, which may be lacking the nucleic acid regions shown on Table 2 or a region with a sequence substantially identical thereto and the following ranges of nucleic acid sequences with reference to SEQ ID NO: 1: 167484-169727, 169778-170575, 170575-171465 and 171462-173444 or a sequence substantially identical thereto. The genome of the strain may be further lacking the following range of nucleic acid sequence with reference to SEQ ID NO: 1: 3088369-3089076 or a sequence substantially identical thereto. The genome of the strain may also be further lacking the following range of nucleic acid sequence with reference to SEQ ID NO: 1: 2820730-2821791 or a sequence substantially identical thereto.

In another embodiment, the invention provides a strain of *E. coli* lacking one or more of the nucleic acid regions shown on any of Tables 1-20, or sequences substantially identical thereto.

In still another embodiment, the invention provides a strain of E. coli lacking one or more of the nucleic acid regions shown on any of Tables 1-20, or sequences substantially identical thereto.

The parent of the reduced genome strain may be E. coli. The parent of the reduced genome strain may also be E. coli MG1655. The genomic sequence of the parent of the reduced genome strain may be the sequence set forth in SEQ ID NO: 1 or a sequence substantially identical thereto.

The strain may comprise a heterologous nucleic acid. The genome of the strain may comprise the heterologous nucleic acid. The heterologous nucleic acid may be a vector, such as a plasmid. The plasmid may also comprise a heterologous nucleic acid. The heterologous nucleic acid may be operatively linked to an expression control sequence. The strain may be used to produce a polypeptide by expressing a polypeptide encoded by the heterologous nucleic acid. The heterologous nucleic acid may be introduced into the strain by transforming the strain with the heterologous nucleic acid. The heterologous nucleic acid may be amplified in the strain.

BRIEF DESCRIPTION OF THE DRAWINGS

FIG. 6 shows the restriction pattern of pCTXVP60 propagated in various strains: (M) molecular weight marker, 1 kbp ladder; (1) MDS41, no insertion; (2) MDS42, no insertion; (3) DH10B, IS10 insertion; (4) DH10B, IS10 insertion/deletion; (5) C600, IS5 insertion; (6) C600, IS1 insertion; and (7) 0600, IS1 insertion. Below the gel, the relative positions of the IS insertions in the CTXVP60 reading frame are diagrammed.

DETAILED DESCRIPTION OF THE INVENTION

Figure 1:
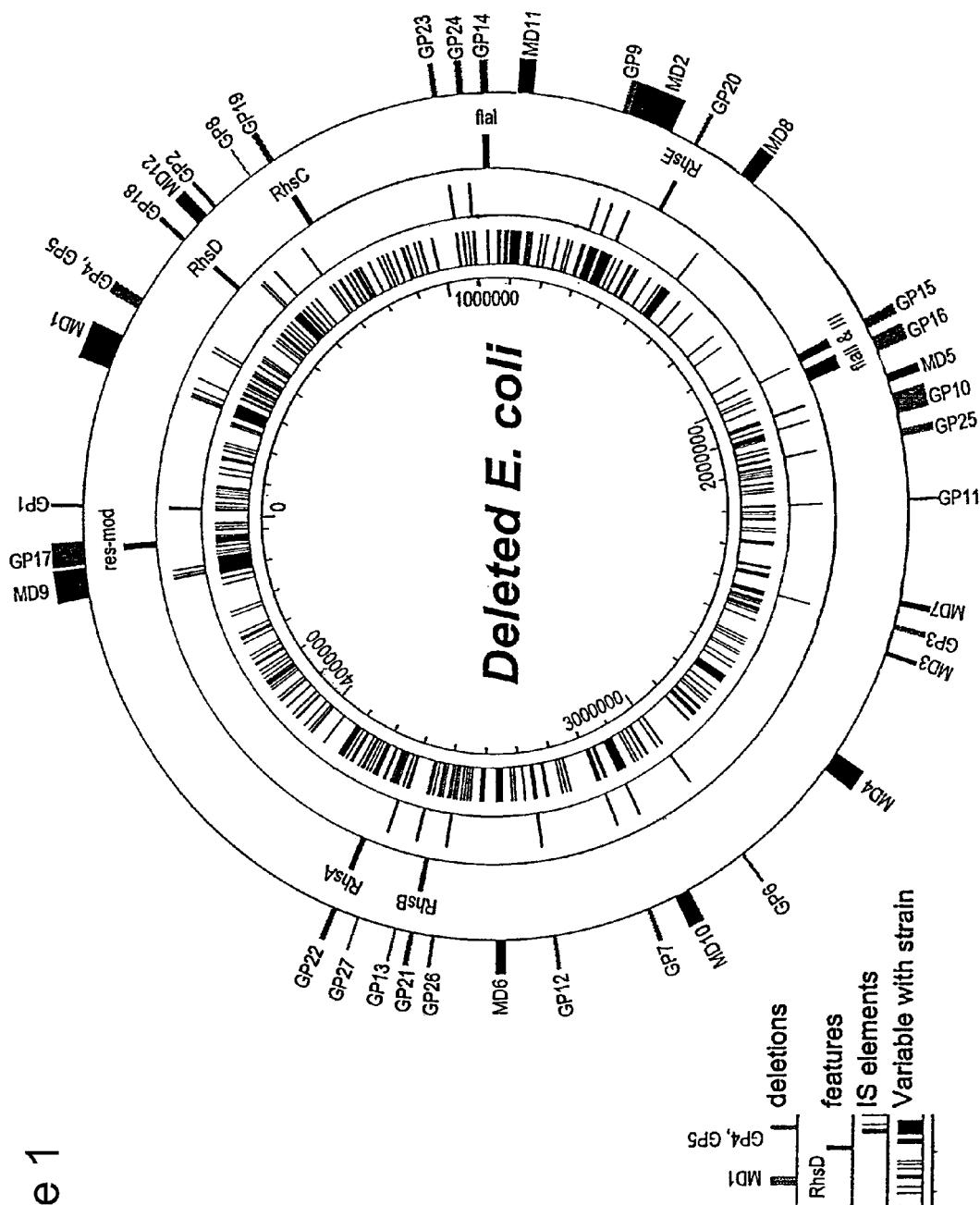
FIG. 1 is an illustration of the original release of the E. coli K-12 genome (strain MG1655-annotation version m54), which natively comprises 4,639,221 nucleotides or base pairs. The inner ring of FIG. 1 shows the scale of the base pair positions without deletions (see also Blattner et al., infra). The next ring progressively outward shows regions of the K-12 genome that are missing or highly altered in a related strain O157:H7, and which are thus potentially delegable from the K-12 genome. The next ring outward shows the positions of the IS elements, both complete and partial, in the native genome. The next ring moving outward shows the positions of the RHS elements A to E and flagellar and restriction regions. The outermost ring shows the location of the deletions actually made to the genome, as described in U.S. Patent Publication No. 20030138937 and International Patent Publication No. WO 2003/070880, the contents of which are incorporated herein by reference, which delete up to about 14 percent of the base pairs in the original K-12 MG1655 genome.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent at issue. Also, the disclosure of ranges is intended as a continuous range including every value between the minimum and maximum values recited as well as any ranges that can be formable thereby.

It is also to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges, and ranges of ratios can be unambiguously derived from the data and numbers presented herein and all represent embodiments of the present invention.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

1. Definitions

"Base pair" used herein may refer to the hydrogen bonded nucleotides of, for example, adenine (A) with thymine (T), or of cytosine (C) with guanine (G) in a double-stranded DNA molecule. In RNA, uracil (U) is substituted for thymine. Base pair may also be used as a unit of measure for DNA length.

"Clone" used in reference to an insert sequence and a vector may mean ligation of the insert sequence into the vector or its introduction by recombination either homologous, site specific or illegitimate as the case may be. When used in reference to an insert sequence, a vector, and a host cell, the term may mean to make copies of a given insert sequence. The term may also refer to a host cell carrying a cloned insert sequence, or to the cloned insert sequence itself.

"Complement," "complementary" or "complementarity" used herein may mean Watson-Crick or Hoogsteen base pairing between nucleotides or nucleotide analogs of nucleic acid molecules. For example, the sequence 5'-A-G-T-3' is complementary to the sequence 3'-T-C-A-5'. Complementarity may be "partial," in which only some of the nucleotides are matched according to the base pairing rules. Or, there may be "complete" or "total" complementarity between the nucleic acids. The degree of complementarity between nucleic acid strands may have effects on the efficiency and strength of hybridization between nucleic acid strands.

"Encoding" or "coding" used herein when referring to a nucleic acid may mean a sequence of nucleotides, which upon transcription into RNA and subsequent translation into protein, would lead to the synthesis of a given protein, peptide or amino acid sequence. Such transcription and translation may actually occur in vitro or in vivo, or may be strictly theoretical based on the standard genetic code.

"Enzyme" used herein may mean a protein which acts as a catalyst to induce a chemical change in other compounds, thereby producing one or more products from one or more substrates. Enzymes are referred to herein using standard nomenclature or by their EC number, as recommended by the Nomenclature Committee of the International Union of Biochemistry and Molecular Biology as of Mar. 11, 2004.

"Expression control sequence" used herein may mean a promoter or array of transcription factor binding sites that direct transcription of a nucleic acid operatively linked thereto.

"Free end" used in reference to a double-stranded nucleic acid may mean a linear nucleic acid with blunt free ends or sticky free ends, or a combination thereof.

"Gene" used herein may refer to a nucleic acid (e.g., DNA or RNA) that comprises a nucleic acid sequence encoding a polypeptide or precursor thereto. The polypeptide can be encoded by a full length coding sequence or by any portion of the coding sequence so long as the desired activity or functional properties (e.g., enzymatic activity, ligand binding, signal transduction, antigenicity etc.) of the full-length or fragment are retained. The term also encompasses the sequences located adjacent to the coding region on both the 5' and 3' ends that contribute to the gene being transcribed into a full-length mRNA. The term "gene" encompasses both cDNA and genomic forms of a gene. A genomic form or clone of a gene may contain the coding region interrupted with non-coding sequences termed (e.g., introns).

"Introduce" or "introduced" when used in reference to adding a nucleic acid to a strain, may mean that the nucleic acid may be integrated into the chromosome of the strain or contained on a vector, such as a plasmid, in the strain.

"Library" used herein may refer to a plurality of vectors each comprising an insert sequence or to a plurality of nucleotide fragments.

"Mutant" or "mutagenesis" used herein may mean any modification to the nucleic acid of a parent strain. Mutagenesis of nucleic acid may be of any type including, but not limited to, deletion, insertion, substitution, rearrangement, and suppressor and point mutations.

"Nucleic acid" used herein may mean any nucleic acid containing molecule including, but not limited to, DNA or RNA. The term encompasses sequences that include any base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5 carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracils, 5-methoxyaminomethyl-2-thiouracil, ÿ-D-maminosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

"Nucleotide" used herein may refer to a monomeric unit of nucleic acid (e.g. DNA or RNA) consisting of a pentose sugar moiety, a phosphate group, and a nitrogenous heterocyclic base. The base may be linked to the sugar moiety via the glycosidic carbon (1' carbon of the pentose). The combination of base and sugar may be called a nucleoside. When the nucleoside contains a phosphate group bonded to the 3' or 5' position of the pentose, it may be referred to as a nucleotide. A sequence of operatively linked nucleotides may be referred to as a "base sequence" or "nucleotide sequence" or "nucleic acid sequence," and may be represented herein by a formula whose left to right orientation is in the conventional direction of 5'-terminus to 3'-terminus.

"Operably linked" used herein may refer to an expression control sequence and downstream polynucleotide, such that productive transcription of the polynucleotide is initiated at the expression control sequence.

"Overexpressing" used herein may mean that the total cellular activity of protein encoded by a gene is increased. The total cellular activity of a protein may be due to increased cellular amounts of a protein, or increased half-life of the protein. Total cellular amounts of a protein may be increased by methods including, but not limited to, amplification of the gene coding said protein or operatively linking a strong promoter to the gene coding said protein.

"Protein" used herein may mean a peptide, polypeptide and protein, whether native or recombinant, as well as fragments, derivatives, homologs, variants and fusions thereof.

"Region of comparison" used herein when referring to a genome may be $1 \times 10^7$, $1.5 \times 10^7$, $2 \times 10^7$, $2.5 \times 10^7$, $3 \times 10^7$, $3.5 \times 10^6$, $4 \times 10^7$ or more nucleotides or base pairs, and when referring to a nucleic acid sequence may be 50, 100, 250, 500, $10^3$, $5 \times 10^3$, $10^4$, $5 \times 10^4$, $10^5$, $5 \times 10^5$, $10^6$ or more nucleotides or more base pairs.

"Stringent hybridization conditions" used herein may mean conditions under which a first nucleic acid sequence will specifically or selectively hybridize to a second nucleic acid sequence, such as in a complex mixture of nucleic acids, but to no other sequences. Stringent conditions are sequence-dependent and will be different in different circumstances. Generally, stringent conditions are selected to be about 5-10° C. lower than the thermal melting point (Tm) for the specific sequence at a defined ionic strength pH. The Tm may be the temperature (under defined ionic strength, pH, and nucleic concentration) at which 50% of the first sequence hybridizes to the second sequence at equilibrium (as the second sequences are present in excess, at Tm, 50% of the first sequence are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short nucleic acid sequences (e.g., about 10-50 nucleotides) and at least about 60° C. for long nucleic acid sequences (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" used herein may mean that a first sequence is at least 60%, 65%, 70%, 75%, 80%, 85%, 90%, 95%, 97%, 98% or 99% identical to the complement of a second sequence over a region of comparison or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical or substantially complementary over a region of comparison. A reference sequence and a test sequence may be aligned, manually or by a computer algorithm (e.g., GAP, BESTFIT, FASTA and TFAST), and the percentage identity calculated by dividing "the total number of identical residues" by "the total number of residues in the reference sequence" and then multiplying by 100.

2. Reduced Genome Strains

Bacteria in their natural environment are exposed to many conditions that are not normally experienced in standard industrial or laboratory growth, and thus carry a large number of condition-dependent, stress-induced genes or otherwise nonessential genes which may not be needed in industrial or laboratory use of the organisms. It was realized that much of the genetic information contained within the genome of a bacteria strain could be deleted without detrimental effect to use of bacteria cultures in processes of industrial or laboratory importance. It was also recognized that a bacterium with a reduced genome might be advantageous over native strains in many industrial and laboratory applications. For example, a bacterium with a reduced genome is at least somewhat less metabolically demanding and thus can produce a desired product more efficiently. In addition, a reduced genome can lead to fewer native products and lower levels of certain native proteins, allowing easier purification of a desired protein from the remaining bacterial proteins. Furthermore, some bacterial genetic sequences are associated with instabilities that can interfere with standard industrial or laboratory practices, and might entail costly and burdensome quality control procedures.

The reduced genome strain may have a genome that is at least two percent (2%), five percent (5%), seven percent (7%) to eight percent (8%) to fourteen percent (14%) to eighteen percent (18%) to twenty percent (20%), to forty percent (40%) to sixty percent (60%) smaller than the genome of its native parental strain. The percentage by which a genome has become smaller after a series of deletions is calculated by dividing "the total number of base pairs deleted after all of the deletions" by "the total number of base pairs in the genome of the parental strain before all of the deletions" and then multiplying by 100.

The reduced genome strain may also have a genome that has about 5% to about 10%, about 10% to about 20%, about 30% to about 40%, or about 60% of its protein encoding genes deleted. The percentage by which a genome has had protein encoding genes deleted is calculated by dividing "the total number of protein encoding genes deleted after all of the deletions" by "the total number of protein encoding genes in the genome of the parental strain before all of the deletions" and then multiplying by 100.

The genes and other nucleic acid sequences deleted from the genome may not adversely affect the rate of survival and proliferation of the reduced genome strain under specific growth conditions. Whether a level of adverse effect is acceptable depends on a specific application. For example, a 30% reduction in proliferation rate may be acceptable for one application but not another. In addition, adverse effect of deleting a nucleic acid sequence from the genome may be reduced by measures such as changing culture conditions. Such measures may turn an unacceptable adverse effect to an acceptable one. The proliferation rate may be increased or approximately the same as the parental strain. The proliferation rate may also be from about 5%, 10%, 15%, 20%, 30%, 40% to about 50% lower than that of the parental strain. The doubling time of the reduced genome strain may range from about thirty minutes to about three hours.

a. Parent

The parental strain may be any bacteria strain or other organism, as well as an intermediate strain from which the reduced genome strain is derived. Representative examples of parent strains include, but are not limited to, *E. coli* strains such as K-12 or B, or a strain with a genome sequence substantially identical thereto. The K-12 strain may be MG1655. The nucleotide sequence of the genome of the parental strain may be partially or completely known. The complete genomic sequence of several strains of *E. coli* and other commonly used laboratory microorganisms is known (see, e.g., Blattner et al, *Science*, 277:1453-74, 1997; GenBank Accession No. U00096; Perna et al, *Nature*, 409, 529-533, 2001; Hayashi et al, *DNA Res.*, 8, 11-22, 2001; Welch et al., *Proc. Natl. Acad. Sci., USA* 99:17020-17024, 2002 and GenBank Accession No. AE014075, each of which is incorporated herein by reference.

The nucleic acid sequence of *E. coli* MG1655 (annotated version m56) is set forth in SEQ ID NO: 1 with a total size of 4,639,675 nucleotides or base pairs. The original release of the genomic sequence of *E. coli* MG1655 was annotated version m54 (4,639,221 nucleotides or base pairs). Each gene that was predicted to occur in the original release of the *E. coli* MG1655 genome was assigned a unique numeric identifier beginning with a lowercase "b". The first predicted gene was thrL with b0001 the last gene was lasT with b4403, since the initial release several new genes have been found which were given unauthenticated b-numbers with a suffix of "a" or "0.1" by various groups for example yaaV. Some of these genes were accepted in the most recent annotation (version m56) and have had new b-numbers assigned starting from b4404. Several genes in the m54 version have since been shown to be merged together or split apart caused by sequencing errors these have all been reissued new b-numbers from b4460 to b4500 and the old b-number deaccessioned.

b. Genomic Deletions

The reduced genome strain may be lacking one or more of the nucleic acid regions set forth on Table 1 or sequences substantially identical thereto. Table 1 provides the following annotated features of the genome for *E. coli* MG1655 (annotated version m56) (SEQ ID NO: 1): Column 1 (Type) lists the type of annotated feature (coding sequence (CDS), prophage, rep_origin, repeat region, rRNA, tRNA, misc_RNA or misc_feature); Column 2 (S) lists the reference strand (+:forward, −: complementary); Column 3 (Left) lists the position of the left end of the feature; Column 4 (Right) lists the position of the right end of the feature; Column 5 (Name) lists the name of the feature; and Column 6 (B) lists the Blattner number or b-number of the feature. The reduced genome strain may be MDS41, MDS42, MDS43, MDS44, MDS45, MDS46, MDS47, MDS48, MDS49, MDS50, MDS51, MDS52, MDS53, MDS54, MDS55, MDS56, MDS57, MDS58, MDS59, MDS60 or a strain with a genome substantially identical thereto. The reduced genome strain may also be MDS42recA⁻ or a strain with a genome substantially identical thereto.

One type of nucleic acid sequence that may be deleted includes those that may adversely affect the stability of the organism or of the gene products of that organism. Such elements that give rise to instability include transposable elements, insertion sequences, and other "selfish DNA" elements that may play a role in genome instability. These elements, either intact or defective, may move from one point to another in the genome or other nucleic acid sequences in the cell, such as a vector. These elements may not be important for bacteria survival and growth in a cultured environment. Positions of the IS elements on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference. Other nucleic acid sequences associated with genomic instability may also be deleted.

Another type of nucleic acid sequence that may be deleted is the restriction modification system genes and other endogenous nucleases whose products may destroy foreign DNA. These genes may not be important for bacterial survival and growth in culture environments. These genes may also interfere with genetic engineering by destroying vectors introduced into a bacterium, Positions of restriction modification system genes on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference. DNA methylase genes, including heterologous genes, may be added back to the deleted strain so as to optimize the strain for certain uses, for example, eukaryotic methylase genes.

Another type of nucleic acid sequence that may be deleted is the flagella gene family, which may provide motility for bacteria. In cultured environments, bacteria motility may not be important for cell survival and growth and the swimming action may be metabolically very expensive, consuming over 1% of the cellular energy to no benefit. Positions of flagella genes on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference.

Another type of nucleic acid sequence that may be deleted is Rhs elements. Rhs elements may share a 3.7 Kb Rhs core, which may be a large homologous repeated region (there may be 5 copies in *E. coli* K-12) that may provide a means for genome rearrangement via homologous recombination. Rhs elements may be accessory elements which largely evolved in some other background and spread to *E. coli* by horizontal exchange after divergence of *E. coli* as a species. Positions of Rhs elements on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference.

Another type of nucleic acid sequence that may be deleted is the non-transcribed regions, which may be less important for cell survival and proliferation. Another type of nucleic acid sequence that can be deleted is the hsd regions, which may encode the major restriction modification gene family. Positions of non-transcribed regions and hsd regions on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference.

Other types of nucleic acid sequence that may be deleted include prophages, pseudogenes, toxin genes, pathogenicity genes, periplasmic protein genes, membrane protein genes, and bacteriophage receptors, such as [tonA] (FhuA) and/or its complete operon [fhu] ABC which encodes the receptor for the lytic phage T1.

Other types of nucleic acid sequences that may be deleted may be identified by comparing the genome of one bacterial strain to one or more others strains. Nucleic acid sequences that are not present in two or three of the strains are less likely to be functionally essential and thus may be candidates for deletion. After the sequence of *E. coli* K-12 (see Blattner, et al., supra), was compared to the sequence of its close relative O157:H7 (See Perna et al., supra), it was discovered that 22% (K-12) and 46% (O157:H7) of the protein encoding genes may be located on strain-specific islands of from one to about 85 kb inserted randomly into a relatively constant backbone. U.S. Patent Publication No. 20030138937 and International Patent Publication No. WO 2003/070880, the contents of which are incorporated herein by reference, describe the comparison of the genomic sequences of *E. coli* strains O157:H7 EDL933 and K-12 MG1655, which led to the identification and deletion of twelve targets resulting in a bacteria strain with a genome that is about 8% smaller. The bacteria with the reduced genome grew at substantially the same rate as the native parent MG1655 strain.

The DNA sequence of a uropathogenic *E. coli* strain CFT073 H7 (see Welch et al., supra), was recently determined and its sequence was compared to the K-12 (MG1655) and O157:H7. Results show that only about 40% of all coding genes found in any one of the genomes are present in all of the genomes and CFT073, K-12 and O157:H7 are composed of 67%, 43% and 68% strain specific island genes. Based on this information, as much as about 60% of the protein coding sequences may be deleted from *E. coli*. It should be noted that there may be genes essential for growth in one strain that are not required for growth in other strains. In such cases, the gene essential for growth of that strain may not be deleted from the strain or if deleted may be replaced with another gene with a complementary function so as to permit growth of the strain.

Other types of nucleic acid sequences that may be deleted are genes coding periplasmic proteins. Gram-negative bacteria, such as *E. coli*, have two cellular membranes, the inner cell membrane and the outer cell membrane, which are separated by a periplasmic space (PS). Nine known and three putative periplasmic protein genes were successfully deleted in constructing MDS40, without significantly affecting the ability of the organism to grow on minimal medium, as shown in International Patent Publication No. WO 2003/070880, the contents of which are incorporated herein by reference. These mutations affect a range of functions, including amino acid uptake, inorganic metabolism, cell membrane maintenance, sugar metabolism, and adhesion. Eliminating periplasmic proteins may reduce the contaminants in recombinant proteins expressed in the periplasm.

Approximately 85 genes have been deleted that code for known or putative membrane proteins, identified by their signal-peptide sequences. Of these 33 may be involved in flagellar structure or biosynthesis; 9 may be involved in fimbrial structure or biosynthesis; and 13 may be involved in general secretory pathways. The remainder may have a variety of known or putative functions in the cell membranes. Many of these proteins may be processed in the periplasmic space. They have also been deleted in constructing MDS40 without significantly affecting the ability of the organism to grow on minimal medium, as shown in International Patent Publication No. WO 2003/070880, the contents of which are incorporated herein by reference.

By searching for signal peptide-like sequences in annotated MG1655 databases, and cross-relating these with the literature, 181 proteins have been identified which may be resident periplasmic proteins. A number of these proteins have been classified according to function into several groups excluding: adhesion and mobility; nutrient and salt uptake, trace element uptake; environmental sensing; defense and protection; and periplasmic protein secretion and processing. Among the genes or full operons which may be deleted are those coding for sugar and amino acid transport proteins, which may not be needed in defined minimal media say for biopharmaceutical production.

One may test the consequence of deleting one or several genes or other nucleic acid sequences from the genome. For example, after one or several genes or other nucleic acid sequences of the genome have been deleted, one can measure the survival and proliferation rate of the resultant bacteria. Although most of the above-identified genes or other nucleic acid sequences may be deleted without detrimental effect for purpose of producing a desired product, it is possible that the deletion of a specific gene or other nucleic acid sequence may have an unacceptable consequence such as cell death or unacceptable level of reduction in proliferation rate. This possibility exists because of redundancies in gene functions and interactions between biological pathways. Some deletions that are viable in a strain without additional deletions will be deleterious only in combination with other deletions. The possibility exists also because of certain methods used to identify deletion candidates. For example, one method used to identify deletion candidates is to compare two E. coli strains and select genes or other DNA sequences that are not present in both strains. While the majority of these genes and other DNA sequences are not likely to be functionally essential, some of them may be important for a unique strain. Another method used to identify deletion candidates is to identify non-transcribed regions and the possibility exists that certain non-transcribed regions may be important for genome stability.

The consequence of deleting one or several genes or other DNA sequences to be tested depends on the purpose of an application. For example, when high production efficiency is the main concern, which is true for many applications, the effect of deletions on proliferation rate and medium consumption rate can be the consequence tested. In this case, the consequence tested can also be more specific as the production speed quantity and yield per cell of a particular product. When eliminating native protein contamination is the main concern, fewer native proteins and lower native protein levels, or the absence of a specific native protein, can be the consequence tested.

Testing the consequence of deleting a gene or other DNA sequence may be important when little is known about the gene or the DNA sequence. This is another viable method to identify deletion candidates in making a bacterium with a reduced genome. This method is particularly useful when candidates identified by other methods have been deleted and additional candidates are being sought.

When the consequence of deleting a gene or other DNA sequence has an effect on the viability of the bacteria under a set of conditions, one alternative to not deleting the specific gene or other DNA sequence is to determine if there are measures that can mitigate the detrimental effects. For example, if deleting lipopolysaccharide (LPS) genes results in poor survival due to more porous cellular membranes caused by the absence from the cellular membranes of the transmembrane domain of the LPS proteins, culture conditions can be changed to accommodate the more porous cellular membranes so that the bacteria lacking the LPS genes can survive just as well as the bacteria carrying the LPS genes.

c. Manner of Making Deletions

The strains may be made by deleting the nucleic acid sequences using any of the several methods known to those of skill in the art for deleting genomic nucleic acid. The nucleic acid sequences may be deleted from the genome without generating any other mutations at the deletion site and without leaving any inserted nucleic acid behind (scarless deletion). If several sequential deletions are being made from a bacterial genome, it may be important not to leave any inserted nucleic acid sequences behind. Such inserted sequences, if they were left behind, may be candidate sites for undesired recombination events that would delete uncharacterized and perhaps important portions of the remaining genome from the bacteria or cause other unanticipated genome rearrangements with untoward effects.

Representative methods for making deletions in the genome of a bacteria are described in U.S. Patent Publication No. 20030138937 and International Patent Publication No. WO 2003/070880, Posfai, G. et al., *J. Bacteriol,* 179: 4426-4428 (1997), Muyrers, J. P. P. et al., *Nucl. Acids Res.* 27:1555-1557 (1999), Datsenko, K. A. et al., *Proc, Natl. Acad. Sci.* 97:6640-6649 (2000) and Posfai, G. et al., *Nucl. Acids Res.* 27: 4409-4415 (1999), each of which is incorporated herein by reference. The deletion methods may be classified to those that are based on linear DNAs and those that are based on suicide plasmids. The methods disclosed in Muyrers, J. P. P. et al., *Nucl. Acids Res.* 27:1555-1557 (1999) and Datsenko, K. A. et al., *Proc. Natl. Acad. Sci.* 97:6640-6649 (2000) are linear DNA-based methods and the methods disclosed in Posfai, G. et al., *J. Bacteriol.* 179: 4426-4428 (1997) and Posfai, G. et al., *Nucl. Acids Res.* 27: 4409-4415 (1999) are suicide plasmid-based methods.

3. Methods a. Products

The reduced genome strain may used for the production of desired products, such as recombinant proteins, nucleic acids, therapeutic products, metabolic intermediates and end products. Representative examples of recombinant proteins include, but are not limited to, insulin, interleukins, cytokines, growth hormones, growth factors, erythropoietin, colony stimulating factors, interferon, antibodies and antibody fragments. Representative examples of therapeutic products include, but are not limited to, a vaccine component, a diagnostic product, or a research reagent. Representative examples of metabolic intermediates and end products include, but are not limited to, vanillin, shikimic acid, amino acids, vitamins, organic acids, and the like, and chemical compounds not naturally produced in the bacteria but produced as a result of metabolic pathway engineering or other genetic manipulation (see, e.g., U.S. Pat. Nos. 6,472,16 and 6,372,476, both of which are incorporated herein by reference).

Recombinant proteins may be expressed into the periplasm or cytoplasm. The expression of proteins in the periplasm is routinely used for industrial use and has been reviewed in Hanahan, [*J. Mol. Biol.*], 166:557-80, 1983; Hockney, [*Trends Biotechnol.*], 12:456-632, 1994; and Hannig et al., [*Trends Biotechnol.*], 16:54-60, 1998, each of which is incorporated herein by reference. Recombinant proteins may be produced in the periplasm by expressing fusion proteins in which they are attached to a signal peptide that causes secretion into the periplasmic space. There the signal peptide may be cleaved off by specific signal peptidases.

Constructs useful for periplasmic expression may comprise a first nucleic acid sequence encoding a signal peptide capable of mediating transport of a protein to the periplasmic space operatively linked to a second nucleic acid sequence encoding the desired protein. The signal sequence may be native to the protein being expressed. The protein transported into the periplasmic space may be biologically active. Expression of the recombinant construct may be under the control of an inducible promoter or a promoter that is constitutively expressed in the host strain. The use of inducible promoters may be advantageous when using the Sec system which may be saturable. For example, [lac]-based promoter/repressor, inducible by the non-metabolizable galactose derivative, IPTG, may be used. Such promoters may allow fine tuning of expression and secretion through the Sec system thereby optimizing periplasmic expression.

The recombinant protein may also be co-expressed with chaperones/disulfide-bond forming enzymes which may provide proper folding of the recombinant protein. Nucleic acid sequences useful for periplasmic expression of recombinant protein include, but are not limited to, those described in U.S. Pat. Nos. 5,747,662; 5,578,464; 6,335,178; and 6,022,952; Thomas et al., Mol-Micro[*Mol Micro*], (2001) 39 (1) 47-53; Weiner et al., [*Cell*], (1998) 93, 93-101; and Current Protocols in Molecular Biology[*Current Protocols in Molecular Biology*] (1994) 16.6.1-16.6.14 (Copyright 2000 by John Wiley [et al.] and Sons), each of which is incorporated herein by reference.

b. Amplification

The reduced genome strain may also be used to clone or amplify a nucleic acid. The reduced genome strain may provide a clean, minimal genetic background that may allow the production of high quality nucleic acids. A reduced genome strain lacking selfish DNA elements, such as IS elements, may also allow the cloning of otherwise toxic genes. The reduced genome strain may also be used to produce a library, such as a genomic library.

c. Vaccine

The reduced genome strain may also be used as a vaccine by introducing heterologous genes encoding antigens capable of inducing an immune response in a host that has been inoculated with the vaccine. Reduced genome vaccines may be DNA based vaccines containing a DNA known to be capable of inducing a desired physiological response in a host (i.e., immune response).

The present invention has multiple aspects, illustrated by the following non-limiting examples.

EXAMPLE 1

Production of MDS40

Reduced genome strain MDS40 was produced as described in International Patent Publication No. WO 2003/070880, which is incorporated herein by reference. Briefly, a series of reduced genome strains (MDS01-MDS40) were produced by making a series of cumulative deletions of nucleic acid sequences from the parental strain *E. coli* MG1655 (annotated version m56) (SEQ ID NO: 1), including those regions shown in Table 2.

EXAMPLE 2

Production of MDS41

Reduced genome strain MDS41 was produced using methods as described in International Patent Publication No. WO 2003/070880 by deleting the following nucleic acid region from parental strain MDS40, with reference to SEQ ID NO: 1:

| Strain | Type | Coordinates | Name | B | Function |
|---|---|---|---|---|---|
| MDS41 | CDS | 167484 ... 169727 | fhuA | b0150 | outer membrane protein receptor for ferrichrome, colicin M, and phages T1, T5, and phi80 |
| MDS41 | CDS | 169778 ... 170575 | fhuC | b0151 | ATP-binding component of hydroxymate-dependent iron transport |
| MDS41 | CDS | 170575 ... 171465 | fhuD | b0152 | hydroxamate-dependent iron uptake cytoplasmic membrane component |
| MDS41 | CDS | 171462 ... 173444 | fhuB | b0153 | hydroxamate-dependent iron uptake cytoplasmic membrane component |

EXAMPLE 3

Production of MDS42

Reduced genome strain MDS42 was produced using methods as described in International Patent Publication No. WO 2003/070880 by deleting the following nucleic acid region from parental strain MDS41, with reference to SEQ ID NO: 1:

| Strain | Type | Coordinates | Name | B | Function |
|---|---|---|---|---|---|
| MDS42 | CDS | 3088369 ... 3089076 | endA | b2945 | DNA-specific endonuclease I |

EXAMPLE 4

Production of MDS42recA⁻

Reduced genome strain MDS42 was produced using methods as described in International Patent Publication No. WO 2003/070880 by deleting the following nucleic acid region from parental strain MDS42, with reference to SEQ ID NO: 1:

| Strain | Type | Coordinates | Name | B | Function |
|---|---|---|---|---|---|
| MDS42recA | CDS | Complement (2820730 ... 2821791) | recA | b2699 | DNA strand exchange and renaturation DNA-dependent ATPase, DNA- and ATP-dependent coprotease |

EXAMPLE 5

Production of MDS43

Reduced genome strain MDS43 was produced using methods as described in International Patent Publication No. WO 2003/070880 by deleting the nucleic acid regions shown in Table 3 from parental strain MDS42, with reference to SEQ ID NO: 1.

EXAMPLE 6

Production of MDS44

Reduced genome strain MDS44 was produced using methods as described in International Patent Publication No. WO 2003/070880 by deleting the following nucleic acid region (also show in Table 4) from parental strain MDS43, with reference to SEQ ID NO: 1:

| Strain | Type | Coordinates | Name | B | Function |
|---|---|---|---|---|---|
| MDS44 | CDS | 2599223...2599840 | hyfA | b2481 | hydrogenase 4 Fe—S subunit |
| MDS44 | CDS | 2599840...2601858 | hyfB | b2482 | hydrogenase 4 membrane subunit |
| MDS44 | CDS | 2601869...2602816 | hyfC | b2483 | hydrogenase 4 membrane subunit |
| MDS44 | CDS | 2602833...2604272 | hyfD | b2484 | hydrogenase 4 membrane subunit |
| MDS44 | CDS | 2604284...2604934 | hyfE | b2485 | hydrogenase 4 membrane subunit |
| MDS44 | CDS | 2604939...2606519 | hyfF | b2486 | hydrogenase 4 membrane subunit |
| MDS44 | CDS | 2606509...2608176 | hyfG | b2487 | hydrogenase 4 subunit |
| MDS44 | CDS | 2608186...2608731 | hyfH | b2488 | hydrogenase 4 Fe—S subunit |
| MDS44 | CDS | 2608728...2609486 | hyfI | b2489 | hydrogenase 4 Fe—S subunit |
| MDS44 | CDS | 2609479...2609892 | hyfJ | b2490 | hydrogenase 4 component J |
| MDS44 | CDS | 2609922...2611934 | hyfR | b2491 | putative 2-component regulator interaction with sigma 54 |
| MDS44 | CDS | 2611956...2612804 | focB | b2492 | probable formate transporter (formate channel 2) |

EXAMPLE 7

Production of MDS45

Reduced genome strain MDS45 was produced using methods as described in International Patent Publication No. WO 2003/070880 by deleting the following nucleic acid region (also show in Table 5) from parental strain MDS44, with reference to SEQ ID NO: 1:

| Strain | Type | Coordinates | Name | B | Function |
|---|---|---|---|---|---|
| MDS45 | CDS | 2318065...2319891 | atoS | b2219 | sensor protein AtoS for response regulator AtoC |
| MDS45 | CDS | 2319888...2321273 | atoC | b2220 | response regulator of ato, ornithine decarboxylase antizyme (sensor ATOS) |
| MDS45 | CDS | 2321469...2322131 | atoD | b2221 | acetyl-CoA:acetoacetyl-CoA transferase alpha subunit |
| MDS45 | CDS | 2322131...2322781 | atoA | b2222 | acetyl-CoA:acetoacetyl-CoA transferase beta subunit |
| MDS45 | CDS | 2322778...2324100 | atoE | b2223 | short chain fatty acid transporter |
| MDS45 | CDS | 2324131...2325315 | atoB | b2224 | acetyl-CoA acetyltransferase |
| MDS45 | CDS | complement(2325389...2326165) | yfaP | b2225 | orf, hypothetical protein |
| MDS45 | CDS | complement(2326170...2327819) | yfaQ | b2226 | orf, hypothetical protein |
| MDS45 | CDS | complement(2327820...2328305) | yfaS_2 | b2227 | orf, hypothetical protein |
| MDS45 | pseudogene | complement(2327820...2332424) | yfaS | b4500 | pseudogene |
| MDS45 | CDS | complement(2328321...2332424) | yfaS_1 | b2228 | putative membrane protein |
| MDS45 | CDS | complement(2332358...2332981) | yfaT | b2229 | orf, hypothetical protein |
| MDS45 | CDS | complement(2332978...2334666) | yfaA | b2230 | orf, hypothetical protein |

EXAMPLE 8

Production of MDS46

Reduced genome strain MDS46 was produced using methods as described in International Patent Publication No. WO 2003/070880 by deleting the following nucleic acid region (also show in Table 6) from parental strain MDS45, with reference to SEQ ID NO: 1:

| Strain | Type | Coordinates | Name | B | Function |
|---|---|---|---|---|---|
| MDS46 | CDS | 3886458 ... 3886532 | tnaL | b3707 | tryptophanase leader peptide |
| MDS46 | CDS | 3886753 ... 3888168 | tnaA | b3708 | tryptophanase |
| MDS46 | CDS | 3888259 ... 3889506 | tnaB | b3709 | low affinity tryptophan permease |
| MDS46 | CDS | 3889638 ... 3890813 | yidY | b3710 | putative transport protein |
| MDS46 | CDS | 3890788 ... 3891747 | yidZ | b3711 | putative transcriptional regulator LYSR-type |
| MDS46 | CDS | 3891892 ... 3892653 | yieE | b3712 | orf, hypothetical protein |
| MDS46 | CDS | 3892675 ... 3893241 | yieF | b3713 | orf, hypothetical protein |
| MDS46 | CDS | complement(3893295 ... 3894632) | yieG | b3714 | putative membrane/transport protein |
| MDS46 | CDS | 3894797 ... 3895462 | yieH | b3715 | putative phosphatase |
| MDS46 | CDS | 3895529 ... 3895996 | yieI | b3716 | orf, hypothetical protein |
| MDS46 | CDS | 3896045 ... 3896632 | yieJ | b3717 | orf, hypothetical protein |
| MDS46 | CDS | complement(3896694 ... 3897416) | yieK | b3718 | pyrimidine-specific nucleoside hydrolase |
| MDS46 | CDS | complement(3897431 ... 3898627) | yieL | b3719 | putative xylanase |
| MDS46 | CDS | complement(3898627 ... 3900243) | yieC | b3720 | putative receptor protein |
| MDS46 | CDS | complement(3900312 ... 3901724) | bglB | b3721 | phospho-beta-glucosidase B; cryptic |
| MDS46 | CDS | complement(3901743 ... 3903620) | bglF | b3722 | PTS system beta-glucosides, enzyme II, cryptic |
| MDS46 | CDS | complement(3903754 ... 3904590) | bglG | b3723 | positive regulation of bgl operon |

EXAMPLE 9

Production of MDS47

Reduced genome strain MDS47 was produced using methods as described in International Patent Publication No. WO 2003/070880 by deleting the following nucleic acid region (also show in Table 7) from parental strain MDS46, with reference to SEQ ID NO: 1:

| Strain | Type | Coordinates | Name | B | Function |
|---|---|---|---|---|---|
| MDS47 | CDS | complement(674793 ... 675770) | ybeQ | b0644 | orf, hypothetical protein |
| MDS47 | CDS | 675934 ... 676641 | ybeR | b0645 | orf, hypothetical protein |
| MDS47 | CDS | 676638 ... 678065 | ybeS | b0646 | putative enzyme of polynucleotide modification |
| MDS47 | CDS | complement(678075 ... 678629) | ybeT | b0647 | orf, hypothetical protein |
| MDS47 | CDS | 678731 ... 679438 | ybeU | b0648 | putative tRNA ligase |
| MDS47 | CDS | 679435 ... 680886 | ybeV | b0649 | orf, hypothetical protein |
| MDS47 | CDS | complement(680946 ... 682616) | hscC | b0650 | putative heatshock protein (Hsp70 family) |

EXAMPLE 10

Production of MDS48

Reduced genome strain MDS48 was produced using methods as described in International Patent Publication No. WO 2003/070880 by deleting the following nucleic acid region (also show in Table 8) from parental strain MDS47, with reference to SEQ ID NO: 1:

| Strain | Type | Coordinates | Name | B | Function |
|---|---|---|---|---|---|
| MDS48 | CDS | complement(4295242 ... 4297389) | fdhF | b4079 | selenopolypeptide subunit of formate dehydrogenase H |
| MDS48 | CDS | complement(4297587 ... 4299053) | yjcP | b4080 | putative enzyme |

-continued

| Strain | Type | Coordinates | Name | B | Function |
|---|---|---|---|---|---|
| MDS48 | CDS | complement(4299050 . . . 4301101) | yjcQ | b4081 | putative enzyme |
| MDS48 | CDS | complement(4301101 . . . 4302132) | yjcR | b4082 | putative membrane protein |
| MDS48 | CDS | complement(4302635 . . . 4304620) | yjcS | b4083 | orf, hypothetical protein |
| MDS48 | CDS | complement(4304893 . . . 4305822) | alsK | b4084 | putative D-allose kinase |
| MDS48 | CDS | complement(4305806 . . . 4306501) | alsE | b4085 | allulose-6-phosphate 3-epimerase |
| MDS48 | CDS | complement(4306512 . . . 4307492) | alsE | b4086 | D-allose ABC transporter |
| MDS48 | CDS | complement(4307471 . . . 4309003) | alsA | b4087 | D-allose ABC transporter |
| MDS48 | CDS | complement(4309130 . . . 4310065) | alsB | b4088 | D-allose ABC transporter |
| MDS48 | CDS | complement(4310124 . . . 4311014) | rpiR | b4089 | transcriptional repressor of rpiB expression |
| MDS48 | CDS | 4311373 . . . 4311822 | rpiB | b4090 | ribose 5-phosphate isomerase B |
| MDS48 | CDS | 4311891 . . . 4312220 | yjdP | b4487 | conserved hypothetical protein |
| MDS48 | CDS | complement(4312367 . . . 4313125) | phnP | b4092 | phosphonate metabolism |
| MDS48 | CDS | complement(4313127 . . . 4313561) | phnO | b4093 | putative regulator, phn operon |
| MDS48 | CDS | complement(4313548 . . . 4314105) | phnN | b4094 | ATP-binding component of phosphonate transport |
| MDS48 | CDS | complement(4314105 . . . 4315241) | phnM | b4095 | phosphonate metabolism |
| MDS48 | CDS | complement(4315238 . . . 4315918) | phnL | b4096 | ATP-binding component of phosphonate transport |
| MDS48 | CDS | complement(4316029 . . . 4316787) | phnK | b4097 | ATP-binding component of phosphonate transport |
| MDS48 | CDS | complement(4316784 . . . 4317629) | phnJ | b4098 | phosphonate metabolism |
| MDS48 | CDS | complement(4317622 . . . 4318686) | phnI | b4099 | phosphonate metabolism |
| MDS48 | CDS | complement(4318686 . . . 4319270) | phnH | b4100 | phosphonate metabolism |
| MDS48 | CDS | complement(4319267 . . . 4319719) | phnG | b4101 | phosphonate metabolism |
| MDS48 | CDS | complement(4319720 . . . 4320445) | phnF | b4102 | putative transcriptional regulator |
| MDS48 | CDS | complement(4320466 . . . 4320834) | phnE_2 | b4103 | orf, hypothetical protein |
| MDS48 | CDS | complement(4320684 . . . 4321304) | phnE | b4104 | membrane channel protein component of Pn transporter |
| MDS48 | CDS | complement(4321359 . . . 4322375) | phnD | b4105 | periplasmic binding protein component of Pn transporter |
| MDS48 | CDS | complement(4322400 . . . 4323188) | phnC | b4106 | ATP-binding component of phosphonate transport |

EXAMPLE 11

Production of MDS49

Reduced genome strain MDS49 was produced using methods as described in International Patent Publication No. WO 2003/070880 by deleting the following nucleic acid region (also show in Table 9) from parental strain MDS48, with reference to SEQ ID NO: 1:

| Strain | Type | Coordinates | Name | B | Function |
|---|---|---|---|---|---|
| MDS49 | CDS | complement(764376 . . . 765098) | farR | b0730 | transcriptional regulator of succinyl-CoA synthetase operon |
| MDS49 | CDS | 765207 . . . 767183 | hrsA | b0731 | protein modification enzyme, induction of ompC |
| MDS49 | CDS | 767201 . . . 769834 | ybgG | b0732 | putative sugar hydrolase |

EXAMPLE 12

Production of MDS50

Reduced genome strain MDS450 was produced using methods as described in International Patent Publication No. WO 2003/070880 by deleting the following nucleic acid region (also show in Table 10) from parental strain MDS49, with reference to SEQ ID NO: 1:

| Strain | Type | Coordinates | Name | B | Function |
|---|---|---|---|---|---|
| MDS50 | CDS | 3737728 . . . 3738981 | avtA | b3572 | alanine-alpha-ketoisovalerate (or valine-pyruvate) transaminase, transaminase C |
| MDS50 | CDS | complement(3739132 . . . 3739605) | yiaI | b3573 | orf, hypothetical protein |
| MDS50 | CDS | complement(3739707 . . . 3740555) | yiaJ | b3574 | transcriptional repressor of the yiaK-S operon. |
| MDS50 | CDS | 3740756 . . . 3741754 | yiaK | b3575 | putative dehydrogenase |
| MDS50 | CDS | 3741766 . . . 3742233 | yiaL | b3576 | putative lipase |
| MDS50 | CDS | 3742351 . . . 3742824 | yiaM | b3577 | orf, hypothetical protein |
| MDS50 | CDS | 3742827 . . . 3744104 | yiaN | b3578 | putative membrane protein |

-continued

| Strain | Type | Coordinates | Name | B | Function |
|---|---|---|---|---|---|
| MDS50 | CDS | 3744117 ... 3745103 | yiaO | b3579 | putative solute-binding transport protein |
| MDS50 | CDS | 3745107 ... 3746603 | lyxK | b3580 | L-xylulose kinase, cryptic |
| MDS50 | CDS | 3746600 ... 3747262 | sgbH | b3581 | probable 3-hexulose 6-phosphate synthase |
| MDS50 | CDS | 3747255 ... 3748115 | sgbU | b3582 | putative 3-hexulose-6-phosphate isomerase |
| MDS50 | CDS | 3748109 ... 3748804 | sgbE | b3583 | L-ribulose-5-phosphate 4-epimerase |
| MDS50 | CDS | complement(3749151 ... 3749891) | yiaT | b3584 | putative outer membrane protein |
| MDS50 | CDS | 3750015 ... 3750989 | yiaU | b3585 | putative transcriptional regulator LYSR-type |
| MDS50 | CDS | complement(3750986 ... 3752122) | yiaV | b3586 | putative membrane protein |
| MDS50 | CDS | complement(3752128 ... 3752451) | yiaW | b3587 | orf, hypothetical protein |

EXAMPLE 13

Production of MDS51

Reduced genome strain MDS51 was produced using methods as described in International Patent Publication No. WO 2003/070880 by deleting the following nucleic acid region (also show in Table 11) from parental strain MDS50, with reference to SEQ ID NO: 1:

| Strain | Type | Coordinates | Name | B | Function |
|---|---|---|---|---|---|
| MDS51 | CDS | 1727111 ... 1731727 | lhr | b1653 | member of ATP-dependent helicase superfamily II |

EXAMPLE 14

Production of MDS52

Reduced genome strain MDS52 was produced using methods as described in International Patent Publication No. WO 2003/070880 by deleting the following nucleic acid region (also show in Table 12) from parental strain MDS51, with reference to SEQ ID NO: 1:

| Strain | Type | Coordinates | Name | B | Function |
|---|---|---|---|---|---|
| MD52 | CDS | complement(2858489 ... 2859286) | ygbI | b2735 | putative DEOR-type transcriptional regulator |
| MD52 | CDS | 2859452 ... 2860360 | ygbJ | b2736 | putative dehydrogenase |
| MD52 | CDS | 2860357 ... 2861523 | ygbK | b2737 | orf, hypothetical protein |
| MD52 | CDS | 2861615 ... 2862253 | ygbL | b2738 | putative epimerase/aldolase |
| MD52 | CDS | 2862258 ... 2863034 | ygbM | b2739 | orf, hypothetical protein |
| MD52 | CDS | 2863123 ... 2864487 | ygbN | b2740 | putative transport protein |

EXAMPLE 15

Production of MDS53

Reduced genome strain MDS53 was produced using methods as described in International Patent Publication No. WO 2003/070880 by deleting the following nucleic acid region (also show in Table 13) from parental strain MDS52, with reference to SEQ ID NO: 1:

| Strain | Type | Coordinates | Name | B | Function |
|---|---|---|---|---|---|
| MDS53 | CDS | complement(2519615 ... 2520499) | xapR | b2405 | regulator for xapA |
| MDS53 | CDS | complement(2520751 ... 2522007) | xapB | b2406 | xanthosine permease |
| MDS53 | CDS | complement(2522067 ... 2522900) | xapA | b2407 | xanthosine phosphorylase |

EXAMPLE 16

Production of MDS54

Reduced genome strain MDS54 was produced using methods as described in International Patent Publication No. WO 2003/070880 by deleting the following nucleic acid region (also show in Table 14) from parental strain MDS53, with reference to SEQ ID NO: 1:

| Strain | Type | Coordinates | Name | B | Function |
|---|---|---|---|---|---|
| MDS54 | CDS | 4085025 ... 4086080 | yiiG | b3896 | orf, hypothetical protein |
| MDS54 | CDS | complement(4086130 ... 4087878) | frvR | b3897 | putative frv operon regulatory protein |
| MDS54 | CDS | complement(4087878 ... 4088948) | frvX | b3898 | frv operon protein |
| MDS54 | CDS | complement(4088938 ... 4090389) | frvB | b3899 | PTS system, fructose-like enzyme IIBC component |
| MDS54 | CDS | complement(4090400 ... 4090846) | frvA | b3900 | PTS system, fructose-specific IIA component |

EXAMPLE 17

Production of MDS55

Reduced genome strain MDS55 was produced using methods as described in International Patent Publication No. WO 2003/070880 by deleting the following nucleic acid region (also show in Table 15) from parental strain MDS54, with reference to SEQ ID NO: 1:

| Strain | Type | Coordinates | Name | B | Function |
|---|---|---|---|---|---|
| MDS55 | CDS | complement (1252308 ... 1255175) | yogV | b1202 | putative adhesion and penetration protein |

EXAMPLE 18

Production of MDS56

Reduced genome strain MDS56 was produced using methods as described in International Patent Publication No. WO 2003/070880 by deleting the following nucleic acid region (also show in Table 16) from parental strain MDS55, with reference to SEQ ID NO: 1:

| Strain | Type | Coordinates | Name | B | Function |
|---|---|---|---|---|---|
| MDS56 | CDS | complement(4486584 ... 4488086) | yjgR | b4263 | orf, hypothetical protein |
| MDS56 | CDS | complement(4488164 ... 4489162) | idnR | b4264 | L-idonate transcriptional regulator |
| MDS56 | CDS | complement(4489229 ... 4490548) | idnT | b4265 | L-idonate transporter |
| MDS56 | CDS | complement(4490610 ... 4491374) | idnO | b4266 | 5-keto-D-gluconate 5-reductase |
| MDS56 | CDS | complement(4491398 ... 4492429) | idnD | b4267 | L-idonate dehydrogenase |
| MDS56 | CDS | 4492646 ... 4493209 | idnK | b4268 | gluconate kinase |

EXAMPLE 19

Production of MDS57

Reduced genome strain MDS57 was produced using methods as described in International Patent Publication No. WO 2003/070880 by deleting the following nucleic acid region (also show in Table 17) from parental strain MDS56, with reference to SEQ ID NO: 1:

| Strain | Type | Coordinates | Name | B | Function |
|---|---|---|---|---|---|
| MDS57 | CDS | complement (643420 ... 644226) | rna | b0611 | RNase I, cleaves phosphodiester bond between any two nucleotides |

EXAMPLE 20

Production of MDS58

Reduced genome strain MDS58 was produced using methods as described in International Patent Publication No. WO 2003/070880 by deleting the following nucleic acid region (also show in Table 18) from parental strain MDS57, with reference to SEQ ID NO: 1:

| Strain | Type | Coordinates | Name | B | Function |
|---|---|---|---|---|---|
| MDS58 | CDS | complement (2474716 ... 2475651) | dsdC | b2364 | D-serine dehydratase (deaminase) transcriptional activator |
| MDS58 | CDS | 2475869 ... 2477206 | dsdX | b2365 | transport system permease (serine) |
| MDS58 | CDS | 2477224 ... 2478552 | dsdA | b2366 | D-serine dehydratase (deaminase) |

EXAMPLE 21

Production of MDS59

Reduced genome strain MDS59 was produced using methods as described in International Patent Publication No. WO 2003/070880 by deleting the following nucleic acid region (also show in Table 19) from parental strain MDS58, with reference to SEQ ID NO: 1:

| Strain | Type | Coordinates | Name | B | Function |
|---|---|---|---|---|---|
| MDS59 | CDS | 879950...881152 | dacC | b0839 | D-alanyl-D-alanine carboxypeptidase penicillin-binding protein 6 |

EXAMPLE 22

Production of MDS60

Reduced genome strain MDS60 was produced using methods as described in International Patent Publication No. WO 2003/070880 by deleting the following nucleic acid region (also show in Table 20) from parental strain MDS59, with reference to SEQ ID NO: 1:

| Strain | Type | Coordinates | Name | B | Function |
|---|---|---|---|---|---|
| MDS60 | CDS | complement(513625...514080) | ybbJ | b0488 | orf, hypothetical protein |
| MDS60 | CDS | complement(514080...514997) | ybbK | b0489 | putative protease |
| MDS60 | CDS | 515143...515820 | ybbL | b0490 | putative ATP-binding component of a transport system |
| MDS60 | CDS | 515807...516586 | ybbM | b0491 | putative metal resistance protein |
| MDS60 | CDS | complement(516649...517503) | ybbN | b0492 | putative thioredoxin-like protein |
| MDS60 | CDS | complement(517564...518373) | ybbO | b0493 | putative oxidoreductase |
| MDS60 | CDS | complement(518363...518989) | tesA | b0494 | acyl-CoA thioesterase I; also functions as protease I |
| MDS60 | CDS | 518957...519643 | ybbA | b0495 | putative ATP-binding component of a transport system |
| MDS60 | CDS | 519640...522054 | ybbP | b0496 | putative oxidoreductase |
| MDS60 | CDS | 522485...526765 | rhsD | b0497 | rhsD protein in rhs element |
| MDS60 | CDS | 526805...527173 | ybbC | b0498 | orf, hypothetical protein |
| MDS60 | CDS | 527173...527883 | ylbH | b0499 | orf, hypothetical protein |
| MDS60 | CDS | 527864...528124 | ybbD | b0500 | orf, hypothetical protein |
| MDS60 | CDS | complement(528869...529240) | ylbJ | b0502 | orf, hypothetical protein |

EXAMPLE 23

Growth Rates of Reduced Genome Strains

Strains MDS41, MDS42, MDS43, MDS44, MDS45, MDS46, MDS47, MDS48, MDS49, MDS50, MDS51, MDS52, MDS53, MDS54, MDS55, MDS56, MDS57, MDS58, MDS59 and MDS60 were characterized for growth on standard microbiological media. Each of the MDS strains can be grown to high cell densities in fed-batch fermentations on minimal medium. In addition, the growth rates were essentially unchanged for each strain relative to the parental strain MG1655.

Figure 2:
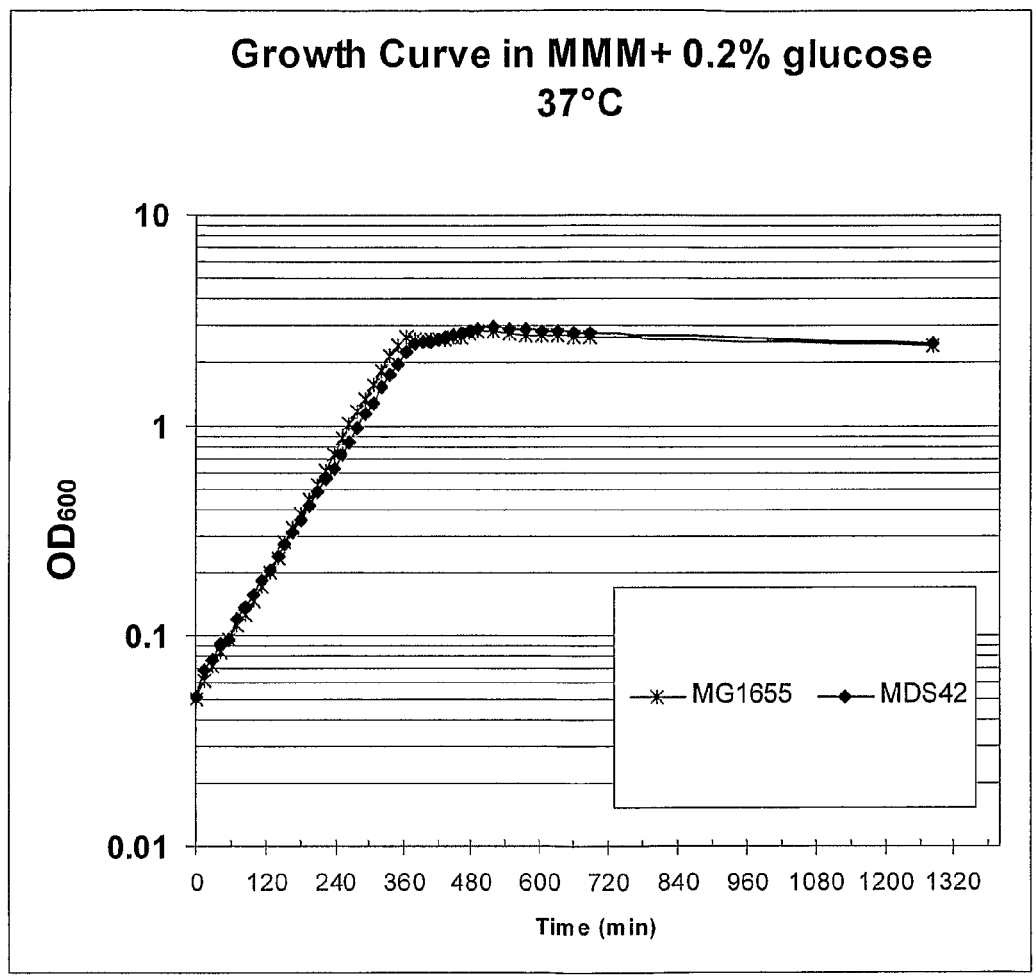
FIG. 2 shows a comparison of the growth rate of MG1655 and MDS42 in MOPS minimal medium at 37° C.

FIG. 2 shows a representative comparison of the growth rate of MG1655 and MDS42 in MOPS minimal medium at 37° C. Doubling time was obtained by measuring $OD_{600}$ of cultures grown in baffled flasks at 37° C. The log linear portion of the growth curve was used to calculate the average doubling times and standard deviation from six replicates on the plate. The doubling time of MG1655 was 61.3 minutes compared to a doubling time of 69.07 minutes for MDS42.

EXAMPLE 24

Transformation Efficiency of Reduced Genome Strains

Strain MDS42 was compared to MG1655 for transformation efficiency. Cells were grown under standard growth conditions to optical density of 0.5 at 600 nm. Cell cultures were then centrifuged, cell pellets were washed several times with water and finally resuspended in water. Approximately 25 ng of either pUC19 or BAC DNA was added to approximately 100 µl of the cell suspension and subjected to electroporation using standard electroporation protocol, e.g., 1.8 kV and resistance of 150 ohms in a 0.1 cm electroporation cuvette using an Invitrogen Electroporator II™ device. As shown below, MDS42 has a substantially higher transformation efficiency compared to MG1655.

| | Electroporation Efficiency (transformants/µg DNA) | |
|---|---|---|
| Strain | pUC19 (2.6 kb) | BAC (150 kb) |
| MDS42 | $4.0 \times 10^9$ | $8.6 \times 10^6$ |
| MG1655 | $3.0 \times 10^7$ | $3.3 \times 10^6$ |

EXAMPLE 25

Protein Expression in Reduced Genome Strains

Figure 3:
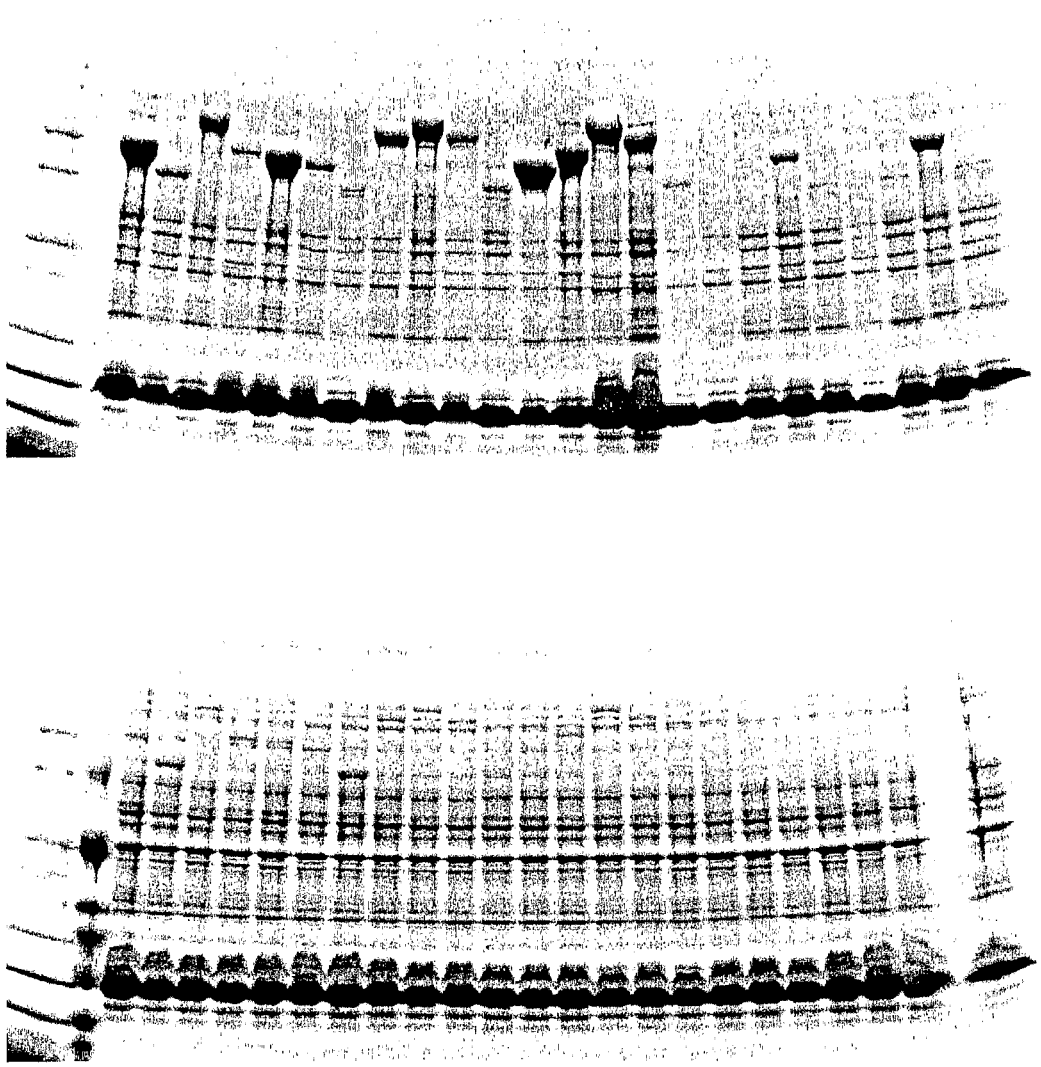
FIG. 3 shows a comparison of the expression of chloramphenicol acetyl transferase (CAT) in MDS42 (top) and MG1655 (bottom).

FIG. 3 shows that expression of recombinant proteins was similar for the MDS and MG1655 strains based on expression of the model protein chloramphenicol acetyl transferase (CAT).

EXAMPLE 26

DNA Production in Reduced Genome Strains

The results below show that the reduced genome strains are able to produce recombinant DNA with yields higher than the native parental strain and other commercial strains.

| DNA Yields (ng/ml) | | |
|---|---|---|
| Strain | pUC19 | PACYC184 |
| MDS42 | 1305.6 | 487.8 |
| MG1655 | 991.2 | 582.6 |
| DH10B | 1228.8 | 195.6 |

| DNA Yields (mg/OD$_{600}$) | | |
|---|---|---|
| Strain | Plasmid A | Plasmid B |
| MDS42recA$^-$ | 4.97 | 6.26 |
| DH10B | 3.05 | 0.26 |

EXAMPLE 27

DNA Stability in Reduced Genome Strains

Figure 4:
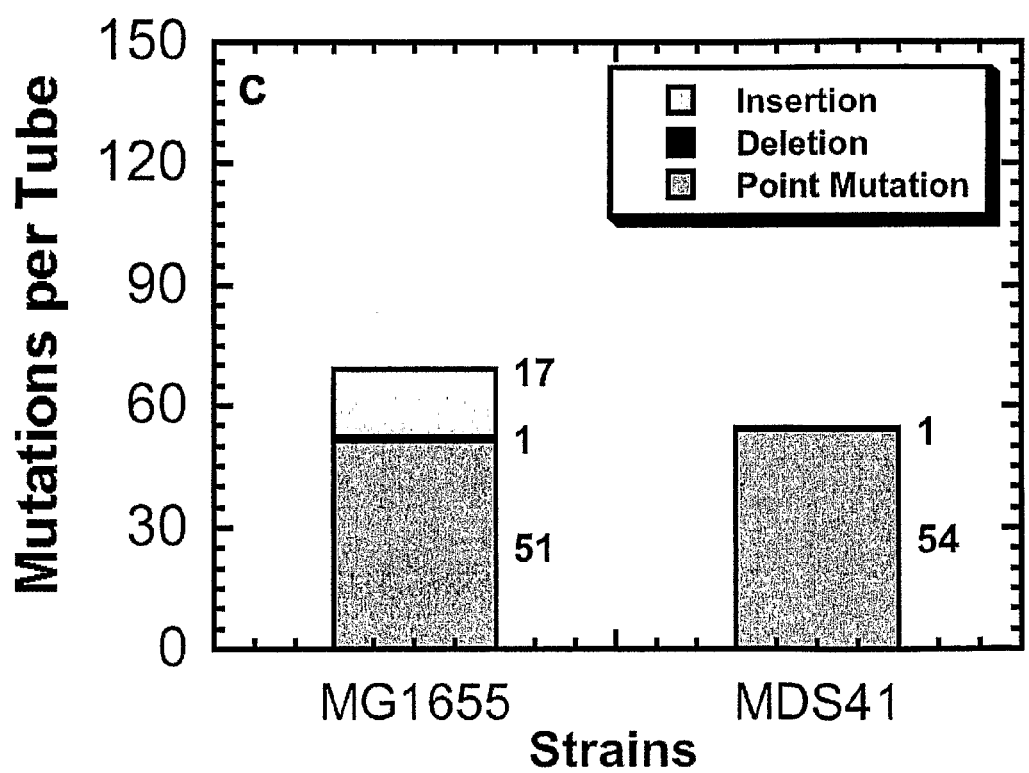
FIG. 4 shows a comparison of the mutation rates in MDS41 and MG1655 based on cycA mutations causing D-cycloserine resistance.

FIG. 4 indicates that the measured frequency of mutation by IS hopping dropped to zero in the reduced genome strains. Interestingly, the frequency of IS insertion events increased by 2.5-fold when CAT was over expressed in MG1655. This indicates that the over-expression of recombinant proteins may induce IS transposition. The reduced genome strains may therefore be a more stable host for protein production.

EXAMPLE 28

DNA Quality in Reduced Genome Strains

Figure 5:
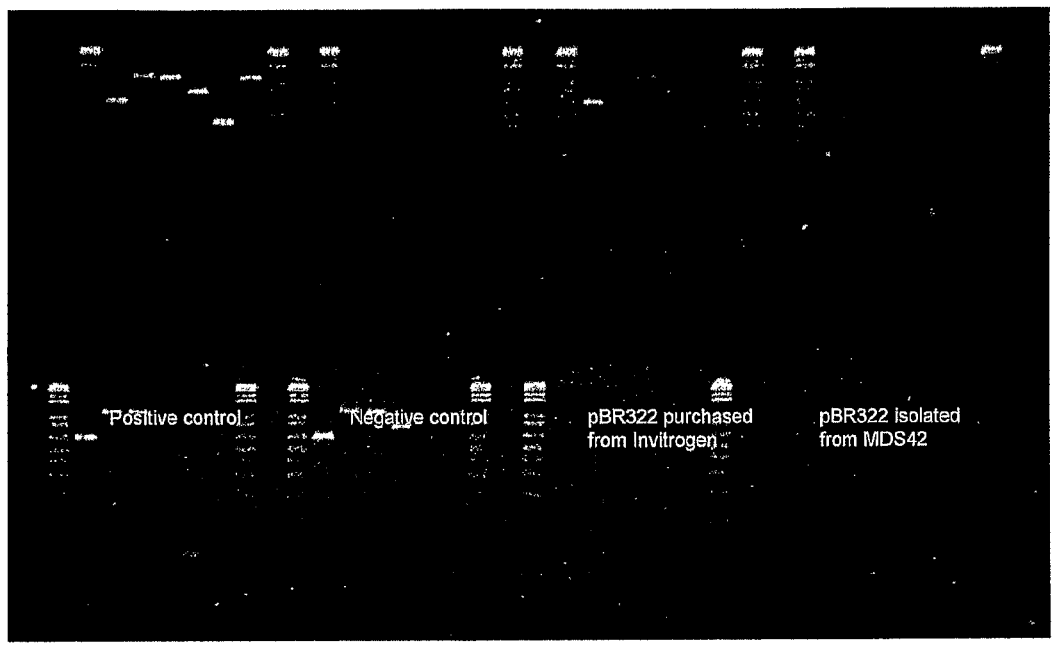
FIG. 5 shows the PCR detection of IS elements in various DNA preparations. Each panel is loaded in the same order: 1 kb+ marker, IS, IS2, IS3, IS5, IS10, IS186, 1kb+ marker, for (1) Positive Control, (2) Negative Control, (3) pBR322 from Invitrogen, and (4) pBR322 produced in MDS42.

To test the quality of DNA obtained from the reduced genome strains, pBR322 isolated from MDS42 and commercially obtained pBR322 were tested for the presence of IS elements by PCR. FIG. 5 indicates that recombinant DNA of high quality may be obtained from the reduced genome strains.

EXAMPLE 29

Cloning of Difficult to Clone Sequence in Reduced Genome Strains

Figure 6:
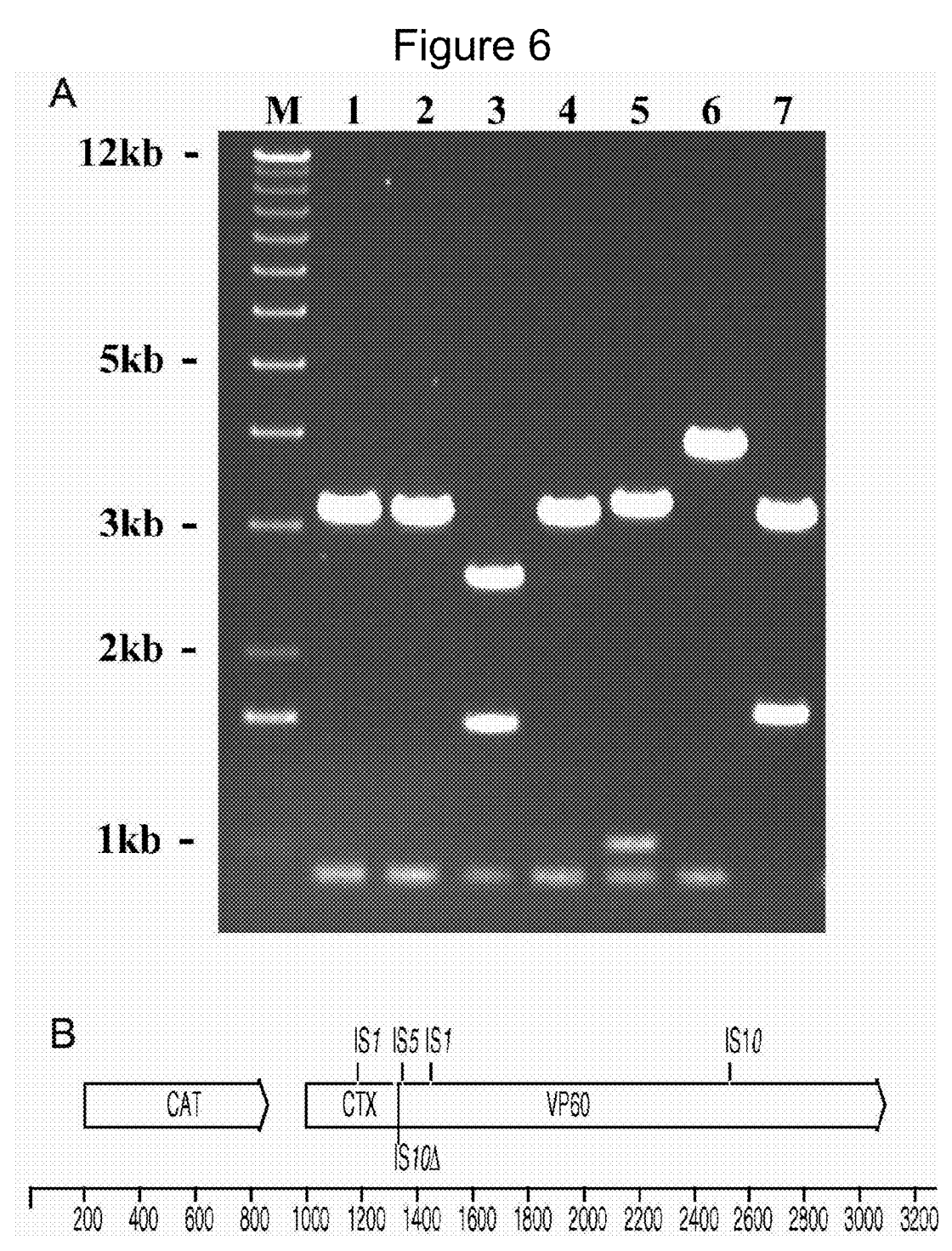

MDS42 was used to prepare pCTXVP60. The plasmid DNA was then propagated in various hosts, isolated, then digested with NcoI and EcoRI. FIG. 6 shows a representative restriction pattern. The fragments were then purified and sequenced. MDS41 (lane 1) and MDS42 (lane 2) did not contain an insertion. DH10B contained an IS1 insertion (lane 3) and also an IS10 insertion/deletion (lane 4). C600 contained an IS5 insertion (lane 5), an IS1 insertion (lanes 6 and 7). This shows that the reduced genome strains may be used to clone sequences that would be difficult to clone (e.g., toxic genes) in other strains.

TABLE 1

| Type | S | Left | Right | Name | B |
|---|---|---|---|---|---|
| CDS | + | 190 | 255 | thrL | b0001 |
| CDS | + | 337 | 2799 | thrA | b0002 |
| CDS | + | 2801 | 3733 | thrB | b0003 |
| CDS | + | 3734 | 5020 | thrC | b0004 |
| CDS | + | 5234 | 5530 | yaaX | b0005 |
| CDS | − | 5683 | 6459 | yaaA | b0006 |
| CDS | − | 6529 | 7959 | yaaJ | b0007 |
| CDS | + | 8238 | 9191 | talB | b0008 |
| CDS | + | 9306 | 9893 | mog | b0009 |
| CDS | − | 9928 | 10494 | yaaH | b0010 |
| CDS | − | 10643 | 11356 | yaaW | b0011 |
| CDS | + | 10830 | 11315 | htgA | b0012 |
| CDS | − | 11382 | 11786 | yaaI | b0013 |
| CDS | + | 12163 | 14079 | dnaK | b0014 |
| CDS | + | 14168 | 15298 | dnaJ | b0015 |
| repeat_region | + | 15388 | 16730 | | |
| CDS | + | 15445 | 16557 | yl81_1 | b0016 |
| CDS | − | 15869 | 16177 | yi82_1 | b0017 |
| CDS | − | 16751 | 16960 | mokC | b0018 |
| CDS | + | 17489 | 18655 | nhaA | b0019 |
| CDS | + | 18715 | 19620 | nhaR | b0020 |
| repeat_region | − | 19796 | 20563 | | |
| CDS | − | 19811 | 20314 | insB_1 | b0021 |
| CDS | − | 20233 | 20508 | insA_1 | b0022 |
| CDS | − | 20815 | 21078 | rpsT | b0023 |
| CDS | + | 21181 | 21399 | yaaY | b0024 |
| CDS | + | 21407 | 22348 | ribF | b0025 |
| CDS | + | 22391 | 25207 | ileS | b0026 |
| CDS | + | 25207 | 25701 | lspA | b0027 |
| CDS | + | 25826 | 26275 | fkpB | b0028 |
| CDS | + | 26277 | 27227 | ispH | b0029 |
| CDS | + | 27293 | 28207 | rihC | b0030 |
| CDS | + | 28374 | 29195 | dapB | b0031 |
| CDS | + | 29651 | 30799 | carA | b0032 |
| CDS | + | 30817 | 34038 | carB | b0033 |
| CDS | + | 34300 | 34695 | caiF | b0034 |
| CDS | − | 34781 | 35371 | caiE | b0035 |
| CDS | − | 35377 | 36270 | caiD | b0036 |
| CDS | − | 36271 | 37839 | caiC | b0037 |
| CDS | − | 37898 | 39115 | caiB | b0038 |
| CDS | − | 39244 | 40386 | caiA | b0039 |
| CDS | − | 40417 | 41931 | caiT | b0040 |
| CDS | + | 42403 | 43173 | fixA | b0041 |
| CDS | + | 43188 | 44129 | fixB | b0042 |
| CDS | + | 44180 | 45466 | fixC | b0043 |
| CDS | + | 45463 | 45750 | fixX | b0044 |
| CDS | + | 45807 | 47138 | yaaU | b0045 |
| CDS | + | 47246 | 47776 | yabF | b0046 |
| CDS | + | 47769 | 49631 | kefC | b0047 |
| CDS | + | 49823 | 50302 | folA | b0048 |
| CDS | − | 50380 | 51222 | apaH | b0049 |
| CDS | − | 51229 | 51606 | apaG | b0050 |
| CDS | − | 51609 | 52430 | ksgA | b0051 |
| CDS | − | 52427 | 53416 | pdxA | b0052 |
| CDS | − | 53416 | 54702 | surA | b0053 |
| CDS | − | 54755 | 57109 | imp | b0054 |
| CDS | + | 57364 | 58179 | djlA | b0055 |
| CDS | + | 58474 | 59124 | yabP | b0056 |
| CDS | + | 59121 | 59279 | yabQ | b0057 |
| CDS | − | 59687 | 60346 | rluA | b0058 |
| CDS | − | 60358 | 63264 | hepA | b0059 |
| CDS | − | 63429 | 65780 | polB | b0060 |
| CDS | − | 65855 | 66550 | araD | b0061 |
| CDS | − | 66835 | 68337 | araA | b0062 |
| CDS | − | 68348 | 70048 | araB | b0063 |
| CDS | + | 70387 | 71265 | araC | b0064 |
| CDS | + | 71351 | 72115 | yabI | b0065 |
| CDS | − | 72229 | 72927 | yabJ | b0066 |
| CDS | − | 72911 | 74521 | yabK | b0067 |
| CDS | − | 74497 | 75480 | tbpA | b0068 |
| CDS | − | 75644 | 77299 | yabN | b0069 |
| CDS | + | 77621 | 78799 | setA | b0070 |
| CDS | − | 78848 | 79453 | leuD | b0071 |
| CDS | − | 79464 | 80864 | leuC | b0072 |
| CDS | − | 80867 | 81958 | leuB | b0073 |
| CDS | − | 81958 | 83529 | leuA | b0074 |
| CDS | − | 83622 | 83708 | leuL | b0075 |
| CDS | + | 84368 | 85312 | leuO | b0076 |

TABLE 1-continued

| Type | S | Left | Right | Name | B |
|---|---|---|---|---|---|
| CDS | + | 85630 | 87354 | ilvI | b0077 |
| CDS | + | 87357 | 87848 | ilvH | b0078 |
| CDS | + | 87860 | 87946 | fruL | b0079 |
| CDS | + | 88028 | 89032 | fruR | b0080 |
| CDS | + | 89634 | 90092 | yabB | b0081 |
| CDS | + | 90094 | 91035 | yabC | b0082 |
| CDS | + | 91032 | 91397 | ftsL | b0083 |
| CDS | + | 91413 | 93179 | ftsI | b0084 |
| CDS | + | 93166 | 94653 | murE | b0085 |
| CDS | + | 94650 | 96008 | murF | b0086 |
| CDS | + | 96002 | 97084 | mraY | b0087 |
| CDS | + | 97087 | 98403 | murD | b0088 |
| CDS | + | 98403 | 99647 | ftsW | b0089 |
| CDS | + | 99644 | 100711 | murG | b0090 |
| CDS | + | 100765 | 102240 | murC | b0091 |
| CDS | + | 102233 | 103153 | ddlB | b0092 |
| CDS | + | 103155 | 103985 | ftsQ | b0093 |
| CDS | + | 103982 | 105244 | ftsA | b0094 |
| CDS | + | 105305 | 106456 | ftsZ | b0095 |
| CDS | + | 106557 | 107474 | lpxC | b0096 |
| CDS | + | 107705 | 108217 | yacA | b0097 |
| CDS | + | 108279 | 110984 | secA | b0098 |
| CDS | + | 111044 | 111433 | mutT | b0099 |
| CDS | − | 111564 | 111698 |  | b0100 |
| CDS | − | 111649 | 111846 | yacG | b0101 |
| CDS | − | 111856 | 112599 | yacF | b0102 |
| CDS | − | 112599 | 113219 | yacE | b0103 |
| CDS | + | 113444 | 114487 | guaC | b0104 |
| CDS | − | 114407 | 114514 |  | b0105 |
| CDS | − | 114522 | 115724 | hofC | b0106 |
| CDS | − | 115714 | 117099 | hofB | b0107 |
| CDS | − | 117109 | 117549 | ppdD | b0108 |
| CDS | − | 117752 | 118645 | nadC | b0109 |
| CDS | + | 118733 | 119284 | ampD | b0110 |
| CDS | + | 119281 | 120135 | ampE | b0111 |
| CDS | − | 120178 | 121551 | aroP | b0112 |
| CDS | + | 122092 | 122856 | pdhR | b0113 |
| CDS | + | 123017 | 125680 | aceE | b0114 |
| CDS | + | 125695 | 127587 | aceF | b0115 |
| CDS | + | 127912 | 129336 | lpdA | b0116 |
| CDS | − | 129407 | 131260 | yacH | b0117 |
| CDS | + | 131615 | 134212 | acnB | b0118 |
| CDS | + | 134388 | 134750 | yacL | b0119 |
| CDS | − | 134788 | 135582 | speD | b0120 |
| CDS | − | 135598 | 136464 | speE | b0121 |
| CDS | − | 136570 | 136917 | yacC | b0122 |
| CDS | + | 137083 | 138633 | cueO | b0123 |
| CDS | − | 138835 | 141225 | gcd | b0124 |
| CDS | + | 141431 | 141967 | hpt | b0125 |
| CDS | − | 142008 | 142670 | yadF | b0126 |
| CDS | + | 142779 | 143705 | yadG | b0127 |
| CDS | + | 143702 | 144472 | yadH | b0128 |
| CDS | + | 144577 | 145017 | yadI | b0129 |
| CDS | + | 145081 | 146310 | yadE | b0130 |
| CDS | − | 146314 | 146694 | panD | b0131 |
| CDS | + | 146698 | 147870 | yadD | b0132 |
| CDS | − | 147944 | 148795 | panC | b0133 |
| CDS | − | 148807 | 149601 | panB | b0134 |
| CDS | − | 149715 | 150953 | yadC | b0135 |
| CDS | − | 151003 | 151599 | yadK | b0136 |
| CDS | − | 151626 | 152231 | yadL | b0137 |
| CDS | − | 152243 | 152812 | yadM | b0138 |
| CDS | − | 152829 | 155426 | htrE | b0139 |
| CDS | − | 155461 | 156201 | ecpD | b0140 |
| CDS | − | 156299 | 156883 | yadN | b0141 |
| CDS | − | 157253 | 157732 | folK | b0142 |
| CDS | − | 157729 | 159126 | pcnB | b0143 |
| CDS | − | 159186 | 160112 | yadB | b0144 |
| CDS | − | 160149 | 160604 | dksA | b0145 |
| CDS | − | 160782 | 161486 | sfsA | b0146 |
| CDS | − | 161501 | 162031 | ligT | b0147 |
| CDS | + | 162105 | 164534 | hrpB | b0148 |
| CDS | + | 164730 | 167264 | mrcB | b0149 |
| CDS | + | 167484 | 169727 | fhuA | b0150 |
| CDS | + | 169778 | 170575 | fhuC | b0151 |
| CDS | + | 170575 | 171465 | fhuD | b0152 |
| CDS | + | 171462 | 173444 | fhuB | b0153 |
| CDS | − | 173602 | 174882 | hemL | b0154 |
| CDS | + | 175107 | 176528 | yadQ | b0155 |
| CDS | + | 176610 | 176954 | yadR | b0156 |
| CDS | − | 177001 | 177624 | yadS | b0157 |
| CDS | − | 177662 | 178462 | yadT | b0158 |
| CDS | − | 178455 | 179153 | pfs | b0159 |
| CDS | + | 179237 | 180754 | dgt | b0160 |
| CDS | + | 180884 | 182308 | degP | b0161 |
| CDS | + | 182463 | 183620 | cdaR | b0162 |
| CDS | − | 183709 | 184095 | yaeH | b0163 |
| CDS | − | 184257 | 185069 | yaeI | b0164 |
| CDS | − | 184987 | 185118 |  | b0165 |
| CDS | − | 185123 | 185947 | dapD | b0166 |
| CDS | − | 185978 | 188650 | glnD | b0167 |
| CDS | − | 188712 | 189506 | map | b0168 |
| CDS | + | 189874 | 190599 | rpsB | b0169 |
| CDS | + | 190857 | 191708 | tsf | b0170 |
| CDS | + | 191855 | 192580 | pyrH | b0171 |
| CDS | + | 192872 | 193429 | frr | b0172 |
| CDS | + | 193521 | 194717 | lspC | b0173 |
| CDS | + | 194903 | 195664 | uppS | b0174 |
| CDS | + | 195677 | 196534 | cdsA | b0175 |
| CDS | + | 196546 | 197898 | yaeL | b0176 |
| CDS | + | 197928 | 200360 | yaeT | b0177 |
| CDS | + | 200482 | 200967 | hlpA | b0178 |
| CDS | + | 200971 | 201996 | lpxD | b0179 |
| CDS | + | 202101 | 202556 | fabZ | b0180 |
| CDS | + | 202560 | 203348 | lpxA | b0181 |
| CDS | + | 203348 | 204496 | lpxB | b0182 |
| CDS | + | 204493 | 205089 | rnhB | b0183 |
| CDS | + | 205126 | 208608 | dnaE | b0184 |
| CDS | + | 208621 | 209580 | accA | b0185 |
| CDS | + | 209679 | 211820 | ldcC | b0186 |
| CDS | + | 211877 | 212266 | yaeR | b0187 |
| CDS | + | 212331 | 213629 | tilS | b0188 |
| CDS | − | 213678 | 213932 | rof | b0189 |
| CDS | + | 214291 | 214836 | yaeQ | b0190 |
| CDS | + | 214833 | 215255 | yaeJ | b0191 |
| CDS | + | 215269 | 215979 | cutF | b0192 |
| CDS | − | 216179 | 217003 | yaeF | b0193 |
| CDS | − | 217057 | 218775 | proS | b0194 |
| CDS | − | 218887 | 219594 | yaeB | b0195 |
| CDS | − | 219591 | 219995 | rcsF | b0196 |
| CDS | − | 220113 | 220928 | metQ | b0197 |
| CDS | − | 220968 | 221621 | metI | b0198 |
| CDS | − | 221614 | 222645 | metN | b0199 |
| CDS | + | 222833 | 223408 | gmhB | b0200 |
| rRNA | + | 223771 | 225312 | rrsH | b0201 |
| tRNA | + | 225381 | 225457 | ileV | b0202 |
| tRNA | + | 225500 | 225575 | alaV | b0203 |
| rRNA | + | 225759 | 228662 | rrlH | b0204 |
| rRNA | + | 228756 | 228875 | rrfH | b0205 |
| tRNA | + | 228928 | 229004 | aspU | b0206 |
| CDS | + | 229167 | 229970 | dkgB | b0207 |
| CDS | − | 229967 | 230881 | yafC | b0208 |
| CDS | + | 231122 | 231922 | yafD | b0209 |
| CDS | + | 231926 | 232549 | yafE | b0210 |
| CDS | − | 232597 | 233955 | mltD | b0211 |
| CDS | − | 234027 | 234782 | gloB | b0212 |
| CDS | + | 234816 | 235538 | yafS | b0213 |
| CDS | + | 235535 | 236002 | rnhA | b0214 |
| CDS | + | 236067 | 236798 | dnaQ | b0215 |
| tRNA | + | 236931 | 237007 | aspV | b0216 |
| CDS | + | 237335 | 238120 | yafT | b0217 |
| CDS | − | 238746 | 239084 | yafU | b0218 |
| CDS | − | 239419 | 240189 | yafV | b0219 |
| CDS | + | 240343 | 240816 | lvy | b0220 |
| CDS | + | 240859 | 243303 | fadE | b0221 |
| CDS | + | 243543 | 244121 | lpcA | b0222 |
| CDS | + | 244327 | 245094 | yafJ | b0223 |
| CDS | − | 245065 | 245805 | yafK | b0224 |
| CDS | − | 245961 | 246239 | yafQ | b0225 |
| CDS | − | 246242 | 246502 | dinJ | b0226 |
| CDS | − | 246731 | 247461 | yafL | b0227 |
| CDS | + | 247637 | 248134 | yafM | b0228 |
| CDS | − | 248358 | 250070 | fhiA | b0229 |
| CDS | + | 250072 | 250827 | mbhA | b0230 |
| CDS | + | 250898 | 251953 | dinB | b0231 |
| CDS | + | 252005 | 252298 | yafN | b0232 |

TABLE 1-continued

| Type | S | Left | Right | Name | B |
|---|---|---|---|---|---|
| CDS | + | 252301 | 252699 | yafO | b0233 |
| CDS | + | 252709 | 253161 | yafP | b0234 |
| CDS | + | 253467 | 253733 | ykfJ | b0235 |
| CDS | + | 253702 | 254202 | prfH | b0236 |
| CDS | − | 254259 | 255716 | pepD | b0237 |
| CDS | + | 255977 | 256435 | gpt | b0238 |
| CDS | + | 256527 | 257771 | yafA | b0239 |
| CDS | + | 257829 | 258230 | crl | b0240 |
| CDS | − | 258269 | 259324 | phoE | b0241 |
| CDS | + | 259612 | 260715 | proB | b0242 |
| CDS | + | 260727 | 261980 | proA | b0243 |
| tRNA | + | 262095 | 262170 | thrW | b0244 |
| CDS | − | 262552 | 262893 | ykfI | b0245 |
| CDS | − | 262914 | 263231 | yafW | b0246 |
| CDS | − | 263480 | 263956 | ykfG | b0247 |
| CDS | − | 263972 | 264430 | yafX | b0248 |
| CDS | − | 264528 | 264767 | ykfF | b0249 |
| CDS | − | 264844 | 265311 | ykfB | b0250 |
| CDS | − | 265334 | 266191 | yafY | b0251 |
| CDS | + | 266408 | 267229 | yafZ | b0252 |
| CDS | − | 267321 | 268184 | ykfA | b0253 |
| CDS | − | 268513 | 269406 | perR | b0254 |
| repeat_region | + | 269430 | 269994 | | |
| CDS | + | 269466 | 269870 | yi91a | |
| repeat_region | + | 269765 | 270985 | | |
| CDS | + | 269827 | 270978 | tra8_1 | b0256 |
| repeat_region | + | 270930 | 271751 | | |
| CDS | + | 271054 | 271479 | | b0257 |
| CDS | + | 272071 | 273216 | ykfC | b0258 |
| repeat_region | + | 273179 | 274373 | | |
| CDS | − | 273325 | 274341 | trs5_1 | b0259 |
| CDS | + | 274549 | 275952 | mmuP | b0260 |
| CDS | + | 275939 | 276871 | mmuM | b0261 |
| CDS | − | 276980 | 278026 | afuC | b0262 |
| CDS | − | 278038 | 278400 | afuB | b0263 |
| repeat_region | − | 278387 | 279154 | | |
| CDS | − | 278402 | 278905 | insB_2 | b0264 |
| CDS | − | 278824 | 279099 | insA_2 | b0265 |
| repeat_region | + | 279155 | 279335 | | |
| CDS | − | 279609 | 279959 | yagB | b0266 |
| CDS | − | 280053 | 281207 | yagA | b0267 |
| CDS | + | 281481 | 282410 | yagE | b0268 |
| CDS | + | 282425 | 284392 | yagF | b0269 |
| CDS | + | 284619 | 286001 | yagG | b0270 |
| CDS | + | 286013 | 287623 | yagH | b0271 |
| CDS | − | 287628 | 288386 | yagI | b0272 |
| CDS | − | 288525 | 289529 | argF | b0273 |
| repeat_region | − | 289858 | 290625 | | |
| CDS | − | 289873 | 290376 | insB_3 | b0274 |
| CDS | − | 290295 | 290570 | insA_3 | b0275 |
| CDS | + | 290724 | 291455 | yagJ | b0276 |
| CDS | − | 291546 | 292172 | yagK | b0277 |
| CDS | − | 292444 | 293142 | yagL | b0278 |
| CDS | − | 293169 | 294023 | yagM | b0279 |
| CDS | − | 294363 | 294803 | yagN | b0280 |
| CDS | − | 294920 | 296320 | intF | b0281 |
| CDS | − | 296605 | 297015 | yagP | b0282 |
| CDS | − | 296994 | 297950 | yagQ | b0283 |
| CDS | − | 297960 | 300158 | yagR | b0284 |
| CDS | − | 300155 | 301111 | yagS | b0285 |
| CDS | − | 301108 | 301797 | yagT | b0286 |
| CDS | + | 302215 | 302829 | yagU | b0287 |
| CDS | − | 303077 | 303406 | ykgJ | b0288 |
| CDS | − | 303719 | 304429 | yagV | b0289 |
| CDS | − | 304398 | 306041 | yagW | b0290 |
| CDS | − | 306031 | 308556 | yagX | b0291 |
| CDS | − | 308582 | 309250 | yagY | b0292 |
| CDS | − | 309308 | 309895 | yagZ | b0293 |
| CDS | − | 309970 | 310560 | yagK | b0294 |
| CDS | + | 311336 | 311563 | ykgL | b0295 |
| CDS | − | 311738 | 312001 | ykgM | b0296 |
| CDS | + | 313581 | 314468 | eaeH | b0297 |
| repeat_region | + | 314453 | 315707 | | |
| CDS | − | 314506 | 314814 | | b0298 |
| CDS | + | 314811 | 315677 | tra5_5 | b0299 |
| CDS | − | 315674 | 316360 | ykgA | b0300 |
| CDS | − | 316950 | 317543 | ykgB | b0301 |
| CDS | − | 317555 | 317791 | ykgI | b0303 |
| CDS | − | 317900 | 319225 | ykgC | b0304 |
| CDS | + | 319451 | 320305 | ykgD | b0305 |
| CDS | + | 320832 | 321551 | ykgE | b0306 |
| CDS | + | 321562 | 322989 | ykgF | b0307 |
| CDS | + | 322982 | 323677 | ykgG | b0308 |
| CDS | − | 323632 | 323844 | | b0309 |
| CDS | − | 323920 | 324588 | ykgH | b0310 |
| CDS | − | 324801 | 326471 | betA | b0311 |
| CDS | − | 326485 | 327957 | betB | b0312 |
| CDS | − | 327971 | 328558 | betI | b0313 |
| CDS | + | 328687 | 330720 | betT | b0314 |
| CDS | + | 331595 | 332683 | yahA | b0315 |
| CDS | − | 332725 | 333657 | yahB | b0316 |
| CDS | − | 333749 | 334246 | yahC | b0317 |
| CDS | + | 334504 | 335109 | yahD | b0318 |
| CDS | + | 335149 | 336012 | yahE | b0319 |
| CDS | + | 336002 | 337549 | yahF | b0320 |
| CDS | + | 337549 | 338967 | yahG | b0321 |
| CDS | + | 339369 | 340339 | yahI | b0323 |
| CDS | + | 340349 | 341731 | yahJ | b0324 |
| CDS | + | 342108 | 343157 | yahK | b0325 |
| CDS | + | 343400 | 344215 | yahL | b0326 |
| CDS | + | 344628 | 344873 | yahM | b0327 |
| CDS | − | 344890 | 345561 | yahN | b0328 |
| CDS | + | 345708 | 345983 | yahO | b0329 |
| CDS | − | 346081 | 347667 | prpR | b0330 |
| CDS | + | 347906 | 348796 | prpB | b0331 |
| CDS | + | 349236 | 350405 | prpC | b0333 |
| CDS | + | 350439 | 351890 | prpD | b0334 |
| CDS | + | 351930 | 353816 | prpE | b0335 |
| CDS | + | 354146 | 355405 | codB | b0336 |
| CDS | + | 355395 | 356678 | codA | b0337 |
| CDS | − | 357015 | 357914 | cynR | b0338 |
| CDS | + | 358023 | 358682 | cynT | b0339 |
| CDS | + | 358713 | 359183 | cynS | b0340 |
| CDS | + | 359216 | 360370 | cynX | b0341 |
| CDS | − | 360473 | 361084 | lacA | b0342 |
| CDS | − | 361150 | 362403 | lacY | b0343 |
| CDS | − | 362455 | 365529 | lacZ | b0344 |
| CDS | − | 365652 | 366734 | lacI | b0345 |
| CDS | − | 366811 | 367758 | mhpR | b0346 |
| CDS | + | 367835 | 369499 | mhpA | b0347 |
| CDS | + | 369501 | 370445 | mhpB | b0348 |
| CDS | + | 370448 | 371329 | mhpC | b0349 |
| CDS | + | 371339 | 372148 | mhpD | b0350 |
| CDS | + | 372145 | 373095 | mhpF | b0351 |
| CDS | + | 373092 | 374105 | mhpE | b0352 |
| CDS | + | 374683 | 375894 | mhpT | b0353 |
| CDS | + | 375996 | 376535 | yaiL | b0354 |
| CDS | − | 376759 | 377592 | frmB | b0355 |
| CDS | − | 377686 | 378795 | frmA | b0356 |
| CDS | − | 378830 | 379105 | frmR | b0357 |
| CDS | − | 379293 | 380066 | yaiO | b0358 |
| CDS | − | 380068 | 380283 | | b0359 |
| repeat_region | − | 380484 | 381814 | | |
| CDS | + | 380530 | 380940 | yi21_1 | b0360 |
| CDS | + | 380898 | 381803 | yi22_1 | b0361 |
| CDS | − | 381728 | 382114 | | b0362 |
| CDS | − | 381963 | 383159 | yaiP | b0363 |
| CDS | − | 383283 | 383840 | yaiS | b0364 |
| CDS | + | 384456 | 385418 | tauA | b0365 |
| CDS | + | 385431 | 386198 | tauB | b0366 |
| CDS | + | 386195 | 387022 | tauC | b0367 |
| CDS | + | 387019 | 387870 | tauD | b0368 |
| CDS | − | 387977 | 388951 | hemB | b0369 |
| CDS | − | 389121 | 389339 | | b0370 |
| CDS | + | 389475 | 390935 | yaiT | b0371 |
| repeat_region | − | 390933 | 392190 | | |
| CDS | + | 390963 | 391829 | tra5_1 | b0372 |
| CDS | − | 391826 | 392134 | | b0373 |
| CDS | + | 392239 | 393642 | yalU | b0374 |
| CDS | + | 393685 | 394353 | yaiV | b0375 |
| CDS | − | 394354 | 395511 | ampH | b0376 |
| CDS | − | 395863 | 397083 | sbmA | b0377 |
| CDS | + | 397096 | 398190 | yaiW | b0378 |
| CDS | − | 398249 | 398557 | yaiY | b0379 |
| CDS | + | 398817 | 399029 | yaiZ | b0380 |
| CDS | − | 399053 | 400147 | ddlA | b0381 |

TABLE 1-continued

| Type | S | Left | Right | Name | B |
|---|---|---|---|---|---|
| CDS | + | 400610 | 400870 | yaiB | b0382 |
| CDS | + | 400971 | 402386 | phoA | b0383 |
| CDS | + | 402505 | 402825 | psiF | b0384 |
| CDS | + | 402927 | 404042 | yaiC | b0385 |
| CDS | − | 404059 | 404868 | proC | b0386 |
| CDS | + | 404988 | 405446 | yaiI | b0387 |
| CDS | + | 405629 | 406153 | aroL | b0388 |
| CDS | + | 406203 | 406394 | yaiA | b0389 |
| CDS | + | 406652 | 407329 | aroM | b0390 |
| CDS | + | 407401 | 407685 | yaiE | b0391 |
| CDS | + | 407893 | 408174 | ykiA | b0392 |
| CDS | − | 408332 | 409243 | yaiD | b0393 |
| CDS | + | 409368 | 410276 | yajF | b0394 |
| CDS | − | 410521 | 411705 | araJ | b0396 |
| CDS | − | 411831 | 414977 | sbcC | b0397 |
| CDS | − | 414974 | 416176 | sbcD | b0398 |
| CDS | + | 416366 | 417055 | phoB | b0399 |
| CDS | + | 417113 | 418408 | phoR | b0400 |
| CDS | + | 418815 | 420134 | brnQ | b0401 |
| CDS | + | 420210 | 421583 | proY | b0402 |
| CDS | + | 421739 | 423556 | malZ | b0403 |
| CDS | − | 423561 | 424142 | yajB | b0404 |
| CDS | + | 424235 | 425305 | queA | b0405 |
| CDS | + | 425361 | 426488 | tgt | b0406 |
| CDS | + | 426511 | 426843 | yajC | b0407 |
| CDS | + | 426871 | 428718 | secD | b0408 |
| CDS | + | 428729 | 429700 | secF | b0409 |
| CDS | + | 429829 | 430176 | yajD | b0410 |
| CDS | − | 430353 | 431237 | tsx | b0411 |
| CDS | − | 431536 | 432075 | yajI | b0412 |
| CDS | + | 432226 | 432675 | ybaD | b0413 |
| CDS | + | 432679 | 433782 | ribD | b0414 |
| CDS | + | 433871 | 434341 | ribE | b0415 |
| CDS | + | 434361 | 434780 | nusB | b0416 |
| CDS | + | 434858 | 435835 | thiL | b0417 |
| CDS | + | 435813 | 436331 | pgpA | b0418 |
| CDS | − | 436385 | 437359 | yajO | b0419 |
| CDS | − | 437539 | 439401 | dxs | b0420 |
| CDS | − | 439426 | 440325 | ispA | b0421 |
| CDS | − | 440325 | 440567 | xseB | b0422 |
| CDS | + | 440773 | 442221 | thiI | b0423 |
| CDS | − | 442275 | 442865 | thiJ | b0424 |
| CDS | − | 442828 | 443739 | apbA | b0425 |
| CDS | + | 443907 | 444398 | yajQ | b0426 |
| CDS | + | 444526 | 445890 | yajR | b0427 |
| CDS | − | 446039 | 446929 | cyoE | b0428 |
| CDS | − | 446941 | 447270 | cyoD | b0429 |
| CDS | − | 447270 | 447884 | cyoC | b0430 |
| CDS | − | 447874 | 449865 | cyoB | b0431 |
| CDS | − | 449887 | 450834 | cyoA | b0432 |
| CDS | − | 451294 | 452769 | ampG | b0433 |
| CDS | − | 452813 | 453391 | yajG | b0434 |
| CDS | + | 453696 | 454013 | bolA | b0435 |
| CDS | + | 454357 | 455655 | tig | b0436 |
| CDS | + | 455901 | 456524 | clpP | b0437 |
| CDS | + | 456650 | 457924 | clpX | b0438 |
| CDS | + | 458112 | 460466 | lon | b0439 |
| CDS | + | 460675 | 460947 | hupB | b0440 |
| CDS | + | 461139 | 463010 | ppiD | b0441 |
| CDS | + | 463161 | 463532 | ybaV | b0442 |
| CDS | + | 463626 | 464024 | ybaW | b0443 |
| CDS | − | 464076 | 464771 | ybaX | b0444 |
| CDS | − | 464836 | 466536 | ybaE | b0445 |
| CDS | + | 466636 | 467454 | cof | b0446 |
| CDS | + | 467607 | 468065 | ybaO | b0447 |
| CDS | + | 468095 | 469867 | mdlA | b0448 |
| CDS | + | 469860 | 471641 | mdlB | b0449 |
| CDS | + | 471822 | 472160 | glnK | b0450 |
| CDS | + | 472190 | 473476 | amtB | b0451 |
| CDS | + | 473525 | 474385 | tesB | b0452 |
| CDS | + | 474603 | 475175 | ybaY | b0453 |
| CDS | | 475206 | 475595 | ybaZ | b0454 |
| misc_RNA | + | 475672 | 475785 | ffs | b0455 |
| CDS | + | 475896 | 476249 | ybaA | b0456 |
| CDS | − | 476291 | 477841 | ylaB | b0457 |
| CDS | − | 478005 | 478475 | ylaC | b0458 |
| CDS | − | 478591 | 479142 | maa | b0459 |
| CDS | − | 479314 | 479532 | hha | b0460 |
| CDS | − | 479558 | 479932 | ybaJ | b0461 |
| CDS | − | 480478 | 483627 | acrB | b0462 |
| CDS | − | 483650 | 484843 | acrA | b0463 |
| CDS | + | 484985 | 485632 | acrR | b0464 |
| CDS | + | 485760 | 489122 | kefA | b0465 |
| CDS | + | 489334 | 489495 | ybaM | b0466 |
| CDS | − | 489509 | 490036 | priC | b0467 |
| CDS | + | 490106 | 490483 | ybaN | b0468 |
| CDS | + | 490636 | 491187 | apt | b0469 |
| CDS | + | 491316 | 493247 | dnaX | b0470 |
| CDS | + | 493300 | 493629 | ybaB | b0471 |
| CDS | + | 493629 | 494234 | recR | b0472 |
| CDS | + | 494344 | 496218 | htpG | b0473 |
| CDS | + | 496399 | 497043 | adk | b0474 |
| CDS | + | 497279 | 498241 | hemH | b0475 |
| CDS | − | 498238 | 499197 | aes | b0476 |
| CDS | + | 499349 | 500653 | gsk | b0477 |
| CDS | − | 500786 | 502462 | ybaL | b0478 |
| CDS | − | 502700 | 503920 | fsr | b0479 |
| CDS | + | 504138 | 505790 | ushA | b0480 |
| CDS | − | 505827 | 506306 | ybaK | b0481 |
| CDS | − | 506510 | 507304 | ybaP | b0482 |
| CDS | + | 507442 | 507783 | ybaQ | b0483 |
| CDS | − | 508099 | 510603 | copA | b0484 |
| CDS | + | 510865 | 511797 | ybaS | b0485 |
| CDS | + | 511800 | 513092 | ybaT | b0486 |
| CDS | + | 513217 | 513624 | cueR | b0487 |
| CDS | − | 513625 | 514080 | ybbJ | b0488 |
| CDS | − | 514080 | 514997 | ybbK | b0489 |
| CDS | + | 515143 | 515820 | ybbL | b0490 |
| CDS | + | 515807 | 516586 | ybbM | b0491 |
| CDS | + | 516649 | 517503 | ybbN | b0492 |
| CDS | − | 517564 | 518373 | ybbO | b0493 |
| CDS | − | 518363 | 518989 | tesA | b0494 |
| CDS | + | 518957 | 519643 | ybbA | b0495 |
| CDS | + | 519640 | 522054 | ybbP | b0496 |
| CDS | + | 522485 | 526765 | rhsD | b0497 |
| CDS | + | 526805 | 527173 | ybbC | b0498 |
| CDS | + | 527173 | 527883 | ylbH | b0499 |
| CDS | + | 527864 | 528124 | ybbD | b0500 |
| CDS | + | 528163 | 528354 | | b0501 |
| CDS | − | 528869 | 529240 | ylbG | b0502 |
| CDS | − | 529356 | 530450 | ybbB | b0503 |
| CDS | − | 530519 | 531445 | ybbS | b0504 |
| CDS | + | 531675 | 532157 | allA | b0505 |
| CDS | + | 532235 | 533050 | allR | b0506 |
| CDS | + | 533140 | 534921 | gcl | b0507 |
| CDS | + | 534934 | 535710 | hyl | b0508 |
| CDS | + | 535810 | 536688 | glxR | b0509 |
| CDS | + | 536720 | 536998 | ybbV | b0510 |
| CDS | + | 536857 | 538311 | allP | b0511 |
| CDS | + | 538377 | 539732 | allB | b0512 |
| CDS | + | 539789 | 541090 | ybbY | b0513 |
| CDS | + | 541112 | 542257 | glxK | b0514 |
| CDS | − | 542485 | 543270 | ylbA | b0515 |
| CDS | − | 543287 | 544516 | allC | b0516 |
| CDS | − | 544538 | 545587 | allD | b0517 |
| CDS | + | 545904 | 547571 | fdrA | b0518 |
| CDS | + | 547838 | 548839 | ylbE | b0519 |
| CDS | + | 548850 | 549665 | ylbF | b0520 |
| CDS | + | 549662 | 550555 | arcC | b0521 |
| CDS | − | 550750 | 551817 | purK | b0522 |
| CDS | − | 551814 | 552323 | purE | b0523 |
| CDS | − | 552441 | 553163 | ybbF | b0524 |
| CDS | − | 553166 | 553660 | pplB | b0525 |
| CDS | + | 553834 | 555219 | cysS | b0526 |
| CDS | − | 555255 | 555776 | ybcI | b0527 |
| CDS | − | 555884 | 556096 | ybcJ | b0528 |
| CDS | − | 556098 | 556964 | folD | b0529 |
| CDS | + | 557435 | 557977 | sfmA | b0530 |
| CDS | + | 558197 | 558889 | sfmC | b0531 |
| CDS | + | 558920 | 561523 | sfmD | b0532 |
| CDS | + | 561565 | 562542 | sfmH | b0533 |
| CDS | + | 562553 | 563068 | sfmF | b0534 |
| CDS | − | 563071 | 563703 | fimZ | b0535 |
| tRNA | + | 563946 | 564022 | argU | b0536 |
| CDS | − | 564038 | 565201 | intD | b0537 |
| CDS | + | 565195 | 565755 | | b0538 |

TABLE 1-continued

| Type | S | Left | Right | Name | B |
|---|---|---|---|---|---|
| CDS | − | 565321 | 565584 | ybcC | b0539 |
| repeat_region | + | 566000 | 567257 | | |
| CDS | + | 566056 | 566364 | | b0540 |
| CDS | + | 566361 | 567227 | tra5_2 | b0541 |
| CDS | + | 567285 | 567470 | | b0542 |
| CDS | + | 567538 | 567870 | emrE | b0543 |
| CDS | + | 568125 | 569651 | ybcK | b0544 |
| CDS | + | 570116 | 570667 | ybcL | b0545 |
| CDS | + | 570677 | 571474 | ybcM | b0546 |
| CDS | + | 571689 | 572144 | ybcN | b0547 |
| CDS | + | 572144 | 572314 | ninE | b0548 |
| CDS | + | 572307 | 572597 | ybcO | b0549 |
| CDS | + | 572594 | 572956 | rus | b0550 |
| CDS | + | 573179 | 573562 | ybcQ | b0551 |
| repeat_region | + | 573814 | 575008 | | |
| CDS | − | 573960 | 574976 | trs5_2 | b0552 |
| CDS | − | 574981 | 576108 | nmpC | b0553 |
| CDS | + | 576621 | 576836 | ybcR | b0554 |
| CDS | + | 576836 | 577333 | ybcS | b0555 |
| CDS | + | 577330 | 577791 | ybcT | b0556 |
| CDS | − | 577823 | 578116 | ybcU | b0557 |
| CDS | − | 578407 | 578817 | ybcV | b0558 |
| CDS | + | 579103 | 579309 | ybcW | b0559 |
| CDS | + | 580057 | 580602 | nohB | b0560 |
| CDS | + | 580757 | 581320 | ybcX | b0561 |
| CDS | − | 581375 | 581959 | ybcY | b0562 |
| CDS | + | 582098 | 582283 | ylcE | b0563 |
| CDS | + | 582904 | 583653 | appY | b0564 |
| CDS | − | 583903 | 584856 | ompT | b0565 |
| CDS | − | 585370 | 586131 | envY | b0566 |
| CDS | − | 586314 | 587204 | ybcH | b0567 |
| CDS | − | 587205 | 590177 | nfrA | b0568 |
| CDS | − | 590164 | 592401 | nfrB | b0569 |
| CDS | − | 592551 | 593993 | cusS | b0570 |
| CDS | − | 593983 | 594666 | cusR | b0571 |
| CDS | + | 594823 | 596196 | cusC | b0572 |
| CDS | + | 596354 | 596686 | ylcC | b0573 |
| CDS | + | 596702 | 597925 | cusB | b0574 |
| CDS | + | 597937 | 601080 | cusA | b0575 |
| CDS | + | 601182 | 602558 | pheP | b0576 |
| CDS | − | 602639 | 603886 | ybdG | b0577 |
| CDS | − | 603994 | 604647 | nfnB | b0578 |
| CDS | − | 604741 | 605109 | ybdF | b0579 |
| CDS | − | 605174 | 605422 | ybdJ | b0580 |
| CDS | − | 605488 | 606606 | ybdK | b0581 |
| repeat_region | + | 607231 | 608573 | | |
| CDS | + | 607288 | 608400 | yiB1_2 | b0582 |
| CDS | − | 608682 | 609311 | | b0583 |
| CDS | − | 609477 | 611717 | fepA | b0584 |
| CDS | + | 612038 | 613162 | fes | b0585 |
| CDS | + | 613380 | 617261 | entF | b0586 |
| CDS | + | 617477 | 618610 | fepE | b0587 |
| CDS | − | 618607 | 619422 | fepC | b0588 |
| CDS | − | 619419 | 620411 | fepG | b0589 |
| CDS | − | 620408 | 621412 | fepD | b0590 |
| CDS | + | 621523 | 622773 | ybdA | b0591 |
| CDS | − | 622777 | 623733 | fepB | b0592 |
| CDS | + | 624108 | 625283 | entC | b0593 |
| CDS | + | 625293 | 626903 | entE | b0594 |
| CDS | + | 626917 | 627774 | entB | b0595 |
| CDS | + | 627774 | 628520 | entA | b0596 |
| CDS | + | 628523 | 628936 | ybdB | b0597 |
| CDS | + | 629117 | 631222 | cstA | b0598 |
| CDS | − | 631612 | 632700 | ybdH | b0599 |
| CDS | + | 632809 | 633969 | ybdL | b0600 |
| CDS | − | 633970 | 634599 | ybdM | b0601 |
| CDS | − | 634572 | 635792 | ybdN | b0602 |
| CDS | − | 635939 | 636841 | ybdO | b0603 |
| CDS | − | 637050 | 637796 | dsbG | b0604 |
| CDS | + | 638168 | 638731 | ahpC | b0605 |
| CDS | + | 638976 | 640541 | ahpF | b0606 |
| CDS | − | 640662 | 641090 | ybdQ | b0607 |
| CDS | − | 641311 | 642549 | ybdR | b0608 |
| CDS | + | 642630 | 643091 | | b0609 |
| CDS | − | 642780 | 643190 | rnk | b0610 |
| CDS | − | 643420 | 644226 | rna | b0611 |
| CDS | − | 644340 | 645803 | citT | b0612 |
| CDS | − | 645854 | 646732 | citG | b0613 |
| CDS | − | 646707 | 647258 | ybdU | b0614 |
| CDS | − | 647262 | 648794 | citF | b0615 |
| CDS | − | 648805 | 649713 | citE | b0616 |
| CDS | − | 649710 | 650006 | citD | b0617 |
| CDS | − | 650021 | 651079 | citC | b0618 |
| CDS | + | 651458 | 653116 | citA | b0619 |
| CDS | + | 653085 | 653765 | citB | b0620 |
| CDS | − | 653806 | 655191 | dcuC | b0621 |
| CDS | + | 655780 | 656340 | crcA | b0622 |
| CDS | + | 656515 | 656724 | cspE | b0623 |
| CDS | − | 656778 | 657161 | crcB | b0624 |
| CDS | + | 657254 | 657481 | ybeH | b0625 |
| CDS | + | 657478 | 658041 | ybeM | b0626 |
| CDS | + | 658170 | 658373 | tatE | b0627 |
| CDS | − | 658474 | 659439 | lipA | b0628 |
| CDS | − | 659648 | 660601 | ybeF | b0629 |
| CDS | − | 660860 | 661501 | lipB | b0630 |
| CDS | − | 661602 | 661865 | ybeD | b0631 |
| CDS | − | 661975 | 663186 | dacA | b0632 |
| CDS | − | 663325 | 664413 | rlpA | b0633 |
| CDS | − | 664424 | 665536 | mrdB | b0634 |
| CDS | − | 665539 | 667440 | mrdA | b0635 |
| CDS | − | 667471 | 667938 | ybeA | b0636 |
| CDS | − | 667942 | 668259 | ybeB | b0637 |
| CDS | − | 668519 | 669130 | phpB | b0638 |
| CDS | − | 669154 | 669795 | nadD | b0639 |
| CDS | − | 669797 | 670828 | holA | b0640 |
| CDS | − | 670828 | 671409 | rlpB | b0641 |
| CDS | − | 671424 | 674006 | leuS | b0642 |
| CDS | + | 674241 | 674723 | ybeL | b0643 |
| CDS | − | 674793 | 675770 | ybeQ | b0644 |
| CDS | + | 675934 | 676641 | ybeR | b0645 |
| CDS | + | 676638 | 678065 | ybeS | b0646 |
| CDS | − | 678075 | 678629 | ybeT | b0647 |
| CDS | + | 678731 | 679438 | ybeU | b0648 |
| CDS | + | 679435 | 680886 | ybeV | b0649 |
| CDS | − | 680946 | 682616 | hscC | b0650 |
| CDS | − | 682700 | 683635 | rihA | b0651 |
| CDS | − | 683753 | 684478 | gltL | b0652 |
| CDS | − | 684478 | 685152 | gltK | b0653 |
| CDS | − | 685152 | 685892 | gltJ | b0654 |
| CDS | − | 686062 | 686970 | gltI | b0655 |
| repeat_region | + | 687074 | 688268 | | |
| CDS | − | 687220 | 688236 | trs5_3 | b0656 |
| CDS | − | 688566 | 690104 | lnt | b0657 |
| CDS | − | 690129 | 691007 | ybeX | b0658 |
| CDS | − | 691097 | 691564 | ybeY | b0659 |
| CDS | − | 691561 | 692640 | ybeZ | b0660 |
| CDS | − | 692754 | 694178 | yleA | b0661 |
| CDS | + | 694324 | 695499 | ubiF | b0662 |
| tRNA | − | 695653 | 695727 | glnX | b0664 |
| tRNA | − | 695765 | 695839 | glnV | b0665 |
| tRNA | − | 695887 | 695963 | metU | b0666 |
| tRNA | − | 695979 | 696053 | glnW | b0668 |
| tRNA | − | 696088 | 696162 | glnU | b0670 |
| tRNA | − | 696186 | 696270 | leuW | b0672 |
| tRNA | − | 696280 | 696356 | metT | b0673 |
| CDS | − | 696736 | 698400 | asnB | b0674 |
| CDS | − | 698797 | 699549 | nagD | b0675 |
| CDS | − | 699597 | 700817 | nagC | b0676 |
| CDS | − | 700826 | 701974 | nagA | b0677 |
| CDS | − | 702034 | 702834 | nagB | b0678 |
| CDS | + | 703167 | 705113 | nagE | b0679 |
| CDS | + | 705316 | 706980 | glnS | b0680 |
| CDS | + | 707557 | 708963 | ybfM | b0681 |
| CDS | + | 709013 | 709339 | ybfN | b0682 |
| CDS | − | 709423 | 709869 | fur | b0683 |
| CDS | − | 710158 | 710688 | fldA | b0684 |
| CDS | − | 710828 | 711121 | ybfE | b0685 |
| CDS | − | 711261 | 712025 | ybfF | b0686 |
| CDS | + | 712210 | 712755 | seqA | b0687 |
| CDS | + | 712781 | 714421 | pgm | b0688 |
| CDS | + | 714635 | 715129 | ybfP | b0689 |
| CDS | − | 715170 | 715580 | ybfG | b0690 |
| CDS | − | 715611 | 715820 | ybfH | b0691 |
| CDS | − | 716169 | 717488 | polE | b0692 |
| CDS | − | 717485 | 719683 | speF | b0693 |
| CDS | − | 720279 | 720956 | kdpE | b0694 |

TABLE 1-continued

| Type | S | Left | Right | Name | B |
|---|---|---|---|---|---|
| CDS | − | 720953 | 723637 | kdpD | b0695 |
| CDS | − | 723630 | 724202 | kdpC | b0696 |
| CDS | − | 724211 | 726259 | kdpB | b0697 |
| CDS | − | 726282 | 727955 | kdpA | b0698 |
| CDS | + | 728357 | 728563 | ybfA | b0699 |
| CDS | + | 728806 | 732999 | rhsC | b0700 |
| CDS | + | 732593 | 732814 |  | b0701 |
| CDS | + | 732999 | 733325 | ybfB | b0702 |
| CDS | + | 733443 | 734876 | ybfO | b0703 |
| CDS | + | 734873 | 735442 | ybfC | b0704 |
| CDS | + | 736123 | 737184 | ybfL | b0705 |
| CDS | + | 737315 | 738076 | ybfD | b0706 |
| CDS | + | 738224 | 738733 | ybgA | b0707 |
| CDS | + | 738730 | 740148 | phrB | b0708 |
| CDS | − | 740298 | 741779 | ybgH | b0709 |
| CDS | + | 742050 | 742793 | ybgI | b0710 |
| CDS | + | 742816 | 743472 | ybgJ | b0711 |
| CDS | + | 743466 | 744398 | ybgK | b0712 |
| CDS | + | 744388 | 745122 | ybgL | b0713 |
| CDS | + | 745158 | 745949 | nei | b0714 |
| CDS | − | 745946 | 746992 | abrB | b0715 |
| CDS | − | 747144 | 748205 | ybgO | b0716 |
| CDS | − | 748202 | 748930 | ybgP | b0717 |
| CDS | − | 748945 | 751392 | ybgQ | b0718 |
| CDS | − | 751452 | 752018 | ybgD | b0719 |
| CDS | − | 752408 | 753691 | gltA | b0720 |
| CDS | + | 754400 | 754789 | sdhC | b0721 |
| CDS | + | 754783 | 755130 | sdhD | b0722 |
| CDS | + | 755130 | 756896 | sdhA | b0723 |
| CDS | + | 756912 | 757628 | sdhB | b0724 |
| CDS | + | 757687 | 757947 |  | b0725 |
| CDS | + | 757929 | 760730 | sucA | b0726 |
| CDS | + | 760745 | 761962 | sucB | b0727 |
| CDS | + | 762237 | 763403 | sucC | b0728 |
| CDS | + | 763403 | 764272 | sucD | b0729 |
| CDS | − | 764376 | 765098 | farR | b0730 |
| CDS | + | 765207 | 767183 | hrsA | b0731 |
| CDS | + | 767201 | 769834 | ybgG | b0732 |
| CDS | + | 770681 | 772249 | cydA | b0733 |
| CDS | + | 772265 | 773404 | cydB | b0734 |
| CDS | + | 773532 | 773825 | ybgE | b0735 |
| CDS | + | 773975 | 774379 | ybgC | b0736 |
| CDS | + | 774376 | 775068 | tolQ | b0737 |
| CDS | + | 775072 | 775500 | tolR | b0738 |
| CDS | + | 775565 | 776830 | tolA | b0739 |
| CDS | + | 776963 | 778255 | tolB | b0740 |
| CDS | + | 778290 | 778811 | pal | b0741 |
| CDS | + | 778821 | 779612 | ybgF | b0742 |
| tRNA | + | 779777 | 779852 | lysT | b0743 |
| tRNA | + | 779988 | 780063 | valT | b0744 |
| tRNA | + | 780066 | 780141 | lysW | b0745 |
| tRNA | + | 780291 | 780366 | valZ | b0746 |
| tRNA | + | 780370 | 780445 | lysY | b0747 |
| tRNA | + | 780592 | 780667 | lysZ | b0748 |
| tRNA | + | 780800 | 780875 | lysQ | b0749 |
| CDS | + | 781308 | 782351 | nadA | b0750 |
| CDS | + | 782389 | 783108 | pnuC | b0751 |
| CDS | − | 783105 | 784046 | ybgR | b0752 |
| CDS | − | 784160 | 784540 | ybgS | b0753 |
| CDS | + | 784856 | 785908 | aroG | b0754 |
| CDS | − | 786066 | 786818 | gpmA | b0755 |
| CDS | − | 787020 | 788060 | galM | b0756 |
| CDS | − | 788054 | 789202 | galK | b0757 |
| CDS | − | 789206 | 790252 | galT | b0758 |
| CDS | − | 790262 | 791278 | galE | b0759 |
| CDS | − | 791539 | 793011 | modF | b0760 |
| CDS | − | 793079 | 793867 | modE | b0761 |
| CDS | + | 793996 | 794145 | ybhT | b0762 |
| CDS | + | 794312 | 795085 | modA | b0763 |
| CDS | + | 795085 | 795774 | modB | b0764 |
| CDS | + | 795777 | 796835 | modC | b0765 |
| CDS | − | 796836 | 797654 | ybhA | b0766 |
| CDS | + | 797809 | 798804 | ybhE | b0767 |
| CDS | − | 798845 | 799861 | ybhD | b0768 |
| CDS | + | 799982 | 801034 | ybhH | b0769 |
| CDS | + | 801110 | 802543 | ybhI | b0770 |
| CDS | + | 802726 | 804987 | ybhJ | b0771 |
| CDS | − | 805221 | 806504 | ybhC | b0772 |
| CDS | − | 806656 | 807132 | ybhB | b0773 |
| CDS | − | 807191 | 808480 | bioA | b0774 |
| CDS | + | 808567 | 809607 | bioB | b0775 |
| CDS | + | 809604 | 810758 | bioF | b0776 |
| CDS | + | 810745 | 811500 | bioC | b0777 |
| CDS | + | 811493 | 812170 | bioD | b0778 |
| CDS | + | 812749 | 814770 | uvrB | b0779 |
| CDS | − | 814962 | 815870 | ybhK | b0780 |
| CDS | + | 816267 | 817256 | moaA | b0781 |
| CDS | + | 817278 | 817790 | moaB | b0782 |
| CDS | + | 817793 | 818278 | moaC | b0783 |
| CDS | + | 818271 | 818516 | moaD | b0784 |
| CDS | + | 818518 | 818970 | moaE | b0785 |
| CDS | + | 819107 | 819811 | ybhL | b0786 |
| CDS | + | 820016 | 820729 | ybhM | b0787 |
| CDS | − | 820765 | 821721 | ybhN | b0788 |
| CDS | − | 821721 | 822962 | ybhO | b0789 |
| CDS | − | 822959 | 823720 | ybhP | b0790 |
| CDS | + | 823853 | 824263 | ybhQ | b0791 |
| CDS | − | 824225 | 825331 | ybhR | b0792 |
| CDS | − | 825342 | 826475 | ybhS | b0793 |
| CDS | − | 826468 | 828204 | ybhF | b0794 |
| CDS | − | 828197 | 829195 | ybhG | b0795 |
| CDS | − | 829195 | 829866 | ybiH | b0796 |
| CDS | + | 830095 | 831459 | rhlE | b0797 |
| CDS | − | 831691 | 832173 | ybiA | b0798 |
| CDS | + | 832293 | 834443 | dinG | b0799 |
| CDS | + | 834471 | 835433 | ybiB | b0800 |
| CDS | + | 835574 | 836659 | ybiC | b0801 |
| CDS | − | 836888 | 837148 | ybiJ | b0802 |
| CDS | − | 837413 | 837679 | ybiI | b0803 |
| CDS | − | 837753 | 838430 | ybiX | b0804 |
| CDS | − | 838472 | 840754 | ybiL | b0805 |
| CDS | − | 841019 | 841279 | ybiM | b0806 |
| CDS | + | 841555 | 842481 | ybiN | b0807 |
| CDS | − | 842478 | 844703 | ybiO | b0808 |
| CDS | − | 844964 | 845686 | glnQ | b0809 |
| CDS | − | 845683 | 846342 | glnP | b0810 |
| CDS | − | 846481 | 847227 | glnH | b0811 |
| CDS | − | 847631 | 848134 | dps | b0812 |
| CDS | − | 848433 | 849320 | ybiF | b0813 |
| CDS | + | 849673 | 850188 | ompX | b0814 |
| CDS | − | 850237 | 851820 | ybiP | b0815 |
| CDS | + | 851894 | 852163 |  | b0816 |
| CDS | + | 852406 | 852873 | mntR | b0817 |
| CDS | + | 852870 | 853988 | ybiR | b0818 |
| CDS | − | 854047 | 854967 | ybiS | b0819 |
| CDS | + | 855186 | 856778 | ybiT | b0820 |
| CDS | − | 857019 | 858284 | ybiU | b0821 |
| CDS | − | 858436 | 859251 | ybiV | b0822 |
| CDS | − | 859397 | 861829 | ybiW | b0823 |
| CDS | − | 861835 | 862761 | ybiY | b0824 |
| CDS | + | 862865 | 863527 | fsa | b0825 |
| CDS | − | 863603 | 864352 | moeB | b0826 |
| CDS | − | 864352 | 865587 | moeA | b0827 |
| CDS | − | 865791 | 866756 | ybiK | b0828 |
| CDS | + | 866776 | 868614 | yliA | b0829 |
| CDS | + | 868634 | 870172 | yliB | b0830 |
| CDS | + | 870190 | 871110 | yliC | b0831 |
| CDS | + | 871113 | 872024 | yliD | b0832 |
| CDS | + | 872202 | 874550 | yliE | b0833 |
| CDS | + | 874558 | 875886 | yliF | b0834 |
| CDS | − | 875933 | 877258 | yliG | b0835 |
| CDS | + | 877471 | 877854 | yliH | b0836 |
| CDS | + | 877965 | 879080 | yliI | b0837 |
| CDS | − | 879077 | 879703 | yliJ | b0838 |
| CDS | + | 879950 | 881152 | dacC | b0839 |
| CDS | − | 881199 | 881957 | deoR | b0840 |
| CDS | − | 882015 | 882611 | ybjG | b0841 |
| CDS | + | 882896 | 884128 | cmr | b0842 |
| CDS | − | 884169 | 884453 | ybjH | b0843 |
| CDS | − | 884539 | 885354 | ybjI | b0844 |
| CDS | − | 885354 | 886562 | ybjJ | b0845 |
| CDS | + | 886646 | 887182 | ybjK | b0846 |
| CDS | + | 887357 | 889042 | ybjL | b0847 |
| CDS | + | 889312 | 889689 | ybjM | b0848 |
| CDS | − | 889719 | 889976 | grxA | b0849 |
| CDS | + | 890136 | 890423 | ybjC | b0850 |

TABLE 1-continued

| Type | S | Left | Right | Name | B |
|---|---|---|---|---|---|
| CDS | + | 890407 | 891129 | nfsA | b0851 |
| CDS | + | 891190 | 892092 | rimK | b0852 |
| CDS | + | 892180 | 892656 | ybjN | b0853 |
| CDS | + | 893007 | 894119 | potF | b0854 |
| CDS | + | 894214 | 895347 | potG | b0855 |
| CDS | + | 895357 | 896310 | potH | b0856 |
| CDS | + | 896307 | 897152 | potI | b0857 |
| CDS | + | 897212 | 897700 | ybjO | b0858 |
| CDS | + | 897741 | 898868 | ybjF | b0859 |
| CDS | − | 899078 | 899798 | artJ | b0860 |
| CDS | − | 900089 | 900757 | artM | b0861 |
| CDS | − | 900757 | 901473 | artQ | b0862 |
| CDS | − | 901480 | 902211 | artI | b0863 |
| CDS | − | 902229 | 902957 | artP | b0864 |
| CDS | − | 903175 | 903690 | ybjP | b0865 |
| CDS | + | 903816 | 904139 | ybjQ | b0866 |
| CDS | + | 904136 | 904966 | ybjR | b0867 |
| CDS | − | 904963 | 905976 | ybjS | b0868 |
| CDS | − | 906075 | 907505 | ybjT | b0869 |
| CDS | − | 907516 | 908517 | ltaE | b0870 |
| CDS | − | 908554 | 910272 | poxB | b0871 |
| CDS | − | 910405 | 911373 | hcr | b0872 |
| CDS | − | 911385 | 913037 | hcp | b0873 |
| CDS | − | 913181 | 914080 | ybjE | b0874 |
| CDS | − | 914575 | 915270 | aqpZ | b0875 |
| CDS | + | 915696 | 917354 | ybjD | b0876 |
| CDS | − | 917351 | 918343 | ybjX | b0877 |
| CDS | + | 918458 | 919573 | macA | b0878 |
| CDS | + | 919570 | 921516 | macB | b0879 |
| CDS | − | 921589 | 921813 | cspD | b0880 |
| CDS | + | 922136 | 922456 | yljA | b0881 |
| CDS | + | 922487 | 924763 | clpA | b0882 |
| tRNA | − | 925107 | 925194 | serW | b0883 |
| CDS | − | 925448 | 925666 | infA | b0884 |
| CDS | − | 925951 | 926655 | aat | b0885 |
| CDS | − | 926697 | 928418 | cydC | b0886 |
| CDS | − | 928419 | 930185 | cydD | b0887 |
| CDS | − | 930308 | 931273 | trxB | b0888 |
| CDS | + | 931818 | 932312 | lrp | b0889 |
| CDS | + | 932447 | 936436 | ftsK | b0890 |
| CDS | + | 936592 | 937206 | lolA | b0891 |
| CDS | + | 937217 | 938560 | ycaJ | b0892 |
| CDS | + | 938651 | 939943 | serS | b0893 |
| CDS | + | 940182 | 942626 | dmsA | b0894 |
| CDS | + | 942637 | 943254 | dmsB | b0895 |
| CDS | + | 943256 | 944119 | dmsC | b0896 |
| CDS | − | 944154 | 944780 | ycaC | b0897 |
| CDS | + | 945094 | 946242 | ycaD | b0898 |
| CDS | + | 946452 | 947882 | ycaM | b0899 |
| CDS | − | 947883 | 948791 | ycaN | b0900 |
| CDS | + | 948891 | 949481 | ycaK | b0901 |
| CDS | − | 949563 | 950303 | pflA | b0902 |
| CDS | − | 950495 | 952777 | pflB | b0903 |
| CDS | − | 952832 | 953689 | focA | b0904 |
| CDS | − | 954095 | 955855 | ycaO | b0905 |
| CDS | + | 955985 | 956677 | ycaP | b0906 |
| CDS | + | 956876 | 957964 | serC | b0907 |
| CDS | + | 958035 | 959318 | aroA | b0908 |
| CDS | + | 959487 | 960251 | ycaL | b0909 |
| CDS | + | 960424 | 961107 | cmk | b0910 |
| CDS | + | 961218 | 962891 | rpsA | b0911 |
| CDS | + | 963051 | 963335 | himD | b0912 |
| CDS | + | 963543 | 965807 | ycaI | b0913 |
| CDS | + | 965844 | 967592 | msbA | b0914 |
| CDS | + | 967589 | 968575 | lpxK | b0915 |
| CDS | + | 968612 | 969844 | ycaQ | b0916 |
| CDS | + | 969896 | 970078 | ycaR | b0917 |
| CDS | + | 970075 | 970821 | kdsB | b0918 |
| CDS | + | 970975 | 971868 | ycbJ | b0919 |
| CDS | − | 971845 | 972624 | ycbC | b0920 |
| CDS | + | 972760 | 973545 | smtA | b0921 |
| CDS | + | 973542 | 974864 | mukF | b0922 |
| CDS | + | 974872 | 975549 | mukE | b0923 |
| CDS | + | 975549 | 980009 | mukB | b0924 |
| CDS | + | 980270 | 982117 | ycbB | b0925 |
| CDS | + | 982298 | 982846 | ycbK | b0926 |
| CDS | + | 982873 | 983520 | ycbL | b0927 |
| CDS | − | 983742 | 984932 | aspC | b0928 |
| CDS | − | 985117 | 986205 | ompF | b0929 |
| CDS | − | 986808 | 988208 | asnS | b0930 |
| CDS | − | 988377 | 989579 | pncB | b0931 |
| CDS | + | 989845 | 992457 | pepN | b0932 |
| CDS | − | 992500 | 993267 | ssuB | b0933 |
| CDS | − | 993264 | 994055 | ssuC | b0934 |
| CDS | − | 994066 | 995211 | ssuD | b0935 |
| CDS | − | 995208 | 996167 | ssuA | b0936 |
| CDS | − | 996160 | 996735 | ssuE | b0937 |
| CDS | + | 997091 | 997630 | ycbQ | b0938 |
| CDS | + | 997713 | 998414 | ycbR | b0939 |
| CDS | + | 998439 | 1001039 | ycbS | b0940 |
| CDS | + | 1001030 | 1002100 | ycbT | b0941 |
| CDS | + | 1002112 | 1002654 | ycbU | b0942 |
| CDS | + | 1002662 | 1003177 | ycbV | b0943 |
| CDS | + | 1003170 | 1003880 | ycbF | b0944 |
| CDS | + | 1003991 | 1005001 | pyrD | b0945 |
| CDS | + | 1005175 | 1005717 | ycbW | b0946 |
| CDS | − | 1005714 | 1006823 | ycbX | b0947 |
| CDS | + | 1007067 | 1009175 | ycbY | b0948 |
| CDS | + | 1009187 | 1011094 | uup | b0949 |
| CDS | + | 1011224 | 1012477 | pqiA | b0950 |
| CDS | + | 1012482 | 1014122 | pqiB | b0951 |
| CDS | + | 1014134 | 1014682 | ymbA | b0952 |
| CDS | + | 1014938 | 1015105 | rmf | b0953 |
| CDS | − | 1015175 | 1015693 | fabA | b0954 |
| CDS | − | 1015762 | 1017522 | ycbZ | b0955 |
| CDS | + | 1017708 | 1018160 | ycbG | b0956 |
| CDS | − | 1018236 | 1019276 | ompA | b0957 |
| CDS | − | 1019633 | 1020142 | sulA | b0958 |
| CDS | + | 1020361 | 1020990 | yccR | b0959 |
| CDS | + | 1020953 | 1023106 | yccS | b0960 |
| CDS | − | 1023125 | 1023571 | yccF | b0961 |
| CDS | + | 1023694 | 1025748 | helD | b0962 |
| CDS | − | 1025780 | 1026238 | mgsA | b0963 |
| CDS | − | 1026334 | 1026996 | yccT | b0964 |
| CDS | + | 1027169 | 1027582 | yccU | b0965 |
| CDS | − | 1027627 | 1027995 | yccV | b0966 |
| CDS | + | 1028002 | 1029105 | yccW | b0967 |
| CDS | + | 1029287 | 1029565 | yccX | b0968 |
| CDS | − | 1029562 | 1029891 | yccK | b0969 |
| CDS | − | 1029982 | 1030641 | yccA | b0970 |
| tRNA | − | 1030848 | 1030935 | serT | b0971 |
| CDS | + | 1031362 | 1032480 | hyaA | b0972 |
| CDS | + | 1032477 | 1034270 | hyaB | b0973 |
| CDS | + | 1034289 | 1034996 | hyaC | b0974 |
| CDS | + | 1034993 | 1035580 | hyaD | b0975 |
| CDS | + | 1035577 | 1035975 | hyaE | b0976 |
| CDS | + | 1035972 | 1036829 | hyaF | b0977 |
| CDS | + | 1036963 | 1038507 | appC | b0978 |
| CDS | + | 1038519 | 1039655 | appB | b0979 |
| CDS | + | 1039840 | 1041138 | appA | b0980 |
| CDS | − | 1041253 | 1043433 | yccC | b0981 |
| CDS | − | 1043453 | 1043899 | yccY | b0982 |
| CDS | − | 1043887 | 1045026 | yccZ | b0983 |
| CDS | + | 1045072 | 1047168 | ymcA | b0984 |
| CDS | + | 1047168 | 1047914 | ymcB | b0985 |
| CDS | + | 1047911 | 1048555 | ymcC | b0986 |
| CDS | + | 1048662 | 1048967 | ymcD | b0987 |
| repeat_region | + | 1049001 | 1049768 | | |
| CDS | + | 1049250 | 1049753 | insB_4 | b0988 |
| CDS | − | 1050186 | 1050398 | cspH | b0989 |
| CDS | + | 1050684 | 1050896 | cspG | b0990 |
| CDS | + | 1051070 | 1051300 | sfa | b0991 |
| CDS | − | 1051512 | 1052585 | yccM | b0992 |
| CDS | − | 1052657 | 1055401 | torS | b0993 |
| CDS | + | 1055484 | 1056512 | torT | b0994 |
| CDS | − | 1056485 | 1057177 | torR | b0995 |
| CDS | + | 1057307 | 1058479 | torC | b0996 |
| CDS | + | 1058479 | 1061025 | torA | b0997 |
| CDS | + | 1061022 | 1061621 | torD | b0998 |
| CDS | − | 1061773 | 1062078 | yccD | b0999 |
| CDS | − | 1062078 | 1062998 | cbpA | b1000 |
| CDS | + | 1063259 | 1064515 | yccE | b1001 |
| CDS | + | 1064808 | 1066049 | agp | b1002 |
| CDS | + | 1066087 | 1066314 | yccJ | b1003 |
| CDS | − | 1066335 | 1066931 | wrbA | b1004 |
| CDS | + | 1067141 | 1067371 | ycdF | b1005 |

TABLE 1-continued

| Type | S | Left | Right | Name | B |
|---|---|---|---|---|---|
| CDS | − | 1067734 | 1069062 | ycdG | b1006 |
| CDS | − | 1069083 | 1069577 | ycdH | b1007 |
| CDS | − | 1069588 | 1070178 | ycdI | b1008 |
| CDS | − | 1070188 | 1070988 | ycdJ | b1009 |
| CDS | − | 1070996 | 1071382 | ycdK | b1010 |
| CDS | − | 1071394 | 1072086 | ycdL | b1011 |
| CDS | − | 1072086 | 1073234 | ycdM | b1012 |
| CDS | + | 1073465 | 1074103 | ycdC | b1013 |
| CDS | − | 1074143 | 1078105 | putA | b1014 |
| CDS | + | 1078528 | 1080036 | putP | b1015 |
| CDS | + | 1080579 | 1080689 | ycdN_1 | b1016 |
| CDS | + | 1080677 | 1081408 | ycdN_2 | b1017 |
| CDS | + | 1081466 | 1082593 | ycdO | b1018 |
| CDS | + | 1082599 | 1083870 | ycdB | b1019 |
| CDS | + | 1084215 | 1085279 | phoH | b1020 |
| CDS | − | 1085329 | 1085742 | ycdP | b1021 |
| CDS | − | 1085744 | 1087069 | ycdQ | b1022 |
| CDS | − | 1087062 | 1089080 | ycdR | b1023 |
| CDS | − | 1089089 | 1091512 | ycdS | b1024 |
| CDS | + | 1092099 | 1093457 | ycdT | b1025 |
| repeat_region | − | 1093468 | 1094725 | | |
| CDS | − | 1093498 | 1094364 | tra5_3 | b1026 |
| CDS | − | 1094361 | 1094669 | | b1027 |
| CDS | + | 1094767 | 1095069 | | b1028 |
| CDS | + | 1095066 | 1096052 | ycdU | b1029 |
| tRNA | − | 1096788 | 1096875 | serX | b1032 |
| CDS | + | 1097109 | 1098047 | ycdW | b1033 |
| CDS | + | 1098102 | 1098839 | ycdX | b1034 |
| CDS | + | 1098863 | 1099417 | ycdY | b1035 |
| CDS | + | 1099519 | 1100010 | ycdZ | b1036 |
| CDS | − | 1100074 | 1100907 | csgG | b1037 |
| CDS | − | 1100934 | 1101350 | csgF | b1038 |
| CDS | − | 1101375 | 1101764 | csgE | b1039 |
| CDS | − | 1101769 | 1102419 | csgD | b1040 |
| CDS | + | 1103174 | 1103629 | csgB | b1041 |
| CDS | + | 1103670 | 1104125 | csgA | b1042 |
| CDS | + | 1104184 | 1104516 | csgC | b1043 |
| CDS | + | 1104637 | 1104948 | ymdA | b1044 |
| CDS | + | 1105043 | 1105576 | ymdB | b1045 |
| CDS | + | 1105578 | 1106999 | ymdC | b1046 |
| CDS | − | 1107007 | 1108164 | mdoC | b1047 |
| CDS | + | 1108558 | 1110093 | mdoG | b1048 |
| CDS | + | 1110086 | 1112629 | mdoH | b1049 |
| CDS | + | 1112802 | 1113029 | yceK | b1050 |
| CDS | − | 1113030 | 1113404 | msyB | b1051 |
| CDS | − | 1113434 | 1113532 | | b1052 |
| CDS | − | 1113487 | 1114713 | yceE | b1053 |
| CDS | − | 1114885 | 1115805 | htrB | b1054 |
| CDS | + | 1116030 | 1117082 | yceA | b1055 |
| CDS | − | 1117124 | 1117699 | yceI | b1056 |
| CDS | − | 1117703 | 1118269 | yceJ | b1057 |
| CDS | − | 1118530 | 1118670 | yceO | b1058 |
| CDS | − | 1118691 | 1119809 | solA | b1059 |
| CDS | − | 1119924 | 1120178 | yceP | b1060 |
| CDS | − | 1120465 | 1120710 | dinI | b1061 |
| CDS | − | 1120784 | 1121830 | pyrC | b1062 |
| CDS | − | 1121936 | 1122496 | yceB | b1063 |
| CDS | − | 1122630 | 1123277 | grxB | b1064 |
| CDS | − | 1123341 | 1124549 | yceL | b1065 |
| CDS | + | 1124785 | 1125369 | rimJ | b1066 |
| CDS | + | 1125380 | 1126027 | yceH | b1067 |
| CDS | + | 1126029 | 1126952 | mviM | b1068 |
| CDS | + | 1127062 | 1128597 | mviN | b1069 |
| CDS | − | 1128637 | 1129053 | flgN | b1070 |
| CDS | − | 1129058 | 1129351 | flgM | b1071 |
| CDS | − | 1129427 | 1130086 | flgA | b1072 |
| CDS | + | 1130241 | 1130657 | flgB | b1073 |
| CDS | + | 1130661 | 1131065 | flgC | b1074 |
| CDS | + | 1131077 | 1131772 | flgD | b1075 |
| CDS | + | 1131797 | 1133005 | flgE | b1076 |
| CDS | + | 1133025 | 1133780 | flgF | b1077 |
| CDS | + | 1133952 | 1134734 | flgG | b1078 |
| CDS | + | 1134787 | 1135485 | flgH | b1079 |
| CDS | + | 1135497 | 1136594 | flgI | b1080 |
| CDS | + | 1136594 | 1137535 | flgJ | b1081 |
| CDS | + | 1137601 | 1139244 | flgK | b1082 |
| CDS | + | 1139256 | 1140209 | flgL | b1083 |
| CDS | − | 1140405 | 1143590 | rne | b1084 |
| CDS | + | 1143725 | 1144045 | | b1085 |
| CDS | + | 1144163 | 1145122 | rluC | b1086 |
| CDS | − | 1145234 | 1145818 | yceF | b1087 |
| CDS | + | 1146017 | 1146538 | yceD | b1088 |
| CDS | + | 1146590 | 1146763 | rpmF | b1089 |
| CDS | + | 1146844 | 1147914 | plsX | b1090 |
| CDS | + | 1147982 | 1148935 | fabH | b1091 |
| CDS | + | 1148951 | 1149880 | fabD | b1092 |
| CDS | + | 1149893 | 1150627 | fabG | b1093 |
| CDS | + | 1150838 | 1151074 | acpP | b1094 |
| CDS | + | 1151162 | 1152403 | fabF | b1095 |
| CDS | + | 1152523 | 1153332 | pabC | b1096 |
| CDS | + | 1153335 | 1154357 | yceG | b1097 |
| CDS | + | 1154347 | 1154988 | tmk | b1098 |
| CDS | + | 1154985 | 1155989 | holB | b1099 |
| CDS | + | 1156000 | 1156797 | ycfH | b1100 |
| CDS | + | 1157092 | 1158525 | ptsG | b1101 |
| CDS | − | 1158585 | 1160774 | fhuE | b1102 |
| CDS | + | 1161108 | 1161467 | ycfF | b1103 |
| CDS | + | 1161470 | 1161847 | ycfL | b1104 |
| CDS | + | 1161861 | 1162502 | ycfM | b1105 |
| CDS | + | 1162483 | 1163307 | ycfN | b1106 |
| CDS | + | 1163318 | 1164343 | nagZ | b1107 |
| CDS | + | 1164366 | 1164908 | ycfP | b1108 |
| CDS | + | 1165308 | 1166612 | ndh | b1109 |
| CDS | + | 1166822 | 1167361 | ycfJ | b1110 |
| CDS | − | 1167423 | 1168055 | ycfQ | b1111 |
| CDS | + | 1168296 | 1168553 | ycfR | b1112 |
| CDS | − | 1168635 | 1169597 | ycfS | b1113 |
| CDS | − | 1169741 | 1173187 | mfd | b1114 |
| CDS | − | 1173315 | 1174388 | ycfT | b1115 |
| CDS | + | 1174650 | 1175849 | ycfU | b1116 |
| CDS | + | 1175842 | 1176543 | ycfV | b1117 |
| CDS | + | 1176543 | 1177787 | ycfW | b1118 |
| CDS | + | 1177816 | 1178727 | ycfX | b1119 |
| CDS | + | 1178743 | 1179582 | cobB | b1120 |
| CDS | − | 1179702 | 1180490 | ycfZ | b1121 |
| CDS | − | 1180487 | 1180948 | ymfA | b1122 |
| CDS | − | 1181006 | 1182052 | potD | b1123 |
| CDS | − | 1182049 | 1182843 | potC | b1124 |
| CDS | − | 1182840 | 1183667 | potB | b1125 |
| CDS | − | 1183681 | 1184817 | potA | b1126 |
| CDS | + | 1185067 | 1186293 | pepT | b1127 |
| CDS | − | 1186342 | 1187463 | ycfD | b1128 |
| CDS | − | 1187539 | 1188999 | phoQ | b1129 |
| CDS | − | 1188999 | 1189670 | phoP | b1130 |
| CDS | − | 1189839 | 1191209 | purB | b1131 |
| CDS | − | 1191213 | 1191854 | ycfC | b1132 |
| CDS | − | 1191890 | 1192996 | trmU | b1133 |
| CDS | − | 1193050 | 1193511 | ymfB | b1134 |
| CDS | − | 1193521 | 1194174 | ymfC | b1135 |
| CDS | + | 1194346 | 1195596 | icdA | b1136 |
| CDS | + | 1196090 | 1196755 | ymfD | b1137 |
| CDS | + | 1196756 | 1197460 | ymfE | b1138 |
| CDS | + | 1197918 | 1198811 | lit | b1139 |
| CDS | − | 1198902 | 1200029 | intE | b1140 |
| CDS | − | 1200010 | 1200255 | | b1141 |
| CDS | − | 1200292 | 1200603 | ymfH | b1142 |
| CDS | + | 1200720 | 1201061 | ymfI | b1143 |
| CDS | − | 1200999 | 1201307 | ymfJ | b1144 |
| CDS | + | 1201482 | 1202156 | ymfK | b1145 |
| CDS | + | 1202247 | 1202447 | | b1146 |
| CDS | + | 1202479 | 1203048 | ymfL | b1147 |
| CDS | + | 1203045 | 1203383 | ymfM | b1148 |
| CDS | + | 1203393 | 1204760 | ymfN | b1149 |
| CDS | + | 1204772 | 1204954 | ymfR | b1150 |
| CDS | + | 1204954 | 1205427 | ymfO | b1151 |
| CDS | + | 1205483 | 1206145 | ymfP | b1152 |
| CDS | + | 1206136 | 1206720 | ymfQ | b1153 |
| CDS | + | 1206724 | 1207353 | ycfK | b1154 |
| CDS | + | 1207355 | 1207768 | ymfS | b1155 |
| CDS | − | 1207740 | 1208342 | tfaE | b1156 |
| CDS | − | 1208342 | 1208878 | stfE | b1157 |
| CDS | + | 1208908 | 1209462 | pin | b1158 |
| CDS | + | 1209569 | 1210402 | mcrA | b1159 |
| CDS | − | 1210903 | 1211226 | ycgW | b1160 |
| CDS | − | 1211926 | 1212330 | ycgX | b1161 |
| CDS | − | 1212551 | 1213282 | ycgE | b1162 |

TABLE 1-continued

| Type | S | Left | Right | Name | B |
|---|---|---|---|---|---|
| CDS | − | 1213487 | 1214698 | ycgF | b1163 |
| CDS | + | 1215012 | 1215248 | ycgZ | b1164 |
| CDS | + | 1215291 | 1215563 | ymgA | b1165 |
| CDS | + | 1215592 | 1215858 | ymgB | b1166 |
| CDS | + | 1215971 | 1216219 | ymgC | b1167 |
| CDS | + | 1216551 | 1218074 | ycgG | b1168 |
| CDS | + | 1220024 | 1220344 | ycgH_1 | b1169 |
| CDS | + | 1220429 | 1221445 | ycgH_2 | b1170 |
| CDS | − | 1221528 | 1221857 | ymgD | b1171 |
| CDS | − | 1221867 | 1222142 |  | b1172 |
| CDS | + | 1222918 | 1223130 |  | b1173 |
| CDS | − | 1223502 | 1223768 | minE | b1174 |
| CDS | − | 1223772 | 1224584 | minD | b1175 |
| CDS | − | 1224608 | 1225303 | minC | b1176 |
| CDS | + | 1225823 | 1226191 | ycgJ | b1177 |
| CDS | − | 1226294 | 1226695 | ycgK | b1178 |
| CDS | + | 1226904 | 1227230 | ycgL | b1179 |
| CDS | + | 1227302 | 1227961 | ycgM | b1180 |
| CDS | + | 1228053 | 1228499 | ycgN | b1181 |
| CDS | − | 1228706 | 1229617 | hlyE | b1182 |
| CDS | + | 1229990 | 1230409 | umuD | b1183 |
| CDS | + | 1230409 | 1231677 | umuC | b1184 |
| CDS | − | 1231723 | 1232253 | dsbB | b1185 |
| CDS | − | 1232399 | 1233940 | nhaB | b1186 |
| CDS | + | 1234161 | 1234880 | fadR | b1187 |
| CDS | − | 1234932 | 1236464 | ycgB | b1188 |
| CDS | + | 1236794 | 1238092 | dadA | b1189 |
| CDS | + | 1238102 | 1239172 | dadX | b1190 |
| CDS | − | 1239558 | 1241294 | ycgO | b1191 |
| CDS | − | 1241389 | 1242303 | ldcA | b1192 |
| CDS | + | 1242303 | 1243014 | mltE | b1193 |
| CDS | − | 1243016 | 1243750 | ycgR | b1194 |
| CDS | + | 1243951 | 1244205 | ymgE | b1195 |
| CDS | + | 1244383 | 1244823 | ycgY | b1196 |
| CDS | − | 1244902 | 1246599 | treA | b1197 |
| CDS | − | 1246919 | 1248337 | dhaM | b1198 |
| CDS | − | 1248348 | 1248980 | dhaL | b1199 |
| CDS | − | 1248991 | 1250061 | dhaK | b1200 |
| CDS | + | 1250289 | 1252208 | dhaR | b1201 |
| CDS | − | 1252308 | 1255175 | ycgV | b1202 |
| CDS | − | 1255944 | 1257035 | ychF | b1203 |
| CDS | − | 1257152 | 1257736 | pth | b1204 |
| CDS | + | 1258014 | 1258292 | ychH | b1205 |
| CDS | − | 1258347 | 1260026 | ychM | b1206 |
| CDS | − | 1260151 | 1261098 | prsA | b1207 |
| CDS | − | 1261249 | 1262100 | ispE | b1208 |
| CDS | − | 1262100 | 1262723 | hemM | b1209 |
| CDS | + | 1262769 | 1264193 | hemA | b1210 |
| CDS | + | 1264235 | 1265317 | prfA | b1211 |
| CDS | + | 1265317 | 1266150 | hemK | b1212 |
| CDS | + | 1266147 | 1266539 | ychQ | b1213 |
| CDS | + | 1266543 | 1267352 | ychA | b1214 |
| CDS | + | 1267388 | 1268242 | kdsA | b1215 |
| CDS | − | 1269972 | 1271072 | chaA | b1216 |
| CDS | + | 1271342 | 1271572 | chaB | b1217 |
| CDS | + | 1271709 | 1272425 | chaC | b1218 |
| CDS | − | 1272469 | 1272822 | ychN | b1219 |
| CDS | + | 1273148 | 1274401 | ychP | b1220 |
| CDS | − | 1274402 | 1275052 | narL | b1221 |
| CDS | − | 1275045 | 1276841 | narX | b1222 |
| CDS | + | 1277180 | 1278571 | narK | b1223 |
| CDS | + | 1279087 | 1282830 | narG | b1224 |
| CDS | + | 1282827 | 1284365 | narH | b1225 |
| CDS | + | 1284362 | 1285072 | narJ | b1226 |
| CDS | + | 1285072 | 1285749 | narI | b1227 |
| CDS | + | 1285932 | 1286207 |  | b1228 |
| CDS | − | 1286310 | 1286411 | tpr | b1229 |
| tRNA | − | 1286467 | 1286551 | tyrV | b1230 |
| tRNA | − | 1286761 | 1286845 | tyrT | b1231 |
| CDS | − | 1287005 | 1287847 | purU | b1232 |
| CDS | − | 1287897 | 1288355 | ychJ | b1233 |
| CDS | + | 1288429 | 1289373 | ychK | b1234 |
| CDS | + | 1289465 | 1290478 | hnr | b1235 |
| CDS | − | 1290680 | 1291588 | galU | b1236 |
| CDS | − | 1291732 | 1292145 | hns | b1237 |
| CDS | + | 1292750 | 1293367 | tdk | b1238 |
| CDS | − | 1293649 | 1294239 | ychG | b1239 |
| CDS | − | 1294191 | 1294421 |  | b1240 |
| CDS | − | 1294669 | 1297344 | adhE | b1241 |
| CDS | + | 1297821 | 1298468 | ychE | b1242 |
| CDS | + | 1299206 | 1300837 | oppA | b1243 |
| CDS | + | 1300923 | 1301843 | oppB | b1244 |
| CDS | + | 1301858 | 1302766 | oppC | b1245 |
| CDS | + | 1302778 | 1303791 | oppD | b1246 |
| CDS | + | 1303788 | 1304792 | oppF | b1247 |
| CDS | − | 1304845 | 1305174 | yciU | b1248 |
| CDS | − | 1305209 | 1306669 | cis | b1249 |
| CDS | − | 1307040 | 1308293 | kch | b1250 |
| CDS | − | 1308593 | 1308889 | yciI | b1251 |
| CDS | + | 1309113 | 1309832 | tonB | b1252 |
| CDS | − | 1309872 | 1310270 | yciA | b1253 |
| CDS | − | 1310375 | 1310914 | ispZ | b1254 |
| CDS | − | 1310944 | 1311687 | yciC | b1255 |
| CDS | + | 1312044 | 1312682 | yciD | b1256 |
| CDS | − | 1312742 | 1313248 | yciE | b1257 |
| CDS | − | 1313294 | 1313794 | yciF | b1258 |
| CDS | − | 1313880 | 1314059 | yciG | b1259 |
| CDS | − | 1314440 | 1315246 | trpA | b1260 |
| CDS | − | 1315246 | 1316439 | trpB | b1261 |
| CDS | − | 1316451 | 1317809 | trpC | b1262 |
| CDS | − | 1317813 | 1319408 | trpD | b1263 |
| CDS | − | 1319408 | 1320970 | trpE | b1264 |
| CDS | − | 1321062 | 1321106 | trpL | b1265 |
| CDS | + | 1321244 | 1322125 | yciV | b1266 |
| CDS | + | 1322122 | 1322742 | yciO | b1267 |
| CDS | + | 1322770 | 1324665 | yciQ | b1268 |
| CDS | + | 1324876 | 1325751 | yciL | b1269 |
| CDS | − | 1325791 | 1326381 | btuR | b1270 |
| CDS | − | 1326378 | 1327136 | yciK | b1271 |
| CDS | + | 1327356 | 1328405 | sohB | b1272 |
| CDS | − | 1328441 | 1328692 | yciN | b1273 |
| CDS | + | 1329072 | 1331669 | topA | b1274 |
| CDS | + | 1331879 | 1332853 | cysB | b1275 |
| CDS | + | 1333855 | 1336530 | acnA | b1276 |
| CDS | − | 1336594 | 1337184 | ribA | b1277 |
| CDS | + | 1337354 | 1338118 | pgpB | b1278 |
| CDS | + | 1338267 | 1338575 | yciS | b1279 |
| CDS | + | 1338582 | 1339751 | yciM | b1280 |
| CDS | + | 1339945 | 1340682 | pyrF | b1281 |
| CDS | + | 1340682 | 1341008 | yciH | b1282 |
| CDS | − | 1341134 | 1341352 | osmB | b1283 |
| CDS | − | 1341621 | 1342370 | yclT | b1284 |
| CDS | − | 1342781 | 1344766 | yciR | b1285 |
| CDS | − | 1345002 | 1346936 | rnb | b1286 |
| CDS | − | 1347004 | 1348131 | yciW | b1287 |
| CDS | − | 1348275 | 1349063 | fabI | b1288 |
| CDS | − | 1349431 | 1349784 | ycjD | b1289 |
| CDS | − | 1349852 | 1350658 | sapF | b1290 |
| CDS | − | 1350660 | 1351652 | sapD | b1291 |
| CDS | − | 1351652 | 1352542 | sapC | b1292 |
| CDS | − | 1352529 | 1353494 | sapB | b1293 |
| CDS | − | 1353491 | 1355134 | sapA | b1294 |
| CDS | − | 1355447 | 1355692 | ymjA | b1295 |
| CDS | − | 1355826 | 1357211 | ycjJ | b1296 |
| CDS | − | 1357514 | 1358932 | ycjK | b1297 |
| CDS | + | 1359144 | 1359908 | ycjL | b1298 |
| CDS | + | 1359935 | 1360492 | ycjC | b1299 |
| CDS | + | 1360767 | 1362254 | aldH | b1300 |
| CDS | + | 1362256 | 1363536 | ordL | b1301 |
| CDS | + | 1363574 | 1364839 | goaG | b1302 |
| CDS | − | 1364959 | 1365936 | pspF | b1303 |
| CDS | + | 1366103 | 1366771 | pspA | b1304 |
| CDS | + | 1366825 | 1367049 | pspB | b1305 |
| CDS | + | 1367049 | 1367408 | pspC | b1306 |
| CDS | + | 1367417 | 1367638 | pspD | b1307 |
| CDS | + | 1367713 | 1368027 | pspE | b1308 |
| CDS | + | 1368240 | 1369919 | ycjM | b1309 |
| CDS | + | 1369933 | 1371225 | ycjN | b1310 |
| CDS | + | 1371246 | 1372127 | ycjO | b1311 |
| CDS | + | 1372114 | 1372956 | ycjP | b1312 |
| CDS | + | 1372987 | 1374039 | ycjQ | b1313 |
| CDS | + | 1374058 | 1374846 | ycjR | b1314 |
| CDS | + | 1374856 | 1375911 | ycjS | b1315 |
| CDS | + | 1375908 | 1378175 | ycjT | b1316 |
| CDS | + | 1378172 | 1378831 | ycjU | b1317 |
| CDS | + | 1378845 | 1379813 | ycjV | b1318 |

TABLE 1-continued

| Type | S | Left | Right | Name | B |
|---|---|---|---|---|---|
| CDS | + | 1379971 | 1380876 | ompG | b1319 |
| CDS | − | 1380987 | 1381985 | ycjW | b1320 |
| CDS | + | 1382141 | 1383538 | ycjX | b1321 |
| CDS | + | 1383535 | 1384596 | ycjF | b1322 |
| CDS | + | 1384744 | 1386285 | tyrR | b1323 |
| CDS | − | 1386329 | 1386835 | tpx | b1324 |
| CDS | + | 1386954 | 1387919 | ycjG | b1325 |
| CDS | − | 1387894 | 1388682 | ycjI | b1326 |
| CDS | − | 1388957 | 1389889 | ycjY | b1327 |
| CDS | + | 1390015 | 1390914 | ycjZ | b1328 |
| CDS | + | 1391251 | 1392864 | mppA | b1329 |
| CDS | − | 1392915 | 1393946 | ynaI | b1330 |
| repeat_region | − | 1394068 | 1395262 | | |
| CDS | + | 1394100 | 1395116 | trs5_4 | b1331 |
| CDS | + | 1395389 | 1395646 | ynaJ | b1332 |
| CDS | − | 1395696 | 1396646 | ydaA | b1333 |
| CDS | − | 1396798 | 1397550 | fnr | b1334 |
| CDS | − | 1397745 | 1398260 | ogt | b1335 |
| CDS | − | 1398271 | 1399797 | abgT | b1336 |
| CDS | − | 1399834 | 1401279 | abgB | b1337 |
| CDS | − | 1401279 | 1402589 | abgA | b1338 |
| CDS | + | 1402765 | 1403673 | abgR | b1339 |
| CDS | + | 1404003 | 1404566 | ydaL | b1340 |
| CDS | + | 1404587 | 1405819 | ydaM | b1341 |
| CDS | + | 1406074 | 1407057 | ydaN | b1342 |
| CDS | + | 1407535 | 1408908 | dbpA | b1343 |
| CDS | − | 1409037 | 1409972 | ydaO | b1344 |
| CDS | − | 1410024 | 1411259 | intR | b1345 |
| CDS | − | 1411261 | 1411476 | xisR | b1346 |
| CDS | − | 1411555 | 1411764 | ydaC | b1347 |
| CDS | − | 1411757 | 1411951 | lar | b1348 |
| CDS | − | 1412008 | 1412817 | recT | b1349 |
| CDS | − | 1412810 | 1415410 | recE | b1350 |
| CDS | − | 1415512 | 1415787 | racC | b1351 |
| CDS | − | 1416032 | 1416253 | kil | b1352 |
| CDS | + | 1416695 | 1417183 | sieB | b1353 |
| CDS | + | 1417192 | 1417368 | | b1354 |
| CDS | − | 1417346 | 1417480 | ydaG | b1355 |
| CDS | − | 1417789 | 1418265 | racR | b1356 |
| CDS | + | 1418389 | 1418685 | ydaS | b1357 |
| CDS | + | 1418708 | 1419130 | ydaT | b1358 |
| CDS | + | 1419143 | 1420000 | ydaU | b1359 |
| CDS | + | 1420007 | 1420753 | ydaV | b1360 |
| CDS | + | 1420776 | 1421336 | ydaW | b1361 |
| CDS | + | 1421369 | 1421668 | rzpR | b1362 |
| CDS | + | 1421806 | 1423263 | trkG | b1363 |
| CDS | + | 1423202 | 1423483 | | b1364 |
| CDS | + | 1423401 | 1423664 | ynaK | b1365 |
| CDS | + | 1423645 | 1424004 | ydaY | b1366 |
| CDS | + | 1424079 | 1424312 | | b1367 |
| CDS | + | 1424478 | 1425506 | ynaA | b1368 |
| CDS | + | 1425482 | 1425637 | | b1369 |
| repeat_region | + | 1425623 | 1426818 | | |
| CDS | − | 1425770 | 1426750 | trs5_5 | b1370 |
| CDS | + | 1426838 | 1427008 | | b1371 |
| CDS | + | 1427073 | 1430435 | stfR | b1372 |
| CDS | + | 1430435 | 1431010 | tfaR | b1373 |
| CDS | − | 1431108 | 1431698 | pinR | b1374 |
| CDS | − | 1432015 | 1432281 | ynaE | b1375 |
| CDS | − | 1433209 | 1433643 | ynaF | b1376 |
| CDS | − | 1433784 | 1434917 | ompN | b1377 |
| CDS | − | 1435284 | 1438808 | ydbK | b1378 |
| CDS | − | 1439345 | 1439767 | hslJ | b1379 |
| CDS | − | 1439878 | 1440867 | ldhA | b1380 |
| CDS | + | 1441075 | 1443714 | ydbH | b1381 |
| CDS | + | 1443711 | 1443896 | ynbE | b1382 |
| CDS | + | 1443904 | 1444230 | ydbL | b1383 |
| CDS | − | 1444402 | 1445307 | feaR | b1384 |
| CDS | + | 1445543 | 1447042 | feaB | b1385 |
| CDS | − | 1447100 | 1449373 | tynA | b1386 |
| CDS | − | 1449621 | 1451666 | paaZ | b1387 |
| CDS | + | 1451951 | 1452880 | paaA | b1388 |
| CDS | + | 1452892 | 1453179 | paaB | b1389 |
| CDS | + | 1453188 | 1453934 | paaC | b1390 |
| CDS | + | 1453949 | 1454446 | paaD | b1391 |
| CDS | + | 1454454 | 1455524 | paaE | b1392 |
| CDS | + | 1455521 | 1456288 | paaF | b1393 |
| CDS | + | 1456288 | 1457076 | paaG | b1394 |
| CDS | + | 1457078 | 1458505 | paaH | b1395 |
| CDS | + | 1458495 | 1458917 | paaI | b1396 |
| CDS | + | 1458917 | 1460122 | paaJ | b1397 |
| CDS | + | 1460149 | 1461462 | paaK | b1398 |
| CDS | + | 1461563 | 1462513 | paaX | b1399 |
| CDS | + | 1462495 | 1463085 | paaY | b1400 |
| CDS | + | 1463416 | 1465974 | ydbA_1 | b1401 |
| repeat_region | + | 1465934 | 1467264 | | |
| CDS | − | 1465945 | 1466850 | yi22_2 | b1402 |
| CDS | − | 1466808 | 1467218 | yi21_2 | b1403 |
| repeat_region | + | 1467320 | 1468540 | | |
| CDS | + | 1467382 | 1468533 | tra8_2 | b1404 |
| CDS | + | 1468714 | 1472037 | ydbA_2 | b1405 |
| CDS | + | 1472245 | 1473105 | ydbC | b1406 |
| CDS | + | 1473168 | 1475474 | ydbD | b1407 |
| CDS | + | 1475645 | 1476250 | ynbA | b1408 |
| CDS | + | 1476250 | 1477146 | ynbB | b1409 |
| CDS | + | 1477162 | 1478919 | ynbC | b1410 |
| CDS | + | 1478933 | 1480225 | ynbD | b1411 |
| CDS | − | 1480279 | 1480884 | acpD | b1412 |
| CDS | + | 1481142 | 1484987 | hrpA | b1413 |
| CDS | + | 1485259 | 1486059 | ydcF | b1414 |
| CDS | + | 1486256 | 1487695 | aldA | b1415 |
| CDS | − | 1487737 | 1487988 | gapC_2 | b1416 |
| CDS | − | 1487985 | 1488737 | gapC_1 | b1417 |
| CDS | + | 1488926 | 1489456 | cybB | b1418 |
| CDS | + | 1489701 | 1489874 | ydcA | b1419 |
| CDS | − | 1489986 | 1490153 | mokB | b1420 |
| CDS | + | 1490494 | 1492134 | trg | b1421 |
| CDS | − | 1492172 | 1493095 | ydcI | b1422 |
| CDS | − | 1493312 | 1494655 | ydcJ | b1423 |
| CDS | + | 1494910 | 1496535 | ydcG | b1424 |
| CDS | − | 1496456 | 1496659 | | b1425 |
| CDS | + | 1496675 | 1496899 | ydcH | b1426 |
| CDS | + | 1496962 | 1497501 | rimL | b1427 |
| CDS | − | 1497493 | 1498473 | ydcK | b1428 |
| CDS | + | 1498597 | 1499589 | tehA | b1429 |
| CDS | + | 1499586 | 1500179 | tehB | b1430 |
| CDS | + | 1500481 | 1501149 | ydcL | b1431 |
| CDS | + | 1501681 | 1502889 | ydcM | b1432 |
| CDS | − | 1502929 | 1504104 | ydcO | b1433 |
| CDS | + | 1504196 | 1504732 | ydcN | b1434 |
| CDS | + | 1504805 | 1506766 | ydcP | b1435 |
| CDS | − | 1506858 | 1507088 | yncJ | b1436 |
| CDS | − | 1507274 | 1507471 | | b1437 |
| CDS | + | 1507511 | 1507948 | ydcQ | b1438 |
| CDS | + | 1508027 | 1509433 | ydcR | b1439 |
| CDS | + | 1509678 | 1510823 | ydcS | b1440 |
| CDS | + | 1510841 | 1511854 | ydcT | b1441 |
| CDS | + | 1511855 | 1512796 | ydcU | b1442 |
| CDS | + | 1512786 | 1513580 | ydcV | b1443 |
| CDS | + | 1513602 | 1515026 | ydcW | b1444 |
| CDS | + | 1515413 | 1515586 | ydcX | b1445 |
| CDS | + | 1515672 | 1515905 | ydcY | b1446 |
| CDS | − | 1515906 | 1516355 | ydcZ | b1447 |
| CDS | − | 1516352 | 1516870 | yncA | b1448 |
| CDS | + | 1517051 | 1518088 | yncB | b1449 |
| CDS | + | 1518286 | 1518951 | yncC | b1450 |
| CDS | + | 1518987 | 1521089 | yncD | b1451 |
| CDS | + | 1521331 | 1522392 | yncE | b1452 |
| CDS | − | 1522505 | 1524004 | ansP | b1453 |
| CDS | + | 1524271 | 1524888 | yncG | b1454 |
| CDS | + | 1524964 | 1525176 | yncH | b1455 |
| CDS | + | 1525914 | 1527962 | rhsE | b1456 |
| CDS | + | 1527946 | 1528428 | ydcD | b1457 |
| CDS | + | 1528610 | 1529356 | | b1458 |
| CDS | + | 1529400 | 1529600 | | b1459 |
| CDS | + | 1529840 | 1530976 | ydcC | b1460 |
| CDS | + | 1531076 | 1531309 | ydcE | b1461 |
| CDS | − | 1531306 | 1531875 | yddH | b1462 |
| CDS | + | 1532048 | 1532893 | nhoA | b1463 |
| CDS | − | 1532989 | 1533882 | yddE | b1464 |
| CDS | − | 1533961 | 1534641 | narV | b1465 |
| CDS | − | 1534638 | 1535333 | narW | b1466 |
| CDS | − | 1535333 | 1536877 | narY | b1467 |
| CDS | − | 1536874 | 1540614 | narZ | b1468 |
| CDS | − | 1540696 | 1542084 | narU | b1469 |
| CDS | − | 1542408 | 1542743 | yddJ | b1470 |

TABLE 1-continued

| Type | S | Left | Right | Name | B |
|---|---|---|---|---|---|
| CDS | − | 1542782 | 1543738 | yddK | b1471 |
| CDS | − | 1543762 | 1544052 |  | b1472 |
| CDS | − | 1544312 | 1545136 | yddG | b1473 |
| CDS | + | 1545425 | 1548472 | fdnG | b1474 |
| CDS | + | 1548485 | 1549369 | fdnH | b1475 |
| CDS | + | 1549362 | 1550015 | fdnI | b1476 |
| CDS | − | 1550422 | 1550784 | yddM | b1477 |
| CDS | − | 1550852 | 1551862 | adhP | b1478 |
| CDS | − | 1551996 | 1553693 | sfcA | b1479 |
| CDS | − | 1553850 | 1553987 | rpsV | b1480 |
| CDS | − | 1554089 | 1554304 | bdm | b1481 |
| CDS | + | 1554649 | 1555080 | osmC | b1482 |
| CDS | − | 1555136 | 1556062 | yddO | b1483 |
| CDS | − | 1556055 | 1557041 | yddP | b1484 |
| CDS | − | 1557038 | 1557934 | yddQ | b1485 |
| CDS | − | 1557931 | 1558953 | yddR | b1486 |
| CDS | − | 1558955 | 1560505 | yddS | b1487 |
| CDS | − | 1560519 | 1561100 | ddpX | b1488 |
| CDS | − | 1561358 | 1563757 | dos | b1489 |
| CDS | − | 1563782 | 1564825 | yddV | b1490 |
| CDS | − | 1565528 | 1566847 | yddW | b1491 |
| CDS | − | 1566978 | 1568513 | xasA | b1492 |
| CDS | − | 1568669 | 1570069 | gadB | b1493 |
| CDS | − | 1570431 | 1573226 | pqqL | b1494 |
| CDS | − | 1573271 | 1575643 | yddB | b1495 |
| CDS | − | 1575681 | 1577366 | yddA | b1496 |
| CDS | − | 1577657 | 1578814 | ydeM | b1497 |
| CDS | − | 1578866 | 1580548 | ydeN | b1498 |
| CDS | − | 1580950 | 1581711 | ydeO | b1499 |
| CDS | − | 1581786 | 1581983 |  | b1500 |
| CDS | − | 1582231 | 1584510 | ydeP | b1501 |
| CDS | − | 1584844 | 1585758 | ydeQ | b1502 |
| CDS | − | 1585817 | 1586320 | ydeR | b1503 |
| CDS | − | 1586333 | 1586863 | ydeS | b1504 |
| CDS | − | 1586877 | 1588025 | ydeT | b1505 |
| CDS | − | 1588381 | 1588560 |  | b1506 |
| CDS | − | 1588878 | 1590200 | hipA | b1507 |
| CDS | − | 1590200 | 1590466 | hipB | b1508 |
| CDS | − | 1590689 | 1592089 | ydeU | b1509 |
| CDS | − | 1592133 | 1596110 | ydeK | b1510 |
| CDS | − | 1596641 | 1598233 | ydeV | b1511 |
| CDS | − | 1598312 | 1599265 | ydeW | b1512 |
| CDS | + | 1599514 | 1601049 | ego | b1513 |
| CDS | + | 1601043 | 1602071 | ydeY | b1514 |
| CDS | + | 1602071 | 1603063 | ydeZ | b1515 |
| CDS | + | 1603075 | 1604097 | yneA | b1516 |
| CDS | + | 1604124 | 1604999 | yneB | b1517 |
| CDS | + | 1605023 | 1605313 | yneC | b1518 |
| CDS | + | 1605370 | 1606128 | tam | b1519 |
| CDS | − | 1606132 | 1607046 | yneE | b1520 |
| CDS | − | 1607253 | 1608704 | uxaB | b1521 |
| CDS | − | 1608931 | 1609878 | yneF | b1522 |
| CDS | − | 1609990 | 1610349 | yneG | b1523 |
| CDS | − | 1610349 | 1611275 | yneH | b1524 |
| CDS | − | 1611339 | 1612727 | yneI | b1525 |
| CDS | + | 1612828 | 1613709 | yneJ | b1526 |
| CDS | + | 1613787 | 1614902 | yneK | b1527 |
| CDS | + | 1615052 | 1616242 | sotB | b1528 |
| CDS | − | 1616267 | 1616932 | marC | b1529 |
| CDS | + | 1617144 | 1617578 | marR | b1530 |
| CDS | + | 1617598 | 1617981 | marA | b1531 |
| CDS | + | 1618013 | 1618231 | marB | b1532 |
| CDS | − | 1618262 | 1619161 | eamA | b1533 |
| CDS | + | 1619356 | 1620543 | ydeE | b1534 |
| CDS | − | 1620984 | 1621874 | ydeH | b1535 |
| CDS | − | 1622129 | 1622521 | ydeI | b1536 |
| CDS | + | 1622797 | 1623315 | ydeJ | b1537 |
| CDS | − | 1623359 | 1625404 | dcp | b1538 |
| CDS | + | 1625541 | 1626287 | ydfG | b1539 |
| CDS | + | 1626376 | 1627062 | ydfH | b1540 |
| CDS | + | 1627239 | 1627442 | ydfZ | b1541 |
| CDS | − | 1627477 | 1628937 | ydfI | b1542 |
| CDS | − | 1629026 | 1630309 | ydfJ | b1543 |
| CDS | + | 1631063 | 1631329 | ydfK | b1544 |
| CDS | + | 1631646 | 1632236 | pinQ | b1545 |
| CDS | − | 1632334 | 1632909 | tfaQ | b1546 |
| CDS | − | 1632909 | 1633871 | stfQ | b1547 |
| CDS | − | 1633822 | 1634391 | nohA | b1548 |
| CDS | + | 1635071 | 1635481 | ydfO | b1549 |
| CDS | − | 1635633 | 1635806 | gnsB | b1550 |
| CDS | − | 1635978 | 1636133 | ynfN | b1551 |
| CDS | − | 1636479 | 1636691 | cspI | b1552 |
| CDS | − | 1637054 | 1637551 | ydfP | b1553 |
| CDS | − | 1637548 | 1638081 | ydfQ | b1554 |
| CDS | − | 1638078 | 1638389 | ydfR | b1555 |
| CDS | − | 1638394 | 1638609 | essQ | b1556 |
| CDS | − | 1639363 | 1639578 | cspB | b1557 |
| CDS | + | 1639879 | 1640091 | cspF | b1558 |
| CDS | + | 1640513 | 1641265 | ydfT | b1559 |
| CDS | − | 1641279 | 1642328 | ydfU | b1560 |
| CDS | − | 1642675 | 1642926 | rem | b1561 |
| CDS | − | 1643143 | 1643298 | hokD | b1562 |
| CDS | − | 1643370 | 1643657 | relE | b1563 |
| CDS | − | 1643657 | 1643896 | relB | b1564 |
| CDS | + | 1643921 | 1644226 | ydfV | b1565 |
| CDS | + | 1644429 | 1644761 | flxA | b1566 |
| CDS | − | 1645198 | 1645347 | ydfW | b1567 |
| CDS | − | 1645370 | 1645660 | ydfX | b1568 |
| CDS | − | 1645644 | 1645874 | dicC | b1569 |
| CDS | + | 1645958 | 1646365 | dicA | b1570 |
| CDS | + | 1646532 | 1646687 | ydfA | b1571 |
| CDS | + | 1646689 | 1646817 | ydfB | b1572 |
| CDS | + | 1646847 | 1647065 | ydfC | b1573 |
| misc_RNA | + | 1647406 | 1647458 | dicF | b1574 |
| CDS | + | 1647633 | 1647821 | dicB | b1575 |
| CDS | + | 1647818 | 1648009 | ydfD | b1576 |
| CDS | + | 1648102 | 1649022 | ydfE | b1577 |
| repeat_region | − | 1648867 | 1649572 |  |  |
| CDS | + | 1648905 | 1649561 |  | b1578 |
| CDS | + | 1649536 | 1650732 | intQ | b1579 |
| CDS | − | 1650920 | 1651939 | rspB | b1580 |
| CDS | − | 1651951 | 1653165 | rspA | b1581 |
| CDS | − | 1653371 | 1653697 | ynfA | b1582 |
| CDS | + | 1653832 | 1654173 | ynfB | b1583 |
| CDS | + | 1654208 | 1654768 | speG | b1584 |
| CDS | − | 1654771 | 1655481 | ynfC | b1585 |
| CDS | + | 1655589 | 1655894 | ynfD | b1586 |
| CDS | + | 1656093 | 1658519 | ynfE | b1587 |
| CDS | + | 1658580 | 1661003 | ynfF | b1588 |
| CDS | + | 1661014 | 1661631 | ynfG | b1589 |
| CDS | + | 1661633 | 1662487 | ynfH | b1590 |
| CDS | + | 1662530 | 1663144 | ynfI | b1591 |
| CDS | + | 1663339 | 1664595 | ynfJ | b1592 |
| CDS | − | 1664548 | 1665243 | ynfK | b1593 |
| CDS | − | 1665368 | 1666588 | mlc | b1594 |
| CDS | − | 1666723 | 1667616 | ynfL | b1595 |
| CDS | + | 1667723 | 1668976 | ynfM | b1596 |
| CDS | + | 1669400 | 1669708 | asr | b1597 |
| CDS | + | 1669984 | 1670805 | ydgD | b1598 |
| CDS | − | 1670844 | 1671173 | ydgE | b1599 |
| CDS | − | 1671160 | 1671525 | ydgF | b1600 |
| CDS | + | 1671937 | 1672971 | ydgG | b1601 |
| CDS | + | 1672996 | 1674384 | pntB | b1602 |
| CDS | + | 1674395 | 1675927 | pntA | b1603 |
| CDS | + | 1676451 | 1677395 | ydgH | b1604 |
| CDS | + | 1677581 | 1678963 | ydgI | b1605 |
| CDS | + | 1679000 | 1679722 | ydgB | b1606 |
| CDS | − | 1679719 | 1680054 | ydgC | b1607 |
| CDS | + | 1680174 | 1680902 | rstA | b1608 |
| CDS | + | 1680906 | 1682207 | rstB | b1609 |
| CDS | + | 1682283 | 1683212 | tus | b1610 |
| CDS | − | 1683209 | 1684612 | fumC | b1611 |
| CDS | − | 1684755 | 1686401 | fumA | b1612 |
| CDS | + | 1686600 | 1687775 | manA | b1613 |
| CDS | + | 1687876 | 1689384 | ydgA | b1614 |
| CDS | − | 1689610 | 1690875 | uidC | b1615 |
| CDS | − | 1690914 | 1692287 | uidB | b1616 |
| CDS | − | 1692284 | 1694095 | uidA | b1617 |
| CDS | − | 1694486 | 1695076 | uidR | b1618 |
| CDS | − | 1695297 | 1696064 | hdhA | b1619 |
| CDS | − | 1696176 | 1697204 | malI | b1620 |
| CDS | + | 1697379 | 1698971 | malX | b1621 |
| CDS | + | 1698981 | 1700153 | malY | b1622 |
| CDS | + | 1700257 | 1701258 | add | b1623 |
| CDS | − | 1701292 | 1702332 | ydgJ | b1624 |
| CDS | + | 1702973 | 1703188 | ydgT | b1625 |

TABLE 1-continued

| Type | S | Left | Right | Name | B |
|---|---|---|---|---|---|
| CDS | + | 1703274 | 1703714 | ydgK | b1626 |
| CDS | + | 1703791 | 1704372 | rnfA | b1627 |
| CDS | + | 1704372 | 1704950 | rnfB | b1628 |
| CDS | + | 1704943 | 1707165 | rnfC | b1629 |
| CDS | + | 1707166 | 1708224 | rnfD | b1630 |
| CDS | + | 1708228 | 1708848 | rnfG | b1631 |
| CDS | + | 1708852 | 1709547 | rnfE | b1632 |
| CDS | + | 1709547 | 1710182 | nth | b1633 |
| CDS | + | 1710793 | 1712295 | ydgR | b1634 |
| CDS | + | 1712401 | 1713006 | gst | b1635 |
| CDS | − | 1713050 | 1713913 | pdxY | b1636 |
| CDS | − | 1713972 | 1715246 | tyrS | b1637 |
| CDS | − | 1715375 | 1716031 | pdxH | b1638 |
| CDS | − | 1716090 | 1716419 | ydhA | b1639 |
| CDS | − | 1716517 | 1717626 | ydhH | b1640 |
| CDS | + | 1717900 | 1718367 | slyB | b1641 |
| CDS | − | 1718414 | 1718848 | slyA | b1642 |
| CDS | + | 1719049 | 1719285 | ydhI | b1643 |
| CDS | + | 1719288 | 1720145 | ydhJ | b1644 |
| CDS | + | 1720145 | 1722157 | ydhK | b1645 |
| CDS | − | 1722158 | 1722679 | sodC | b1646 |
| CDS | − | 1722760 | 1723656 | ydhF | b1647 |
| CDS | − | 1723705 | 1723944 | ydhL | b1648 |
| CDS | + | 1724131 | 1724646 | ydhM | b1649 |
| CDS | + | 1724683 | 1725780 | nemA | b1650 |
| CDS | + | 1725861 | 1726268 | gloA | b1651 |
| CDS | + | 1726371 | 1727018 | rnt | b1652 |
| CDS | + | 1727111 | 1731727 | lhr | b1653 |
| CDS | − | 1731778 | 1732125 | ydhD | b1654 |
| CDS | + | 1732459 | 1733274 | ydhO | b1655 |
| CDS | + | 1733402 | 1733983 | sodB | b1656 |
| CDS | − | 1734145 | 1735314 | ydhP | b1657 |
| CDS | + | 1735868 | 1736893 | purR | b1658 |
| CDS | − | 1736890 | 1737822 | ydhB | b1659 |
| CDS | + | 1737935 | 1739146 | ydhC | b1660 |
| CDS | + | 1739437 | 1740585 | cfa | b1661 |
| CDS | − | 1740625 | 1741266 | ribC | b1662 |
| CDS | + | 1741481 | 1742854 | norM | b1663 |
| CDS | − | 1742895 | 1744151 | ydhQ | b1664 |
| tRNA | + | 1744459 | 1744535 | valU | b1665 |
| tRNA | + | 1744540 | 1744616 | valW | b1666 |
| CDS | + | 1744724 | 1745029 | ydhR | b1667 |
| CDS | + | 1745155 | 1746759 | ydhS | b1668 |
| CDS | − | 1746771 | 1747583 | ydhT | b1669 |
| CDS | − | 1747587 | 1748372 | ydhU | b1670 |
| CDS | − | 1748369 | 1749037 | ydhX | b1671 |
| CDS | − | 1749101 | 1749748 | ydhW | b1672 |
| CDS | − | 1749752 | 1751854 | ydhV | b1673 |
| CDS | + | 1751875 | 1752501 | ydhY | b1674 |
| CDS | − | 1752956 | 1753165 | ydhZ | b1675 |
| CDS | + | 1753722 | 1755134 | pykF | b1676 |
| CDS | + | 1755445 | 1755681 | lpp | b1677 |
| CDS | − | 1755745 | 1756749 | ynhG | b1678 |
| CDS | − | 1756898 | 1757314 | sufE | b1679 |
| CDS | − | 1757327 | 1758547 | sufS | b1680 |
| CDS | − | 1758544 | 1759815 | sufD | b1681 |
| CDS | − | 1759790 | 1760536 | sufC | b1682 |
| CDS | − | 1760546 | 1762033 | sufB | b1683 |
| CDS | − | 1762042 | 1762410 | sufA | b1684 |
| CDS | − | 1762958 | 1763227 | ydiH | b1685 |
| CDS | − | 1763246 | 1763656 | ydiI | b1686 |
| CDS | − | 1763653 | 1766709 | ydiJ | b1687 |
| CDS | + | 1767098 | 1768210 | ydiK | b1688 |
| CDS | + | 1768639 | 1768995 | ydiL | b1689 |
| CDS | + | 1769095 | 1770309 | ydiM | b1690 |
| CDS | + | 1770536 | 1771801 | ydiN | b1691 |
| CDS | + | 1771813 | 1772679 | ydiB | b1692 |
| CDS | + | 1772710 | 1773468 | aroD | b1693 |
| CDS | + | 1773611 | 1775206 | ydiF | b1694 |
| CDS | + | 1775220 | 1776371 | ydiO | b1695 |
| CDS | − | 1776414 | 1777325 | ydiP | b1696 |
| CDS | + | 1777641 | 1778405 | ydiQ | b1697 |
| CDS | + | 1778425 | 1779363 | ydiR | b1698 |
| CDS | + | 1779419 | 1780708 | ydiS | b1699 |
| CDS | + | 1780705 | 1780998 | ydiT | b1700 |
| CDS | + | 1781001 | 1782701 | ydiD | b1701 |
| CDS | − | 1782758 | 1785136 | ppsA | b1702 |
| CDS | + | 1785469 | 1786302 | ydiA | b1703 |
| CDS | + | 1786459 | 1787505 | aroH | b1704 |
| CDS | + | 1787637 | 1787828 | ydiE | b1705 |
| CDS | − | 1787832 | 1789268 | ydiU | b1706 |
| CDS | − | 1789331 | 1790044 | ydiV | b1707 |
| CDS | − | 1790291 | 1790755 | nlpC | b1708 |
| CDS | − | 1790833 | 1791582 | btuD | b1709 |
| CDS | − | 1791582 | 1792133 | btuE | b1710 |
| CDS | − | 1792196 | 1793176 | btuC | b1711 |
| CDS | − | 1793277 | 1793576 | himA | b1712 |
| CDS | − | 1793581 | 1795968 | pheT | b1713 |
| CDS | − | 1795983 | 1796966 | pheS | b1714 |
| CDS | − | 1797250 | 1797294 | pheM | b1715 |
| CDS | − | 1797417 | 1797773 | rplT | b1716 |
| CDS | − | 1797826 | 1798023 | rpmI | b1717 |
| CDS | − | 1798120 | 1798662 | infC | b1718 |
| CDS | − | 1798666 | 1800594 | thrS | b1719 |
| CDS | + | 1801118 | 1801591 | arpB_1 | b1720 |
| CDS | + | 1801602 | 1803017 | arpB_2 | b1721 |
| CDS | − | 1803269 | 1804107 | ydiY | b1722 |
| CDS | + | 1804394 | 1805323 | pfkB | b1723 |
| CDS | + | 1805424 | 1805714 | ydiZ | b1724 |
| CDS | + | 1805820 | 1806680 | yniA | b1725 |
| CDS | − | 1806721 | 1807257 | yniB | b1726 |
| CDS | + | 1807404 | 1808072 | yniC | b1727 |
| CDS | + | 1808235 | 1808825 | ydjM | b1728 |
| CDS | + | 1808958 | 1810349 | ydjN | b1729 |
| CDS | − | 1810353 | 1811168 | ydjO | b1730 |
| CDS | − | 1811445 | 1811708 | cedA | b1731 |
| CDS | + | 1811891 | 1814152 | katE | b1732 |
| CDS | − | 1814410 | 1815159 | ydjC | b1733 |
| CDS | − | 1815172 | 1816524 | celF | b1734 |
| CDS | − | 1816629 | 1817471 | celD | b1735 |
| CDS | − | 1817479 | 1817829 | celC | b1736 |
| CDS | − | 1817880 | 1819238 | celB | b1737 |
| CDS | − | 1819323 | 1819643 | celA | b1738 |
| CDS | − | 1819942 | 1820280 | osmE | b1739 |
| CDS | + | 1820482 | 1821309 | nadE | b1740 |
| CDS | + | 1821539 | 1822426 | ydjQ | b1741 |
| CDS | − | 1822386 | 1822961 | ydjR | b1742 |
| CDS | − | 1823164 | 1823649 | spy | b1743 |
| CDS | − | 1823979 | 1824947 | astE | b1744 |
| CDS | − | 1824940 | 1826283 | astB | b1745 |
| CDS | − | 1826280 | 1827758 | astD | b1746 |
| CDS | − | 1827755 | 1828789 | astA | b1747 |
| CDS | − | 1828786 | 1830006 | astC | b1748 |
| CDS | + | 1830452 | 1831258 | xthA | b1749 |
| CDS | + | 1831425 | 1832135 | ydjX | b1750 |
| CDS | + | 1832140 | 1832817 | ydjY | b1751 |
| CDS | + | 1832832 | 1833539 | ydjZ | b1752 |
| CDS | + | 1833539 | 1834087 | ynjA | b1753 |
| CDS | + | 1834097 | 1835263 | ynjB | b1754 |
| CDS | + | 1835281 | 1836771 | ynjC | b1755 |
| CDS | + | 1836771 | 1837424 | ynjD | b1756 |
| CDS | + | 1837491 | 1838798 | ynjE | b1757 |
| CDS | − | 1838807 | 1839427 | ynjF | b1758 |
| CDS | − | 1839514 | 1839921 | nudG | b1759 |
| CDS | − | 1839887 | 1840159 | ynjH | b1760 |
| CDS | + | 1840395 | 1841738 | gdhA | b1761 |
| CDS | − | 1841855 | 1842895 | ynjI | b1762 |
| CDS | − | 1843023 | 1844984 | topB | b1763 |
| CDS | − | 1844989 | 1846032 | selD | b1764 |
| CDS | − | 1846149 | 1846700 | ydjA | b1765 |
| CDS | + | 1846861 | 1848717 | sppA | b1766 |
| CDS | + | 1848884 | 1849900 | ansA | b1767 |
| CDS | + | 1849911 | 1850552 | pncA | b1768 |
| CDS | − | 1850645 | 1852003 | ydjE | b1769 |
| CDS | − | 1852120 | 1852878 | ydjF | b1770 |
| CDS | − | 1853015 | 1853995 | ydjG | b1771 |
| CDS | − | 1854005 | 1854952 | ydjH | b1772 |
| CDS | − | 1854957 | 1855793 | ydjI | b1773 |
| CDS | − | 1855814 | 1856857 | ydjJ | b1774 |
| CDS | − | 1856874 | 1858253 | ydjK | b1775 |
| CDS | − | 1858280 | 1859356 | ydjL | b1776 |
| CDS | − | 1859726 | 1859998 | yeaC | b1777 |
| CDS | − | 1860040 | 1860453 | yeaA | b1778 |
| CDS | + | 1860795 | 1861790 | gapA | b1779 |
| CDS | − | 1861874 | 1862758 | yeaD | b1780 |
| CDS | − | 1862806 | 1863660 | yeaE | b1781 |

TABLE 1-continued

| Type | S | Left | Right | Name | B |
|---|---|---|---|---|---|
| CDS | − | 1863750 | 1864496 | mipA | b1782 |
| CDS | + | 1864932 | 1866866 | yeaG | b1783 |
| CDS | + | 1866979 | 1868262 | yeaH | b1784 |
| CDS | + | 1868409 | 1869884 | yeaI | b1785 |
| CDS | + | 1870065 | 1871555 | yeaJ | b1786 |
| CDS | + | 1871598 | 1872101 | yeaK | b1787 |
| CDS | − | 1872102 | 1872206 | | b1788 |
| CDS | + | 1872376 | 1872822 | yeaL | b1789 |
| CDS | − | 1872779 | 1873600 | yeaM | b1790 |
| CDS | + | 1873697 | 1874878 | yeaN | b1791 |
| CDS | + | 1874933 | 1875280 | yeaO | b1792 |
| CDS | − | 1875302 | 1875556 | yoaF | b1793 |
| CDS | + | 1875739 | 1876764 | yeaP | b1794 |
| CDS | − | 1877031 | 1877279 | yeaQ | b1795 |
| CDS | − | 1877427 | 1877609 | yoaG | b1796 |
| CDS | − | 1877613 | 1877972 | yeaR | b1797 |
| CDS | − | 1878145 | 1878783 | yeaS | b1798 |
| CDS | − | 1878910 | 1879833 | yeaT | b1799 |
| CDS | + | 1879936 | 1881021 | yeaU | b1800 |
| CDS | + | 1881212 | 1882657 | yeaV | b1801 |
| CDS | + | 1882689 | 1883813 | yeaW | b1802 |
| CDS | + | 1883869 | 1884834 | yeaX | b1803 |
| CDS | − | 1884888 | 1886015 | rnd | b1804 |
| CDS | − | 1886085 | 1887770 | fadD | b1805 |
| CDS | − | 1887975 | 1888556 | yeaY | b1806 |
| CDS | − | 1888596 | 1889291 | yeaZ | b1807 |
| CDS | − | 1889349 | 1891259 | yoaA | b1808 |
| CDS | + | 1891391 | 1891735 | yoaB | b1809 |
| CDS | + | 1892097 | 1892456 | yoaC | b1810 |
| CDS | − | 1892576 | 1892755 | yoaH | b1811 |
| CDS | + | 1892829 | 1894190 | pabB | b1812 |
| CDS | + | 1894194 | 1894772 | yeaB | b1813 |
| CDS | + | 1894956 | 1896320 | sdaA | b1814 |
| CDS | + | 1896451 | 1898049 | yoaD | b1815 |
| CDS | − | 1898053 | 1899609 | yoaE | b1816 |
| CDS | + | 1900072 | 1901043 | manX | b1817 |
| CDS | + | 1901106 | 1901906 | manY | b1818 |
| CDS | + | 1901910 | 1902770 | manZ | b1819 |
| CDS | + | 1902825 | 1903283 | yobD | b1820 |
| CDS | + | 1903712 | 1904278 | yebN | b1821 |
| CDS | − | 1904275 | 1905084 | rrmA | b1822 |
| CDS | − | 1905250 | 1905459 | cspC | b1823 |
| CDS | − | 1905472 | 1905615 | yobF | b1824 |
| CDS | − | 1906285 | 1906572 | yebO | b1825 |
| CDS | − | 1906647 | 1906790 | yobG | b1826 |
| CDS | − | 1907332 | 1908123 | kdgR | b1827 |
| CDS | + | 1908300 | 1909673 | yebQ | b1828 |
| CDS | − | 1909719 | 1910600 | htpX | b1829 |
| CDS | − | 1910792 | 1912840 | prc | b1830 |
| CDS | − | 1912860 | 1913558 | proQ | b1831 |
| CDS | − | 1913655 | 1914206 | yebR | b1832 |
| CDS | + | 1914282 | 1915565 | yebS | b1833 |
| CDS | + | 1915534 | 1918167 | yebT | b1834 |
| CDS | + | 1918247 | 1919686 | yebU | b1835 |
| CDS | + | 1919804 | 1920040 | yebV | b1836 |
| CDS | + | 1920145 | 1920336 | yebW | b1837 |
| CDS | − | 1920337 | 1920993 | pphA | b1838 |
| CDS | − | 1921389 | 1921730 | yebY | b1839 |
| CDS | − | 1921743 | 1922615 | yebZ | b1840 |
| CDS | − | 1922619 | 1922993 | yobA | b1841 |
| CDS | + | 1923132 | 1923362 | holE | b1842 |
| CDS | + | 1923464 | 1924120 | yobB | b1843 |
| CDS | + | 1924144 | 1924806 | exoX | b1844 |
| CDS | − | 1924803 | 1926863 | ptrB | b1845 |
| CDS | − | 1927072 | 1927731 | yebE | b1846 |
| CDS | − | 1928058 | 1928426 | yebF | b1847 |
| CDS | − | 1928481 | 1928771 | yebG | b1848 |
| CDS | + | 1928905 | 1930083 | purT | b1849 |
| CDS | − | 1930139 | 1930780 | eda | b1850 |
| CDS | − | 1930817 | 1932628 | edd | b1851 |
| CDS | − | 1932863 | 1934338 | zwf | b1852 |
| CDS | + | 1934676 | 1935545 | yebK | b1853 |
| CDS | + | 1935673 | 1937115 | pykA | b1854 |
| CDS | + | 1937246 | 1938217 | msbB | b1855 |
| CDS | − | 1938337 | 1939659 | yebA | b1856 |
| CDS | − | 1939675 | 1940607 | znuA | b1857 |
| CDS | + | 1940686 | 1941441 | znuC | b1858 |
| CDS | + | 1941438 | 1942223 | znuB | b1859 |
| CDS | − | 1942370 | 1943380 | ruvB | b1860 |
| CDS | − | 1943389 | 1944000 | ruvA | b1861 |
| CDS | + | 1944275 | 1944877 | yebB | b1862 |
| CDS | − | 1944879 | 1945400 | ruvC | b1863 |
| CDS | − | 1945435 | 1946175 | yebC | b1864 |
| CDS | − | 1946204 | 1946656 | ntpA | b1865 |
| CDS | − | 1946774 | 1948546 | aspS | b1866 |
| CDS | + | 1948856 | 1949422 | yecD | b1867 |
| CDS | + | 1949419 | 1950237 | yecE | b1868 |
| CDS | + | 1950290 | 1950685 | yecN | b1869 |
| CDS | + | 1950726 | 1951469 | yecO | b1870 |
| CDS | + | 1951466 | 1952437 | yecP | b1871 |
| CDS | − | 1952602 | 1955031 | torZ | b1872 |
| CDS | − | 1955056 | 1956156 | torY | b1873 |
| CDS | − | 1956544 | 1957290 | cutC | b1874 |
| CDS | − | 1957304 | 1957870 | yecM | b1875 |
| CDS | + | 1958086 | 1959819 | argS | b1876 |
| CDS | + | 1959996 | 1960484 | yecT | b1877 |
| CDS | − | 1960604 | 1960996 | flhE | b1878 |
| CDS | − | 1960996 | 1963074 | flhA | b1879 |
| CDS | − | 1963067 | 1964215 | flhB | b1880 |
| CDS | − | 1964417 | 1965061 | cheZ | b1881 |
| CDS | − | 1965072 | 1965461 | cheY | b1882 |
| CDS | − | 1965476 | 1966525 | cheB | b1883 |
| CDS | − | 1966528 | 1967388 | cheR | b1884 |
| CDS | − | 1967407 | 1969008 | tap | b1885 |
| CDS | − | 1969054 | 1970715 | tar | b1886 |
| CDS | − | 1970860 | 1971363 | cheW | b1887 |
| CDS | − | 1971384 | 1973348 | cheA | b1888 |
| CDS | − | 1973353 | 1974279 | motB | b1889 |
| CDS | − | 1974276 | 1975163 | motA | b1890 |
| CDS | − | 1975290 | 1975868 | flhC | b1891 |
| CDS | − | 1975871 | 1976230 | flhD | b1892 |
| repeat_region | − | 1976527 | 1977294 | | |
| CDS | − | 1976542 | 1977045 | insB_5 | b1893 |
| CDS | − | 1976964 | 1977239 | insA_5 | b1894 |
| CDS | + | 1977777 | 1978205 | yecG | b1895 |
| CDS | − | 1978212 | 1979636 | otsA | b1896 |
| CDS | − | 1979611 | 1980411 | otsB | b1897 |
| CDS | − | 1981579 | 1983093 | araG | b1900 |
| CDS | − | 1983163 | 1984152 | araF | b1901 |
| CDS | + | 1984949 | 1985452 | yecI | b1902 |
| CDS | + | 1985468 | 1985806 | | b1903 |
| CDS | + | 1986246 | 1986569 | yecR | b1904 |
| CDS | + | 1986740 | 1987237 | ftn | b1905 |
| CDS | − | 1987275 | 1987514 | yecH | b1906 |
| CDS | + | 1987705 | 1988916 | tyrP | b1907 |
| CDS | − | 1988978 | 1989643 | yecA | b1908 |
| tRNA | − | 1989839 | 1989925 | leuZ | b1909 |
| tRNA | − | 1989938 | 1990011 | cysT | b1910 |
| tRNA | − | 1990066 | 1990141 | glyW | b1911 |
| CDS | − | 1990293 | 1990841 | pgsA | b1912 |
| CDS | − | 1990898 | 1992730 | uvrC | b1913 |
| CDS | − | 1992727 | 1993383 | uvrY | b1914 |
| CDS | + | 1993842 | 1994066 | yecF | b1915 |
| CDS | − | 1994134 | 1994856 | sdiA | b1916 |
| CDS | − | 1995086 | 1995838 | yecC | b1917 |
| CDS | − | 1995835 | 1996503 | yecS | b1918 |
| CDS | − | 1996518 | 1997504 | yedO | b1919 |
| CDS | − | 1997609 | 1998409 | fliY | b1920 |
| CDS | − | 1998497 | 1999048 | fliZ | b1921 |
| CDS | + | 1999094 | 1999813 | fliA | b1922 |
| CDS | − | 2000134 | 2001630 | fliC | b1923 |
| CDS | + | 2001896 | 2003302 | fliD | b1924 |
| CDS | + | 2003327 | 2003737 | fliS | b1925 |
| CDS | + | 2003737 | 2004102 | fliT | b1926 |
| CDS | + | 2004180 | 2005667 | amyA | b1927 |
| CDS | − | 2005701 | 2006114 | yedD | b1928 |
| CDS | + | 2006301 | 2007506 | yedE | b1929 |
| CDS | + | 2007503 | 2007736 | yedF | b1930 |
| CDS | + | 2007845 | 2008513 | yedK | b1931 |
| CDS | + | 2008624 | 2009103 | yedL | b1932 |
| CDS | − | 2009372 | 2009563 | yedN_2 | b1933 |
| CDS | − | 2009573 | 2009893 | yedN_1 | b1934 |
| CDS | − | 2010025 | 2010375 | yedM | b1935 |
| CDS | + | 2010526 | 2010804 | | b1936 |
| CDS | − | 2010724 | 2011038 | fliE | b1937 |
| CDS | + | 2011253 | 2012911 | fliF | b1938 |

TABLE 1-continued

| Type | S | Left | Right | Name | B |
|---|---|---|---|---|---|
| CDS | + | 2012904 | 2013899 | fliG | b1939 |
| CDS | + | 2013892 | 2014578 | fliH | b1940 |
| CDS | + | 2014578 | 2015951 | fliI | b1941 |
| CDS | + | 2015970 | 2016413 | fliJ | b1942 |
| CDS | + | 2016410 | 2017537 | fliK | b1943 |
| CDS | + | 2017642 | 2018106 | fliL | b1944 |
| CDS | + | 2018111 | 2019115 | fliM | b1945 |
| CDS | + | 2019112 | 2019525 | fliN | b1946 |
| CDS | + | 2019528 | 2019893 | fliO | b1947 |
| CDS | + | 2019893 | 2020630 | fliP | b1948 |
| CDS | + | 2020640 | 2020909 | fliQ | b1949 |
| CDS | + | 2020917 | 2021702 | fliR | b1950 |
| CDS | + | 2021992 | 2022615 | rcsA | b1951 |
| CDS | − | 2022659 | 2022847 | dsrB | b1952 |
| CDS | + | 2023010 | 2023237 | yodD | b1953 |
| misc_RNA | − | 2023251 | 2023337 | dsrA | b1954 |
| CDS | + | 2023535 | 2024350 | yedP | b1955 |
| CDS | − | 2024347 | 2026041 | yedQ | b1956 |
| CDS | − | 2026212 | 2026394 | yodC | b1957 |
| CDS | − | 2026473 | 2027390 | yedI | b1958 |
| CDS | + | 2027563 | 2028483 | yedA | b1959 |
| CDS | − | 2028472 | 2028942 | vsr | b1960 |
| CDS | − | 2028923 | 2030341 | dcm | b1961 |
| CDS | − | 2030408 | 2031103 | yedJ | b1962 |
| CDS | − | 2031143 | 2031508 | yedR | b1963 |
| CDS | + | 2032075 | 2032560 | yedS_1 | b1964 |
| CDS | + | 2032570 | 2032779 | yedS_2 | b1965 |
| CDS | + | 2032863 | 2033267 | yedS_3 | b1966 |
| CDS | + | 2033859 | 2034710 | yedU | b1967 |
| CDS | − | 2034818 | 2036176 | yedV | b1968 |
| CDS | − | 2036847 | 2036876 | yedW | b1969 |
| CDS | − | 2036980 | 2037393 | yedX | b1970 |
| CDS | + | 2037502 | 2038506 | yedY | b1971 |
| CDS | + | 2038507 | 2039142 | yedZ | b1972 |
| CDS | + | 2039399 | 2040049 | yodA | b1973 |
| CDS | + | 2040392 | 2040922 | yodB | b1974 |
| tRNA | − | 2041492 | 2041581 | serU | b1975 |
| CDS | + | 2041675 | 2042472 | yeeI | b1976 |
| tRNA | + | 2042573 | 2042648 | asnT | b1977 |
| CDS | + | 2042935 | 2050038 | yeeJ | b1978 |
| CDS | − | 2050300 | 2050626 | yeeL_2 | b1979 |
| CDS | − | 2050648 | 2051352 | yeeL_1 | b1980 |
| CDS | + | 2051667 | 2052983 | shiA | b1981 |
| CDS | + | 2053085 | 2054539 | amn | b1982 |
| CDS | + | 2054882 | 2055598 | yeeN | b1983 |
| tRNA | − | 2056051 | 2056126 | asnW | b1984 |
| CDS | − | 2056227 | 2057870 | yeeO | b1985 |
| RNA | + | 2057875 | 2057950 | asnU | b1986 |
| CDS | + | 2057988 | 2058938 | cbl | b1987 |
| CDS | − | 2059040 | 2059957 | nac | b1988 |
| tRNA | + | 2060284 | 2060359 | asnV | b1989 |
| CDS | − | 2060415 | 2061347 | erfK | b1990 |
| CDS | − | 2061412 | 2062491 | cobT | b1991 |
| CDS | − | 2062503 | 2063246 | cobS | b1992 |
| CDS | − | 2063243 | 2063788 | cobU | b1993 |
| repeat_region | + | 2064183 | 2065377 | | |
| CDS | − | 2064329 | 2065345 | trs5_6 | b1994 |
| CDS | + | 2066659 | 2067051 | | b1995 |
| repeat_region | + | 2066965 | 2068295 | | |
| CDS | − | 2066976 | 2067881 | yi22_3 | b1996 |
| CDS | − | 2067839 | 2068249 | yi21_3 | b1997 |
| CDS | + | 2068268 | 2068528 | | b1998 |
| CDS | + | 2068810 | 2069235 | yeeP | b1999 |
| CDS | + | 2069563 | 2072682 | flu | b2000 |
| CDS | + | 2072803 | 2074335 | yeeR | b2001 |
| CDS | + | 2074332 | 2074778 | yeeS | b2002 |
| CDS | + | 2074841 | 2075062 | yeeT | b2003 |
| CDS | + | 2075136 | 2075504 | yeeU | b2004 |
| CDS | + | 2075593 | 2075967 | yeeV | b2005 |
| CDS | + | 2075964 | 2076158 | yeeW | b2006 |
| CDS | − | 2077056 | 2077451 | yeeX | b2007 |
| CDS | − | 2077557 | 2078615 | yeeA | b2008 |
| CDS | − | 2078813 | 2079286 | sbmC | b2009 |
| CDS | − | 2079405 | 2080571 | dacD | b2010 |
| CDS | + | 2080780 | 2082207 | sbcB | b2011 |
| CDS | − | 2082250 | 2082477 | yeeD | b2012 |
| CDS | − | 2082491 | 2083549 | yeeE | b2013 |
| CDS | − | 2083728 | 2085086 | yeeF | b2014 |
| CDS | − | 2085353 | 2086282 | yeeY | b2015 |
| CDS | − | 2086328 | 2087152 | yeeZ | b2016 |
| CDS | − | 2087486 | 2087737 | yefM | b2017 |
| CDS | + | 2088020 | 2088070 | hisL | b2018 |
| CDS | + | 2088216 | 2089115 | hisG | b2019 |
| CDS | + | 2089121 | 2090425 | hisD | b2020 |
| CDS | + | 2090422 | 2091492 | hisC | b2021 |
| CDS | + | 2091492 | 2092559 | hisB | b2022 |
| CDS | + | 2092559 | 2093149 | hisH | b2023 |
| CDS | + | 2093149 | 2093886 | hisA | b2024 |
| CDS | + | 2093868 | 2094644 | hisF | b2025 |
| CDS | + | 2094638 | 2095249 | hisI | b2026 |
| CDS | − | 2095345 | 2096325 | cld | b2027 |
| CDS | − | 2096471 | 2097637 | ugd | b2028 |
| CDS | − | 2097886 | 2099292 | gnd | b2029 |
| repeat_region | + | 2099773 | 2100967 | | |
| CDS | − | 2099919 | 2100935 | trs5_7 | b2030 |
| CDS | − | 2099420 | 2101413 | wbbL | b2031 |
| CDS | − | 2101415 | 2102533 | wbbK | b2032 |
| CDS | − | 2102518 | 2103108 | wbbJ | b2033 |
| CDS | − | 2103089 | 2104081 | wbbI | b2034 |
| CDS | − | 2104084 | 2105250 | rfc | b2035 |
| CDS | − | 2105250 | 2106353 | glf | b2036 |
| CDS | − | 2106361 | 2107608 | rfbX | b2037 |
| CDS | − | 2107605 | 2108162 | rfbC | b2038 |
| CDS | − | 2108162 | 2109043 | rfbA | b2039 |
| CDS | − | 2109101 | 2110000 | rfbD | b2040 |
| CDS | − | 2110000 | 2111085 | rfbB | b2041 |
| CDS | − | 2111458 | 2112351 | galF | b2042 |
| CDS | − | 2112526 | 2113920 | wcaM | b2043 |
| CDS | − | 2113931 | 2115151 | wcaL | b2044 |
| CDS | − | 2115148 | 2116428 | wcaK | b2045 |
| CDS | − | 2116704 | 2118182 | wzxC | b2046 |
| CDS | − | 2118184 | 2119578 | wcaJ | b2047 |
| CDS | − | 2119633 | 2121003 | cpsG | b2048 |
| CDS | − | 2121108 | 2122544 | cpsB | b2049 |
| CDS | − | 2122547 | 2123770 | wcaI | b2050 |
| CDS | − | 2123767 | 2124246 | wcaH | b2051 |
| CDS | − | 2124249 | 2125214 | wcaG | b2052 |
| CDS | − | 2125217 | 2126338 | gmd | b2053 |
| CDS | − | 2126364 | 2126912 | wcaF | b2054 |
| CDS | − | 2126928 | 2127674 | wcaE | b2055 |
| CDS | − | 2127685 | 2128902 | wcaD | b2056 |
| CDS | − | 2128877 | 2130094 | wcaC | b2057 |
| CDS | − | 2130091 | 2130579 | wcaB | b2058 |
| CDS | − | 2130582 | 2131421 | wcaA | b2059 |
| CDS | − | 2131514 | 2133676 | wzc | b2060 |
| CDS | − | 2133679 | 2134122 | wzb | b2061 |
| CDS | − | 2134128 | 2135267 | wza | b2062 |
| CDS | + | 2135926 | 2137509 | yegH | b2063 |
| CDS | − | 2137783 | 2139636 | asmA | b2064 |
| CDS | − | 2139658 | 2140239 | dcd | b2065 |
| CDS | − | 2140331 | 2140972 | udk | b2066 |
| CDS | + | 2141290 | 2144607 | yegE | b2067 |
| CDS | − | 2144716 | 2145564 | alkA | b2068 |
| CDS | + | 2145698 | 2147050 | yegD | b2069 |
| CDS | + | 2147063 | 2149009 | yegI | b2070 |
| CDS | + | 2149209 | 2149670 | yegJ | b2071 |
| CDS | + | 2149735 | 2150496 | yegK | b2072 |
| CDS | − | 2150493 | 2151152 | yegL | b2073 |
| CDS | + | 2152040 | 2153287 | yegM | b2074 |
| CDS | + | 2153287 | 2156409 | yegN | b2075 |
| CDS | + | 2156410 | 2159487 | yegO | b2076 |
| CDS | + | 2159488 | 2160903 | yegB | b2077 |
| CDS | + | 2160900 | 2162303 | baeS | b2078 |
| CDS | + | 2162300 | 2163022 | baeR | b2079 |
| CDS | + | 2163213 | 2163545 | yegP | b2080 |
| CDS | + | 2163692 | 2165053 | yegQ | b2081 |
| CDS | − | 2165326 | 2165544 | ogrK | b2082 |
| CDS | − | 2165626 | 2165844 | yegZ | b2083 |
| CDS | − | 2165759 | 2166025 | | b2084 |
| CDS | − | 2166013 | 2166330 | yegR | b2085 |
| CDS | + | 2166736 | 2167635 | yegS | b2086 |
| CDS | − | 2167717 | 2168163 | gatR_1 | b2087 |
| repeat_region | + | 2168195 | 2169452 | | |
| CDS | + | 2168251 | 2168559 | | b2088 |
| CDS | + | 2168556 | 2169422 | tra5_4 | b2089 |
| CDS | − | 2169419 | 2169757 | gatR_2 | b2090 |

TABLE 1-continued

| Type | S | Left | Right | Name | B |
|---|---|---|---|---|---|
| CDS | − | 2169857 | 2170897 | gatD | b2091 |
| CDS | − | 2170945 | 2172300 | gatC | b2092 |
| CDS | − | 2172304 | 2172588 | gatB | b2093 |
| CDS | − | 2172619 | 2173071 | gatA | b2094 |
| CDS | − | 2173081 | 2174343 | gatZ | b2095 |
| CDS | − | 2174372 | 2175226 | gatY | b2096 |
| CDS | − | 2175534 | 2176586 | fbaB | b2097 |
| CDS | + | 2176843 | 2178120 | yegT | b2098 |
| CDS | + | 2178117 | 2179121 | yegU | b2099 |
| CDS | + | 2179118 | 2180083 | yegV | b2100 |
| CDS | − | 2180057 | 2180803 | yegW | b2101 |
| CDS | − | 2180855 | 2181673 | yegX | b2102 |
| CDS | − | 2181738 | 2182538 | thiD | b2103 |
| CDS | − | 2182535 | 2183323 | thiM | b2104 |
| CDS | − | 2183546 | 2183818 | yohL | b2105 |
| CDS | + | 2183939 | 2184763 | yohM | b2106 |
| CDS | + | 2184982 | 2185320 | yohN | b2107 |
| CDS | − | 2185402 | 2186436 | yehA | b2108 |
| CDS | − | 2186452 | 2188932 | yehB | b2109 |
| CDS | − | 2188948 | 2189667 | yehC | b2110 |
| CDS | − | 2189702 | 2190244 | yehD | b2111 |
| CDS | − | 2190537 | 2190818 | yehE | b2112 |
| CDS | − | 2191081 | 2192190 | mrp | b2113 |
| CDS | + | 2192322 | 2194355 | metG | b2114 |
| CDS | + | 2194496 | 2195320 | molR_1 | b2115 |
| CDS | + | 2195432 | 2197369 | molR_2 | b2116 |
| CDS | + | 2197344 | 2198291 | molR_3 | b2117 |
| CDS | + | 2198301 | 2201933 | yehI | b2118 |
| CDS | + | 2202618 | 2203706 | yehL | b2119 |
| CDS | + | 2203717 | 2205996 | yehM | b2120 |
| CDS | + | 2205989 | 2207125 | yehP | b2121 |
| CDS | + | 2207122 | 2208966 | yehQ | b2122 |
| CDS | + | 2209247 | 2209708 | yehR | b2123 |
| CDS | − | 2209748 | 2210218 | yehS | b2124 |
| CDS | − | 2210265 | 2210984 | yehT | b2125 |
| CDS | − | 2210981 | 2212666 | yehU | b2126 |
| CDS | + | 2212888 | 2213619 | yehV | b2127 |
| CDS | − | 2213767 | 2214498 | yehW | b2128 |
| CDS | − | 2214503 | 2215429 | yehX | b2129 |
| CDS | − | 2215422 | 2216579 | yehY | b2130 |
| CDS | − | 2216586 | 2217503 | yehZ | b2131 |
| CDS | − | 2217714 | 2220011 | bglX | b2132 |
| CDS | + | 2220207 | 2221922 | dld | b2133 |
| CDS | − | 2221960 | 2222892 | pbpG | b2134 |
| CDS | − | 2223066 | 2223653 | yohC | b2135 |
| CDS | + | 2223823 | 2224401 | yohD | b2136 |
| CDS | − | 2224531 | 2225292 | yohF | b2137 |
| CDS | − | 2225345 | 2226433 | yohG | b2138 |
| CDS | − | 2226571 | 2226708 | yohH | b2139 |
| CDS | − | 2227460 | 2228407 | yohI | b2140 |
| CDS | + | 2228646 | 2229044 | yohJ | b2141 |
| CDS | + | 2229041 | 2229736 | yohK | b2142 |
| CDS | + | 2229866 | 2230750 | cdd | b2143 |
| CDS | + | 2230900 | 2231619 | sanA | b2144 |
| CDS | + | 2231622 | 2231861 | yeiS | b2145 |
| CDS | + | 2232055 | 2233293 | yeiT | b2146 |
| CDS | + | 2233287 | 2234522 | yeiA | b2147 |
| CDS | − | 2234765 | 2235775 | mglC | b2148 |
| CDS | − | 2235791 | 2237311 | mglA | b2149 |
| CDS | − | 2237372 | 2238370 | mglB | b2150 |
| CDS | − | 2238650 | 2239690 | galS | b2151 |
| CDS | − | 2239832 | 2240989 | yeiB | b2152 |
| CDS | − | 2241006 | 2241674 | folE | b2153 |
| CDS | + | 2241932 | 2242768 | yeiG | b2154 |
| CDS | − | 2242800 | 2244791 | cirA | b2155 |
| CDS | − | 2245085 | 2246554 | lysP | b2156 |
| CDS | − | 2246759 | 2247640 | yeiE | b2157 |
| CDS | + | 2247739 | 2248788 | yeiH | b2158 |
| CDS | − | 2248862 | 2249719 | nfo | b2159 |
| CDS | + | 2249722 | 2250810 | yeiI | b2160 |
| CDS | − | 2250917 | 2252167 | yeiJ | b2161 |
| CDS | − | 2252267 | 2253208 | rihB | b2162 |
| CDS | + | 2253377 | 2254036 | yeiL | b2163 |
| CDS | + | 2254107 | 2255357 | yeiM | b2164 |
| CDS | − | 2255451 | 2256389 | yeiN | b2165 |
| CDS | − | 2256377 | 2257318 | yeiC | b2166 |
| CDS | − | 2257741 | 2259432 | fruA | b2167 |
| CDS | − | 2259449 | 2260387 | fruK | b2168 |
| CDS | − | 2260387 | 2261517 | fruB | b2169 |
| CDS | + | 2261885 | 2263066 | setB | b2170 |
| CDS | + | 2263472 | 2264044 | yeiP | b2171 |
| CDS | + | 2264267 | 2265733 | yeiQ | b2172 |
| CDS | + | 2265851 | 2266837 | yeiR | b2173 |
| CDS | + | 2266876 | 2267589 | yeiU | b2174 |
| CDS | + | 2268001 | 2268567 | spr | b2175 |
| CDS | + | 2268748 | 2270304 | rtn | b2176 |
| CDS | + | 2270386 | 2272200 | yejA | b2177 |
| CDS | + | 2272201 | 2273295 | yejB | b2178 |
| CDS | + | 2273295 | 2274320 | yejE | b2179 |
| CDS | + | 2274322 | 2275911 | yejF | b2180 |
| CDS | − | 2275915 | 2276259 | yejG | b2181 |
| CDS | − | 2276592 | 2277782 | bcr | b2182 |
| CDS | − | 2277810 | 2278505 | rsuA | b2183 |
| CDS | + | 2278654 | 2280414 | yejH | b2184 |
| CDS | + | 2280539 | 2280823 | rplY | b2185 |
| CDS | − | 2280962 | 2281969 | yejK | b2186 |
| CDS | + | 2282151 | 2282378 | yejL | b2187 |
| CDS | + | 2282398 | 2284158 | yejM | b2188 |
| tRNA | + | 2284233 | 2284309 | proL | b2189 |
| CDS | − | 2284412 | 2286922 | yejO | b2190 |
| CDS | − | 2286927 | 2287049 |  | b2191 |
| repeat_region | + | 2286941 | 2288135 |  |  |
| CDS | − | 2287087 | 2288103 | trs5_8 | b2192 |
| CDS | + | 2288522 | 2289169 | narP | b2193 |
| CDS | − | 2289389 | 2290432 | ccmH | b2194 |
| CDS | − | 2290429 | 2290986 | ccmG | b2195 |
| CDS | − | 2290983 | 2292926 | ccmF | b2196 |
| CDS | − | 2292923 | 2293402 | ccmE | b2197 |
| CDS | − | 2293399 | 2293608 | ccmD | b2198 |
| CDS | − | 2293605 | 2294342 | ccmC | b2199 |
| CDS | − | 2294384 | 2295046 | ccmB | b2200 |
| CDS | − | 2295043 | 2295666 | ccmA | b2201 |
| CDS | − | 2295679 | 2296281 | napC | b2202 |
| CDS | − | 2296291 | 2296740 | napB | b2203 |
| CDS | − | 2296737 | 2297600 | napH | b2204 |
| CDS | − | 2297587 | 2298282 | napG | b2205 |
| CDS | − | 2298289 | 2300775 | napA | b2206 |
| CDS | − | 2300772 | 2301035 | napD | b2207 |
| CDS | − | 2301025 | 2301519 | napF | b2208 |
| CDS | + | 2301927 | 2302415 | eco | b2209 |
| CDS | − | 2303130 | 2304776 | mqo | b2210 |
| CDS | − | 2304994 | 2306637 | yojI | b2211 |
| CDS | − | 2306713 | 2307363 | alkB | b2212 |
| CDS | − | 2307363 | 2308427 | ada | b2213 |
| CDS | − | 2308501 | 2309556 | yojL | b2214 |
| CDS | − | 2309668 | 2310771 | ompC | b2215 |
| CDS | + | 2311510 | 2314182 | yojN | b2216 |
| CDS | + | 2314199 | 2314849 | rcsB | b2217 |
| CDS | − | 2315049 | 2317850 | rcsC | b2218 |
| CDS | + | 2318065 | 2319891 | atoS | b2219 |
| CDS | + | 2319888 | 2321273 | atoC | b2220 |
| CDS | + | 2321469 | 2322131 | atoD | b2221 |
| CDS | + | 2322131 | 2322781 | atoA | b2222 |
| CDS | + | 2322778 | 2324100 | atoE | b2223 |
| CDS | + | 2324131 | 2325315 | atoB | b2224 |
| CDS | − | 2325389 | 2326165 | yfaP | b2225 |
| CDS | − | 2326170 | 2327819 | yfaQ | b2226 |
| CDS | − | 2327820 | 2328305 | yfaS_2 | b2227 |
| CDS | − | 2328321 | 2332424 | yfaS_1 | b2228 |
| CDS | − | 2332358 | 2332981 | yfaT | b2229 |
| CDS | − | 2332978 | 2334666 | yfaA | b2230 |
| CDS | − | 2334815 | 2337442 | gyrA | b2231 |
| CDS | + | 2337589 | 2338311 | ubiG | b2232 |
| CDS | − | 2338439 | 2342191 | yfaL | b2233 |
| CDS | + | 2342887 | 2345172 | nrdA | b2234 |
| CDS | + | 2345406 | 2346536 | nrdB | b2235 |
| CDS | + | 2346536 | 2346790 | yfaE | b2236 |
| CDS | − | 2346844 | 2347494 | inaA | b2237 |
| CDS | + | 2347709 | 2347915 | yfaH | b2238 |
| CDS | − | 2347957 | 2349033 | glpQ | b2239 |
| CDS | − | 2349038 | 2350396 | glpT | b2240 |
| CDS | + | 2350669 | 2352297 | glpA | b2241 |
| CDS | + | 2352287 | 2353546 | glpB | b2242 |
| CDS | + | 2353543 | 2354733 | glpC | b2243 |
| CDS | + | 2354926 | 2355825 | yfaD | b2244 |
| CDS | − | 2356064 | 2356867 |  | b2245 |

TABLE 1-continued

| Type | S | Left | Right | Name | B |
|---|---|---|---|---|---|
| CDS | − | 2356885 | 2358174 | yfaV | b2246 |
| CDS | − | 2358231 | 2359448 | yfaW | b2247 |
| CDS | − | 2359451 | 2360233 | yfaX | b2248 |
| CDS | − | 2360453 | 2361655 |  | b2249 |
| CDS | − | 2361755 | 2362297 | yfaZ | b2250 |
| CDS | + | 2362576 | 2363001 | yfaO | b2251 |
| CDS | − | 2363040 | 2363642 | ais | b2252 |
| CDS | + | 2363932 | 2365089 | yfbE | b2253 |
| CDS | + | 2365093 | 2366061 | yfbF | b2254 |
| CDS | + | 2366061 | 2368043 | yfbG | b2255 |
| CDS | + | 2368040 | 2368930 |  | b2256 |
| CDS | + | 2368930 | 2370582 | arnT | b2257 |
| CDS | + | 2370914 | 2371300 | yfbJ | b2258 |
| CDS | − | 2371294 | 2371560 | pmrD | b2259 |
| CDS | − | 2371670 | 2373025 | menE | b2260 |
| CDS | − | 2373022 | 2373984 | menC | b2261 |
| CDS | − | 2373984 | 2374841 | menB | b2262 |
| CDS | − | 2374856 | 2375614 | yfbB | b2263 |
| CDS | − | 2375611 | 2377281 | menD | b2264 |
| CDS | − | 2377370 | 2378665 | menF | b2265 |
| CDS | − | 2378744 | 2379049 | elaB | b2266 |
| CDS | − | 2379104 | 2379565 | elaA | b2267 |
| CDS | + | 2379630 | 2380547 | elaC | b2268 |
| CDS | + | 2380735 | 2381946 | elaD | b2269 |
| CDS | − | 2382017 | 2383744 | yfbK | b2270 |
| CDS | + | 2383882 | 2384853 | yfbL | b2271 |
| CDS | + | 2384956 | 2385459 | yfbM | b2272 |
| CDS | − | 2385732 | 2386448 | yfbN | b2273 |
| CDS | + | 2386603 | 2387079 |  | b2274 |
| CDS | + | 2387135 | 2387986 |  | b2275 |
| CDS | − | 2388070 | 2389347 | nuoN | b2276 |
| CDS | − | 2389534 | 2391063 | nuoM | b2277 |
| CDS | − | 2391227 | 2393068 | nuoL | b2278 |
| CDS | − | 2393065 | 2393367 | nuoK | b2279 |
| CDS | − | 2393364 | 2393918 | nuoJ | b2280 |
| CDS | − | 2393930 | 2394472 | nuoI | b2281 |
| CDS | − | 2394487 | 2395464 | nuoH | b2282 |
| CDS | − | 2395461 | 2398193 | nuoG | b2283 |
| CDS | − | 2398240 | 2399577 | nuoF | b2284 |
| CDS | − | 2399574 | 2400074 | nuoE | b2285 |
| CDS | − | 2400077 | 2401879 | nuoC | b2286 |
| CDS | − | 2401973 | 2402635 | nuoB | b2287 |
| CDS | − | 2402651 | 2403094 | nuoA | b2288 |
| CDS | − | 2403725 | 2404663 | lrhA | b2289 |
| CDS | + | 2405583 | 2406800 | yfbQ | b2290 |
| CDS | + | 2406884 | 2407483 |  | b2291 |
| CDS | − | 2407542 | 2409374 | yfbS | b2292 |
| CDS | − | 2409461 | 2410111 | yfbT | b2293 |
| CDS | − | 2410122 | 2410616 | yfbU | b2294 |
| CDS | − | 2410699 | 2411154 |  | b2295 |
| CDS | + | 2411492 | 2412694 | ackA | b2296 |
| CDS | + | 2412769 | 2414913 | pta | b2297 |
| CDS | + | 2415103 | 2416623 | yfcC | b2298 |
| CDS | − | 2416656 | 2417198 |  | b2299 |
| CDS | − | 2417256 | 2417810 | yfcE | b2300 |
| CDS | − | 2417863 | 2418507 | yfcF | b2301 |
| CDS | + | 2418643 | 2419290 | yfcG | b2302 |
| CDS | + | 2419347 | 2419709 | folX | b2303 |
| CDS | + | 2419730 | 2420623 | yfcH | b2304 |
| CDS | − | 2420671 | 2421561 | yfcI | b2305 |
| CDS | − | 2421758 | 2422531 | hisP | b2306 |
| CDS | − | 2422539 | 2423255 | hisM | b2307 |
| CDS | − | 2423252 | 2423938 | hisQ | b2308 |
| CDS | − | 2424028 | 2424810 | hisJ | b2309 |
| CDS | − | 2425031 | 2425813 | argT | b2310 |
| CDS | − | 2426079 | 2426648 | ubiX | b2311 |
| CDS | − | 2426743 | 2428260 | purF | b2312 |
| CDS | − | 2428297 | 2428785 | cvpA | b2313 |
| CDS | − | 2429044 | 2429706 | dedD | b2314 |
| CDS | − | 2429696 | 2430964 | folC | b2315 |
| CDS | − | 2431034 | 2431948 | accD | b2316 |
| CDS | − | 2432104 | 2432763 | dedA | b2317 |
| CDS | − | 2432846 | 2433658 | truA | b2318 |
| CDS | − | 2433658 | 2434671 | usg | b2319 |
| CDS | − | 2434737 | 2435873 | pdxB | b2320 |
| CDS | + | 2435972 | 2436967 | flk | b2321 |
| CDS | − | 2436964 | 2438142 |  | b2322 |
| CDS | − | 2438407 | 2439627 | fabB | b2323 |
| CDS | + | 2439786 | 2441792 |  | b2324 |
| CDS | − | 2441913 | 2442191 | yfcL | b2325 |
| CDS | − | 2442225 | 2442773 | yfcM | b2326 |
| CDS | − | 2442773 | 2443582 | yfcA | b2327 |
| CDS | − | 2443582 | 2444406 | mepA | b2328 |
| CDS | − | 2444410 | 2445495 | aroC | b2329 |
| CDS | − | 2445530 | 2446462 | yfcB | b2330 |
| CDS | + | 2446628 | 2447179 | yfcN | b2331 |
| CDS | − | 2447250 | 2448071 |  | b2332 |
| CDS | − | 2448073 | 2448612 | yfcP | b2333 |
| CDS | − | 2448609 | 2449097 |  | b2334 |
| CDS | − | 2449094 | 2449606 |  | b2335 |
| CDS | − | 2449606 | 2450358 | yfcS | b2336 |
| CDS | − | 2450378 | 2451274 |  | b2337 |
| CDS | − | 2451287 | 2453023 | yfcU | b2338 |
| CDS | − | 2453105 | 2453668 |  | b2339 |
| CDS | − | 2454349 | 2454834 | sixA | b2340 |
| CDS | − | 2455037 | 2457181 | yfcX | b2341 |
| CDS | − | 2457181 | 2458491 | yfcY | b2342 |
| CDS | − | 2458672 | 2458956 | yfcZ | b2343 |
| CDS | + | 2459322 | 2460668 | fadL | b2344 |
| CDS | + | 2461034 | 2462092 |  | b2345 |
| CDS | − | 2462274 | 2463029 | vacJ | b2346 |
| CDS | + | 2463323 | 2464255 | yfdC | b2347 |
| tRNA | + | 2464331 | 2464405 | argW | b2348 |
| CDS | + | 2464567 | 2465724 | intS | b2349 |
| CDS | + | 2465877 | 2466239 | yfdG | b2350 |
| CDS | + | 2466236 | 2467156 | yfdH | b2351 |
| CDS | + | 2467153 | 2468484 | yfdI | b2352 |
| CDS | + | 2468825 | 2469127 | tfaS | b2353 |
| CDS | − | 2469099 | 2469539 | yfdK | b2354 |
| CDS | − | 2469566 | 2470084 | yfdL | b2355 |
| CDS | − | 2470134 | 2470409 | yfdM | b2356 |
| CDS | − | 2470409 | 2470903 | yfdN | b2357 |
| CDS | − | 2470900 | 2471268 | yfdO | b2358 |
| CDS | + | 2471542 | 2471988 | yfdP | b2359 |
| CDS | + | 2472054 | 2472878 | yfdQ | b2360 |
| CDS | + | 2473006 | 2473542 | yfdR | b2361 |
| CDS | + | 2473533 | 2473895 | yfdS | b2362 |
| CDS | + | 2473895 | 2474200 | yfdT | b2363 |
| CDS | − | 2474716 | 2475651 | dsdC | b2364 |
| CDS | + | 2475869 | 2477206 | dsdX | b2365 |
| CDS | + | 2477224 | 2478552 | dsdA | b2366 |
| CDS | − | 2478660 | 2480198 | emrY | b2367 |
| CDS | − | 2480198 | 2481361 | emrK | b2368 |
| CDS | + | 2481777 | 2482391 | evgA | b2369 |
| CDS | + | 2482396 | 2485989 | evgS | b2370 |
| CDS | − | 2486045 | 2487190 | yfdE | b2371 |
| CDS | − | 2487264 | 2488208 | yfdV | b2372 |
| CDS | − | 2488278 | 2489972 | yfdU | b2373 |
| CDS | − | 2490026 | 2491276 | yfdW | b2374 |
| CDS | − | 2491789 | 2492424 | yfdX | b2375 |
| CDS | + | 2492720 | 2492995 | ypdI | b2376 |
| CDS | − | 2493072 | 2493314 | yfdY | b2377 |
| CDS | + | 2493667 | 2494587 | ddg | b2378 |
| CDS | − | 2495079 | 2496317 | yfdZ | b2379 |
| CDS | + | 2496693 | 2498390 | ypdA | b2380 |
| CDS | + | 2498405 | 2499139 | ypdB | b2381 |
| CDS | + | 2499152 | 2500009 | ypdC | b2382 |
| CDS | − | 2500012 | 2502507 | ypdD | b2383 |
| CDS | − | 2502532 | 2503569 | ypdE | b2384 |
| CDS | − | 2503569 | 2504654 | ypdF | b2385 |
| CDS | − | 2504669 | 2505916 | ypdG | b2386 |
| CDS | − | 2505938 | 2506264 | ypdH | b2387 |
| CDS | − | 2506483 | 2507448 | glk | b2388 |
| CDS | + | 2507652 | 2508908 | yfeO | b2389 |
| CDS | + | 2509023 | 2509349 | ypeC | b2390 |
| CDS | − | 2509490 | 2510728 | mntH | b2392 |
| CDS | − | 2511064 | 2512266 | nupC | b2393 |
| repeat_region | + | 2512296 | 2513638 |  |  |
| CDS | + | 2512353 | 2513465 | yi81_3 | b2394 |
| CDS | − | 2513665 | 2515854 | yfeA | b2395 |
| tRNA | − | 2516063 | 2516138 | alaX | b2396 |
| tRNA | − | 2516178 | 2516253 | alaW | b2397 |
| CDS | + | 2516489 | 2516833 | yfeC | b2398 |
| CDS | + | 2516835 | 2517227 | yfeD | b2399 |
| CDS | − | 2517279 | 2518694 | gltX | b2400 |
| tRNA | + | 2518953 | 2519028 | valU | b2401 |

TABLE 1-continued

| Type | S | Left | Right | Name | B |
|---|---|---|---|---|---|
| tRNA | + | 2519073 | 2519148 | valX | b2402 |
| tRNA | + | 2519195 | 2519270 | valY | b2403 |
| tRNA | + | 2519275 | 2519350 | lysV | b2404 |
| CDS | − | 2519615 | 2520499 | xapR | b2405 |
| CDS | − | 2520751 | 2522007 | xapB | b2406 |
| CDS | − | 2522067 | 2522900 | xapA | b2407 |
| CDS | + | 2523149 | 2523913 | yfeN | b2408 |
| CDS | − | 2523952 | 2524878 | yfeR | b2409 |
| CDS | + | 2524968 | 2525966 | yfeH | b2410 |
| CDS | − | 2526183 | 2528198 | ligA | b2411 |
| CDS | − | 2528269 | 2529255 | zipA | b2412 |
| CDS | + | 2529485 | 2530246 | cysZ | b2413 |
| CDS | + | 2530431 | 2531402 | cysK | b2414 |
| CDS | + | 2531786 | 2532043 | ptsH | b2415 |
| CDS | + | 2532088 | 2533815 | ptsI | b2416 |
| CDS | + | 2533856 | 2534365 | crr | b2417 |
| CDS | − | 2534408 | 2535259 | pdxK | b2418 |
| CDS | + | 2535364 | 2535738 | yfeK | b2419 |
| CDS | + | 2535771 | 2536505 | yfeS | b2420 |
| CDS | − | 2536694 | 2537605 | cysM | b2421 |
| CDS | − | 2537739 | 2538836 | cysA | b2422 |
| CDS | − | 2538826 | 2539701 | cysW | b2423 |
| CDS | − | 2539701 | 2540534 | cysU | b2424 |
| CDS | − | 2540534 | 2541550 | cysP | b2425 |
| CDS | − | 2541854 | 2542645 | ucpA | b2426 |
| CDS | − | 2542774 | 2543631 | yfeT | b2427 |
| CDS | + | 2543795 | 2544691 | yfeU | b2428 |
| CDS | + | 2544695 | 2546119 | yfeV | b2429 |
| CDS | + | 2546124 | 2547428 | yfeW | b2430 |
| CDS | − | 2547668 | 2548567 | yfeX | b2431 |
| CDS | − | 2548663 | 2549238 | yfeY | b2432 |
| CDS | − | 2549299 | 2549748 | yfeZ | b2433 |
| CDS | − | 2549735 | 2550160 | ypeA | b2434 |
| CDS | + | 2550374 | 2551243 | amiA | b2435 |
| CDS | + | 2551247 | 2552146 | hemF | b2436 |
| CDS | − | 2552152 | 2553204 | yfeG | b2437 |
| CDS | − | 2553250 | 2553750 | yffI | b2438 |
| CDS | − | 2553763 | 2554422 | eutL | b2439 |
| CDS | − | 2554432 | 2555319 | eutC | b2440 |
| CDS | − | 2555340 | 2556701 | eutB | b2441 |
| CDS | + | 2556793 | 2558088 | intZ | b2442 |
| CDS | + | 2558279 | 2558920 |  | b2443 |
| CDS | + | 2559390 | 2559635 |  | b2444 |
| CDS | + | 2559632 | 2560015 | yffN | b2445 |
| CDS | + | 2560133 | 2560549 | yffO | b2446 |
| CDS | + | 2560546 | 2561139 |  | b2447 |
| CDS | + | 2561599 | 2561991 | yffQ | b2448 |
| CDS | + | 2562002 | 2562394 |  | b2449 |
| CDS | + | 2562515 | 2563354 | yffS | b2450 |
| CDS | − | 2563503 | 2564906 | eutA | b2451 |
| CDS | − | 2564903 | 2566129 | eutH | b2452 |
| CDS | − | 2566346 | 2567533 | eutG | b2453 |
| CDS | − | 2567523 | 2568359 | eutJ | b2454 |
| CDS | − | 2568370 | 2569773 | eutE | b2455 |
| CDS | − | 2569785 | 2570072 | cchB | b2456 |
| CDS | − | 2570178 | 2570472 | cchA | b2457 |
| CDS | − | 2570511 | 2571527 | eutI | b2458 |
| CDS | − | 2571524 | 2572327 | eutT | b2459 |
| CDS | − | 2572324 | 2573025 | eutQ | b2460 |
| CDS | − | 2573000 | 2573479 | eutP | b2461 |
| CDS | − | 2573492 | 2573827 | ypfE | b2462 |
| CDS | − | 2574120 | 2576399 | maeB | b2463 |
| CDS | + | 2576688 | 2577638 | talA | b2464 |
| CDS | + | 2577658 | 2579661 | tktB | b2465 |
| CDS | − | 2579756 | 2580799 | ypfG | b2466 |
| CDS | − | 2580925 | 2581500 | yffH | b2467 |
| CDS | − | 2581568 | 2583547 | aegA | b2468 |
| CDS | + | 2583753 | 2585453 | narQ | b2469 |
| CDS | + | 2585617 | 2588730 | acrD | b2470 |
| CDS | + | 2589269 | 2589625 | yffB | b2471 |
| CDS | + | 2589629 | 2590756 | dapE | b2472 |
| CDS | − | 2591094 | 2591792 | ypfH | b2473 |
| CDS | − | 2591866 | 2593881 | ypfI | b2474 |
| CDS | − | 2593896 | 2594759 |  | b2475 |
| CDS | − | 2594927 | 2595640 | purC | b2476 |
| CDS | − | 2595853 | 2596887 | nlpB | b2477 |
| CDS | − | 2596904 | 2597782 | dapA | b2478 |
| CDS | + | 2597928 | 2598500 | gcvR | b2479 |
| CDS | + | 2598500 | 2598970 | bcp | b2480 |
| CDS | + | 2599223 | 2599840 | hyfA | b2481 |
| CDS | + | 2599840 | 2601858 | hyfB | b2482 |
| CDS | + | 2601869 | 2602816 | hyfC | b2483 |
| CDS | + | 2602833 | 2604272 | hyfD | b2484 |
| CDS | + | 2604284 | 2604934 | hyfE | b2485 |
| CDS | + | 2604939 | 2606519 | hyfF | b2486 |
| CDS | + | 2606509 | 2608176 | hyfG | b2487 |
| CDS | + | 2608186 | 2608731 | hyfH | b2488 |
| CDS | + | 2608728 | 2609486 | hyfI | b2489 |
| CDS | + | 2609479 | 2609892 | hyfJ | b2490 |
| CDS | + | 2609922 | 2611934 | hyfR | b2491 |
| CDS | + | 2611956 | 2612804 | focB | b2492 |
| CDS | − | 2612842 | 2613903 | perM | b2493 |
| CDS | + | 2614116 | 2615579 |  | b2494 |
| CDS | + | 2615600 | 2615959 | yfgD | b2495 |
| CDS | − | 2616097 | 2616843 | hda | b2496 |
| CDS | − | 2616893 | 2618182 | uraA | b2497 |
| CDS | − | 2618268 | 2618894 | upp | b2498 |
| CDS | + | 2619219 | 2620256 | purM | b2499 |
| CDS | + | 2620256 | 2620894 | purN | b2500 |
| CDS | + | 2621066 | 2623132 | ppk | b2501 |
| CDS | + | 2623137 | 2624678 | ppx | b2502 |
| CDS | − | 2624717 | 2626960 | yfgF | b2503 |
| CDS | + | 2627312 | 2627503 | yfgG | b2504 |
| CDS | + | 2627814 | 2628332 | yfgH | b2505 |
| CDS | + | 2628348 | 2628887 | yfgI | b2506 |
| CDS | − | 2628980 | 2630557 | guaA | b2507 |
| CDS | − | 2630626 | 2632092 | guaB | b2508 |
| CDS | + | 2632254 | 2633624 | xseA | b2509 |
| CDS | − | 2633621 | 2633836 | yfgJ | b2510 |
| CDS | − | 2633906 | 2635378 | yfgK | b2511 |
| CDS | − | 2635496 | 2636674 | yfgL | b2512 |
| CDS | − | 2636685 | 2637305 | yfgM | b2513 |
| CDS | − | 2637323 | 2638597 | hisS | b2514 |
| CDS | − | 2638708 | 2639826 | ispG | b2515 |
| CDS | − | 2639853 | 2640866 | yfgA | b2516 |
| CDS | − | 2641151 | 2642305 | yfgB | b2517 |
| CDS | − | 2642455 | 2642886 | ndk | b2518 |
| CDS | − | 2643035 | 2645347 | pbpC | b2519 |
| CDS | − | 2645348 | 2650309 | yfhM | b2520 |
| CDS | + | 2650516 | 2651361 | sseA | b2521 |
| CDS | − | 2652179 | 2652955 | sseB | b2522 |
| CDS | − | 2653097 | 2654380 | pepB | b2523 |
| CDS | − | 2654558 | 2654758 | yfhJ | b2524 |
| CDS | − | 2654770 | 2655105 | fdx | b2525 |
| CDS | − | 2655107 | 2656957 | hscA | b2526 |
| CDS | − | 2656974 | 2657489 | hscB | b2527 |
| CDS | − | 2657585 | 2657908 | iscA | b2528 |
| CDS | − | 2657925 | 2658311 | iscU | b2529 |
| CDS | − | 2658339 | 2659553 | iscS | b2530 |
| CDS | − | 2659665 | 2660153 | iscR | b2531 |
| CDS | − | 2660605 | 2661345 | yfhQ | b2532 |
| CDS | + | 2661464 | 2662267 | suhB | b2533 |
| CDS | + | 2662385 | 2663266 | yfhR | b2534 |
| CDS | + | 2663457 | 2664737 | csiE | b2535 |
| CDS | + | 2664729 | 2665868 | hcaT | b2536 |
| CDS | − | 2666028 | 2666918 | hcaR | b2537 |
| CDS | + | 2667054 | 2668415 | hcaE | b2538 |
| CDS | + | 2668412 | 2668930 | hcaF | b2539 |
| CDS | + | 2668930 | 2669250 | hcaC | b2540 |
| CDS | + | 2669247 | 2670059 | hcaB | b2541 |
| CDS | + | 2670069 | 2671271 | hcaD | b2542 |
| CDS | + | 2671296 | 2671790 | yphA | b2543 |
| CDS | − | 2671838 | 2672710 | yphB | b2544 |
| CDS | − | 2672722 | 2673783 | yphC | b2545 |
| CDS | − | 2673849 | 2674847 | yphD | b2546 |
| CDS | − | 2674872 | 2676383 | yphE | b2547 |
| CDS | − | 2676406 | 2677389 | yphF | b2548 |
| CDS | − | 2677486 | 2680767 | yphG | b2549 |
| CDS | + | 2680885 | 2682078 | yphH | b2550 |
| CDS | − | 2682276 | 2683529 | glyA | b2551 |
| CDS | + | 2683857 | 2685047 | hmpA | b2552 |
| CDS | − | 2685092 | 2685430 | glnB | b2553 |
| CDS | − | 2685491 | 2686825 | yfhA | b2554 |
| CDS | − | 2686815 | 2687528 | yfhG | b2555 |
| CDS | − | 2687693 | 2689120 | yfhK | b2556 |
| CDS | − | 2689678 | 2693565 | purL | b2557 |

TABLE 1-continued

| Type | S | Left | Right | Name | B |
|---|---|---|---|---|---|
| CDS | + | 2693961 | 2695379 | yfhD | b2558 |
| CDS | − | 2695376 | 2695912 | tadA | b2559 |
| CDS | − | 2695937 | 2696572 | yfhB | b2560 |
| CDS | + | 2696781 | 2697629 | yfhH | b2561 |
| CDS | + | 2697685 | 2697945 | yfhL | b2562 |
| CDS | − | 2698640 | 2699020 | acpS | b2563 |
| CDS | − | 2699020 | 2699751 | pdxJ | b2564 |
| CDS | − | 2699763 | 2700491 | recO | b2565 |
| CDS | − | 2700503 | 2701408 | era | b2566 |
| CDS | − | 2701405 | 2702085 | rnc | b2567 |
| CDS | − | 2702357 | 2703331 | lepB | b2568 |
| CDS | − | 2703347 | 2705146 | lepA | b2569 |
| CDS | − | 2705344 | 2705823 | rseC | b2570 |
| CDS | − | 2705820 | 2706776 | rseB | b2571 |
| CDS | − | 2706776 | 2707426 | rseA | b2572 |
| CDS | − | 2707459 | 2708034 | rpoE | b2573 |
| CDS | + | 2708442 | 2710064 | nadB | b2574 |
| CDS | − | 2710049 | 2710786 | yfiC | b2575 |
| CDS | + | 2710918 | 2712252 | srmB | b2576 |
| CDS | − | 2712461 | 2713342 | yfiE | b2577 |
| CDS | + | 2713445 | 2714032 | yfiK | b2578 |
| CDS | − | 2714088 | 2714471 | yfiD | b2579 |
| CDS | + | 2714776 | 2715465 | ung | b2580 |
| CDS | − | 2715513 | 2716550 | yfiF | b2581 |
| CDS | + | 2716757 | 2717176 | trxC | b2582 |
| CDS | + | 2717245 | 2717943 | yfiP | b2583 |
| CDS | + | 2717975 | 2720635 | yfiQ | b2584 |
| CDS | + | 2720749 | 2722104 | pssA | b2585 |
| CDS | + | 2722201 | 2722473 | yfiM | b2586 |
| CDS | − | 2722470 | 2723768 | kgtP | b2587 |
| rRNA | − | 2724091 | 2724210 | rrfG | b2588 |
| rRNA | − | 2724303 | 2727206 | rrlG | b2589 |
| tRNA | − | 2727391 | 2727466 | gltW | b2590 |
| rRNA | − | 2727638 | 2729179 | rrsG | b2591 |
| CDS | − | 2729622 | 2732195 | clpB | b2592 |
| CDS | − | 2732325 | 2733056 | yfiH | b2593 |
| CDS | − | 2733053 | 2734033 | rluD | b2594 |
| CDS | + | 2734168 | 2734905 | yfiO | b2595 |
| CDS | + | 2734935 | 2735141 | | b2596 |
| CDS | + | 2735176 | 2735517 | yfiA | b2597 |
| CDS | + | 2735621 | 2735668 | pheL | b2598 |
| CDS | + | 2735767 | 2736927 | pheA | b2599 |
| CDS | − | 2736970 | 2738091 | tyrA | b2600 |
| CDS | − | 2738102 | 2739172 | aroF | b2601 |
| CDS | + | 2739382 | 2739747 | yfiL | b2602 |
| CDS | + | 2739897 | 2740415 | yfiR | b2603 |
| CDS | + | 2740405 | 2741631 | yfiN | b2604 |
| CDS | + | 2741647 | 2742129 | yfiB | b2605 |
| CDS | − | 2742205 | 2742552 | rplS | b2606 |
| CDS | − | 2742594 | 2743361 | trmD | b2607 |
| CDS | − | 2743392 | 2743940 | rimM | b2608 |
| CDS | − | 2743959 | 2744207 | rpsP | b2609 |
| CDS | − | 2744456 | 2745817 | ffh | b2610 |
| CDS | + | 2745909 | 2746775 | ypjD | b2611 |
| CDS | − | 2748137 | 2748730 | grpE | b2614 |
| CDS | + | 2748853 | 2749731 | yfjB | b2615 |
| CDS | − | 2749817 | 2751478 | recN | b2616 |
| CDS | + | 2751627 | 2751968 | smpA | b2617 |
| CDS | − | 2752030 | 2752320 | yfjF | b2618 |
| CDS | − | 2752310 | 2752786 | yfjG | b2619 |
| CDS | + | 2752918 | 2753400 | smpB | b2620 |
| misc_RNA | + | 2753615 | 2753977 | ssrA | b2621 |
| CDS | + | 2754181 | 2755422 | intA | b2622 |
| CDS | − | 2755666 | 2756622 | yfjH | b2623 |
| CDS | + | 2756666 | 2756878 | alpA | b2624 |
| CDS | + | 2757007 | 2758416 | yfjI | b2625 |
| CDS | + | 2758569 | 2759195 | yfjJ | b2626 |
| CDS | − | 2759373 | 2761562 | yfjK | b2627 |
| CDS | − | 2761526 | 2763175 | yfjL | b2628 |
| CDS | − | 2763535 | 2763798 | yfjM | b2629 |
| CDS | + | 2763940 | 2765013 | yfjN | b2630 |
| CDS | + | 2765006 | 2765377 | yfjO | b2631 |
| CDS | + | 2765732 | 2766595 | yfjP | b2632 |
| CDS | + | 2766687 | 2767508 | yfjQ | b2633 |
| CDS | + | 2767725 | 2768426 | yfjR | b2634 |
| CDS | + | 2768467 | 2768703 | ypjK | b2635 |
| CDS | + | 2768703 | 2769146 | yfjS | b2636 |
| CDS | + | 2769170 | 2769637 | yfjT | b2637 |
| CDS | − | 2769862 | 2770176 | yfjU | b2638 |
| CDS | − | 2770189 | 2770707 | | b2639 |
| CDS | − | 2770858 | 2771058 | | b2640 |
| CDS | − | 2770998 | 2771180 | | b2641 |
| CDS | + | 2771340 | 2773043 | yfjW | b2642 |
| CDS | + | 2773941 | 2774399 | yfjX | b2643 |
| CDS | + | 2774408 | 2774890 | yfjY | b2644 |
| CDS | + | 2775137 | 2775454 | yfjZ | b2645 |
| CDS | + | 2775475 | 2775804 | ypjF | b2646 |
| CDS | − | 2776168 | 2780748 | ypjA | b2647 |
| CDS | − | 2781087 | 2781230 | pinH | b2648 |
| CDS | − | 2781660 | 2782451 | | b2649 |
| CDS | − | 2782551 | 2783033 | | b2650 |
| CDS | + | 2783243 | 2783374 | | b2651 |
| tRNA | − | 2783784 | 2783859 | ileY | b2652 |
| CDS | − | 2783822 | 2783995 | | b2653 |
| CDS | + | 2784419 | 2784751 | | b2654 |
| CDS | + | 2785664 | 2786260 | | b2657 |
| CDS | + | 2786399 | 2786671 | | b2658 |
| CDS | + | 2787007 | 2787984 | | b2659 |
| CDS | + | 2788004 | 2789272 | ygaF | b2660 |
| CDS | + | 2789295 | 2790743 | gabD | b2661 |
| CDS | + | 2790757 | 2792037 | gabT | b2662 |
| CDS | + | 2792275 | 2793675 | gabP | b2663 |
| CDS | + | 2793696 | 2794358 | ygaE | b2664 |
| CDS | − | 2794359 | 2794808 | ygaU | b2665 |
| CDS | − | 2794892 | 2795050 | yqaE | b2666 |
| CDS | + | 2795233 | 2795532 | | b2667 |
| CDS | + | 2795542 | 2796066 | ygaP | b2668 |
| CDS | − | 2796113 | 2796517 | stpA | b2669 |
| CDS | + | 2797186 | 2797635 | | b2670 |
| CDS | + | 2797672 | 2798016 | ygaC | b2671 |
| CDS | + | 2798156 | 2798497 | ygaM | b2672 |
| CDS | + | 2798745 | 2798990 | nrdH | b2673 |
| CDS | + | 2798987 | 2799397 | nrdI | b2674 |
| CDS | + | 2799370 | 2801514 | nrdE | b2675 |
| CDS | + | 2801524 | 2802483 | nrdF | b2676 |
| CDS | + | 2802837 | 2804039 | proV | b2677 |
| CDS | + | 2804032 | 2805096 | proW | b2678 |
| CDS | + | 2805154 | 2806146 | proX | b2679 |
| CDS | + | 2806338 | 2806604 | | b2680 |
| CDS | + | 2806634 | 2807515 | | b2681 |
| CDS | + | 2807639 | 2808376 | ygaZ | b2682 |
| CDS | + | 2808366 | 2808701 | ygaH | b2683 |
| CDS | + | 2808792 | 2809322 | emrR | b2684 |
| CDS | + | 2809449 | 2810621 | emrA | b2685 |
| CDS | + | 2810638 | 2812176 | emrB | b2686 |
| CDS | − | 2812240 | 2812755 | ygaG | b2687 |
| CDS | − | 2812905 | 2814461 | gshA | b2688 |
| CDS | − | 2814534 | 2814962 | yqaA | b2689 |
| CDS | − | 2814959 | 2815525 | yqaB | b2690 |
| tRNA | − | 2815806 | 2815882 | argQ | b2691 |
| tRNA | − | 2816081 | 2816157 | argZ | b2692 |
| tRNA | − | 2816220 | 2816296 | argY | b2693 |
| tRNA | − | 2816495 | 2816571 | argV | b2694 |
| tRNA | − | 2816575 | 2816667 | serV | b2695 |
| CDS | − | 2816983 | 2817168 | csrA | b2696 |
| CDS | − | 2817403 | 2820033 | alaS | b2697 |
| CDS | − | 2820161 | 2820661 | oraA | b2698 |
| CDS | − | 2820730 | 2821791 | recA | b2699 |
| CDS | − | 2821871 | 2822368 | ygaD | b2700 |
| CDS | − | 2822513 | 2823598 | mltB | b2701 |
| CDS | + | 2823854 | 2824417 | srlA | b2702 |
| CDS | + | 2824414 | 2825373 | srlE | b2703 |
| CDS | + | 2825384 | 2825755 | srlB | b2704 |
| CDS | + | 2825759 | 2826538 | srlD | b2705 |
| CDS | + | 2826643 | 2827002 | gutM | b2706 |
| CDS | + | 2827069 | 2827842 | srlR | b2707 |
| CDS | + | 2827835 | 2828800 | gutQ | b2708 |
| CDS | − | 2828797 | 2830311 | ygaA | b2709 |
| CDS | + | 2830498 | 2831937 | norV | b2710 |
| CDS | + | 2831934 | 2833067 | ygbD | b2711 |
| CDS | − | 2833195 | 2835447 | hypF | b2712 |
| CDS | − | 2835600 | 2836127 | hydN | b2713 |
| CDS | − | 2836276 | 2837289 | ascG | b2714 |
| CDS | + | 2837546 | 2839003 | ascF | b2715 |
| CDS | + | 2839012 | 2840436 | ascB | b2716 |
| CDS | − | 2840595 | 2841065 | hycI | b2717 |

TABLE 1-continued

| Type | S | Left | Right | Name | B |
|---|---|---|---|---|---|
| CDS | − | 2841058 | 2841468 | hycH | b2718 |
| CDS | − | 2841465 | 2842232 | hycG | b2719 |
| CDS | − | 2842232 | 2842774 | hycF | b2720 |
| CDS | − | 2842784 | 2844493 | hycE | b2721 |
| CDS | − | 2844511 | 2845434 | hycD | b2722 |
| CDS | − | 2845437 | 2847263 | hycC | b2723 |
| CDS | − | 2847260 | 2847871 | hycB | b2724 |
| CDS | − | 2847996 | 2848457 | hycA | b2725 |
| CDS | + | 2848669 | 2849019 | hypA | b2726 |
| CDS | + | 2849023 | 2849895 | hypB | b2727 |
| CDS | + | 2849886 | 2850158 | hypC | b2728 |
| CDS | + | 2850158 | 2851279 | hypD | b2729 |
| CDS | + | 2851318 | 2852286 | hypE | b2730 |
| CDS | + | 2852360 | 2854438 | fhlA | b2731 |
| CDS | − | 2854475 | 2854828 | ygbA | b2732 |
| CDS | + | 2855115 | 2857676 | mutS | b2733 |
| CDS | + | 2857782 | 2858438 | pphB | b2734 |
| CDS | − | 2858489 | 2859286 | ygbI | b2735 |
| CDS | + | 2859452 | 2860360 | ygbJ | b2736 |
| CDS | + | 2860357 | 2861523 | ygbK | b2737 |
| CDS | + | 2861615 | 2862253 | ygbL | b2738 |
| CDS | + | 2862258 | 2863034 | ygbM | b2739 |
| CDS | + | 2863123 | 2864487 | ygbN | b2740 |
| CDS | − | 2864581 | 2865573 | rpoS | b2741 |
| CDS | − | 2865636 | 2866775 | nlpD | b2742 |
| CDS | − | 2866915 | 2867541 | pcm | b2743 |
| CDS | − | 2867535 | 2868296 | surE | b2744 |
| CDS | − | 2868277 | 2869326 | ygbO | b2745 |
| CDS | − | 2869323 | 2869802 | ispF | b2746 |
| CDS | − | 2869802 | 2870512 | ispD | b2747 |
| CDS | − | 2870531 | 2870842 | ygbQ | b2748 |
| CDS | − | 2871036 | 2871359 | ygbE | b2749 |
| CDS | − | 2871409 | 2872014 | cysC | b2750 |
| CDS | − | 2872014 | 2873441 | cysN | b2751 |
| CDS | − | 2873443 | 2874351 | cysD | b2752 |
| CDS | + | 2874603 | 2875640 | iap | b2753 |
| CDS | − | 2876591 | 2876875 | ygbF | b2754 |
| CDS | − | 2876877 | 2877794 | ygbT | b2755 |
| CDS | − | 2877810 | 2878409 | ygcH | b2756 |
| CDS | − | 2878396 | 2879070 | ygcI | b2757 |
| CDS | − | 2879073 | 2880164 | ygcJ | b2758 |
| CDS | − | 2880177 | 2880659 | ygcK | b2759 |
| CDS | − | 2880652 | 2882160 | ygcL | b2760 |
| CDS | − | 2882575 | 2885241 | ygcN | b2761 |
| CDS | − | 2885600 | 2886334 | cysH | b2762 |
| CDS | − | 2886409 | 2888121 | cysI | b2763 |
| CDS | − | 2888121 | 2889920 | cysJ | b2764 |
| CDS | + | 2890236 | 2890601 | ygcM | b2765 |
| CDS | + | 2890679 | 2891950 | ygcN | b2766 |
| CDS | + | 2891941 | 2892201 | ygcO | b2767 |
| CDS | + | 2892218 | 2892793 | ygcP | b2768 |
| CDS | − | 2892941 | 2893801 | ygcQ | b2769 |
| CDS | − | 2893798 | 2894577 | ygcR | b2770 |
| CDS | − | 2894555 | 2895892 | ygcS | b2771 |
| CDS | − | 2897510 | 2898295 | ygcW | b2774 |
| CDS | + | 2898614 | 2899891 | yqcE | b2775 |
| CDS | + | 2899918 | 2901396 | ygcE | b2776 |
| CDS | − | 2902769 | 2903440 | ygcF | b2777 |
| CDS | + | 2903733 | 2904605 | ygcG | b2778 |
| CDS | − | 2904665 | 2905963 | eno | b2779 |
| CDS | − | 2906051 | 2907688 | pyrG | b2780 |
| CDS | − | 2907916 | 2908707 | mazG | b2781 |
| CDS | − | 2908778 | 2909113 | chpA | b2782 |
| CDS | − | 2909113 | 2909361 | chpR | b2783 |
| CDS | − | 2909439 | 2911673 | relA | b2784 |
| CDS | − | 2911721 | 2913022 | rumA | b2785 |
| CDS | + | 2913079 | 2915835 | barA | b2786 |
| CDS | − | 2916067 | 2917407 | gudD | b2787 |
| CDS | − | 2917428 | 2918768 | gudX | b2788 |
| CDS | − | 2918770 | 2920122 | gudP | b2789 |
| CDS | − | 2920557 | 2921006 | yqcA | b2790 |
| CDS | − | 2921024 | 2921806 | yqcB | b2791 |
| CDS | − | 2921806 | 2922135 | yqcC | b2792 |
| CDS | − | 2922757 | 2923302 | syd | b2793 |
| CDS | + | 2923370 | 2924218 | yqcD | b2794 |
| CDS | + | 2924330 | 2925694 | ygdH | b2795 |
| CDS | + | 2926251 | 2927540 | sdaC | b2796 |
| CDS | + | 2927598 | 2928965 | sdaB | b2797 |
| CDS | + | 2928987 | 2929832 | exo | b2798 |
| CDS | − | 2929887 | 2931038 | fucO | b2799 |
| CDS | − | 2931063 | 2931710 | fucA | b2800 |
| CDS | + | 2932257 | 2933573 | fucP | b2801 |
| CDS | + | 2933606 | 2935381 | fucI | b2802 |
| CDS | + | 2935460 | 2936908 | fucK | b2803 |
| CDS | + | 2936910 | 2937332 | fucU | b2804 |
| CDS | + | 2937390 | 2938121 | fucR | b2805 |
| CDS | − | 2938165 | 2939265 | ygdE | b2806 |
| CDS | − | 2939258 | 2939653 | ygdD | b2807 |
| CDS | − | 2939672 | 2940589 | gcvA | b2808 |
| CDS | − | 2940940 | 2941167 | ygdI | b2809 |
| CDS | + | 2941359 | 2942564 | csdA | b2810 |
| CDS | + | 2942564 | 2943007 | ygdK | b2811 |
| CDS | − | 2943058 | 2943864 | ygdL | b2812 |
| CDS | − | 2944103 | 2945200 | mltA | b2813 |
| tRNA | + | 2945409 | 2945485 | metZ | b2814 |
| tRNA | + | 2945519 | 2945595 | metW | b2815 |
| tRNA | + | 2945629 | 2945705 | metV | b2816 |
| CDS | − | 2945779 | 2947032 | amiC | b2817 |
| CDS | + | 2947264 | 2948595 | argA | b2818 |
| CDS | − | 2948657 | 2950483 | recD | b2819 |
| CDS | − | 2950483 | 2954025 | recB | b2820 |
| CDS | − | 2954018 | 2956906 | ptr | b2821 |
| CDS | − | 2957082 | 2960450 | recC | b2822 |
| CDS | − | 2960463 | 2960786 | ppdC | b2823 |
| CDS | − | 2960771 | 2961178 | ygdB | b2824 |
| CDS | − | 2961175 | 2961738 | ppdB | b2825 |
| CDS | − | 2961729 | 2962199 | ppdA | b2826 |
| CDS | − | 2962383 | 2963177 | thyA | b2827 |
| CDS | − | 2963184 | 2964059 | lgt | b2828 |
| CDS | − | 2964210 | 2966456 | ptsP | b2829 |
| CDS | − | 2966469 | 2966999 | ygdP | b2830 |
| CDS | + | 2967684 | 2968373 | mutH | b2831 |
| CDS | + | 2968442 | 2969155 | ygdQ | b2832 |
| CDS | + | 2969223 | 2969511 | ygdR | b2833 |
| CDS | + | 2969619 | 2970659 | tas | b2834 |
| CDS | − | 2970691 | 2971884 | ygeD | b2835 |
| CDS | + | 2971877 | 2974036 | aas | b2836 |
| CDS | + | 2974621 | 2975652 | galR | b2837 |
| CDS | − | 2975659 | 2976921 | lysA | b2838 |
| CDS | + | 2977043 | 2977978 | lysR | b2839 |
| CDS | − | 2977965 | 2978657 | ygeA | b2840 |
| CDS | − | 2978786 | 2980204 | araE | b2841 |
| CDS | − | 2980519 | 2981280 | kduD | b2842 |
| CDS | − | 2981310 | 2982146 | kduI | b2843 |
| CDS | − | 2982433 | 2983614 | yqeF | b2844 |
| CDS | + | 2983869 | 2985098 | yqeG | b2845 |
| CDS | + | 2985558 | 2986190 | yqeH | b2846 |
| CDS | + | 2986524 | 2987333 | yqeI | b2847 |
| CDS | + | 2987326 | 2987808 | yqeJ | b2848 |
| CDS | − | 2987957 | 2988382 | yqeK | b2849 |
| CDS | + | 2988576 | 2989022 | ygeF | b2850 |
| CDS | + | 2989290 | 2989781 | ygeG | b2851 |
| CDS | + | 2990116 | 2991492 | ygeH | b2852 |
| CDS | + | 2991660 | 2991878 | ygeI | b2853 |
| CDS | + | 2992063 | 2992437 |  | b2854 |
| CDS | − | 2992482 | 2992925 | ygeK | b2855 |
| CDS | − | 2992959 | 2993114 |  | b2856 |
| CDS | − | 2993336 | 2993767 |  | b2857 |
| CDS | − | 2993770 | 2994042 |  | b2858 |
| CDS | − | 2993984 | 2994409 |  | b2859 |
| repeat_region | + | 2994383 | 2995713 |  |  |
| CDS | − | 2994394 | 2995299 | yi22_4 | b2860 |
| CDS | − | 2995667 | 2995667 | yi21_4 | b2861 |
| CDS | − | 2995711 | 2996010 | ygeP | b2862 |
| CDS | − | 2996056 | 2996850 | ygeQ | b2863 |
| tRNA | − | 2997006 | 2997079 | glyU | b2864 |
| CDS | − | 2997158 | 2997913 | ygeR | b2865 |
| CDS | + | 2998367 | 3000625 | xdhA | b2866 |
| CDS | + | 3000636 | 3001514 | xdhB | b2867 |
| CDS | + | 3001511 | 3001990 | xdhC | b2868 |
| CDS | − | 3002030 | 3003808 | ygeV | b2869 |
| CDS | + | 3004284 | 3005474 | ygeW | b2870 |
| CDS | + | 3005532 | 3006728 | ygeX | b2871 |
| CDS | + | 3006786 | 3007997 | ygeY | b2872 |
| CDS | + | 3008050 | 3009435 | ygeZ | b2873 |
| CDS | + | 3009483 | 3010415 | yqeA | b2874 |

TABLE 1-continued

| Type | S | Left | Right | Name | B |
|---|---|---|---|---|---|
| CDS | − | 3010636 | 3012261 | yqeB | b2875 |
| CDS | − | 3012309 | 3013079 | yqeC | b2876 |
| CDS | + | 3013182 | 3013760 | ygfJ | b2877 |
| CDS | + | 3014082 | 3017180 | ygfK | b2878 |
| CDS | + | 3017183 | 3018511 | ssnA | b2879 |
| CDS | + | 3018562 | 3019341 | ygfM | b2880 |
| CDS | + | 3019338 | 3022208 | xdhD | b2881 |
| CDS | + | 3022373 | 3023773 | ygfO | b2882 |
| CDS | + | 3023788 | 3025107 | guaD | b2883 |
| CDS | − | 3026546 | 3027034 | ygfS | b2886 |
| CDS | − | 3027034 | 3028953 | ygfT | b2887 |
| CDS | + | 3029389 | 3030837 | ygfU | b2888 |
| CDS | + | 3031087 | 3031635 | idi | b2889 |
| CDS | − | 3031679 | 3033196 | lysS | b2890 |
| CDS | − | 3033206 | 3034304 | prfB | b2891 |
| CDS | − | 3034395 | 3036128 | recJ | b2892 |
| CDS | − | 3036134 | 3036844 | dsbC | b2893 |
| CDS | − | 3036869 | 3037765 | xerD | b2894 |
| CDS | + | 3037877 | 3038398 | fldB | b2895 |
| CDS | − | 3038438 | 3038845 | ygfX | b2896 |
| CDS | − | 3038826 | 3039092 | ygfY | b2897 |
| CDS | + | 3039335 | 3040315 | ygfZ | b2898 |
| CDS | − | 3040511 | 3041170 | yqfA | b2899 |
| CDS | − | 3041334 | 3041645 | yqfB | b2900 |
| CDS | + | 3041684 | 3043123 | bglA | b2901 |
| CDS | − | 3043180 | 3043923 | ygfF | b2902 |
| CDS | − | 3044190 | 3047063 | gcvP | b2903 |
| CDS | − | 3047182 | 3047571 | gcvH | b2904 |
| CDS | − | 3047595 | 3048689 | gcvT | b2905 |
| CDS | − | 3049137 | 3050339 | visC | b2906 |
| CDS | − | 3050362 | 3051540 | ubiH | b2907 |
| CDS | − | 3051537 | 3052862 | pepP | b2908 |
| CDS | − | 3052888 | 3053466 | ygfB | b2909 |
| CDS | + | 3053634 | 3053963 | ygfE | b2910 |
| misc_RNA | + | 3054005 | 3054187 | ssrS | b2911 |
| CDS | + | 3054263 | 3054811 | ygfA | b2912 |
| CDS | − | 3055200 | 3056432 | serA | b2913 |
| CDS | − | 3056688 | 3057347 | rpiA | b2914 |
| CDS | − | 3057403 | 3057633 | yqfE | b2915 |
| CDS | + | 3057775 | 3058668 | iciA | b2916 |
| CDS | + | 3058872 | 3061016 | sbm | b2917 |
| CDS | + | 3061009 | 3062004 | argK | b2918 |
| CDS | + | 3062015 | 3062800 | ygfG | b2919 |
| CDS | + | 3062824 | 3064302 | ygfH | b2920 |
| CDS | − | 3064299 | 3065195 | ygfI | b2921 |
| CDS | − | 3065362 | 3066102 | yggE | b2922 |
| CDS | − | 3066195 | 3066830 | yggA | b2923 |
| CDS | − | 3066969 | 3067829 | yggB | b2924 |
| CDS | − | 3068187 | 3069266 | fbaA | b2925 |
| CDS | − | 3069481 | 3070644 | pgk | b2926 |
| CDS | − | 3070694 | 3071713 | epd | b2927 |
| CDS | − | 3071998 | 3072711 | yggC | b2928 |
| CDS | − | 3072708 | 3073217 | yggD | b2929 |
| CDS | − | 3073239 | 3074204 | yggF | b2930 |
| CDS | − | 3075493 | 3076881 | cmtA | b2933 |
| CDS | − | 3076909 | 3077352 | cmtB | b2934 |
| CDS | − | 3077666 | 3079657 | tktA | b2935 |
| CDS | + | 3079935 | 3080693 | yggG | b2936 |
| CDS | − | 3080899 | 3081819 | speB | b2937 |
| CDS | − | 3081957 | 3083933 | speA | b2938 |
| CDS | − | 3083942 | 3084088 | yqgB | b2939 |
| CDS | + | 3084209 | 3084424 | yqgC | b2940 |
| CDS | − | 3084421 | 3084672 | yqgD | b2941 |
| CDS | + | 3084728 | 3085882 | metK | b2942 |
| CDS | + | 3086306 | 3087700 | galP | b2943 |
| CDS | + | 3087777 | 3088274 | sprT | b2944 |
| CDS | + | 3088369 | 3089076 | endA | b2945 |
| CDS | + | 3089156 | 3089887 | yggJ | b2946 |
| CDS | + | 3089900 | 3090850 | gshB | b2947 |
| CDS | + | 3090959 | 3091522 | yqgE | b2948 |
| CDS | + | 3091522 | 3091938 | yqgF | b2949 |
| CDS | − | 3092122 | 3093102 | yggR | b2950 |
| CDS | + | 3093120 | 3093824 | yggS | b2951 |
| CDS | + | 3093842 | 3094408 | yggT | b2952 |
| CDS | + | 3094405 | 3094695 | yggU | b2953 |
| CDS | + | 3094703 | 3095296 | yggV | b2954 |
| CDS | + | 3095289 | 3096425 | yggW | b2955 |
| CDS | − | 3096580 | 3097587 | yggM | b2956 |
| CDS | − | 3097704 | 3098750 | ansB | b2957 |
| CDS | − | 3098926 | 3099645 | yggN | b2958 |
| CDS | − | 3099829 | 3100155 | yggL | b2959 |
| CDS | − | 3100155 | 3100874 | yggH | b2960 |
| CDS | + | 3101035 | 3102087 | mutY | b2961 |
| CDS | + | 3102115 | 3102390 | yggX | b2962 |
| CDS | + | 3102455 | 3103534 | mltC | b2963 |
| CDS | + | 3103736 | 3104992 | nupG | b2964 |
| CDS | − | 3105042 | 3107177 | speC | b2965 |
| CDS | + | 3107575 | 3108282 | yqgA | b2966 |
| tRNA | + | 3108388 | 3108463 | pheV | b2967 |
| CDS | − | 3108612 | 3109148 | yghD | b2968 |
| CDS | − | 3109150 | 3110010 | yghE | b2969 |
| CDS | − | 3110076 | 3110942 | yghF | b2970 |
| CDS | − | 3111089 | 3111499 | yghG | b2971 |
| CDS | − | 3111565 | 3112374 | pppA | b2972 |
| CDS | − | 3117619 | 3119301 | yghK | b2975 |
| CDS | − | 3119656 | 3121827 | glcB | b2976 |
| CDS | − | 3121849 | 3122253 | glcG | b2977 |
| CDS | − | 3124544 | 3126043 | glcD | b2979 |
| CDS | + | 3126294 | 3127058 | glcC | b2980 |
| CDS | − | 3127065 | 3128237 | yghO | b2981 |
| repeat_region | − | 3128168 | 3129362 | | |
| CDS | + | 3128200 | 3129216 | trs5_9 | b2982 |
| CDS | − | 3129363 | 3130430 | yghQ | b2983 |
| CDS | − | 3130476 | 3131234 | yghR | b2984 |
| CDS | − | 3131266 | 3131979 | yghS | b2985 |
| CDS | + | 3132153 | 3132845 | yghT | b2986 |
| CDS | − | 3132894 | 3134393 | pitB | b2987 |
| CDS | − | 3134685 | 3136544 | gss | b2988 |
| CDS | + | 3136749 | 3137615 | yghU | b2989 |
| CDS | − | 3137738 | 3137986 | hybG | b2990 |
| CDS | − | 3137999 | 3138340 | hybF | b2991 |
| CDS | − | 3138333 | 3138821 | hybE | b2992 |
| CDS | − | 3138814 | 3139308 | hybD | b2993 |
| CDS | − | 3139308 | 3141011 | hybC | b2994 |
| CDS | − | 3141008 | 3142186 | hybB | b2995 |
| CDS | − | 3142176 | 3143162 | hybA | b2996 |
| CDS | − | 3143165 | 3144283 | hybO | b2997 |
| CDS | − | 3144472 | 3144759 | yghW | b2998 |
| CDS | − | 3144878 | 3145288 | | b2999 |
| CDS | − | 3145288 | 3145641 | | b3000 |
| CDS | + | 3145919 | 3146959 | yghZ | b3001 |
| CDS | − | 3146999 | 3147493 | yqhA | b3002 |
| CDS | + | 3147684 | 3148568 | yghA | b3003 |
| CDS | + | 3148744 | 3148989 | | b3004 |
| CDS | + | 3148840 | 3149265 | exbD | b3005 |
| CDS | + | 3149272 | 3150006 | exbB | b3006 |
| CDS | − | 3149999 | 3150154 | | b3007 |
| CDS | + | 3150258 | 3151445 | metC | b3008 |
| CDS | + | 3151585 | 3152244 | yghB | b3009 |
| CDS | − | 3152284 | 3153240 | yqhC | b3010 |
| CDS | + | 3153377 | 3154540 | yqhD | b3011 |
| CDS | + | 3154645 | 3155472 | dkgA | b3012 |
| CDS | + | 3155672 | 3156598 | yqhG | b3013 |
| CDS | + | 3156649 | 3156906 | yqhH | b3014 |
| CDS | − | 3159279 | 3160691 | sufI | b3017 |
| CDS | − | 3160766 | 3161503 | plsC | b3018 |
| CDS | − | 3161737 | 3163995 | parC | b3019 |
| CDS | − | 3164133 | 3165740 | ygiS | b3020 |
| CDS | − | 3165873 | 3166268 | ygiT | b3021 |
| CDS | − | 3166270 | 3166566 | ygiU | b3022 |
| CDS | − | 3166771 | 3167253 | | b3023 |
| CDS | + | 3167306 | 3167698 | ygiW | b3024 |
| CDS | + | 3167850 | 3168509 | ygiX | b3025 |
| CDS | + | 3168506 | 3169855 | ygiY | b3026 |
| CDS | + | 3169901 | 3170233 | ygiZ | b3027 |
| CDS | + | 3170552 | 3171133 | mdaB | b3028 |
| CDS | + | 3171164 | 3171478 | ygiN | b3029 |
| CDS | − | 3171526 | 3173418 | parE | b3030 |
| CDS | − | 3173447 | 3174028 | yqiA | b3031 |
| CDS | − | 3174028 | 3174855 | cpdA | b3032 |
| CDS | − | 3174880 | 3175302 | yqiB | b3033 |
| CDS | − | 3175303 | 3175932 | yqiE | b3034 |
| CDS | + | 3176137 | 3177618 | tolC | b3035 |
| CDS | + | 3177618 | 3177878 | ygiA | b3036 |
| CDS | + | 3177862 | 3178437 | ygiB | b3037 |
| CDS | + | 3178443 | 3179603 | ygiC | b3038 |

TABLE 1-continued

| Type | S | Left | Right | Name | B |
|---|---|---|---|---|---|
| CDS | − | 3179641 | 3180456 | ygiD | b3039 |
| CDS | + | 3180572 | 3181345 | ygiE | b3040 |
| CDS | − | 3181835 | 3182488 | ribB | b3041 |
| CDS | + | 3182862 | 3183152 | yqiC | b3042 |
| CDS | + | 3183436 | 3183987 | ygiL | b3043 |
| repeat_region | − | 3184118 | 3185448 | | |
| CDS | + | 3184164 | 3184574 | yi21_5 | b3044 |
| CDS | + | 3184532 | 3185437 | yi22_5 | b3045 |
| CDS | + | 3185422 | 3187887 | yqiG | b3046 |
| CDS | + | 3187903 | 3188652 | yqiH | b3047 |
| CDS | + | 3188654 | 3189718 | yqiI | b3048 |
| CDS | − | 3189761 | 3189961 | glgS | b3049 |
| CDS | + | 3190230 | 3190859 | yqiJ | b3050 |
| CDS | + | 3190886 | 3192547 | yqiK | b3051 |
| CDS | − | 3193342 | 3194775 | rfaE | b3052 |
| CDS | − | 3194823 | 3197663 | glnE | b3053 |
| CDS | − | 3197686 | 3198987 | ygiF | b3054 |
| CDS | + | 3199229 | 3199849 | ygiM | b3055 |
| CDS | + | 3199913 | 3201151 | cca | b3056 |
| CDS | − | 3201332 | 3202153 | bacA | b3057 |
| CDS | − | 3202243 | 3202611 | ygiG | b3058 |
| CDS | + | 3202716 | 3203333 | ygiH | b3059 |
| CDS | − | 3203346 | 3204278 | ygiP | b3060 |
| CDS | + | 3204485 | 3205396 | ttdA | b3061 |
| CDS | + | 3205393 | 3205998 | ttdB | b3062 |
| CDS | + | 3206046 | 3207509 | ygjE | b3063 |
| CDS | − | 3207552 | 3208565 | ygjD | b3064 |
| CDS | + | 3208803 | 3209018 | rpsU | b3065 |
| CDS | + | 3209129 | 3210874 | dnaG | b3066 |
| CDS | + | 3211069 | 3212910 | rpoD | b3067 |
| CDS | − | 3212989 | 3213495 | ygjF | b3068 |
| tRNA | + | 3213620 | 3213695 | ileX | b3069 |
| CDS | − | 3213749 | 3214513 | yqjH | b3070 |
| CDS | + | 3214801 | 3215424 | yqjI | b3071 |
| CDS | − | 3215578 | 3217098 | aer | b3072 |
| CDS | + | 3217489 | 3218895 | ygjG | b3073 |
| CDS | − | 3218937 | 3219269 | ygjH | b3074 |
| CDS | + | 3219488 | 3220471 | ebgR | b3075 |
| CDS | + | 3220655 | 3223747 | ebgA | b3076 |
| CDS | + | 3223744 | 3224193 | ebgC | b3077 |
| CDS | + | 3224256 | 3225689 | ygjI | b3078 |
| CDS | + | 3225823 | 3226893 | ygjJ | b3079 |
| CDS | + | 3226910 | 3229261 | ygjK | b3080 |
| CDS | + | 3229687 | 3231705 | fadH | b3081 |
| CDS | − | 3231750 | 3232166 | ygjM | b3082 |
| CDS | − | 3232163 | 3232477 | ygjN | b3083 |
| CDS | − | 3232761 | 3233897 | ygjO | b3084 |
| CDS | + | 3233982 | 3234485 | ygjP | b3085 |
| CDS | + | 3234562 | 3235254 | ygjQ | b3086 |
| CDS | + | 3235315 | 3236319 | ygjR | b3087 |
| CDS | + | 3236602 | 3237567 | ygjT | b3088 |
| CDS | + | 3237966 | 3239210 | ygjU | b3089 |
| CDS | − | 3239215 | 3239766 | ygjV | b3090 |
| CDS | − | 3239849 | 3241336 | uxaA | b3091 |
| CDS | − | 3241351 | 3242763 | uxaC | b3092 |
| CDS | + | 3243126 | 3244544 | exuT | b3093 |
| CDS | + | 3244674 | 3245450 | exuR | b3094 |
| CDS | + | 3245795 | 3246457 | yqjA | b3095 |
| CDS | + | 3246461 | 3246844 | yqjB | b3096 |
| CDS | + | 3246991 | 3247359 | yqjC | b3097 |
| CDS | + | 3247397 | 3247702 | yqjD | b3098 |
| CDS | + | 3247705 | 3248109 | yqjE | b3099 |
| CDS | + | 3248099 | 3248398 | yqjK | b3100 |
| CDS | + | 3248584 | 3248976 | yqjF | b3101 |
| CDS | + | 3249046 | 3250032 | yqjG | b3102 |
| CDS | + | 3250326 | 3250691 | yhaH | b3103 |
| CDS | + | 3250933 | 3251289 | yhaI | b3104 |
| CDS | − | 3251340 | 3252236 | yhaJ | b3105 |
| CDS | + | 3252341 | 3253042 | yhaK | b3106 |
| CDS | + | 3253065 | 3253229 | yhaL | b3107 |
| CDS | − | 3254701 | 3255969 | yhaO | b3110 |
| CDS | − | 3257743 | 3258132 | tdcF | b3113 |
| CDS | − | 3258146 | 3260440 | tdcE | b3114 |
| CDS | − | 3260474 | 3261694 | tdcD | b3115 |
| CDS | − | 3261708 | 3263039 | tdcC | b3116 |
| CDS | − | 3263061 | 3264050 | tdcB | b3117 |
| CDS | − | 3264149 | 3265087 | tdcA | b3118 |
| CDS | + | 3265402 | 3265620 | tdcR | b3119 |
| CDS | + | 3265876 | 3266415 | yhaB | b3120 |
| CDS | + | 3266437 | 3267624 | yhaC | b3121 |
| misc_RNA | − | 3268238 | 3268614 | rnpB | b3123 |
| CDS | − | 3268647 | 3269873 | garK | b3124 |
| CDS | − | 3269889 | 3270779 | garR | b3125 |
| CDS | − | 3270809 | 3271579 | garL | b3126 |
| CDS | − | 3271595 | 3272929 | garP | b3127 |
| CDS | + | 3273304 | 3274875 | garD | b3128 |
| CDS | + | 3275024 | 3275359 | sohA | b3129 |
| CDS | + | 3275359 | 3275823 | yhaV | b3130 |
| CDS | − | 3275878 | 3276687 | agaR | b3131 |
| CDS | + | 3276936 | 3278216 | agaZ | b3132 |
| CDS | + | 3278239 | 3278712 | agaV | b3133 |
| CDS | + | 3278723 | 3279124 | agaW | b3134 |
| CDS | + | 3279144 | 3279647 | agaA | b3135 |
| CDS | + | 3279998 | 3281152 | agaS | b3136 |
| CDS | + | 3281165 | 3282025 | agaY | b3137 |
| CDS | + | 3282192 | 3282668 | agaB | b3138 |
| CDS | + | 3282707 | 3283510 | agaC | b3139 |
| CDS | + | 3283500 | 3284291 | agaD | b3140 |
| CDS | + | 3284292 | 3285047 | agaI | b3141 |
| CDS | + | 3285448 | 3286032 | yraH | b3142 |
| CDS | + | 3286112 | 3286807 | yraI | b3143 |
| CDS | + | 3286836 | 3289352 | yraJ | b3144 |
| CDS | + | 3289363 | 3290454 | yraK | b3145 |
| CDS | − | 3290497 | 3291357 | yraL | b3146 |
| CDS | + | 3291422 | 3293458 | yraM | b3147 |
| CDS | + | 3293416 | 3293811 | yraN | b3148 |
| CDS | + | 3293831 | 3294421 | yraO | b3149 |
| CDS | + | 3294431 | 3295006 | yraP | b3150 |
| CDS | − | 3295120 | 3296160 | yraQ | b3151 |
| CDS | − | 3296233 | 3296868 | yraR | b3152 |
| CDS | + | 3296996 | 3297514 | yhbO | b3153 |
| CDS | − | 3297494 | 3297937 | yhbP | b3154 |
| CDS | + | 3297988 | 3298290 | yhbQ | b3155 |
| CDS | − | 3298277 | 3298780 | yhbS | b3156 |
| CDS | − | 3298774 | 3299298 | yhbT | b3157 |
| CDS | + | 3299507 | 3300502 | yhbU | b3158 |
| CDS | + | 3300511 | 3301389 | yhbV | b3159 |
| CDS | + | 3301470 | 3302477 | yhbW | b3160 |
| CDS | − | 3302595 | 3303839 | mtr | b3161 |
| CDS | − | 3303993 | 3305882 | deaD | b3162 |
| CDS | − | 3306062 | 3306946 | nlpI | b3163 |
| CDS | − | 3307055 | 3309259 | pnp | b3164 |
| CDS | − | 3309437 | 3309706 | rpsO | b3165 |
| CDS | − | 3309855 | 3310799 | truB | b3166 |
| CDS | − | 3310799 | 3311200 | rbfA | b3167 |
| CDS | − | 3311364 | 3314036 | infB | b3168 |
| CDS | − | 3314061 | 3315548 | nusA | b3169 |
| CDS | − | 3315576 | 3316028 | yhbC | b3170 |
| tRNA | − | 3316235 | 3316311 | metY | b3171 |
| CDS | + | 3316659 | 3318002 | argG | b3172 |
| CDS | − | 3318010 | 3319635 | yhbX | b3173 |
| tRNA | − | 3320094 | 3320180 | leuU | b3174 |
| CDS | − | 3320195 | 3320527 | secG | b3175 |
| CDS | − | 3320755 | 3322092 | glmM | b3176 |
| CDS | − | 3322085 | 3322933 | folP | b3177 |
| CDS | − | 3323023 | 3324957 | hflB | b3178 |
| CDS | − | 3325057 | 3325686 | rrmJ | b3179 |
| CDS | + | 3325812 | 3326105 | yhbY | b3180 |
| CDS | − | 3326261 | 3326737 | greA | b3181 |
| CDS | + | 3326985 | 3328418 | dacB | b3182 |
| CDS | − | 3328604 | 3329776 | yhbZ | b3183 |
| CDS | − | 3329792 | 3330757 | yhbE | b3184 |
| CDS | − | 3330884 | 3331141 | rpmA | b3185 |
| CDS | − | 3331162 | 3331473 | rplU | b3186 |
| CDS | + | 3331732 | 3332703 | ispB | b3187 |
| CDS | + | 3332931 | 3333209 | nlp | b3188 |
| CDS | − | 3333257 | 3334516 | murA | b3189 |
| CDS | − | 3334571 | 3334825 | yrbA | b3190 |
| CDS | − | 3334985 | 3335278 | yrbB | b3191 |
| CDS | − | 3335278 | 3335913 | yrbC | b3192 |
| CDS | − | 3335932 | 3336483 | yrbD | b3193 |
| CDS | − | 3336488 | 3337270 | yrbE | b3194 |
| CDS | − | 3337278 | 3338087 | yrbF | b3195 |
| CDS | + | 3338297 | 3339274 | yrbG | b3196 |
| CDS | + | 3339288 | 3340274 | yrbH | b3197 |
| CDS | + | 3340295 | 3340861 | yrbI | b3198 |

TABLE 1-continued

| Type | S | Left | Right | Name | B |
|---|---|---|---|---|---|
| CDS | + | 3340858 | 3341433 | yrbK | b3199 |
| CDS | + | 3341402 | 3341959 | yhbN | b3200 |
| CDS | + | 3341966 | 3342691 | yhbG | b3201 |
| CDS | + | 3342739 | 3344172 | rpoN | b3202 |
| CDS | + | 3344195 | 3344482 | yhbH | b3203 |
| CDS | + | 3344600 | 3345091 | ptsN | b3204 |
| CDS | + | 3345137 | 3345991 | yhbJ | b3205 |
| CDS | + | 3345988 | 3346260 | ptsO | b3206 |
| CDS | + | 3346474 | 3347106 | yrbL | b3207 |
| CDS | − | 3347103 | 3347831 | mtgA | b3208 |
| CDS | − | 3347828 | 3348481 | yhbL | b3209 |
| CDS | − | 3348711 | 3351047 | arcB | b3210 |
| CDS | − | 3351143 | 3352072 | yhcC | b3211 |
| CDS | + | 3352654 | 3357207 | gltB | b3212 |
| CDS | + | 3357220 | 3358638 | gltD | b3213 |
| CDS | + | 3359198 | 3359962 | gltF | b3214 |
| CDS | + | 3360134 | 3360808 | yhcA | b3215 |
| CDS | + | 3360829 | 3363210 | yhcD | b3216 |
| CDS | + | 3363207 | 3363686 | yhcE | b3217 |
| repeat_region | + | 3363578 | 3364772 | | |
| CDS | − | 3363724 | 3364740 | trs5_10 | b3218 |
| CDS | + | 3364948 | 3365664 | yhcF | b3219 |
| CDS | + | 3365849 | 3366976 | yhcG | b3220 |
| CDS | − | 3367036 | 3367500 | yhcH | b3221 |
| CDS | − | 3367497 | 3368372 | nanK | b3222 |
| CDS | − | 3368369 | 3369058 | nanE | b3223 |
| CDS | − | 3369106 | 3370224 | nanT | b3224 |
| CDS | − | 3370705 | 3371598 | nanA | b3225 |
| CDS | − | 3371720 | 3372511 | nanR | b3226 |
| CDS | + | 3372891 | 3374258 | dcuD | b3227 |
| CDS | − | 3374178 | 3374798 | sspB | b3228 |
| CDS | − | 3374804 | 3375442 | sspA | b3229 |
| CDS | − | 3375837 | 3376229 | rpsI | b3230 |
| CDS | − | 3376245 | 3376673 | rplM | b3231 |
| CDS | − | 3376892 | 3378019 | yhcM | b3232 |
| CDS | + | 3378213 | 3378611 | yhcB | b3233 |
| CDS | + | 3378765 | 3380132 | degQ | b3234 |
| CDS | + | 3380222 | 3381289 | degS | b3235 |
| CDS | − | 3381352 | 3382290 | mdh | b3236 |
| CDS | + | 3382725 | 3383195 | argR | b3237 |
| CDS | + | 3383560 | 3383823 | yhcN | b3238 |
| CDS | − | 3383879 | 3384151 | yhcO | b3239 |
| CDS | − | 3384243 | 3386210 | yhcP | b3240 |
| CDS | − | 3386216 | 3387148 | yhcQ | b3241 |
| CDS | − | 3387156 | 3387359 | yhcR | b3242 |
| CDS | + | 3387542 | 3388471 | yhcS | b3243 |
| CDS | − | 3388605 | 3390050 | tldD | b3244 |
| CDS | − | 3394348 | 3395817 | rng | b3247 |
| CDS | − | 3395807 | 3396400 | yhdE | b3248 |
| CDS | − | 3396409 | 3396897 | mreD | b3249 |
| CDS | − | 3396897 | 3398000 | mreC | b3250 |
| CDS | − | 3398066 | 3399109 | mreB | b3251 |
| CDS | − | 3399414 | 3401354 | yhdA | b3252 |
| CDS | + | 3401506 | 3402480 | yhdH | b3253 |
| CDS | − | 3402538 | 3402639 | | b3254 |
| CDS | + | 3403458 | 3403928 | accB | b3255 |
| CDS | + | 3403939 | 3405288 | accC | b3256 |
| CDS | + | 3405397 | 3405639 | yhdT | b3257 |
| CDS | + | 3405629 | 3407080 | panF | b3258 |
| CDS | + | 3407092 | 3407973 | prmA | b3259 |
| CDS | + | 3408302 | 3409267 | yhdG | b3260 |
| CDS | + | 3409293 | 3409589 | fis | b3261 |
| CDS | + | 3409675 | 3410559 | yhdJ | b3262 |
| CDS | + | 3410643 | 3410822 | yhdU | b3263 |
| CDS | − | 3410825 | 3411487 | envR | b3264 |
| CDS | + | 3411886 | 3413043 | acrE | b3265 |
| CDS | + | 3413055 | 3416159 | acrF | b3266 |
| CDS | + | 3416412 | 3416633 | yhdV | b3267 |
| CDS | + | 3417171 | 3418088 | yhdW | b3268 |
| CDS | + | 3418156 | 3419337 | yhdX | b3269 |
| CDS | + | 3419347 | 3420450 | yhdY | b3270 |
| CDS | + | 3420458 | 3421216 | yhdZ | b3271 |
| rRNA | − | 3421445 | 3421564 | rrfF | b3272 |
| tRNA | − | 3421602 | 3421677 | thrV | b3273 |
| rRNA | − | 3421690 | 3421809 | rrfD | b3274 |
| rRNA | − | 3421902 | 3424805 | rrlD | b3275 |
| tRNA | − | 3424980 | 3425055 | alaU | b3276 |
| tRNA | − | 3425098 | 3425174 | ileU | b3277 |
| rRNA | − | 3425243 | 3426784 | rrsD | b3278 |
| CDS | + | 3427258 | 3427812 | yrdA | b3279 |
| CDS | − | 3427788 | 3428045 | yrdB | b3280 |
| CDS | − | 3428042 | 3428860 | aroE | b3281 |
| CDS | − | 3428865 | 3429437 | yrdC | b3282 |
| CDS | − | 3429442 | 3429984 | yrdD | b3283 |
| CDS | − | 3430013 | 3430486 | smg | b3284 |
| CDS | + | 3431712 | 3432221 | def | b3287 |
| CDS | + | 3432236 | 3433183 | fmt | b3288 |
| CDS | + | 3433229 | 3434518 | rsmB | b3289 |
| CDS | + | 3434540 | 3435916 | trkA | b3290 |
| CDS | + | 3436046 | 3436456 | mscL | b3291 |
| CDS | − | 3436727 | 3437152 | zntR | b3292 |
| CDS | − | 3437163 | 3437531 | yhdN | b3293 |
| CDS | − | 3437638 | 3438021 | rplQ | b3294 |
| CDS | − | 3438062 | 3439051 | rpoA | b3295 |
| CDS | − | 3439077 | 3439697 | rpsD | b3296 |
| CDS | − | 3439731 | 3440120 | rpsK | b3297 |
| CDS | − | 3440137 | 3440493 | rpsM | b3298 |
| CDS | − | 3440640 | 3440756 | rpmJ | b3299 |
| CDS | − | 3440788 | 3442119 | prlA | b3300 |
| CDS | − | 3442127 | 3442561 | rplO | b3301 |
| CDS | − | 3442565 | 3442744 | rpmD | b3302 |
| CDS | − | 3442748 | 3443251 | rpsE | b3303 |
| CDS | − | 3443266 | 3443619 | rplR | b3304 |
| CDS | − | 3443629 | 3444162 | rplF | b3305 |
| CDS | − | 3444175 | 3444567 | rpsH | b3306 |
| CDS | − | 3444601 | 3444906 | rpsN | b3307 |
| CDS | − | 3444921 | 3445460 | rplE | b3308 |
| CDS | − | 3445475 | 3445789 | rplX | b3309 |
| CDS | − | 3445800 | 3446171 | rplN | b3310 |
| CDS | − | 3446336 | 3446590 | rpsQ | b3311 |
| CDS | − | 3446590 | 3446781 | rpmC | b3312 |
| CDS | − | 3446781 | 3447191 | rplP | b3313 |
| CDS | − | 3447204 | 3447905 | rpsC | b3314 |
| CDS | − | 3447923 | 3448255 | rplV | b3315 |
| CDS | − | 3448270 | 3448548 | rpsS | b3316 |
| CDS | − | 3448565 | 3449386 | rplB | b3317 |
| CDS | − | 3449404 | 3449706 | rplW | b3318 |
| CDS | − | 3449703 | 3450308 | rplD | b3319 |
| CDS | − | 3450319 | 3450948 | rplC | b3320 |
| CDS | − | 3450981 | 3451292 | rpsJ | b3321 |
| CDS | − | 3451530 | 3451949 | pioO | b3322 |
| CDS | − | 3451951 | 3453420 | gspA | b3323 |
| CDS | + | 3453600 | 3454415 | gspC | b3324 |
| CDS | + | 3454399 | 3456351 | gspD | b3325 |
| CDS | + | 3456361 | 3457842 | gspE | b3326 |
| CDS | + | 3457839 | 3459035 | gspF | b3327 |
| CDS | + | 3459045 | 3459482 | gspG | b3328 |
| CDS | + | 3459490 | 3459999 | gspH | b3329 |
| CDS | + | 3459996 | 3460373 | gspI | b3330 |
| CDS | + | 3460366 | 3460953 | gspJ | b3331 |
| CDS | + | 3460946 | 3461929 | gspK | b3332 |
| CDS | + | 3461944 | 3463107 | gspL | b3333 |
| CDS | + | 3463104 | 3463565 | gspM | b3334 |
| CDS | + | 3463565 | 3464242 | gspO | b3335 |
| CDS | − | 3464271 | 3464747 | bfr | b3336 |
| CDS | − | 3464819 | 3465013 | bfd | b3337 |
| CDS | − | 3465182 | 3467875 | chiA | b3338 |
| CDS | − | 3468167 | 3469351 | tufA | b3339 |
| CDS | − | 3469422 | 3471536 | fusA | b3340 |
| CDS | − | 3471564 | 3472103 | rpsG | b3341 |
| CDS | − | 3472200 | 3472574 | rpsL | b3342 |
| CDS | − | 3472700 | 3472987 | yheL | b3343 |
| CDS | − | 3472995 | 3473354 | yheM | b3344 |
| CDS | − | 3473354 | 3473740 | yheN | b3345 |
| CDS | − | 3473740 | 3474462 | yheO | b3346 |
| CDS | − | 3474629 | 3475441 | fkpA | b3347 |
| CDS | + | 3475662 | 3475880 | slyX | b3348 |
| CDS | − | 3475929 | 3476519 | slyD | b3349 |
| CDS | − | 3476824 | 3478629 | kefB | b3350 |
| CDS | − | 3478629 | 3479183 | yheR | b3351 |
| CDS | − | 3479311 | 3481224 | yheS | b3352 |
| CDS | + | 3481224 | 3482246 | yheT | b3353 |
| CDS | + | 3482240 | 3482458 | yheU | b3354 |
| CDS | + | 3482512 | 3483381 | prkB | b3355 |
| CDS | − | 3483436 | 3483840 | yhfA | b3356 |
| CDS | + | 3484142 | 3484774 | crp | b3357 |

TABLE 1-continued

| Type | S | Left | Right | Name | B |
|---|---|---|---|---|---|
| CDS | + | 3484813 | 3486915 | yhfK | b3358 |
| CDS | − | 3486982 | 3488202 | argD | b3359 |
| CDS | − | 3488288 | 3488851 | pabA | b3360 |
| CDS | − | 3488883 | 3489485 | fic | b3361 |
| CDS | − | 3489475 | 3489642 | yhfG | b3362 |
| CDS | − | 3489747 | 3490319 | ppiA | b3363 |
| CDS | + | 3490590 | 3491771 | yhfC | b3364 |
| CDS | + | 3492033 | 3494576 | nirB | b3365 |
| CDS | + | 3494573 | 3494899 | nirD | b3366 |
| CDS | + | 3495025 | 3495831 | nirC | b3367 |
| CDS | + | 3495850 | 3497223 | cysG | b3368 |
| CDS | + | 3497470 | 3497637 | yhfL | b3369 |
| CDS | + | 3497932 | 3499269 | yhfM | b3370 |
| CDS | + | 3499290 | 3500312 | yhfN | b3371 |
| CDS | + | 3501189 | 3501974 | yhfQ | b3374 |
| CDS | + | 3502074 | 3502805 | yhfR | b3375 |
| CDS | − | 3502957 | 3504042 | yhfS | b3376 |
| CDS | − | 3504054 | 3505358 | yhfT | b3377 |
| CDS | − | 3505370 | 3505723 | yhfU | b3378 |
| CDS | − | 3505734 | 3506612 | yhfV | b3379 |
| CDS | − | 3506609 | 3507835 | yhfW | b3380 |
| CDS | − | 3507835 | 3508998 | yhfX | b3381 |
| CDS | − | 3509082 | 3509444 | yhfY | b3382 |
| CDS | − | 3509461 | 3510366 | yhfZ | b3383 |
| CDS | − | 3510656 | 3511660 | trpS | b3384 |
| CDS | − | 3511653 | 3512411 | gph | b3385 |
| CDS | − | 3512404 | 3513081 | rpe | b3386 |
| CDS | − | 3513099 | 3513935 | dam | b3387 |
| CDS | − | 3514042 | 3515328 | damX | b3388 |
| CDS | − | 3515420 | 3516508 | aroB | b3389 |
| CDS | − | 3516565 | 3517086 | aroK | b3390 |
| CDS | − | 3517487 | 3518725 | hofQ | b3391 |
| CDS | − | 3518637 | 3519041 | yrfA | b3392 |
| CDS | − | 3519031 | 3519471 | yrfB | b3393 |
| CDS | − | 3519455 | 3519994 | yrfC | b3394 |
| CDS | − | 3519994 | 3520773 | yrfD | b3395 |
| CDS | + | 3520893 | 3523445 | mrcA | b3396 |
| CDS | − | 3523611 | 3524171 | yrfE | b3397 |
| CDS | + | 3524491 | 3526626 | yrfF | b3398 |
| CDS | + | 3526691 | 3527359 | yrfG | b3399 |
| CDS | + | 3527370 | 3527771 | hslR | b3400 |
| CDS | + | 3527796 | 3528674 | hslO | b3401 |
| CDS | − | 3528737 | 3530461 | yhgE | b3402 |
| CDS | + | 3530840 | 3532462 | pckA | b3403 |
| CDS | − | 3532538 | 3533890 | envZ | b3404 |
| CDS | − | 3533887 | 3534606 | ompR | b3405 |
| CDS | + | 3534834 | 3535310 | greB | b3406 |
| CDS | + | 3535407 | 3537728 | yhgF | b3407 |
| CDS | + | 3538185 | 3538412 | feoA | b3408 |
| CDS | + | 3538429 | 3540750 | feoB | b3409 |
| CDS | + | 3540750 | 3540986 | yhgG | b3410 |
| CDS | + | 3541189 | 3542067 | yhgA | b3411 |
| CDS | − | 3542096 | 3542866 | bioH | b3412 |
| CDS | + | 3542904 | 3543587 | yhgH | b3413 |
| CDS | + | 3543646 | 3544221 | yhgI | b3414 |
| CDS | + | 3544581 | 3545897 | gntT | b3415 |
| CDS | − | 3546008 | 3548092 | malQ | b3416 |
| CDS | − | 3548102 | 3550495 | malP | b3417 |
| CDS | + | 3551107 | 3553812 | malT | b3418 |
| CDS | − | 3554875 | 3556101 | rtcB | b3421 |
| CDS | + | 3556290 | 3557888 | rtcR | b3422 |
| CDS | − | 3557870 | 3558628 | glpR | b3423 |
| CDS | − | 3558645 | 3559475 | glpG | b3424 |
| CDS | − | 3559520 | 3559846 | glpE | b3425 |
| CDS | + | 3560036 | 3561541 | glpD | b3426 |
| CDS | − | 3561747 | 3562028 | yzgL | b3427 |
| CDS | − | 3562157 | 3564604 | glgP | b3428 |
| CDS | − | 3564623 | 3566056 | glgA | b3429 |
| CDS | − | 3566056 | 3567351 | glgC | b3430 |
| CDS | − | 3567369 | 3569342 | glgX | b3431 |
| CDS | − | 3569339 | 3571525 | glgB | b3432 |
| CDS | − | 3571798 | 3572901 | asd | b3433 |
| CDS | + | 3573094 | 3573687 | yhgN | b3434 |
| CDS | − | 3575088 | 3575615 | gntK | b3437 |
| CDS | − | 3575754 | 3576749 | gntR | b3438 |
| CDS | − | 3576973 | 3577668 | yhhW | b3439 |
| CDS | − | 3577791 | 3578828 | yhhX | b3440 |
| CDS | + | 3579161 | 3579649 | yhhY | b3441 |
| CDS | + | 3579886 | 3581064 | yhhZ | b3442 |
| CDS | + | 3581064 | 3581477 | yrhA | b3443 |
| repeat_region | + | 3581451 | 3582218 | | |
| CDS | + | 3581506 | 3581781 | insA_6 | b3444 |
| CDS | + | 3581700 | 3582203 | insB_6 | b3445 |
| CDS | + | 3582782 | 3583066 | yrhB | b3446 |
| CDS | − | 3583104 | 3584846 | ggt | b3447 |
| CDS | + | 3584966 | 3585406 | yhhA | b3448 |
| CDS | − | 3585393 | 3586136 | ugpQ | b3449 |
| CDS | − | 3586133 | 3587203 | ugpC | b3450 |
| CDS | − | 3587205 | 3588050 | ugpE | b3451 |
| CDS | − | 3588047 | 3588934 | ugpA | b3452 |
| CDS | − | 3589032 | 3590348 | ugpB | b3453 |
| CDS | − | 3590747 | 3591460 | livF | b3454 |
| CDS | − | 3591462 | 3592229 | livG | b3455 |
| CDS | − | 3592226 | 3593503 | livM | b3456 |
| CDS | − | 3593500 | 3594426 | livH | b3457 |
| CDS | − | 3594474 | 3595583 | livK | b3458 |
| CDS | + | 3596007 | 3596390 | yhhK | b3459 |
| CDS | − | 3596578 | 3597681 | livJ | b3460 |
| CDS | − | 3597952 | 3598806 | rpoH | b3461 |
| CDS | − | 3599051 | 3600109 | ftsX | b3462 |
| CDS | − | 3600102 | 3600770 | ftsE | b3463 |
| CDS | − | 3600773 | 3602266 | ftsY | b3464 |
| CDS | + | 3602416 | 3603012 | yhhF | b3465 |
| CDS | + | 3603002 | 3603271 | yhhL | b3466 |
| CDS | − | 3603274 | 3603633 | yhhM | b3467 |
| CDS | + | 3603774 | 3604400 | yhhN | b3468 |
| CDS | + | 3604474 | 3606672 | zntA | b3469 |
| CDS | − | 3606774 | 3607019 | sirA | b3470 |
| CDS | + | 3607240 | 3607905 | yhhQ | b3471 |
| CDS | + | 3607978 | 3608535 | dcrB | b3472 |
| CDS | − | 3608539 | 3609756 | yhhS | b3473 |
| CDS | + | 3609888 | 3610937 | yhhT | b3474 |
| CDS | + | 3610992 | 3611579 | acpT | b3475 |
| CDS | + | 3611690 | 3613264 | nikA | b3476 |
| CDS | + | 3613264 | 3614208 | nikB | b3477 |
| CDS | + | 3614205 | 3615038 | nikC | b3478 |
| CDS | + | 3615038 | 3615802 | nikD | b3479 |
| CDS | + | 3615799 | 3616605 | nikE | b3480 |
| CDS | + | 3616611 | 3617012 | nikR | b3481 |
| CDS | + | 3617215 | 3621450 | rhsB | b3482 |
| CDS | + | 3621422 | 3621805 | yhhH | b3483 |
| CDS | + | 3622401 | 3623537 | yhhI | b3484 |
| CDS | − | 3623702 | 3624826 | yhhJ | b3485 |
| CDS | − | 3624826 | 3627561 | yhiH | b3486 |
| CDS | − | 3627558 | 3628625 | yhiI | b3487 |
| CDS | − | 3628991 | 3630613 | yhiJ | b3488 |
| CDS | − | 3630875 | 3631267 | yhiK | b3489 |
| CDS | − | 3631243 | 3632481 | yhiL | b3490 |
| CDS | + | 3632864 | 3633916 | yhiM | b3491 |
| CDS | − | 3634231 | 3635433 | yhiN | b3492 |
| CDS | + | 3635665 | 3637164 | pitA | b3493 |
| CDS | − | 3637408 | 3637743 | yhiO | b3494 |
| CDS | + | 3638134 | 3638568 | uspA | b3495 |
| CDS | + | 3638885 | 3640354 | yhiP | b3496 |
| CDS | − | 3640403 | 3641155 | yhiQ | b3497 |
| CDS | − | 3641163 | 3643205 | prlC | b3498 |
| CDS | + | 3643408 | 3644250 | yhiR | b3499 |
| CDS | + | 3644322 | 3645674 | gor | b3500 |
| CDS | + | 3646551 | 3646904 | arsR | b3501 |
| CDS | + | 3646958 | 3648247 | arsB | b3502 |
| CDS | + | 3648260 | 3648685 | arsC | b3503 |
| CDS | + | 3649314 | 3650096 | yhiS | b3504 |
| repeat_region | + | 3650059 | 3651253 | | |
| CDS | − | 3650205 | 3651221 | trs5_11 | b3505 |
| CDS | + | 3651984 | 3652550 | slp | b3506 |
| CDS | + | 3652706 | 3653236 | yhiF | b3507 |
| CDS | − | 3653278 | 3653925 | yhiD | b3508 |
| CDS | − | 3653989 | 3654315 | hdeB | b3509 |
| CDS | − | 3654431 | 3654763 | hdeA | b3510 |
| CDS | + | 3655018 | 3655590 | hdeD | b3511 |
| CDS | + | 3656389 | 3656916 | yhiE | b3512 |
| CDS | + | 3657255 | 3658412 | yhiU | b3513 |
| CDS | + | 3658437 | 3661550 | yhiV | b3514 |
| CDS | − | 3661913 | 3662641 | yhiW | b3515 |
| CDS | − | 3663009 | 3663833 | gadX | b3516 |
| CDS | − | 3664203 | 3665603 | gadA | b3517 |

TABLE 1-continued

| Type | S | Left | Right | Name | B |
|---|---|---|---|---|---|
| CDS | − | 3665814 | 3667211 | yhjA | b3518 |
| CDS | + | 3667615 | 3669264 | treF | b3519 |
| CDS | − | 3669315 | 3669917 | yhjB | b3520 |
| CDS | + | 3670365 | 3671336 | yhjC | b3521 |
| CDS | + | 3671385 | 3672398 | yhjD | b3522 |
| CDS | + | 3672809 | 3674131 | yhjE | b3523 |
| CDS | − | 3674313 | 3676388 | yhjG | b3524 |
| CDS | − | 3676443 | 3677210 | yhjH | b3525 |
| CDS | + | 3677442 | 3678371 | kdgK | b3526 |
| CDS | − | 3678467 | 3679963 | yhjJ | b3527 |
| CDS | − | 3680184 | 3681470 | dctA | b3528 |
| CDS | − | 3681653 | 3683602 | yhjK | b3529 |
| CDS | − | 3683723 | 3687196 | yhjL | b3530 |
| CDS | − | 3687178 | 3688284 | bcsC | b3531 |
| CDS | − | 3688291 | 3690630 | yhjN | b3532 |
| CDS | − | 3690641 | 3693259 | yhjO | b3533 |
| CDS | − | 3693256 | 3693984 | yhjQ | b3534 |
| CDS | − | 3694020 | 3694208 | yhjR | b3535 |
| CDS | + | 3694481 | 3696052 | yhjS | b3536 |
| CDS | + | 3696049 | 3696240 | yhjT | b3537 |
| CDS | + | 3696237 | 3697916 | yhjU | b3538 |
| CDS | + | 3698586 | 3699857 | yhjV | b3539 |
| CDS | − | 3699887 | 3700891 | dppF | b3540 |
| CDS | − | 3700888 | 3701871 | dppD | b3541 |
| CDS | − | 3701882 | 3702784 | dppC | b3542 |
| CDS | − | 3702794 | 3703813 | dppB | b3543 |
| CDS | − | 3704121 | 3705728 | dppA | b3544 |
| tRNA | − | 3706639 | 3706715 | proK | b3545 |
| CDS | − | 3706807 | 3708498 | yhjW | b3546 |
| CDS | − | 3708822 | 3710030 | yhjX | b3547 |
| CDS | − | 3710259 | 3710957 | yhjY | b3548 |
| CDS | + | 3711115 | 3711678 | tag | b3549 |
| CDS | + | 3711675 | 3712115 | yiaC | b3550 |
| CDS | − | 3712084 | 3714363 | bisC | b3551 |
| CDS | + | 3714570 | 3715229 | yiaD | b3552 |
| CDS | + | 3715333 | 3716307 | tkrA | b3553 |
| CDS | − | 3716357 | 3717067 | yiaF | b3554 |
| CDS | + | 3717501 | 3717791 | yiaG | b3555 |
| CDS | + | 3718072 | 3718284 | cspA | b3556 |
| repeat_region | + | 3718656 | 3720098 | | |
| CDS | + | 3718703 | 3719224 | yi5A | b3557 |
| CDS | + | 3719221 | 3720072 | t150 | b3558 |
| CDS | − | 3720351 | 3722420 | glyS | b3559 |
| CDS | − | 3722430 | 3723341 | glyQ | b3560 |
| CDS | + | 3723910 | 3724905 | yiaH | b3561 |
| CDS | − | 3724947 | 3725384 | yiaA | b3562 |
| CDS | − | 3725430 | 3725771 | yiaB | b3563 |
| CDS | − | 3725940 | 3727394 | xylB | b3564 |
| CDS | − | 3727466 | 3728788 | xylA | b3565 |
| CDS | + | 3729154 | 3730146 | xylF | b3566 |
| CDS | + | 3730224 | 3731765 | xylG | b3567 |
| CDS | + | 3731743 | 3732924 | xylH | b3568 |
| CDS | + | 3733002 | 3734180 | xylR | b3569 |
| CDS | − | 3734376 | 3735200 | bax | b3570 |
| CDS | + | 3735520 | 3737550 | malS | b3571 |
| CDS | + | 3737728 | 3738981 | avtA | b3572 |
| CDS | − | 3739132 | 3739605 | yiaI | b3573 |
| CDS | − | 3739707 | 3740555 | yiaJ | b3574 |
| CDS | + | 3740756 | 3741754 | yiaK | b3575 |
| CDS | + | 3741766 | 3742233 | yiaL | b3576 |
| CDS | + | 3742351 | 3742824 | yiaM | b3577 |
| CDS | + | 3742827 | 3744104 | yiaN | b3578 |
| CDS | + | 3744117 | 3745103 | yiaO | b3579 |
| CDS | + | 3745107 | 3746603 | lyxK | b3580 |
| CDS | + | 3746600 | 3747262 | sgbH | b3581 |
| CDS | + | 3747255 | 3748115 | sgbU | b3582 |
| CDS | + | 3748109 | 3748804 | sgbE | b3583 |
| CDS | − | 3749151 | 3749891 | yiaT | b3584 |
| CDS | + | 3750015 | 3750989 | yiaU | b3585 |
| CDS | − | 3750986 | 3752122 | yiaV | b3586 |
| CDS | − | 3752128 | 3752451 | yiaW | b3587 |
| CDS | − | 3752996 | 3754534 | aldB | b3588 |
| CDS | − | 3754699 | 3755850 | yiaY | b3589 |
| CDS | − | 3756040 | 3757884 | selB | b3590 |
| CDS | − | 3757881 | 3759272 | selA | b3591 |
| CDS | − | 3759370 | 3759978 | yibF | b3592 |
| CDS | + | 3760206 | 3764339 | rhsA | b3593 |
| CDS | + | 3764360 | 3765202 | yibA | b3594 |
| CDS | + | 3765244 | 3765945 | yibJ | b3595 |
| CDS | + | 3766200 | 3766661 | yibG | b3596 |
| CDS | − | 3768266 | 3769402 | yibH | b3597 |
| CDS | − | 3769405 | 3769767 | yibI | b3598 |
| CDS | + | 3770304 | 3772217 | mtlA | b3599 |
| CDS | + | 3772447 | 3773595 | mtlD | b3600 |
| CDS | + | 3773595 | 3774182 | mtlR | b3601 |
| CDS | + | 3774688 | 3775050 | yibL | b3602 |
| CDS | + | 3775422 | 3777077 | lldP | b3603 |
| CDS | + | 3777077 | 3777853 | lldR | b3604 |
| CDS | + | 3777850 | 3779040 | lldD | b3605 |
| CDS | + | 3779238 | 3779711 | ylbK | b3606 |
| CDS | − | 3779764 | 3780585 | cysE | b3607 |
| CDS | − | 3780665 | 3781684 | gpsA | b3608 |
| CDS | − | 3781684 | 3782151 | secB | b3609 |
| CDS | − | 3782214 | 3782465 | grxC | b3610 |
| CDS | − | 3782607 | 3783038 | yibN | b3611 |
| CDS | + | 3783283 | 3784827 | yibO | b3612 |
| CDS | + | 3784861 | 3786120 | yibP | b3613 |
| CDS | + | 3786124 | 3787083 | yibQ | b3614 |
| CDS | − | 3787070 | 3788104 | yibD | b3615 |
| CDS | − | 3788343 | 3789368 | tdh | b3616 |
| CDS | − | 3789378 | 3790574 | kbl | b3617 |
| CDS | − | 3790849 | 3791706 | htrL | b3618 |
| CDS | + | 3792010 | 3792942 | rfaD | b3619 |
| CDS | + | 3792952 | 3793998 | rfaF | b3620 |
| CDS | + | 3794002 | 3794961 | rfaC | b3621 |
| CDS | + | 3794971 | 3796230 | rfaL | b3622 |
| CDS | − | 3796262 | 3797335 | rfaK | b3623 |
| CDS | − | 3797368 | 3798219 | rfaZ | b3624 |
| CDS | − | 3798290 | 3798988 | rfaY | b3625 |
| CDS | − | 3799006 | 3800022 | rfaJ | b3626 |
| CDS | − | 3800062 | 3801081 | rfaI | b3627 |
| CDS | − | 3801081 | 3802190 | rfaB | b3628 |
| CDS | − | 3802204 | 3803139 | rfaS | b3629 |
| CDS | − | 3803176 | 3803973 | rfaP | b3630 |
| CDS | − | 3803966 | 3805090 | rfaG | b3631 |
| CDS | − | 3805087 | 3806121 | rfaQ | b3632 |
| CDS | + | 3806563 | 3807840 | kdtA | b3633 |
| CDS | + | 3807848 | 3808327 | coaD | b3634 |
| CDS | − | 3808366 | 3809175 | mutM | b3635 |
| CDS | − | 3809273 | 3809440 | rpmG | b3636 |
| CDS | − | 3809461 | 3809697 | rpmB | b3637 |
| CDS | − | 3809914 | 3810582 | radC | b3638 |
| CDS | + | 3810754 | 3811974 | dfp | b3639 |
| CDS | + | 3811955 | 3812410 | dut | b3640 |
| CDS | + | 3812517 | 3813113 | ttk | b3641 |
| CDS | − | 3813150 | 3813791 | pyrE | b3642 |
| CDS | − | 3813886 | 3814572 | rph | b3643 |
| CDS | + | 3814699 | 3815562 | yicC | b3644 |
| CDS | + | 3815783 | 3816607 | dinD | b3645 |
| CDS | + | 3816897 | 3817514 | yicG | b3646 |
| CDS | − | 3817511 | 3819193 | yicF | b3647 |
| CDS | + | 3819451 | 3820074 | gmk | b3648 |
| CDS | + | 3820129 | 3820404 | rpoZ | b3649 |
| CDS | + | 3820423 | 3822531 | spoT | b3650 |
| CDS | + | 3822538 | 3823227 | trmH | b3651 |
| CDS | + | 3823233 | 3825314 | recG | b3652 |
| CDS | + | 3825483 | 3826688 | gltS | b3653 |
| CDS | + | 3826968 | 3828359 | yicE | b3654 |
| CDS | + | 3828480 | 3830189 | yicH | b3655 |
| CDS | − | 3830242 | 3832560 | yicI | b3656 |
| CDS | − | 3832570 | 3833952 | yicJ | b3657 |
| tRNA | + | 3834245 | 3834339 | selC | b3658 |
| CDS | + | 3834976 | 3836160 | yicK | b3659 |
| CDS | + | 3836271 | 3837194 | yicL | b3660 |
| CDS | − | 3837198 | 3838016 | nlpA | b3661 |
| CDS | − | 3838572 | 3839927 | yicM | b3662 |
| CDS | + | 3839973 | 3840425 | yicN | b3663 |
| CDS | − | 3840478 | 3841812 | yicO | b3664 |
| CDS | + | 3841987 | 3843753 | ade | b3665 |
| CDS | − | 3843799 | 3845190 | uhpT | b3666 |
| CDS | − | 3845328 | 3846647 | uhpC | b3667 |
| CDS | − | 3846657 | 3848159 | uhpB | b3668 |
| CDS | − | 3848159 | 3848749 | uhpA | b3669 |
| CDS | − | 3848825 | 3849115 | ilvN | b3670 |
| CDS | − | 3849119 | 3850807 | ilvB | b3671 |
| CDS | − | 3850913 | 3851011 | ivbL | b3672 |

TABLE 1-continued

| Type | S | Left | Right | Name | B |
|---|---|---|---|---|---|
| CDS | + | 3851945 | 3853129 | emrD | b3673 |
| CDS | − | 3853137 | 3853634 | yidF | b3674 |
| CDS | − | 3853631 | 3853993 | yidG | b3675 |
| CDS | − | 3853983 | 3854330 | yidH | b3676 |
| CDS | + | 3854438 | 3854887 | yidI | b3677 |
| CDS | − | 3854934 | 3856427 | yidJ | b3678 |
| CDS | − | 3856424 | 3858139 | yidK | b3679 |
| CDS | + | 3858276 | 3859199 | yidL | b3680 |
| CDS | − | 3859372 | 3860010 | glvG | b3681 |
| CDS | − | 3860010 | 3860495 | glvB | b3682 |
| CDS | − | 3860520 | 3861626 | glvC | b3683 |
| CDS | + | 3861922 | 3862638 | yidP | b3684 |
| CDS | − | 3862635 | 3864296 | yidE | b3685 |
| CDS | − | 3864492 | 3864920 | ibpB | b3686 |
| CDS | − | 3865032 | 3865445 | ibpA | b3687 |
| CDS | + | 3865751 | 3866083 | yidQ | b3688 |
| CDS | − | 3866085 | 3867299 | yidR | b3689 |
| CDS | + | 3867400 | 3868464 | yidS | b3690 |
| CDS | − | 3868461 | 3869753 | dgoT | b3691 |
| CDS | − | 3871619 | 3872497 | dgoK | b3693 |
| CDS | + | 3873461 | 3874117 | yidX | b3696 |
| CDS | − | 3874163 | 3874975 | yidA | b3697 |
| CDS | − | 3875090 | 3875488 | yidB | b3698 |
| CDS | − | 3875728 | 3878142 | gyrB | b3699 |
| CDS | − | 3878171 | 3879244 | recF | b3700 |
| CDS | − | 3879244 | 3880344 | dnaN | b3701 |
| CDS | − | 3880349 | 3881752 | dnaA | b3702 |
| CDS | + | 3882359 | 3882499 | rpmH | b3703 |
| CDS | + | 3882516 | 3882875 | rnpA | b3704 |
| CDS | + | 3883099 | 3884745 | yidC | b3705 |
| CDS | + | 3884719 | 3886215 | trmE | b3706 |
| CDS | + | 3886458 | 3886532 | tnaL | b3707 |
| CDS | + | 3886753 | 3888168 | tnaA | b3708 |
| CDS | + | 3888259 | 3889506 | tnaB | b3709 |
| CDS | + | 3889638 | 3890813 | yidY | b3710 |
| CDS | + | 3890788 | 3891747 | yidZ | b3711 |
| CDS | + | 3891892 | 3892653 | yieE | b3712 |
| CDS | + | 3892675 | 3893241 | yieF | b3713 |
| CDS | − | 3893295 | 3894632 | yieG | b3714 |
| CDS | + | 3894797 | 3895462 | yieH | b3715 |
| CDS | + | 3895529 | 3895996 | yieI | b3716 |
| CDS | + | 3896045 | 3896632 | yieJ | b3717 |
| CDS | − | 3896694 | 3897416 | yieK | b3718 |
| CDS | − | 3897431 | 3898627 | yieL | b3719 |
| CDS | − | 3898627 | 3900243 | yieC | b3720 |
| CDS | − | 3900312 | 3901724 | bglB | b3721 |
| CDS | − | 3901743 | 3903620 | bglF | b3722 |
| CDS | − | 3903754 | 3904590 | bglG | b3723 |
| CDS | − | 3904876 | 3905601 | phoU | b3724 |
| CDS | − | 3905616 | 3906389 | pstB | b3725 |
| CDS | − | 3906572 | 3907462 | pstA | b3726 |
| CDS | − | 3907462 | 3908421 | pstC | b3727 |
| CDS | − | 3908508 | 3909548 | pstS | b3728 |
| CDS | − | 3909862 | 3911691 | glmS | b3729 |
| CDS | − | 3911853 | 3913223 | glmU | b3730 |
| CDS | − | 3913576 | 3913995 | atpC | b3731 |
| CDS | − | 3914016 | 3915398 | atpD | b3732 |
| CDS | − | 3915425 | 3916288 | atpG | b3733 |
| CDS | − | 3916339 | 3917880 | atpA | b3734 |
| CDS | − | 3917893 | 3918426 | atpH | b3735 |
| CDS | − | 3918441 | 3918911 | atpF | b3736 |
| CDS | − | 3918973 | 3919212 | atpE | b3737 |
| CDS | − | 3919259 | 3920074 | atpB | b3738 |
| CDS | − | 3920083 | 3920463 | atpI | b3739 |
| CDS | − | 3921080 | 3921703 | gidB | b3740 |
| CDS | − | 3921767 | 3923656 | gidA | b3741 |
| rep_origin | + | 3923767 | 3923998 |  | b4489 |
| CDS | − | 3924035 | 3924478 | mioC | b3742 |
| CDS | − | 3924568 | 3925026 | asnC | b3743 |
| CDS | + | 3925178 | 3926170 | asnA | b3744 |
| CDS | − | 3926175 | 3927626 | yieM | b3745 |
| CDS | − | 3927620 | 3929116 | yieN | b3746 |
| CDS | + | 3929339 | 3931207 | kup | b3747 |
| CDS | + | 3931374 | 3931793 | rbsD | b3748 |
| CDS | + | 3931801 | 3933306 | rbsA | b3749 |
| CDS | + | 3933311 | 3934276 | rbsC | b3750 |
| CDS | + | 3934301 | 3935191 | rbsB | b3751 |
| CDS | + | 3935317 | 3936246 | rbsK | b3752 |
| CDS | + | 3936250 | 3937242 | rbsR | b3753 |
| CDS | − | 3937208 | 3938635 | yieO | b3754 |
| CDS | − | 3938658 | 3939350 | yieP | b3755 |
| rRNA | + | 3939831 | 3941372 | rrsC | b3756 |
| tRNA | + | 3941458 | 3941533 | gltU | b3757 |
| rRNA | + | 3941727 | 3944630 | rrlC | b3758 |
| rRNA | + | 3944723 | 3944842 | rrfC | b3759 |
| tRNA | + | 3944895 | 3944971 | aspT | b3760 |
| tRNA | + | 3944980 | 3945055 | trpT | b3761 |
| CDS | + | 3946109 | 3946447 | yifE | b3764 |
| CDS | − | 3946472 | 3948022 | yifB | b3765 |
| CDS | + | 3948345 | 3948443 | ilvL | b3766 |
| CDS | + | 3948583 | 3949566 | ilvG_1 | b3767 |
| CDS | + | 3949646 | 3950227 | ilvG_2 | b3768 |
| CDS | + | 3950224 | 3950487 | ilvM | b3769 |
| CDS | + | 3950507 | 3951436 | ilvE | b3770 |
| CDS | + | 3951501 | 3953351 | ilvD | b3771 |
| CDS | + | 3953354 | 3954898 | ilvA | b3772 |
| CDS | − | 3954950 | 3955843 | ilvY | b3773 |
| CDS | + | 3955993 | 3957468 | ilvC | b3774 |
| CDS | − | 3957555 | 3957836 | ppiC | b3775 |
| CDS | − | 3958035 | 3958310 |  | b3776 |
| CDS | − | 3958265 | 3958483 | yifN | b3777 |
| CDS | + | 3958700 | 3960721 | rep | b3778 |
| CDS | − | 3960768 | 3962252 | gppA | b3779 |
| CDS | − | 3962388 | 3963653 | rhlB | b3780 |
| CDS | + | 3963784 | 3964113 | trxA | b3781 |
| CDS | + | 3964254 | 3964355 | rhoL | b3782 |
| CDS | + | 3964440 | 3965699 | rho | b3783 |
| CDS | + | 3965939 | 3967042 | rfe | b3784 |
| CDS | + | 3967054 | 3968100 | wzzE | b3785 |
| CDS | + | 3968156 | 3969286 | wecB | b3786 |
| CDS | + | 3969283 | 3970545 | wecC | b3787 |
| CDS | + | 3970545 | 3971612 | rffG | b3788 |
| CDS | + | 3971631 | 3972512 | rffH | b3789 |
| CDS | + | 3972619 | 3973164 | wecD | b3790 |
| CDS | + | 3973169 | 3974299 | wecE | b3791 |
| CDS | + | 3974301 | 3975551 | wzxE | b3792 |
| CDS | + | 3976624 | 3977976 | wzyE | b3793 |
| CDS | + | 3977979 | 3978719 | wecG | b3794 |
| CDS | + | 3978910 | 3980295 | yifK | b3795 |
| tRNA | + | 3980398 | 3980474 | argX | b3796 |
| tRNA | + | 3980532 | 3980608 | hisR | b3797 |
| tRNA | + | 3980629 | 3980715 | leuT | b3798 |
| tRNA | + | 3980758 | 3980834 | proM | b3799 |
| CDS | + | 3980981 | 3982216 | aslB | b3800 |
| CDS | − | 3982375 | 3984030 | aslA | b3801 |
| CDS | − | 3984709 | 3985905 | hemY | b3802 |
| CDS | − | 3985908 | 3987089 | hemX | b3803 |
| CDS | − | 3987111 | 3987851 | hemD | b3804 |
| CDS | − | 3987848 | 3988789 | hemC | b3805 |
| CDS | + | 3989176 | 3991722 | cyaA | b3806 |
| CDS | − | 3991762 | 3992082 | cyaY | b3807 |
| CDS | + | 3991873 | 3992358 | yzcX | b3808 |
| CDS | + | 3992785 | 3993609 | dapF | b3809 |
| CDS | + | 3993606 | 3994313 | yigA | b3810 |
| CDS | + | 3994310 | 3995206 | xerC | b3811 |
| CDS | + | 3995206 | 3995922 | yigB | b3812 |
| CDS | + | 3996006 | 3998168 | uvrD | b3813 |
| CDS | + | 3999449 | 4000399 | corA | b3816 |
| CDS | − | 4000442 | 4000822 | yigF | b3817 |
| CDS | − | 4000836 | 4001216 | yigG | b3818 |
| CDS | − | 4001311 | 4002201 | rarD | b3819 |
| CDS | − | 4002253 | 4002720 | yigI | b3820 |
| CDS | + | 4002885 | 4003754 | pldA | b3821 |
| CDS | + | 4003887 | 4005716 | recQ | b3822 |
| CDS | − | 4005780 | 4006400 | rhtC | b3823 |
| CDS | − | 4006462 | 4007082 | rhtB | b3824 |
| CDS | + | 4007193 | 4008215 | pldB | b3825 |
| CDS | + | 4008223 | 4009023 | yigL | b3826 |
| CDS | + | 4009099 | 4009998 | yigM | b3827 |
| CDS | − | 4009886 | 4010839 | metR | b3828 |
| CDS | + | 4011076 | 4013337 | metE | b3829 |
| CDS | − | 4013377 | 4014192 | ysgA | b3830 |
| CDS | + | 4014454 | 4015215 | udp | b3831 |
| CDS | + | 4015356 | 4016783 | yigN | b3832 |
| CDS | + | 4016878 | 4017633 | ubiE | b3833 |
| CDS | + | 4017647 | 4018252 | yigP | b3834 |

TABLE 1-continued

| Type | S | Left | Right | Name | B |
|---|---|---|---|---|---|
| CDS | + | 4018249 | 4019889 | ubiB | b3835 |
| CDS | + | 4019968 | 4020237 | tatA | b3836 |
| CDS | + | 4020241 | 4020756 | tatB | b3838 |
| CDS | + | 4020759 | 4021535 | tatC | b3839 |
| CDS | − | 4022356 | 4022844 | rfaH | b3842 |
| CDS | + | 4023011 | 4024504 | ubiD | b3843 |
| CDS | + | 4024550 | 4025251 | fre | b3844 |
| CDS | − | 4025632 | 4026795 | fadA | b3845 |
| CDS | − | 4026805 | 4028994 | fadB | b3846 |
| CDS | + | 4029184 | 4030515 | pepQ | b3847 |
| CDS | + | 4030515 | 4031129 | yigZ | b3848 |
| CDS | + | 4031168 | 4032619 | trkH | b3849 |
| CDS | + | 4032631 | 4033176 | hemG | b3850 |
| rRNA | + | 4033554 | 4035095 | rrsA | b3851 |
| tRNA | + | 4035164 | 4035240 | ileT | b3852 |
| tRNA | + | 4035283 | 4035358 | alaT | b3853 |
| rRNA | + | 4035542 | 4038446 | rrlA | b3854 |
| rRNA | + | 4038540 | 4038659 | rrfA | b3855 |
| CDS | − | 4038929 | 4039441 | mobB | b3856 |
| CDS | − | 4039438 | 4040022 | mobA | b3857 |
| CDS | + | 4040092 | 4040361 | yihD | b3858 |
| CDS | + | 4040438 | 4041424 | yihE | b3859 |
| CDS | + | 4041441 | 4042067 | dsbA | b3860 |
| CDS | + | 4042222 | 4043652 | yihF | b3861 |
| CDS | − | 4043693 | 4044625 | yihG | b3862 |
| CDS | + | 4044989 | 4047775 | polA | b3863 |
| misc_RNA | + | 4047922 | 4048030 | spf | b3864 |
| CDS | − | 4048156 | 4048752 | yihA | b3865 |
| CDS | + | 4049370 | 4049879 | yihI | b3866 |
| CDS | + | 4050068 | 4051441 | hemN | b3867 |
| CDS | − | 4051892 | 4053301 | glnB | b3868 |
| CDS | − | 4053313 | 4054362 | glnL | b3869 |
| CDS | − | 4054648 | 4056057 | glnA | b3870 |
| CDS | + | 4056430 | 4058253 | bipA | b3871 |
| CDS | + | 4058470 | 4059180 | yihL | b3872 |
| CDS | + | 4059188 | 4060168 | yihM | b3873 |
| CDS | + | 4060270 | 4061535 | yihN | b3874 |
| CDS | − | 4061626 | 4062318 | yshA | b3875 |
| CDS | − | 4062386 | 4063789 | yihO | b3876 |
| CDS | − | 4063832 | 4065238 | yihP | b3877 |
| CDS | + | 4065263 | 4067299 | yihQ | b3878 |
| CDS | − | 4067498 | 4068424 | yihR | b3879 |
| CDS | − | 4068538 | 4069779 | yihS | b3880 |
| CDS | − | 4069796 | 4070674 | yihT | b3881 |
| CDS | − | 4070698 | 4071594 | yihU | b3882 |
| CDS | + | 4071762 | 4072658 | yihV | b3883 |
| CDS | + | 4072692 | 4073477 | yihW | b3884 |
| CDS | + | 4073576 | 4074175 | yihX | b3885 |
| CDS | + | 4074169 | 4075041 | rbn | b3886 |
| CDS | + | 4075038 | 4075475 | dtd | b3887 |
| CDS | + | 4075472 | 4076461 | yiiD | b3888 |
| CDS | + | 4077314 | 4077532 | yiiE | b3889 |
| CDS | + | 4077774 | 4077992 | yiiF | b3890 |
| CDS | − | 4078322 | 4079251 | fdhE | b3891 |
| CDS | − | 4079248 | 4079883 | fdoI | b3892 |
| CDS | − | 4079900 | 4080782 | fdoH | b3893 |
| CDS | − | 4080795 | 4083845 | fdoG | b3894 |
| CDS | + | 4084039 | 4084872 | fdhD | b3895 |
| CDS | + | 4085025 | 4086080 | yiiG | b3896 |
| CDS | − | 4086130 | 4087878 | frvR | b3897 |
| CDS | − | 4087878 | 4088948 | frvX | b3898 |
| CDS | − | 4088938 | 4090389 | frvB | b3899 |
| CDS | − | 4090400 | 4090846 | frvA | b3900 |
| CDS | − | 4091147 | 4091461 | yiiL | b3901 |
| CDS | − | 4091471 | 4092295 | rhaD | b3902 |
| CDS | − | 4092746 | 4094005 | rhaA | b3903 |
| CDS | − | 4094002 | 4095471 | rhaB | b3904 |
| CDS | + | 4095759 | 4096595 | rhaS | b3905 |
| CDS | + | 4096579 | 4097517 | rhaR | b3906 |
| CDS | − | 4097514 | 4098548 | rhaT | b3907 |
| CDS | + | 4098833 | 4099453 | sodA | b3908 |
| CDS | + | 4099713 | 4100696 | kdgT | b3909 |
| CDS | + | 4100845 | 4101519 | yiiM | b3910 |
| CDS | − | 4101625 | 4102998 | cpxA | b3911 |
| CDS | − | 4102995 | 4103693 | cpxR | b3912 |
| CDS | + | 4104492 | 4105394 | yiiP | b3915 |
| CDS | + | 4105575 | 4106537 | pfkA | b3916 |
| CDS | + | 4106857 | 4107846 | sbp | b3917 |
| CDS | + | 4107953 | 4108708 | cdh | b3918 |
| CDS | − | 4108763 | 4109530 | tpiA | b3919 |
| CDS | − | 4109638 | 4110237 | yiiQ | b3920 |
| CDS | + | 4110338 | 4110778 | yiiR | b3921 |
| CDS | + | 4110990 | 4111289 | yiiS | b3922 |
| CDS | + | 4111316 | 4111744 | yiiT | b3923 |
| CDS | − | 4111749 | 4112495 | fpr | b3924 |
| CDS | − | 4112592 | 4113602 | glpX | b3925 |
| CDS | − | 4113737 | 4115245 | glpK | b3926 |
| CDS | − | 4115268 | 4116113 | glpF | b3927 |
| CDS | + | 4116538 | 4116783 | yiiU | b3928 |
| CDS | − | 4116868 | 4117353 | menG | b3929 |
| CDS | − | 4117446 | 4118372 | menA | b3930 |
| CDS | − | 4118439 | 4119770 | hslU | b3931 |
| CDS | − | 4119780 | 4120310 | hslV | b3932 |
| CDS | + | 4120403 | 4121362 | ftsN | b3933 |
| CDS | − | 4121454 | 4122479 | cytR | b3934 |
| CDS | − | 4122635 | 4124833 | priA | b3935 |
| CDS | + | 4125036 | 4125248 | rpmE | b3936 |
| CDS | − | 4125309 | 4125917 | yiiX | b3937 |
| CDS | − | 4126101 | 4126418 | metJ | b3938 |
| CDS | + | 4126695 | 4127855 | metB | b3939 |
| CDS | + | 4127858 | 4130290 | metL | b3940 |
| CDS | + | 4130639 | 4131529 | metF | b3941 |
| CDS | + | 4131858 | 4134038 | katG | b3942 |
| CDS | + | 4134131 | 4135036 | yijE | b3943 |
| CDS | − | 4135063 | 4135680 | yijF | b3944 |
| CDS | − | 4135955 | 4137058 | gldA | b3945 |
| CDS | − | 4137069 | 4137731 | talC | b3946 |
| CDS | − | 4137743 | 4140244 | ptsA | b3947 |
| CDS | + | 4140553 | 4141632 | frwC | b3949 |
| CDS | + | 4141647 | 4141967 | frwB | b3950 |
| CDS | + | 4142018 | 4144315 | pflD | b3951 |
| CDS | + | 4144281 | 4145159 | pflC | b3952 |
| CDS | + | 4145161 | 4145502 | frwD | b3953 |
| CDS | − | 4145489 | 4146340 | yijO | b3954 |
| CDS | − | 4146555 | 4148288 | yijP | b3955 |
| CDS | − | 4148470 | 4151121 | ppc | b3956 |
| CDS | − | 4151719 | 4152870 | argE | b3957 |
| CDS | + | 4153024 | 4154028 | argC | b3958 |
| CDS | + | 4154039 | 4154812 | argB | b3959 |
| CDS | + | 4154873 | 4156246 | argH | b3960 |
| CDS | + | 4156513 | 4157430 | oxyR | b3961 |
| CDS | − | 4157413 | 4158813 | udhA | b3962 |
| CDS | + | 4159090 | 4159794 | yijC | b3963 |
| CDS | + | 4159794 | 4160153 | yijD | b3964 |
| CDS | − | 4160193 | 4161293 | trmA | b3965 |
| CDS | + | 4161662 | 4163506 | btuB | b3966 |
| CDS | + | 4163451 | 4164308 | murI | b3967 |
| rRNA | + | 4164682 | 4166223 | rrsB | b3968 |
| tRNA | + | 4166395 | 4166470 | gltT | b3969 |
| rRNA | + | 4166664 | 4169569 | rrlB | b3970 |
| rRNA | + | 4169660 | 4169779 | rrfB | b3971 |
| CDS | + | 4170080 | 4171108 | murB | b3972 |
| CDS | + | 4171105 | 4172070 | birA | b3973 |
| CDS | + | 4172099 | 4173049 | coaA | b3974 |
| CDS | | 4173236 | 4173391 | | b3975 |
| tRNA | + | 4173411 | 4173486 | thrU | b3976 |
| tRNA | + | 4173495 | 4173579 | tyrU | b3977 |
| tRNA | + | 4173696 | 4173770 | glyT | b3978 |
| tRNA | + | 4173777 | 4173852 | thrT | b3979 |
| CDS | + | 4173967 | 4175151 | tufB | b3980 |
| CDS | + | 4175381 | 4175764 | secE | b3981 |
| CDS | + | 4175766 | 4176311 | nusG | b3982 |
| CDS | + | 4176470 | 4176898 | rplK | b3983 |
| CDS | + | 4176902 | 4177606 | rplA | b3984 |
| CDS | + | 4178019 | 4178516 | rplJ | b3985 |
| CDS | + | 4178583 | 4178948 | rplL | b3986 |
| CDS | + | 4179268 | 4183296 | rpoB | b3987 |
| CDS | + | 4183373 | 4187596 | rpoC | b3988 |
| CDS | + | 4187809 | 4188348 | htrC | b3989 |
| CDS | − | 4188758 | 4189891 | thiH | b3990 |
| CDS | − | 4189888 | 4190658 | thiG | b3991 |
| CDS | − | 4190844 | 4191599 | thiF | b3992 |
| CDS | − | 4191592 | 4192227 | thiE | b3993 |
| CDS | − | 4192227 | 4194122 | thiC | b3994 |
| CDS | − | 4194355 | 4194831 | rsd | b3995 |
| CDS | + | 4194926 | 4195699 | nudC | b3996 |

TABLE 1-continued

| Type | S | Left | Right | Name | B |
|---|---|---|---|---|---|
| CDS | + | 4195739 | 4196803 | hemE | b3997 |
| CDS | + | 4196813 | 4197484 | nfi | b3998 |
| CDS | + | 4197527 | 4198117 | yjaG | b3999 |
| CDS | + | 4198304 | 4198576 | hupA | b4000 |
| CDS | + | 4198589 | 4199284 | yjaH | b4001 |
| CDS | − | 4199286 | 4199711 | zraP | b4002 |
| CDS | + | 4199949 | 4201346 | zraS | b4003 |
| CDS | + | 4201343 | 4202668 | zraR | b4004 |
| CDS | − | 4202665 | 4203954 | purD | b4005 |
| CDS | − | 4203966 | 4205555 | purH | b4006 |
| rRNA | + | 4206170 | 4207711 | rrsE | b4007 |
| tRNA | + | 4207797 | 4207872 | gltV | b4008 |
| rRNA | + | 4208066 | 4210969 | rrlE | b4009 |
| rRNA | + | 4211063 | 4211182 | rrfE | b4010 |
| CDS | + | 4211257 | 4211640 | yjaA | b4011 |
| CDS | − | 4211703 | 4212146 | yjaB | b4012 |
| CDS | + | 4212303 | 4213232 | metA | b4013 |
| CDS | + | 4213501 | 4215102 | aceB | b4014 |
| CDS | + | 4215132 | 4216436 | aceA | b4015 |
| CDS | + | 4216619 | 4218355 | aceK | b4016 |
| CDS | − | 4218324 | 4220510 | arpA | b4017 |
| CDS | − | 4220827 | 4221651 | iclR | b4018 |
| CDS | + | 4221851 | 4225534 | metH | b4019 |
| CDS | + | 4225754 | 4227385 | yjbB | b4020 |
| CDS | − | 4227476 | 4228165 | pepE | b4021 |
| CDS | + | 4228377 | 4229249 | yjbC | b4022 |
| CDS | − | 4229382 | 4229654 | yjbD | b4023 |
| CDS | − | 4229907 | 4231256 | lysC | b4024 |
| CDS | + | 4231781 | 4233430 | pgi | b4025 |
| CDS | + | 4233929 | 4234171 | yjbE | b4026 |
| CDS | + | 4234285 | 4234923 | yjbF | b4027 |
| CDS | + | 4234920 | 4235657 | yjbG | b4028 |
| CDS | + | 4235657 | 4237753 | yjbH | b4029 |
| CDS | + | 4238348 | 4238758 | yjbA | b4030 |
| CDS | − | 4238802 | 4240277 | xylE | b4031 |
| CDS | − | 4240649 | 4241539 | malG | b4032 |
| CDS | − | 4241554 | 4243098 | malF | b4033 |
| CDS | − | 4243252 | 4244442 | malE | b4034 |
| CDS | + | 4244807 | 4245922 | malK | b4035 |
| CDS | + | 4245994 | 4247334 | lamB | b4036 |
| CDS | + | 4247577 | 4248497 | malM | b4037 |
| CDS | + | 4248978 | 4250306 | yjbI | b4038 |
| CDS | + | 4250529 | 4251026 | ubiC | b4039 |
| CDS | + | 4251039 | 4251911 | ubiA | b4040 |
| CDS | − | 4252066 | 4254489 | plsB | b4041 |
| CDS | + | 4254660 | 4255028 | dgkA | b4042 |
| CDS | + | 4255138 | 4255746 | lexA | b4043 |
| CDS | + | 4255765 | 4257144 | dinF | b4044 |
| CDS | + | 4257260 | 4257469 | yjbJ | b4045 |
| CDS | − | 4257511 | 4258026 | zur | b4046 |
| CDS | + | 4258344 | 4258598 | yjbL | b4047 |
| CDS | + | 4258622 | 4259329 | yjbM | b4048 |
| CDS | + | 4259692 | 4260729 | yjbN | b4049 |
| CDS | + | 4260863 | 4261105 | yjbO | b4050 |
| CDS | − | 4261271 | 4262254 | qor | b4051 |
| CDS | + | 4262337 | 4263752 | dnaB | b4052 |
| CDS | + | 4263805 | 4264884 | alr | b4053 |
| CDS | + | 4265137 | 4266330 | tyrB | b4054 |
| CDS | + | 4267437 | 4268150 | aphA | b4055 |
| CDS | + | 4268261 | 4268677 | yjbQ | b4056 |
| CDS | + | 4268681 | 4269037 | yjbR | b4057 |
| CDS | − | 4269072 | 4271894 | uvrA | b4058 |
| CDS | + | 4272148 | 4272684 | ssb | b4059 |
| CDS | − | 4272783 | 4273064 | yjcB | b4060 |
| CDS | + | 4273494 | 4275080 | yjcC | b4061 |
| CDS | − | 4275083 | 4275406 | soxS | b4062 |
| CDS | + | 4275492 | 4275956 | soxR | b4063 |
| CDS | + | 4276502 | 4277851 | yjcD | b4064 |
| CDS | − | 4278003 | 4279652 | yjcE | b4065 |
| CDS | − | 4279806 | 4281098 | yjcF | b4066 |
| CDS | − | 4281276 | 4282925 | actP | b4067 |
| CDS | − | 4282922 | 4283236 | yjcH | b4068 |
| CDS | − | 4283436 | 4285394 | acs | b4069 |
| CDS | + | 4285787 | 4287223 | nrfA | b4070 |
| CDS | + | 4287268 | 4287834 | nrfB | b4071 |
| CDS | + | 4287831 | 4288502 | nrfC | b4072 |
| CDS | + | 4288499 | 4289455 | nrfD | b4073 |
| CDS | + | 4289535 | 4291193 | nrfE | b4074 |
| CDS | + | 4291186 | 4291569 | nrfF | b4075 |
| CDS | + | 4291566 | 4292162 | nrfG | b4076 |
| CDS | + | 4292504 | 4293817 | gltP | b4077 |
| CDS | − | 4294459 | 4295148 | yjcO | b4078 |
| CDS | − | 4295242 | 4297389 | fdhF | b4079 |
| CDS | − | 4297587 | 4299053 | yjcP | b4080 |
| CDS | − | 4299050 | 4301101 | yjcQ | b4081 |
| CDS | − | 4301101 | 4302132 | yjcR | b4082 |
| CDS | − | 4302635 | 4304620 | yjcS | b4083 |
| CDS | − | 4304893 | 4305822 | alsK | b4084 |
| CDS | − | 4305806 | 4306501 | alsE | b4085 |
| CDS | − | 4306512 | 4307492 | alsC | b4086 |
| CDS | − | 4307471 | 4309003 | alsA | b4087 |
| CDS | − | 4309130 | 4310065 | alsB | b4088 |
| CDS | − | 4310124 | 4311014 | rpiR | b4089 |
| CDS | + | 4311373 | 4311822 | rpiB | b4090 |
| CDS | − | 4312367 | 4313125 | phnP | b4092 |
| CDS | − | 4313127 | 4313561 | phnO | b4093 |
| CDS | − | 4313548 | 4314105 | phnN | b4094 |
| CDS | − | 4314105 | 4315241 | phnM | b4095 |
| CDS | − | 4315238 | 4315918 | phnL | b4096 |
| CDS | − | 4316029 | 4316787 | phnK | b4097 |
| CDS | − | 4316784 | 4317629 | phnJ | b4098 |
| CDS | − | 4317622 | 4318686 | phnI | b4099 |
| CDS | − | 4318686 | 4319270 | phnH | b4100 |
| CDS | − | 4319267 | 4319719 | phnG | b4101 |
| CDS | − | 4319720 | 4320445 | phnF | b4102 |
| CDS | − | 4320466 | 4320834 |  | b4103 |
| CDS | − | 4320684 | 4321304 | phnE | b4104 |
| CDS | − | 4321359 | 4322375 | phnD | b4105 |
| CDS | − | 4322400 | 4323188 | phnC | b4106 |
| CDS | − | 4323321 | 4323764 | phnB | b4107 |
| CDS | − | 4324422 | 4324757 | phnA | b4108 |
| CDS | + | 4325158 | 4327386 | yjdA | b4109 |
| CDS | + | 4327383 | 4328261 | yjcZ | b4110 |
| CDS | + | 4328525 | 4330027 | proP | b4111 |
| CDS | − | 4330204 | 4331295 | basS | b4112 |
| CDS | − | 4331305 | 4331973 | basR | b4113 |
| CDS | − | 4331970 | 4333613 | yjdB | b4114 |
| CDS | − | 4333717 | 4335054 | yjdE | b4115 |
| CDS | − | 4335191 | 4335952 | adiY | b4116 |
| CDS | − | 4336277 | 4338547 | adiA | b4117 |
| CDS | − | 4338743 | 4339651 | melR | b4118 |
| CDS | + | 4339934 | 4341289 | melA | b4119 |
| CDS | + | 4341404 | 4342813 | melB | b4120 |
| CDS | − | 4342952 | 4343581 | yjdF | b4121 |
| CDS | − | 4343703 | 4345349 | fumB | b4122 |
| CDS | − | 4345427 | 4346767 | dcuB | b4123 |
| CDS | + | 4347338 | 4348057 | dcuR | b4124 |
| CDS | + | 4348054 | 4349685 | dcuS | b4125 |
| CDS | + | 4349866 | 4350096 | yjdI | b4126 |
| CDS | + | 4350108 | 4350380 | yjdJ | b4127 |
| CDS | + | 4350607 | 4350903 | yjdK | b4128 |
| CDS | − | 4351223 | 4352740 | lysU | b4129 |
| CDS | − | 4352977 | 4354434 | yjdL | b4130 |
| CDS | − | 4354493 | 4356640 | cadA | b4131 |
| CDS | − | 4356720 | 4358054 | cadB | b4132 |
| CDS | − | 4358419 | 4359957 | cadC | b4133 |
| tRNA | − | 4360574 | 4360649 | pheU | b4134 |
| CDS | − | 4360756 | 4361331 | yjdC | b4135 |
| CDS | − | 4361368 | 4363065 | dsbD | b4136 |
| CDS | − | 4363041 | 4363379 | cutA | b4137 |
| CDS | − | 4363495 | 4364796 | dcuA | b4138 |
| CDS | − | 4364914 | 4366350 | aspA | b4139 |
| CDS | + | 4366687 | 4367163 | fxsA | b4140 |
| CDS | − | 4367179 | 4368435 | yjeH | b4141 |
| CDS | + | 4368711 | 4369004 | groS | b4142 |
| CDS | + | 4369048 | 4370694 | groL | b4143 |
| CDS | + | 4370832 | 4371185 | yjeI | b4144 |
| CDS | − | 4371388 | 4372257 | yjeJ | b4145 |
| CDS | − | 4372652 | 4373680 | yjeK | b4146 |
| CDS | + | 4373722 | 4374288 | efp | b4147 |
| CDS | + | 4374898 | 4375215 | sugE | b4148 |
| CDS | − | 4375212 | 4375745 | blc | b4149 |
| CDS | − | 4375834 | 4376967 | ampC | b4150 |
| CDS | − | 4377030 | 4377389 | frdD | b4151 |
| CDS | − | 4377400 | 4377795 | frdC | b4152 |
| CDS | − | 4377806 | 4378540 | frdB | b4153 |

TABLE 1-continued

| Type | S | Left | Right | Name | B |
|---|---|---|---|---|---|
| CDS | − | 4378533 | 4380341 | frdA | b4154 |
| CDS | + | 4380666 | 4381643 | yjeA | b4155 |
| CDS | + | 4381862 | 4383364 | yjeM | b4156 |
| CDS | + | 4383416 | 4383730 | yjeN | b4157 |
| CDS | + | 4383727 | 4384041 | yjeO | b4158 |
| CDS | − | 4384070 | 4387393 | yjeP | b4159 |
| CDS | − | 4387415 | 4388383 | psd | b4160 |
| CDS | − | 4388480 | 4389532 | yjeQ | b4161 |
| CDS | + | 4389627 | 4390172 | orn | b4162 |
| tRNA | + | 4390383 | 4390458 | glyV | b4163 |
| tRNA | + | 4390495 | 4390570 | glyX | b4164 |
| tRNA | + | 4390606 | 4390681 | glyY | b4165 |
| CDS | − | 4390951 | 4392090 | yjeS | b4166 |
| CDS | + | 4392089 | 4393636 | yjeF | b4167 |
| CDS | + | 4393608 | 4394069 | yjeE | b4168 |
| CDS | + | 4394088 | 4395425 | amiB | b4169 |
| CDS | + | 4395435 | 4397282 | mutL | b4170 |
| CDS | + | 4397275 | 4398225 | miaA | b4171 |
| CDS | + | 4398311 | 4398619 | hfq | b4172 |
| CDS | + | 4398695 | 4399975 | hflX | b4173 |
| CDS | + | 4400061 | 4401320 | hflK | b4174 |
| CDS | + | 4401323 | 4402327 | hflC | b4175 |
| CDS | + | 4402409 | 4402606 | yjeT | b4176 |
| CDS | + | 4402710 | 4404008 | purA | b4177 |
| CDS | + | 4404213 | 4404638 | yjeB | b4178 |
| CDS | + | 4404677 | 4407118 | rnr | b4179 |
| CDS | + | 4407298 | 4408029 | yjfH | b4180 |
| CDS | + | 4408156 | 4408557 | yjfI | b4181 |
| CDS | + | 4408576 | 4409274 | yjfJ | b4182 |
| CDS | + | 4409325 | 4409984 | yjfK | b4183 |
| CDS | + | 4410002 | 4410400 | yjfL | b4184 |
| CDS | + | 4410410 | 4411048 | yjfM | b4185 |
| CDS | + | 4411051 | 4412214 | yjfC | b4186 |
| CDS | + | 4412298 | 4413923 | aidB | b4187 |
| CDS | − | 4414040 | 4414315 | yjfN | b4188 |
| CDS | − | 4414464 | 4414793 | yjfO | b4189 |
| CDS | + | 4414975 | 4415724 | yjfP | b4190 |
| CDS | − | 4415721 | 4416476 | yjfQ | b4191 |
| CDS | − | 4416584 | 4417648 | yjfR | b4192 |
| CDS | + | 4418003 | 4419400 | sgaT | b4193 |
| CDS | + | 4419416 | 4419721 | sgaB | b4194 |
| CDS | + | 4419731 | 4420195 | ptxA | b4195 |
| CDS | + | 4420209 | 4420859 | sgaH | b4196 |
| CDS | + | 4420869 | 4421723 | sgaU | b4197 |
| CDS | + | 4421723 | 4422409 | sgaE | b4198 |
| CDS | − | 4422539 | 4422814 | yjfY | b4199 |
| CDS | + | 4423141 | 4423536 | rpsF | b4200 |
| CDS | + | 4423543 | 4423857 | priB | b4201 |
| CDS | + | 4423862 | 4424089 | rpsR | b4202 |
| CDS | + | 4424131 | 4424580 | rplI | b4203 |
| CDS | − | 4424651 | 4425445 | yjfZ | b4204 |
| CDS | + | 4425792 | 4426118 | ytfA | b4205 |
| CDS | − | 4426102 | 4426740 | ytfB | b4206 |
| CDS | + | 4426958 | 4427578 | fklB | b4207 |
| CDS | + | 4427887 | 4429299 | cycA | b4208 |
| CDS | − | 4429344 | 4430006 | ytfE | b4209 |
| CDS | + | 4430114 | 4431088 | ytfF | b4210 |
| CDS | − | 4431187 | 4432047 | ytfG | b4211 |
| CDS | + | 4432136 | 4432516 | ytfH | b4212 |
| CDS | − | 4432645 | 4434588 | cpdB | b4213 |
| CDS | + | 4434778 | 4435518 | cysQ | b4214 |
| CDS | + | 4435730 | 4436668 | ytfI | b4215 |
| CDS | − | 4436731 | 4437285 | ytfJ | b4216 |
| CDS | + | 4437610 | 4437816 | ytfK | b4217 |
| CDS | − | 4437895 | 4439238 | ytfL | b4218 |
| CDS | − | 4439561 | 4440199 | msrA | b4219 |
| CDS | + | 4440405 | 4442138 | ytfM | b4220 |
| CDS | + | 4442135 | 4445914 | ytfN | b4221 |
| CDS | + | 4445917 | 4446258 | ytfP | b4222 |
| CDS | − | 4445999 | 4446268 | yzfA | b4223 |
| CDS | + | 4446470 | 4446721 | chpS | b4224 |
| CDS | + | 4446715 | 4447065 | chpB | b4225 |
| CDS | − | 4447145 | 4447675 | ppa | b4226 |
| CDS | + | 4447985 | 4448941 | ytfQ | b4227 |
| CDS | + | 4450597 | 4451619 | ytfT | b4230 |
| CDS | + | 4451606 | 4452601 | yjfF | b4231 |
| CDS | − | 4452634 | 4453632 | fbp | b4232 |
| CDS | + | 4453808 | 4455181 | mpl | b4233 |

TABLE 1-continued

| Type | S | Left | Right | Name | B |
|---|---|---|---|---|---|
| CDS | − | 4455337 | 4455888 | yjgA | b4234 |
| CDS | + | 4455982 | 4457334 | pmbA | b4235 |
| CDS | + | 4457576 | 4457878 | cybC | b4236 |
| CDS | − | 4457923 | 4458387 | nrdG | b4237 |
| CDS | − | 4458545 | 4460683 | nrdD | b4238 |
| CDS | − | 4461077 | 4462732 | treC | b4239 |
| CDS | − | 4462782 | 4464203 | treB | b4240 |
| CDS | − | 4464322 | 4465269 | treR | b4241 |
| CDS | + | 4465648 | 4468344 | mgtA | b4242 |
| CDS | − | 4468550 | 4468936 | yjgF | b4243 |
| CDS | − | 4469009 | 4469470 | pyrI | b4244 |
| CDS | − | 4469483 | 4470418 | pyrB | b4245 |
| CDS | − | 4470422 | 4470556 | pyrL | b4246 |
| CDS | + | 4470536 | 4470868 | yjgG | b4247 |
| CDS | − | 4470837 | 4471232 | yjgH | b4248 |
| CDS | − | 4471363 | 4472076 | yjgI | b4249 |
| CDS | + | 4472250 | 4472414 |  | b4250 |
| CDS | + | 4472147 | 4472740 | yjgJ | b4251 |
| CDS | + | 4472885 | 4473337 | yjgK | b4252 |
| CDS | + | 4473460 | 4475274 | yjgL | b4253 |
| CDS | − | 4475330 | 4476334 | argI | b4254 |
| CDS | + | 4476496 | 4476912 | yjgD | b4255 |
| CDS | − | 4477057 | 4477560 | yjgM | b4256 |
| CDS | + | 4477753 | 4478949 | yjgN | b4257 |
| CDS | − | 4479005 | 4481860 | valS | b4258 |
| CDS | − | 4481860 | 4482303 | holC | b4259 |
| CDS | − | 4482463 | 4483974 | pepA | b4260 |
| CDS | + | 4484241 | 4485341 | yjgP | b4261 |
| CDS | + | 4485341 | 4486423 | yjgQ | b4262 |
| CDS | + | 4486584 | 4488086 | yjgR | b4263 |
| CDS | + | 4488184 | 4489162 | idnR | b4264 |
| CDS | − | 4489229 | 4490548 | idnT | b4265 |
| CDS | − | 4490610 | 4491374 | idnO | b4266 |
| CDS | − | 4491398 | 4492429 | idnD | b4267 |
| CDS | + | 4492646 | 4493209 | idnK | b4268 |
| CDS | + | 4493213 | 4494232 | yjgB | b4269 |
| tRNA | + | 4494428 | 4494512 | leuX | b4270 |
| CDS | + | 4494773 | 4495963 | intB | b4271 |
| repeat_region |  | 4496204 | 4497534 |  |  |
| CDS | + | 4496250 | 4496660 | yi21_6 | b4272 |
| CDS | + | 4496618 | 4497523 | yi22_6 | b4273 |
| CDS | + | 4497622 | 4497957 | yjgW | b4274 |
| CDS | − | 4498066 | 4498512 | yjgX | b4275 |
| CDS | − | 4498455 | 4498814 | yjgY | b4276 |
| CDS | + | 4499283 | 4499612 | yjgZ | b4277 |
| repeat_region | − | 4500113 | 4501538 |  |  |
| CDS | − | 4500126 | 4501454 | yi41 | b4278 |
| CDS | + | 4502081 | 4503298 | yjhB | b4279 |
| CDS | + | 4503310 | 4504428 | yjhC | b4280 |
| CDS | − | 4504649 | 4504879 | yjhD | b4281 |
| CDS | + | 4504884 | 4505132 | yjhE | b4282 |
| repeat_region | + | 4505138 | 4505475 |  |  |
| CDS | + | 4505220 | 4505486 | yi91b | b4283 |
| repeat_region | − | 4505482 | 4506702 |  |  |
| CDS | + | 4505489 | 4506640 | tra8_3 | b4284 |
| repeat_region | − | 4506703 | 4507029 |  |  |
| CDS | + | 4506981 | 4507577 |  | b4285 |
| repeat_region | + | 4507030 | 4507824 |  |  |
| CDS | + | 4507743 | 4508156 |  | b4286 |
| CDS | − | 4508713 | 4509480 | fecE | b4287 |
| CDS | − | 4509481 | 4510437 | fecD | b4288 |
| CDS | − | 4510434 | 4511432 | fecC | b4289 |
| CDS | − | 4511429 | 4512331 | fecB | b4290 |
| CDS | − | 4512376 | 4514700 | fecA | b4291 |
| CDS | − | 4514787 | 4515740 | fecR | b4292 |
| CDS | − | 4515737 | 4516258 | fecI | b4293 |
| repeat_region | + | 4516495 | 4517262 |  |  |
| CDS | + | 4516550 | 4516825 | insA_7 | b4294 |
| CDS | − | 4517361 | 4518347 | yjhU | b4295 |
| CDS | − | 4518694 | 4520043 | yjhF | b4296 |
| CDS | + | 4520150 | 4522117 | yjhG | b4297 |
| CDS | + | 4522128 | 4523033 | yjhH | b4298 |
| CDS | − | 4523038 | 4523826 | yjhI | b4299 |
| CDS | − | 4524129 | 4524911 | sgcR | b4300 |
| CDS | − | 4524928 | 4525560 | sgcE | b4301 |
| CDS | − | 4525572 | 4526003 | sgcA | b4302 |
| CDS | − | 4526134 | 4526940 | sgcQ | b4303 |
| CDS | − | 4526953 | 4528266 | sgcC | b4304 |

TABLE 1-continued

| Type | S | Left | Right | Name | B |
|---|---|---|---|---|---|
| CDS | − | 4528553 | 4529674 | sgcX | b4305 |
| CDS | − | 4530460 | 4531206 | yjhP | b4306 |
| CDS | − | 4531262 | 4531807 | yjhQ | b4307 |
| CDS | + | 4533038 | 4534054 | yjhR | b4308 |
| CDS | − | 4534637 | 4535617 | yjhS | b4309 |
| CDS | − | 4535682 | 4536788 | yjhT | b4310 |
| CDS | − | 4536808 | 4537524 | yjhA | b4311 |
| CDS | + | 4538980 | 4539582 | fimB | b4312 |
| CDS | + | 4540060 | 4540656 | fimE | b4313 |
| CDS | + | 4541138 | 4541686 | fimA | b4314 |
| CDS | + | 4541751 | 4542290 | fimI | b4315 |
| CDS | + | 4542327 | 4543052 | fimC | b4316 |
| CDS | + | 4543119 | 4545755 | fimD | b4317 |
| CDS | + | 4545765 | 4546295 | fimF | b4318 |
| CDS | + | 4546308 | 4546811 | fimG | b4319 |
| CDS | + | 4546831 | 4547733 | fimH | b4320 |
| CDS | − | 4547976 | 4549319 | gntP | b4321 |
| CDS | + | 4549659 | 4550843 | uxuA | b4322 |
| CDS | + | 4550924 | 4552384 | uxuB | b4323 |
| CDS | + | 4552599 | 4553372 | uxuR | b4324 |
| CDS | − | 4553513 | 4554343 | yjiC | b4325 |
| CDS | + | 4555016 | 4555408 | yjiD | b4326 |
| CDS | − | 4555401 | 4556312 | yjiE | b4327 |
| CDS | − | 4556377 | 4557549 | iadA | b4328 |
| CDS | − | 4557562 | 4558023 | yjiG | b4329 |
| CDS | − | 4558020 | 4558703 | yjiH | b4330 |
| CDS | + | 4558953 | 4559507 | kptA | b4331 |
| CDS | − | 4559520 | 4560698 | yjiJ | b4332 |
| CDS | − | 4560766 | 4561734 | yjiK | b4333 |
| CDS | − | 4561945 | 4562712 | yjiL | b4334 |
| CDS | − | 4562722 | 4563873 | yjiM | b4335 |
| CDS | − | 4563989 | 4565269 | yjiN | b4336 |
| CDS | − | 4565310 | 4566542 | yjiO | b4337 |
| CDS | + | 4567021 | 4567332 | yjiP | b4338 |
| CDS | + | 4567381 | 4567941 | yjiQ | b4339 |
| CDS | − | 4568185 | 4569597 | yjiR | b4340 |
| CDS | + | 4569774 | 4569938 | yjiS | b4341 |
| CDS | + | 4570437 | 4571954 | yjiT | b4342 |
| CDS | − | 4574935 | 4575981 | mcrC | b4345 |
| CDS | − | 4575981 | 4577360 | mcrB | b4346 |
| CDS | − | 4577522 | 4577920 | yjiW | b4347 |
| CDS | − | 4578091 | 4579485 | hsdS | b4348 |
| CDS | − | 4579482 | 4581071 | hsdM | b4349 |
| CDS | − | 4581272 | 4584838 | hsdR | b4350 |
| CDS | + | 4584972 | 4585886 | mrr | b4351 |
| CDS | − | 4585932 | 4586888 | yjiA | b4352 |
| CDS | − | 4586899 | 4587102 | yjiX | b4353 |
| CDS | − | 4587152 | 4589302 | yjiY | b4354 |
| CDS | + | 4589680 | 4591335 | tsr | b4355 |
| CDS | − | 4591384 | 4592745 | yjiZ | b4356 |
| CDS | − | 4592960 | 4593874 | yjjM | b4357 |
| CDS | + | 4594013 | 4595035 | yjjN | b4358 |
| CDS | − | 4595173 | 4597464 | mdoB | b4359 |
| CDS | − | 4597718 | 4598212 | yjjA | b4360 |
| CDS | − | 4598261 | 4598998 | dnaC | b4361 |
| CDS | − | 4599001 | 4599540 | dnaT | b4362 |
| CDS | − | 4599647 | 4599973 | yjjB | b4363 |
| CDS | − | 4600111 | 4600881 | yjjP | b4364 |
| CDS | + | 4601500 | 4602225 | yjjQ | b4365 |
| CDS | + | 4602237 | 4602860 | bglJ | b4366 |
| CDS | − | 4602898 | 4603686 | fhuF | b4367 |
| tRNA | − | 4604102 | 4604188 | leuV | b4368 |
| tRNA | − | 4604223 | 4604309 | leuP | b4369 |
| tRNA | − | 4604338 | 4604424 | leuQ | b4370 |
| CDS | + | 4604692 | 4605723 | rsmC | b4371 |
| CDS | + | 4605826 | 4606239 | holD | b4372 |
| CDS | + | 4606208 | 4606654 | rimI | b4373 |
| CDS | + | 4606669 | 4607346 | yjjG | b4374 |
| CDS | + | 4607437 | 4609026 | prfC | b4375 |
| CDS | + | 4609419 | 4610024 | osmY | b4376 |
| CDS | + | 4610434 | 4611507 | yjjU | b4377 |
| CDS | + | 4611504 | 4612283 | yjjV | b4378 |
| CDS | − | 4612703 | 4613566 | yjjW | b4379 |
| CDS | − | 4613538 | 4615088 | yjjI | b4380 |
| CDS | + | 4615346 | 4616125 | deoC | b4381 |
| CDS | + | 4616252 | 4617574 | deoA | b4382 |
| CDS | + | 4617626 | 4618849 | deoB | b4383 |
| CDS | + | 4618906 | 4619625 | deoD | b4384 |
| CDS | + | 4619792 | 4621123 | yjjJ | b4385 |
| CDS | − | 4621124 | 4622140 | lplA | b4386 |
| CDS | − | 4622168 | 4622812 | smp | b4387 |
| CDS | + | 4622918 | 4623886 | serB | b4388 |
| CDS | + | 4623935 | 4625317 | sms | b4389 |
| CDS | + | 4625338 | 4626570 | nadR | b4390 |
| CDS | − | 4626878 | 4628545 | yjjK | b4391 |
| CDS | + | 4628756 | 4630693 | slt | b4392 |
| CDS | + | 4630783 | 4631109 | trpR | b4393 |
| CDS | − | 4631256 | 4631768 | yjjX | b4394 |
| CDS | + | 4631820 | 4632467 | gpmB | b4395 |
| CDS | − | 4632464 | 4633333 | rob | b4396 |
| CDS | + | 4633544 | 4634017 | creA | b4397 |
| CDS | + | 4634030 | 4634719 | creB | b4398 |
| CDS | + | 4634719 | 4636143 | creC | b4399 |
| CDS | + | 4636201 | 4637553 | creD | b4400 |
| CDS | − | 4637613 | 4638329 | arcA | b4401 |
| CDS | + | 4638425 | 4638565 | yjjY | b4402 |
| CDS | + | 4638965 | 4639651 | lasT | b4403 |
| CDS | − | 4190660 | 4190860 | thiS | b4407 |
| CDS | + | 4374340 | 4374465 | ecnA | b4410 |
| CDS | + | 4374576 | 4374722 | ecnB | b4411 |
| CDS | + | 1702575 | 1702700 | blr | b4409 |
| misc_RNA | − | 2922178 | 2922537 | csrB | b4408 |
| CDS | − | 213925 | 214125 | yaeP | b4406 |
| misc_RNA | + | 16952 | 17006 | sokC | b4413 |
| misc_RNA | + | 189712 | 189847 | t44 | b4414 |
| misc_RNA | + | 852175 | 852263 | rybA | b4416 |
| misc_RNA | − | 887199 | 887277 | rybB | b4417 |
| misc_RNA | + | 1145812 | 1145980 | sraB | b4418 |
| misc_RNA | + | 1268546 | 1268621 | rdlA | b4420 |
| misc_RNA | + | 1269081 | 1269146 | rdlB | b4422 |
| misc_RNA | + | 1269616 | 1269683 | rdlC | b4424 |
| misc_RNA | − | 1286289 | 1286459 | rtT | b4425 |
| misc_RNA | + | 1403833 | 1403918 | IS061 | b4426 |
| misc_RNA | + | 1435145 | 1435253 | micC | b4427 |
| misc_RNA | + | 1490143 | 1490195 | sokB | b4429 |
| misc_RNA | − | 1762737 | 1762804 | rydB | b4430 |
| misc_RNA | + | 1768396 | 1768500 | rprA | b4431 |
| misc_RNA | + | 1921090 | 1921338 | ryeA | b4432 |
| misc_RNA | − | 1921188 | 1921308 | ryeB | b4433 |
| misc_RNA | − | 1985863 | 1986022 | IS092 | b4434 |
| misc_RNA | + | 2069339 | 2069542 | IS102 | b4435 |
| misc_RNA | + | 2151299 | 2151447 | ryeC | b4436 |
| misc_RNA | + | 2151634 | 2151776 | ryeD | b4437 |
| misc_RNA | + | 2165136 | 2165221 | ryeE | b4438 |
| misc_RNA | + | 2311106 | 2311198 | micF | b4439 |
| misc_RNA | + | 2651877 | 2652180 | ryfA | b4440 |
| misc_RNA | − | 2689214 | 2689362 | tke1 | b4441 |
| misc_RNA | + | 2812823 | 2812897 | sraD | b4442 |
| misc_RNA | + | 2940718 | 2940922 | gcvB | b4443 |
| misc_RNA | + | 2974124 | 2974211 | rygA | b4444 |
| misc_RNA | + | 2974332 | 2974407 | rygB | b4445 |
| misc_RNA | + | 3054837 | 3054987 | rygC | b4446 |
| misc_RNA | + | 3192773 | 3192922 | rygD | b4447 |
| misc_RNA | + | 3236396 | 3236583 | sraF | b4448 |
| misc_RNA | + | 3309247 | 3309420 | sraG | b4449 |
| misc_RNA | + | 3348599 | 3348706 | ryhA | b4450 |
| misc_RNA | + | 3578946 | 3579039 | ryhB | b4451 |
| misc_RNA | + | 3662887 | 3662991 | IS183 | b4452 |
| misc_RNA | + | 3698159 | 3698222 | rdlD | b4454 |
| misc_RNA | + | 3984455 | 3984626 | ryiA | b4456 |
| misc_RNA | + | 4049059 | 4049303 | csrC | b4457 |
| misc_RNA | − | 4156308 | 4156417 | oxyS | b4458 |
| misc_RNA | − | 4275950 | 4276089 | ryjA | b4459 |
| CDS | − | 16751 | 16903 | hokC | b4412 |
| CDS | + | 607059 | 607211 | hokE | b4415 |
| CDS | − | 1268391 | 1268498 | ldrA | b4419 |
| CDS | − | 1268926 | 1269033 | ldrB | b4421 |
| CDS | − | 1269461 | 1269568 | ldrC | b4423 |
| CDS | + | 1489946 | 1490095 | hokB | b4428 |
| CDS | − | 3698003 | 3698110 | ldrD | b4453 |
| CDS | − | 3718471 | 3718623 | hokA | b4455 |
| misc_feature | − | 1588774 | 1588801 | | |
| CDS | − | 1980578 | 1981567 | araH | b4460 |
| CDS | − | 2895986 | 2897440 | | b4463 |
| CDS | − | 3074201 | 3075478 | yggP | b4465 |
| CDS | − | 3112572 | 3117134 | yghJ | b4466 |

TABLE 1-continued

| Type | S | Left | Right | Name | B |
|---|---|---|---|---|---|
| CDS | − | 3122258 | 3123481 | glcF | b4467 |
| CDS | − | 3123492 | 3124544 | glcE | b4468 |
| CDS | − | 3156949 | 3159168 | ygiQ | b4469 |
| CDS | − | 3253363 | 3254673 | yhaM | b4470 |
| CDS | − | 3256307 | 3257671 | tdcG | b4471 |
| CDS | − | 3390480 | 3394280 | yhdP | b4472 |
| CDS | − | 3430458 | 3431582 | smf | b4473 |
| CDS | − | 3553855 | 3554871 | rtcA | b4475 |
| CDS | − | 3573744 | 3575084 | gntU | b4476 |
| CDS | − | 3869873 | 3871021 | dgoD | b4478 |
| CDS | − | 3871018 | 3871635 | dgoA | b4477 |
| CDS | − | 3872494 | 3873183 | dgoR | b4479 |
| CDS | − | 3945151 | 3945990 | hdfR | b4480 |
| CDS | − | 3998315 | 3999079 | yigE | b4482 |
| CDS | + | 2746886 | 2748082 | yfjD | b4461 |
| CDS | + | 2784770 | 2785456 | ygaR | b4462 |
| CDS | + | 3025143 | 3026510 | ygfQ | b4464 |
| CDS | + | 3500362 | 3501192 | frlC | b4474 |
| CDS | + | 3975548 | 3976627 | rffT | b4481 |
| CDS | + | 4021577 | 4022359 | tatD | b4483 |
| CDS | + | 4103843 | 4104343 | cpxP | b4484 |
| CDS | + | 4449081 | 4450583 | ytfR | b4485 |
| CDS | + | 4572158 | 4574878 | yjiV | b4486 |
| CDS | + | 4311891 | 4312220 | yjdP | b4487 |
| CDS | + | 3948583 | 3950227 | ilvG | b4488 |
| prophage | + | 262182 | 296489 | | |
| prophage | + | 564025 | 585326 | | |
| prophage | + | 1195443 | 1210646 | | |
| prophage | + | 1409949 | 1433008 | | |
| prophage | + | 1630310 | 1650778 | | |
| prophage | + | 2064183 | 2077055 | | |
| prophage | + | 2464407 | 2474621 | | |
| prophage | + | 2556721 | 2563510 | | |
| prophage | + | 2753971 | 2776001 | | |
| prophage | + | 4494563 | 4534632 | | |
| CDS | + | 2474332 | 2474532 | torI | b4501 |
| CDS | − | 2263063 | 2263317 | yeiW | b4502 |

TABLE 2

| Strain | Type | Coordinates | Name | B | Function |
|---|---|---|---|---|---|
| MDS01 | CDS | complement(262552 . . . 262893) | | b0245 | orf, hypothetical protein |
| MDS01 | CDS | complement(262914 . . . 263231) | yafW | b0246 | orf, hypothetical protein |
| MDS01 | CDS | complement(263480 . . . 263956) | ykfG | b0247 | putative DNA repair protein |
| MDS01 | CDS | complement(263972 . . . 264430) | yafX | b0248 | orf, hypothetical protein |
| MDS01 | CDS | complement(264528 . . . 264767) | ykfF | b0249 | orf, hypothetical protein |
| MDS01 | CDS | complement(264844 . . . 265311) | ykfB | b0250 | orf, hypothetical protein |
| MDS01 | CDS | complement(265334 . . . 266191) | yafY | b0251 | hypothetical transcriptional regulator |
| MDS01 | CDS | complement(266408 . . . 267244) | yafZ | b0252 | orf, hypothetical protein |
| MDS01 | CDS | complement(267321 . . . 268187) | ykfA | b0253 | putative GTP-binding protein |
| MDS01 | CDS | complement(268513 . . . 269406) | perR | b0254 | peroxide resistance protein |
| MDS01 | CDS | 269466 . . . 269870 | yi91a | b0255 | |
| MDS01 | CDS | 269827 . . . 270978 | tra8_1 | b0256 | IS30 transposase |
| MDS01 | CDS | 271054 . . . 271479 | | b0257 | putative transposase |
| MDS01 | CDS | 272086 . . . 273216 | ykfC | b0258 | orf, hypothetical protein |
| MDS01 | CDS | complement(273325 . . . 274341) | trs5_1 | b0259 | IS5 transposase |
| MDS01 | CDS | 274525 . . . 275952 | ykfB | b0260 | orf, hypothetical protein |
| MDS01 | CDS | 275939 . . . 276871 | yafY | b0261 | hypothetical transcriptional regulator |
| MDS01 | CDS | complement(276980 . . . 278038) | afuC | b0262 | putative ATP-binding component of a transport system |
| MDS01 | CDS | complement(278038 . . . 278400) | | b0263 | |
| MDS01 | CDS | complement(278402 . . . 278905) | insB_2 | b0264 | IS1 protein InsB |
| MDS01 | CDS | complement(278824 . . . 279099) | insA_2 | b0265 | IS1 protein InsA |
| MDS01 | CDS | complement(279609 . . . 279986) | yagB | b0266 | orf, hypothetical protein |
| MDS01 | CDS | complement(280053 . . . 281207) | yagA | b0267 | orf, hypothetical protein |
| MDS01 | CDS | 281481 . . . 282410 | yagE | b0268 | putative lyase/synthase |
| MDS01 | CDS | 282425 . . . 284392 | yagF | b0269 | putative dehydratase |
| MDS01 | CDS | 284619 . . . 286001 | yagG | b0270 | putative permease |
| MDS01 | CDS | 286013 . . . 287623 | yagH | b0271 | putative beta-xylosidase (EC 3.2.1.37 |
| MDS01 | CDS | complement(287628 . . . 288386) | yagI | b0272 | putative regulator |
| MDS01 | CDS | complement(288525 . . . 289529) | argF | b0273 | ornithine carbamoyltransferase 2, chain F |
| MDS01 | CDS | complement(289873 . . . 290376) | insB_3 | b0274 | IS1 protein InsB |
| MDS01 | CDS | complement(290295 . . . 290570) | insA_3 | b0275 | IS1 protein InsA |
| MDS01 | CDS | 290724 . . . 291455 | yagJ | b0276 | orf, hypothetical protein |
| MDS01 | CDS | complement(291546 . . . 292172) | yagK | b0277 | orf, hypothetical protein |
| MDS01 | CDS | complement(292444 . . . 293142) | yagL | b0278 | DNA-binding protein |
| MDS01 | CDS | complement(293169 . . . 294023) | yagM | b0279 | orf, hypothetical protein |
| MDS01 | CDS | complement(294363 . . . 294803) | yagN | b0280 | orf, hypothetical protein |
| MDS01 | CDS | complement(294920 . . . 296320) | intF | b0281 | putative phage integrase |
| MDS01 | CDS | complement(296605 . . . 297015) | yagP | b0282 | putative transcriptional regulator LYSR-type |
| MDS01 | CDS | complement(296994 . . . 297950) | yagQ | b0283 | orf, hypothetical protein |
| MDS01 | CDS | complement(297960 . . . 300158) | yagR | b0284 | orf, hypothetical protein |
| MDS01 | CDS | complement(300155 . . . 301111) | yagS | b0285 | orf, hypothetical protein |
| MDS01 | CDS | complement(301108 . . . 301797) | yagT | b0286 | putative xanthine dehydrogenase (EC 1.1.1.20 |
| MDS01 | CDS | 302215 . . . 302829 | yagU | b0287 | orf, hypothetical protein |
| MDS01 | CDS | complement(303077 . . . 303406) | ykgJ | b0288 | putative ferredoxin |
| MDS01 | CDS | complement(303719 . . . 304474) | yagV | b0289 | orf, hypothetical protein |
| MDS01 | CDS | complement(304398 . . . 306041) | yagW | b0290 | putative receptor |
| MDS01 | CDS | complement(306031 . . . 308556) | yagX | b0291 | putative enzyme |
| MDS01 | CDS | complement(308582 . . . 309250) | yagY | b0292 | orf, hypothetical protein |

TABLE 2-continued

| Strain | Type | Coordinates | Name | B | Function |
|---|---|---|---|---|---|
| MDS01 | CDS | complement(309308 . . . 309895) | yagZ | b0293 | orf, hypothetical protein |
| MDS01 | CDS | complement(309970 . . . 310560) | ykgK | b0294 | putative regulator |
| MDS01 | CDS | 311336 . . . 311563 | ykgL | b0295 | orf, hypothetical protein |
| MDS01 | CDS | complement(311738 . . . 312001) | ykgM | b0296 | putative ribosomal protein |
| MDS01 | CDS | 313581 . . . 314468 | eaeH | b0297 | attaching and effacing protein, pathogenesis factor |
| MDS01 | CDS | 314506 . . . 314814 | | b0298 | |
| MDS01 | CDS | 314811 . . . 315677 | tra5_5 | b0299 | |
| MDS01 | CDS | complement(315674 . . . 316393) | ykgA | b0300 | putative ARAC-type regulatory protein |
| MDS01 | CDS | complement(316950 . . . 317552) | ykgB | b0301 | orf, hypothetical protein |
| MDS01 | CDS | complement(317555 . . . 317806) | ykgI | b0303 | orf, hypothetical protein |
| MDS01 | CDS | complement(317900 . . . 319252) | ykgC | b0304 | putative oxidoreductase |
| MDS01 | CDS | 319451 . . . 320305 | ykgD | b0305 | putative ARAC-type regulatory protein |
| MDS01 | CDS | 320832 . . . 321551 | ykgE | b0306 | putative dehydrogenase subunit |
| MDS01 | CDS | 321562 . . . 322989 | ykgF | b0307 | orf, hypothetical protein |
| MDS01 | CDS | 322829 . . . 323677 | ykgG | b0308 | putative transporter |
| MDS01 | CDS | complement(323632 . . . 323844) | | b0309 | orf, hypothetical protein |
| MDS01 | CDS | complement(323920 . . . 324588) | ykgH | b0310 | orf, hypothetical protein |
| MDS02 | CDS | complement(1398271 . . . 1399803) | ydaH | b1336 | |
| MDS02 | CDS | complement(1399834 . . . 1401279) | | b1337 | |
| MDS02 | CDS | complement(1401279 . . . 1402604) | ydaJ | b1338 | |
| MDS02 | CDS | 1402765 . . . 1403673 | ydaK | b1339 | putative transcriptional regulator LYSR-type |
| MDS02 | CDS | 1404003 . . . 1404566 | ydaL | b1340 | orf, hypothetical protein |
| MDS02 | CDS | complement(1404587 . . . 1405879) | | b1341 | orf, hypothetical protein |
| MDS02 | CDS | 1406074 . . . 1407057 | | b1342 | orf, hypothetical protein |
| MDS02 | CDS | 1407535 . . . 1408908 | dbpA | b1343 | ATP-dependent RNA helicase |
| MDS02 | CDS | complement(1409037 . . . 1409972) | ydaO | b1344 | orf, hypothetical protein |
| MDS02 | CDS | complement(1410024 . . . 1411259) | | b1345 | |
| MDS02 | CDS | complement(1411261 . . . 1411500) | ydaQ | b1346 | putative lambdoid prophage Rac excisionase |
| MDS02 | CDS | complement(1411555 . . . 1411764) | ydaC | b1347 | orf, hypothetical protein |
| MDS02 | CDS | complement(1411757 . . . 1411951) | lar | b1348 | restriction alleviation and modification enhancement |
| MDS02 | CDS | complement(1412008 . . . 1412817) | recT | b1349 | recombinase, DNA renaturation |
| MDS02 | CDS | complement(1412810 . . . 1415410) | recE | b1350 | exonuclease VIII, ds DNA exonuclease 5' --> 3' specific |
| MDS02 | CDS | complement(1415512 . . . 1415787) | racC | b1351 | RacC protein |
| MDS02 | CDS | complement(1416032 . . . 1416265) | kil | b1352 | Kil protein (killing function) of lambdoid prophage Rac |
| MDS02 | CDS | 1416572 . . . 1417183 | sieB | b1353 | phage superinfection exclusion protein |
| MDS02 | CDS | 1417192 . . . 1417368 | | b1354 | orf, hypothetical protein |
| MDS02 | CDS | complement(1417346 . . . 1417525) | | b1355 | orf, hypothetical protein |
| MDS02 | CDS | complement(1417789 . . . 1418265) | ydaR | b1356 | |
| MDS02 | CDS | 1418389 . . . 1418685 | ydaS | b1357 | orf, hypothetical protein |
| MDS02 | CDS | 1418708 . . . 1419130 | ydaT | b1358 | orf, hypothetical protein |
| MDS02 | CDS | 1419143 . . . 1420000 | ydaU | b1359 | orf, hypothetical protein |
| MDS02 | CDS | 1420007 . . . 1420753 | | b1360 | putative DNA replication factor |
| MDS02 | CDS | 1420725 . . . 1421336 | ydaW | b1361 | orf, hypothetical protein |
| MDS02 | CDS | 1421363 . . . 1421668 | | b1362 | putative Rac prophage endopeptidase |
| MDS02 | CDS | 1421806 . . . 1423263 | trkG | b1363 | |
| MDS02 | CDS | 1423202 . . . 1423483 | | b1364 | orf, hypothetical protein |
| MDS02 | CDS | 1423401 . . . 1423664 | | b1365 | orf, hypothetical protein |
| MDS02 | CDS | 1423645 . . . 1424004 | ydaY | b1366 | orf, hypothetical protein |
| MDS02 | CDS | 1424079 . . . 1424312 | | b1367 | orf, hypothetical protein |
| MDS02 | CDS | 1424478 . . . 1425506 | | b1368 | putative alpha helix protein |
| MDS02 | CDS | 1425482 . . . 1425637 | | b1369 | orf, hypothetical protein |
| MDS02 | CDS | complement(1425770 . . . 1426750) | trs5_5 | b1370 | |
| MDS02 | CDS | 1426547 . . . 1427008 | | b1371 | orf, hypothetical protein |
| MDS02 | CDS | 1427067 . . . 1430435 | | b1372 | |
| MDS02 | CDS | 1430435 . . . 1431010 | | b1373 | tail fiber assembly protein homolog from lambdoid prophage Rac |
| MDS02 | CDS | complement(1431108 . . . 1431698) | | b1374 | |
| MDS02 | CDS | complement(1432015 . . . 1432281) | ynaE | b1375 | orf, hypothetical protein |
| MDS02 | CDS | complement(1433209 . . . 1433715) | | b1376 | ynaF putative filament protein |
| MDS02 | CDS | complement(1433784 . . . 1434917) | | b1377 | |
| MDS02 | CDS | complement(1435284 . . . 1438808) | ydbK | b1378 | putative oxidoreductase, Fe—S subunit |
| MDS02 | CDS | complement(1439345 . . . 1439767) | hslJ | b1379 | heat shock protein HslJ |
| MDS02 | CDS | complement(1439878 . . . 1440867) | ldhA | b1380 | fermentative D-lactate dehydrogenase NAD-dependent |
| MDS02 | CDS | 1441075 . . . 1443714 | ydbH | b1381 | orf, hypothetical protein |
| MDS02 | CDS | 1443711 . . . 1443896 | ynbE | b1382 | orf, hypothetical protein |
| MDS02 | CDS | 1443898 . . . 1444230 | ydbL | b1383 | orf, hypothetical protein |
| MDS02 | CDS | complement(1444402 . . . 1445307) | feaR | b1384 | regulatory protein for 2-phenylethylamine catabolism |
| MDS02 | CDS | 1445540 . . . 1447042 | feaB | b1385 | phenylacetaldehyde dehydrogenase |
| MDS02 | CDS | complement(1447100 . . . 1449373) | tynA | b1386 | copper amine oxidase (tyramine oxidase) |

TABLE 2-continued

| Strain | Type | Coordinates | Name | B | Function |
|---|---|---|---|---|---|
| MDS02 | CDS | complement(1449621 . . . 1451666) | maoC | b1387 | |
| MDS02 | CDS | 1451951 . . . 1452880 | ydbO | b1388 | |
| MDS02 | CDS | 1452892 . . . 1453179 | ynbF | b1389 | |
| MDS02 | CDS | 1453188 . . . 1453934 | ydbP | b1390 | |
| MDS02 | CDS | 1453943 . . . 1454446 | | b1391 | |
| MDS02 | CDS | 1454454 . . . 1455524 | | b1392 | |
| MDS02 | CDS | 1455521 . . . 1456288 | ydbS | b1393 | |
| MDS02 | CDS | 1456288 . . . 1457076 | | b1394 | |
| MDS02 | CDS | 1457078 . . . 1458505 | ydbU | b1395 | |
| MDS02 | CDS | 1458495 . . . 1458917 | | b1396 | |
| MDS02 | CDS | 1458917 . . . 1460122 | | b1397 | |
| MDS02 | CDS | 1460149 . . . 1461462 | | b1398 | |
| MDS02 | CDS | 1461563 . . . 1462513 | | b1399 | |
| MDS02 | CDS | 1462495 . . . 1463085 | | b1400 | |
| MDS02 | CDS | 1463416 . . . 1465974 | ydbA_1 | b1401 | |
| MDS02 | CDS | complement(1465945 . . . 1466850) | yi22_2 | b1402 | IS2 hypothetical protein |
| MDS02 | CDS | complement(1466808 . . . 1467218) | yi21_2 | b1403 | IS2 hypothetical protein |
| MDS02 | CDS | 1467382 . . . 1468533 | tra8_2 | b1404 | IS30 transposase |
| MDS02 | CDS | 1468714 . . . 1472037 | ydbA_2 | b1405 | |
| MDS02 | CDS | 1472245 . . . 1473105 | ydbC | b1406 | putative dehydrogenase |
| MDS02 | CDS | 1473162 . . . 1475474 | ydbD | b1407 | orf, hypothetical protein |
| MDS02 | CDS | 1475639 . . . 1476250 | | b1408 | |
| MDS02 | CDS | 1476250 . . . 1477146 | | b1409 | putative phosphatidate cytidiltransferase |
| MDS02 | CDS | 1477162 . . . 1478919 | | b1410 | orf, hypothetical protein |
| MDS02 | CDS | 1478933 . . . 1480225 | ynbD | b1411 | putative enzymes |
| MDS02 | misc_RNA | complement(1403676 . . . 1403833) | IS061 | b4426 | |
| MDS02 | misc_RNA | 1435145 . . . 1435252 | tke8 | b4427 | |
| MDS03 | CDS | complement(2555340 . . . 2556743) | eutB | b2441 | ethanolamine ammonia-lyase, heavy chain |
| MDS03 | CDS | 2556793 . . . 2558088 | | b2442 | putative prophage integrase |
| MDS03 | CDS | 2558279 . . . 2558920 | | b2443 | orf, hypothetical protein |
| MDS03 | CDS | 2559390 . . . 2559635 | | b2444 | orf, hypothetical protein |
| MDS03 | CDS | 2559632 . . . 2560015 | | b2445 | orf, hypothetical protein |
| MDS03 | CDS | 2560133 . . . 2560549 | | b2446 | orf, hypothetical protein |
| MDS03 | CDS | 2560546 . . . 2561139 | | b2447 | orf, hypothetical protein |
| MDS03 | CDS | 2561599 . . . 2561991 | | b2448 | orf, hypothetical protein |
| MDS03 | CDS | 2562002 . . . 2562394 | | b2449 | orf, hypothetical protein |
| MDS03 | CDS | 2562515 . . . 2563354 | | b2450 | orf, hypothetical protein |
| MDS04 | CDS | 2754181 . . . 2755422 | intA | b2622 | prophage CP4-57 integrase |
| MDS04 | CDS | complement(2755666 . . . 2756622) | yfjH | b2623 | putative histone |
| MDS04 | CDS | 2756666 . . . 2756878 | alpA | b2624 | prophage CP4-57 regulatory protein alpA |
| MDS04 | CDS | 2757007 . . . 2758416 | yfjI | b2625 | orf, hypothetical protein |
| MDS04 | CDS | 2758569 . . . 2759195 | yfjJ | b2626 | orf, hypothetical protein |
| MDS04 | CDS | complement(2759373 . . . 2761562) | yfjK | b2627 | orf, hypothetical protein |
| MDS04 | CDS | complement(2761559 . . . 2763175) | yfjL | b2628 | orf, hypothetical protein |
| MDS04 | CDS | complement(2763535 . . . 2763798) | yfjM | b2629 | orf, hypothetical protein |
| MDS04 | CDS | 2763940 . . . 2765013 | yfjN | b2630 | putative cell division protein |
| MDS04 | CDS | 2765057 . . . 2765377 | yfjO | b2631 | orf, hypothetical protein |
| MDS04 | CDS | 2765732 . . . 2766595 | yfjP | b2632 | putative GTP-binding protein |
| MDS04 | CDS | 2766687 . . . 2767508 | yfjQ | b2633 | orf, hypothetical protein |
| MDS04 | CDS | 2767725 . . . 2768426 | yfjR | b2634 | orf, hypothetical protein |
| MDS04 | CDS | 2768311 . . . 2768703 | | b2635 | orf, hypothetical protein |
| MDS04 | CDS | 2768454 . . . 2769146 | | b2636 | orf, hypothetical protein |
| MDS04 | CDS | 2769170 . . . 2769637 | yfjT | b2637 | orf, hypothetical protein |
| MDS04 | CDS | complement(2769862 . . . 2770176) | | b2638 | orf, hypothetical protein |
| MDS04 | CDS | complement(2770189 . . . 2770707) | | b2639 | putative pump protein |
| MDS04 | CDS | complement(2770858 . . . 2771058) | | b2640 | orf, hypothetical protein |
| MDS04 | CDS | complement(2770998 . . . 2771114) | | b2641 | orf, hypothetical protein |
| MDS04 | CDS | 2771340 . . . 2773043 | yfjW | b2642 | orf, hypothetical protein |
| MDS04 | CDS | 2773941 . . . 2774399 | yfjX | b2643 | orf, hypothetical protein |
| MDS04 | CDS | 2774408 . . . 2774890 | yfjY | b2644 | putative DNA repair protein |
| MDS04 | CDS | 2775137 . . . 2775454 | yfjZ | b2645 | orf, hypothetical protein |
| MDS04 | CDS | 2775475 . . . 2775804 | ypjF | b2646 | orf, hypothetical protein |
| MDS04 | CDS | complement(2776168 . . . 2780877) | ypjA | b2647 | putative ATP-binding component of a transport system |
| MDS04 | CDS | complement(2781087 . . . 2781230) | | b2648 | orf, hypothetical protein |
| MDS04 | CDS | complement(2781660 . . . 2782451) | | b2649 | orf, hypothetical protein |
| MDS04 | CDS | complement(2782551 . . . 2783033) | | b2650 | orf, hypothetical protein |
| MDS04 | CDS | 2783243 . . . 2783374 | | b2651 | orf, hypothetical protein |
| MDS04 | tRNA | complement(2783784 . . . 2783859) | ileY | b2652 | tRNA-Ile |
| MDS04 | CDS | complement(2783822 . . . 2783995) | | b2653 | orf, hypothetical protein |
| MDS04 | CDS | 2784419 . . . 2784751 | | b2654 | orf, hypothetical protein |
| MDS04 | CDS | 2785628 . . . 2786260 | | b2657 | putative enzyme |
| MDS04 | CDS | 2786399 . . . 2786671 | | b2658 | orf, hypothetical protein |
| MDS04 | CDS | 2786902 . . . 2787984 | | b2659 | orf, hypothetical protein |
| MDS04 | CDS | 2787938 . . . 2789272 | ygaF | b2660 | orf, hypothetical protein |

TABLE 2-continued

| Strain | Type | Coordinates | Name | B | Function |
|---|---|---|---|---|---|
| MDS04 | CDS | 2784770 . . . 2785456 | ygaR | b4462 | orf, hypothetical protein |
| MDS05 | CDS | complement(2064329 . . . 2065345) | trs5_6 | b1994 | IS5 transposase |
| MDS05 | CDS | 2066632 . . . 2067051 | | b1995 | orf, hypothetical protein |
| MDS05 | CDS | complement(2066976 . . . 2067881) | yi22_3 | b1996 | IS2 hypothetical protein |
| MDS05 | CDS | complement(2067839 . . . 2068249) | yi21_3 | b1997 | IS2 hypothetical protein |
| MDS05 | CDS | 2068268 . . . 2068528 | | b1998 | orf, hypothetical protein |
| MDS05 | CDS | 2068525 . . . 2069235 | yeeP | b1999 | putative histone |
| MDS05 | CDS | 2069563 . . . 2072682 | flu | b2000 | antigen 43, phase-variable bipartite outer membrane fluffing protein |
| MDS05 | CDS | 2072797 . . . 2074335 | | b2001 | orf, hypothetical protein |
| MDS05 | CDS | 2074332 . . . 2074778 | yeeS | b2002 | putative DNA repair protein, RADC family |
| MDS05 | CDS | 2074841 . . . 2075062 | yeeT | b2003 | orf, hypothetical protein |
| MDS05 | CDS | 2075136 . . . 2075504 | yeeU | b2004 | putative structural protein |
| MDS05 | CDS | 2075593 . . . 2075967 | yeeV | b2005 | orf, hypothetical protein |
| MDS05 | CDS | 2075964 . . . 2076158 | yeeW | b2006 | orf, hypothetical protein |
| MDS05 | CDS | complement(2077056 . . . 2077451) | yeeX | b2007 | putative alpha helix protein |
| MDS05 | CDS | complement(2077557 . . . 2078615) | yeeA | b2008 | orf, hypothetical protein |
| MDS05 | misc_RNA | 2069339 . . . 2069542 | | b4435 | IS102 |
| MDS06 | CDS | complement(3451530 . . . 3451949) | | b3322 | calcium-binding protein required for initiation of chromosome replication |
| MDS06 | CDS | complement(3451951 . . . 3453420) | yheD | b3323 | putative export protein A for general secretion pathway (GSP) |
| MDS06 | CDS | 3453600 . . . 3454415 | yheE | b3324 | |
| MDS06 | CDS | 3454387 . . . 3456351 | yheF | b3325 | |
| MDS06 | CDS | 3456361 . . . 3457842 | yheG | b3326 | |
| MDS06 | CDS | 3457839 . . . 3459035 | hofF | b3327 | |
| MDS06 | CDS | 3459045 . . . 3459482 | hofG | b3328 | |
| MDS06 | CDS | 3459490 . . . 3459999 | hofH | b3329 | |
| MDS06 | CDS | 3459957 . . . 3460373 | yheH | b3330 | |
| MDS06 | CDS | 3460366 . . . 3460953 | yheI | b3331 | |
| MDS06 | CDS | 3460946 . . . 3461929 | yheJ | b3332 | |
| MDS06 | CDS | 3461941 . . . 3463107 | yheK | b3333 | |
| MDS06 | CDS | 3463080 . . . 3463565 | pshM | b3334 | |
| MDS06 | CDS | 3463565 . . . 3464242 | hofD | b3335 | |
| MDS06 | CDS | complement(3464271 . . . 3464747) | bfr | b3336 | bacterioferrin, an iron storage homoprotein |
| MDS06 | CDS | complement(3464819 . . . 3465013) | yheA | b3337 | |
| MDS06 | CDS | complement(3465182 . . . 3467875) | yheB | b3338 | |
| MDS07 | CDS | 2464567 . . . 2465724 | intC | b2349 | |
| MDS07 | CDS | 2465877 . . . 2466239 | | b2350 | |
| MDS07 | CDS | 2471542 . . . 2471988 | | b2350 | orf, hypothetical protein |
| MDS07 | CDS | 2466236 . . . 2467156 | | b2351 | |
| MDS07 | CDS | 2467153 . . . 2468484 | | b2352 | putative ligase |
| MDS07 | CDS | 2468783 . . . 2469127 | | b2353 | |
| MDS07 | CDS | complement(2469099 . . . 2469539) | | b2354 | orf, hypothetical protein |
| MDS07 | CDS | complement(2469566 . . . 2470084) | yfdL | b2355 | putative RNA polymerase beta |
| MDS07 | CDS | complement(2470134 . . . 2470442) | yfdM | b2356 | orf, hypothetical protein |
| MDS07 | CDS | complement(2470409 . . . 2470903) | yfdN | b2357 | orf, hypothetical protein |
| MDS07 | CDS | complement(2470900 . . . 2471268) | yfdO | b2358 | orf, hypothetical protein |
| MDS07 | CDS | 2472054 . . . 2472878 | | b2360 | orf, hypothetical protein |
| MDS07 | CDS | 2472979 . . . 2473542 | | b2361 | orf, hypothetical protein |
| MDS07 | CDS | 2473533 . . . 2473895 | | b2362 | orf, hypothetical protein |
| MDS07 | CDS | 2473895 . . . 2474200 | | b2363 | orf, hypothetical protein |
| MDS08 | CDS | 1625541 . . . 1626287 | ydfG | b1539 | putative oxidoreductase |
| MDS08 | CDS | 1626376 . . . 1627062 | ydfH | b1540 | orf, hypothetical protein |
| MDS08 | CDS | 1627239 . . . 1627442 | | b1541 | orf, hypothetical protein |
| MDS08 | CDS | complement(1627477 . . . 1628937) | ydfI | b1542 | putative oxidoreductase |
| MDS08 | CDS | complement(1629026 . . . 1630309) | | b1543 | putative transport protein |
| MDS08 | CDS | 1631063 . . . 1631329 | ydfK | b1544 | orf, hypothetical protein |
| MDS08 | CDS | 1631646 . . . 1632236 | | b1545 | |
| MDS08 | CDS | complement(1632334 . . . 1632909) | ydfM | b1546 | tail fiber assembly protein homolog from lambdoid prophage Qin |
| MDS08 | CDS | complement(1632909 . . . 1633871) | | b1547 | |
| MDS08 | CDS | complement(1633822 . . . 1634391) | nohA | b1548 | DNA packaging protein NU1 homolog from lambdoid prophages |
| MDS08 | CDS | 1635056 . . . 1635481 | ydfO | b1549 | orf, hypothetical protein |
| MDS08 | CDS | complement(1635633 . . . 1635809) | | b1550 | |
| MDS08 | CDS | complement(1635978 . . . 1636169) | | b1551 | orf, hypothetical protein |
| MDS08 | CDS | complement(1636479 . . . 1636691) | cspI | b1552 | cold shock-like protein |
| MDS08 | CDS | complement(1637054 . . . 1637551) | | b1553 | orf, hypothetical protein |
| MDS08 | CDS | complement(1637548 . . . 1638081) | | b1554 | |
| MDS08 | CDS | complement(1638078 . . . 1638389) | | b1555 | orf, hypothetical protein |
| MDS08 | CDS | complement(1638394 . . . 1638684) | | b1556 | |
| MDS08 | CDS | complement(1639363 . . . 1639578) | cspB | b1557 | |
| MDS08 | CDS | 1639879 . . . 1640091 | cspF | b1558 | |
| MDS08 | CDS | complement(1640513 . . . 1641295) | | b1559 | |
| MDS08 | CDS | complement(1641279 . . . 1642367) | | b1560 | orf, hypothetical protein |

TABLE 2-continued

| Strain | Type | Coordinates | Name | B | Function |
|---|---|---|---|---|---|
| MDS08 | CDS | complement(1642675 ... 1642926) | rem | b1561 | orf, hypothetical protein |
| MDS08 | CDS | complement(1643143 ... 1643298) | hokD | b1562 | polypeptide destructive to membrane potential |
| MDS08 | CDS | complement(1643370 ... 1643657) | relE | b1563 | orf, hypothetical protein |
| MDS08 | CDS | complement(1643657 ... 1643896) | relB | b1564 | negative regulator of translation |
| MDS08 | CDS | 1643921 ... 1644226 | | b1565 | orf, hypothetical protein |
| MDS08 | CDS | 1644429 ... 1644761 | flxA | b1566 | orf, hypothetical protein |
| MDS08 | CDS | complement(1645198 ... 1645347) | | b1567 | orf, hypothetical protein |
| MDS08 | CDS | complement(1645370 ... 1645660) | | b1568 | orf, hypothetical protein |
| MDS08 | CDS | complement(1645644 ... 1645874) | dicC | b1569 | regulator of dicB |
| MDS08 | CDS | 1645958 ... 1646365 | dicA | b1570 | regulator of dicB |
| MDS08 | CDS | 1646532 ... 1646687 | ydfA | b1571 | orf, hypothetical protein |
| MDS08 | CDS | 1646647 ... 1646817 | ydfB | b1572 | orf, hypothetical protein |
| MDS08 | CDS | 1646847 ... 1647065 | ydfC | b1573 | orf, hypothetical protein |
| MDS08 | misc_RNA | 1647406 ... 1647458 | dicF | b1574 | DicF antisense RNA, inhibits ftsZ translation |
| MDS08 | CDS | 1647633 ... 1647821 | dicB | b1575 | inhibition of cell division |
| MDS08 | CDS | 1647818 ... 1648009 | ydfD | b1576 | orf, hypothetical protein |
| MDS08 | CDS | 1648102 ... 1649022 | ydfE | b1577 | orf, hypothetical protein |
| MDS08 | CDS | 1648905 ... 1649561 | | b1578 | orf, hypothetical protein |
| MDS08 | CDS | 1649536 ... 1650732 | | b1579 | |
| MDS09 | CDS | complement(4493213 ... 4494274) | yjgB | b4269 | putative oxidoreductase |
| MDS09 | tRNA | 4494428 ... 4494512 | leuX | b4270 | tRNA-Leu |
| MDS09 | CDS | 4494773 ... 4495963 | intB | b4271 | prophage P4 integrase |
| MDS09 | CDS | 4496250 ... 4496660 | yi21_6 | b4272 | IS2 hypothetical protein |
| MDS09 | CDS | 4496618 ... 4497523 | yi22_6 | b4273 | IS2 hypothetical protein |
| MDS09 | CDS | 4497622 ... 4497957 | yjgW | b4274 | orf, hypothetical protein |
| MDS09 | CDS | complement(4498066 ... 4498512) | yjgX | b4275 | orf, hypothetical protein |
| MDS09 | CDS | complement(4498455 ... 4498904) | yjgY | b4276 | orf, hypothetical protein |
| MDS09 | CDS | 4499283 ... 4499612 | yjgZ | b4277 | orf, hypothetical protein |
| MDS09 | CDS | complement(4500126 ... 4501454) | yi41 | b4278 | IS4 hypothetical protein |
| MDS09 | CDS | 4502021 ... 4503298 | yjhB | b4279 | putative transport protein |
| MDS09 | CDS | 4503295 ... 4504428 | yjhC | b4280 | putative dehydrogenase |
| MDS09 | CDS | complement(4504649 ... 4505023) | yjhD | b4281 | orf, hypothetical protein |
| MDS09 | CDS | 4504929 ... 4505132 | yjhE | b4282 | orf, hypothetical protein |
| MDS09 | CDS | 4505184 ... 4505486 | yi91b | b4283 | |
| MDS09 | CDS | complement(4505489 ... 4506640) | tra8_3 | b4284 | IS30 transposase |
| MDS09 | CDS | 4506981 ... 4507577 | | b4285 | putative transposase |
| MDS09 | CDS | 4507743 ... 4508156 | | b4286 | orf, hypothetical protein |
| MDS09 | CDS | complement(4508713 ... 4509480) | fecE | b4287 | ATP-binding component of citrate-dependent |
| MDS09 | CDS | complement(4509481 ... 4510437) | fecD | b4288 | citrate-dependent iron transport, membrane-bound protein |
| MDS09 | CDS | complement(4510434 ... 4511432) | fecC | b4289 | citrate-dependent iron(III) transport protein, cytosolic |
| MDS09 | CDS | complement(4511429 ... 4512337) | fecB | b4290 | citrate-dependent iron transport, periplasmic protein |
| MDS09 | CDS | complement(4512376 ... 4514700) | fecA | b4291 | outer membrane receptor; citrate-dependent iron |
| MDS09 | CDS | complement(4514787 ... 4515740) | fecR | b4292 | outer membrane receptor; citrate-dependent iron transport, outer membrane receptor |
| MDS09 | CDS | complement(4515737 ... 4516258) | fecI | b4293 | probable RNA polymerase sigma factor |
| MDS09 | CDS | 4516550 ... 4516825 | insA_7 | b4294 | IS1 protein InsA |
| MDS09 | CDS | complement(4517361 ... 4518161) | yjhU | b4295 | orf, hypothetical protein |
| MDS09 | CDS | complement(4518694 ... 4520043) | yjhF | b4296 | putative transport system permease |
| MDS09 | CDS | complement(4520150 ... 4522117) | yjhG | b4297 | putative dehydratase |
| MDS09 | CDS | complement(4522128 ... 4523087) | yjhH | b4298 | putative lyase/synthase |
| MDS09 | CDS | complement(4523038 ... 4523826) | yjhI | b4299 | putative regulator |
| MDS09 | CDS | complement(4524129 ... 4524911) | sgcR | b4300 | putative DEOR-type transcriptional regulator |
| MDS09 | CDS | complement(4524928 ... 4525560) | sgcE | b4301 | putative epimerase |
| MDS09 | CDS | complement(4525572 ... 4526003) | sgcA | b4302 | putative PTS system enzyme II A component |
| MDS09 | CDS | complement(4526134 ... 4526940) | sgcQ | b4303 | putative nucleoside triphosphatase |
| MDS09 | CDS | complement(4526953 ... 4528266) | sgcC | b4304 | putative PTS system enzyme IIC component |
| MDS09 | CDS | complement(4528553 ... 4529704) | sgcX | b4305 | putative lyase/synthase |
| MDS09 | CDS | complement(4530460 ... 4531206) | yjhP | b4306 | putative methyltransferase |
| MDS09 | CDS | complement(4531262 ... 4531807) | yjhQ | b4307 | orf, hypothetical protein |
| MDS09 | CDS | 4533038 ... 4534054 | yjhR | b4308 | putative frameshift suppressor" |
| MDS09 | CDS | complement(4534637 ... 4535617) | yjhS | b4309 | orf, hypothetical protein |
| MDS09 | CDS | complement(4535682 ... 4536896) | yjhT | b4310 | orf, hypothetical protein |
| MDS09 | CDS | complement(4536808 ... 4537533) | yjhA | b4311 | orf, hypothetical protein |
| MDS09 | CDS | 4538980 ... 4539582 | fimB | b4312 | recombinase involved in phase variation; regulator for fimA" |

TABLE 2-continued

| Strain | Type | Coordinates | Name | B | Function |
|---|---|---|---|---|---|
| MDS09 | CDS | 4540060 . . . 4540656 | fimE | b4313 | recombinase involved in phase variation; regulator for fimA" |
| MDS09 | CDS | 4541138 . . . 4541686 | fimA | b4314 | major type 1 subunit fimbrin (pilin) |
| MDS09 | CDS | 4541643 . . . 4542290 | fimI | b4315 | fimbrial protein |
| MDS09 | CDS | 4542327 . . . 4543052 | fimC | b4316 | periplasmic chaperone, required for type 1 fimbriae |
| MDS09 | CDS | 4543119 . . . 4545755 | fimD | b4317 | outer membrane protein; export and assembly of type 1 fimbriae, interrupted |
| MDS09 | CDS | 4545765 . . . 4546295 | fimF | b4318 | fimbrial morphology |
| MDS09 | CDS | 4546308 . . . 4546811 | fimG | b4319 | fimbrial morphology |
| MDS09 | CDS | 4546831 . . . 4547733 | fimH | b4320 | minor fimbrial subunit, D-mannose specific adhesin |
| MDS10 | CDS | complement(3108612 . . . 3109148) | yghD | b2968 | putative secretion pathway protein |
| MDS10 | CDS | complement(3109150 . . . 3110010) | yghE | b2969 | putative general secretion pathway for protein export (GSP) |
| MDS10 | CDS | complement(3110076 . . . 3110942) |  | b2970 | putative general secretion pathway for protein export (GSP) |
| MDS10 | CDS | complement(3111089 . . . 3111499) |  | b2971 | orf, hypothetical protein |
| MDS10 | CDS | complement(3111565 . . . 3112497) |  | b2972 |  |
| MDS10 | CDS | complement(3117619 . . . 3119301) | yghK | b2975 | putative permease |
| MDS10 | CDS | complement(3119656 . . . 3121827) | glcB | b2976 | malate synthase G |
| MDS10 | CDS | complement(3121849 . . . 3122253) | glcG | b2977 | orf, hypothetical protein |
| MDS10 | CDS | complement(3124544 . . . 3126043) | glcD | b2979 | glycolate oxidase subunit D |
| MDS10 | CDS | 3126294 . . . 3127058 | glcC | b2980 | transcriptional activator for glc operon |
| MDS10 | CDS | complement(3127065 . . . 3128237) |  | b2981 | orf, hypothetical protein |
| MDS10 | CDS | 3128200 . . . 3129216 | trs5_9 | b2982 | IS5 transposase |
| MDS10 | CDS | complement(3129363 . . . 3130430) | yghQ | b2983 | orf, hypothetical protein |
| MDS10 | CDS | complement(3130476 . . . 3131234) | yghR | b2984 | orf, hypothetical protein |
| MDS10 | CDS | complement(3131266 . . . 3131979) | yghS | b2985 | orf, hypothetical protein |
| MDS10 | CDS | 3132153 . . . 3132845 | yghT | b2986 | orf, hypothetical protein |
| MDS10 | CDS | complement(3132894 . . . 3134393) | pitB | b2987 | low-affinity phosphate transport |
| MDS10 | CDS | complement(3112572 . . . 3117134) | yghJ | b4466 | putative lipoprotein |
| MDS10 | CDS | complement(3122258 . . . 3123481) | glcF | b4467 | glycolate oxidase iron-sulfur subunit |
| MDS10 | CDS | complement(3123492 . . . 3124544) | glcE | b4468 | glycolate oxidase iron-sulfur subunit |
| MDS11 | CDS | complement(1196090 . . . 1196755) | ymfD | b1137 | orf, hypothetical protein |
| MDS11 | CDS | complement(1196756 . . . 1197460) | ymfE | b1138 | orf, hypothetical protein |
| MDS11 | CDS | 1197918 . . . 1198811 | lit | b1139 | phage T4 late gene expression; at locus of e14 element |
| MDS11 | CDS | complement(1198902 . . . 1200029) | intE | b1140 | prophage e14 integrase |
| MDS11 | CDS | complement(1200010 . . . 1200255) |  | b1141 |  |
| MDS11 | CDS | complement(1200292 . . . 1200603) | ymfH | b1142 |  |
| MDS11 | CDS | 1200675 . . . 1201061 | ymfI | b1143 |  |
| MDS11 | CDS | complement(1200999 . . . 1201283) | ymfJ | b1144 |  |
| MDS11 | CDS | complement(1201482 . . . 1202156) |  | b1145 |  |
| MDS11 | CDS | 1201944 . . . 1202447 |  | b1146 |  |
| MDS11 | CDS | 1202479 . . . 1203048 | ymfL | b1147 |  |
| MDS11 | CDS | 1203045 . . . 1203383 | ymfM | b1148 |  |
| MDS11 | CDS | 1203393 . . . 1204760 | ymfN | b1149 |  |
| MDS11 | CDS | 1204772 . . . 1204954 | ymfR | b1150 |  |
| MDS11 | CDS | 1204954 . . . 1205427 | ymfO | b1151 |  |
| MDS11 | CDS | 1205354 . . . 1206145 |  | b1152 |  |
| MDS11 | CDS | 1206136 . . . 1206720 |  | b1153 |  |
| MDS11 | CDS | 1206724 . . . 1207353 | ycfK | b1154 |  |
| MDS11 | CDS | 1207355 . . . 1207768 |  | b1155 |  |
| MDS11 | CDS | complement(1207740 . . . 1208342) | ycfA | b1156 |  |
| MDS11 | CDS | complement(1208342 . . . 1208881) |  | b1157 |  |
| MDS11 | CDS | 1208908 . . . 1209462 | pin | b1158 | inversion of adjacent DNA; at locus of e14 element |
| MDS11 | CDS | 1209569 . . . 1210402 | mcrA | b1159 | restriction of DNA at 5-methylcytosine residues; at locus of e14 element |
| MDS11 | CDS | complement(1210903 . . . 1211226) | ycgW | b1160 | orf, hypothetical protein |
| MDS11 | CDS | complement(1211926 . . . 1212330) | ycgX | b1161 | orf, hypothetical protein |
| MDS11 | CDS | complement(1212551 . . . 1213282) | ycgE | b1162 | putative transcriptional regulator |
| MDS11 | CDS | complement(1213487 . . . 1214698) |  | b1163 | orf, hypothetical protein |
| MDS11 | CDS | 1215012 . . . 1215248 | ycgZ | b1164 | orf, hypothetical protein |
| MDS11 | CDS | 1215291 . . . 1215563 | ymgA | b1165 | orf, hypothetical protein |
| MDS11 | CDS | 1215592 . . . 1215858 | ymgB | b1166 | orf, hypothetical protein |
| MDS11 | CDS | 1215971 . . . 1216219 | ymgC | b1167 | orf, hypothetical protein |
| MDS11 | CDS | 1216509 . . . 1218074 |  | b1168 | putative proteases |
| MDS11 | CDS | 1218824 . . . 1220344 |  | b1169 | putative ATP-binding component of a transport system |
| MDS11 | CDS | 1220429 . . . 1221445 |  | b1170 |  |
| MDS11 | CDS | complement(1221528 . . . 1221863) |  | b1171 | orf, hypothetical protein |
| MDS11 | CDS | complement(1221867 . . . 1222151) |  | b1172 | orf, hypothetical protein |
| MDS12 | CDS | complement(564038 . . . 565201) | intD | b0537 | prophage DLP12 integrase |
| MDS12 | CDS | 565195 . . . 565755 |  | b0538 | putative sensory transduction regulator |
| MDS12 | CDS | complement(565321 . . . 565584) |  | b0539 |  |

TABLE 2-continued

| Strain | Type | Coordinates | Name | B | Function |
|---|---|---|---|---|---|
| MDS12 | CDS | 566056 . . . 566364 | | b0540 | |
| MDS12 | CDS | 566361 . . . 567227 | tra5_2 | b0541 | |
| MDS12 | CDS | 567333 . . . 567470 | | b0542 | orf, hypothetical protein |
| MDS12 | CDS | 567538 . . . 567870 | emrE | b0543 | methylviologen resistance |
| MDS12 | CDS | 568125 . . . 569651 | ybcK | b0544 | orf, hypothetical protein |
| MDS12 | CDS | 570116 . . . 570667 | ybcL | b0545 | orf, hypothetical protein |
| MDS12 | CDS | 570677 . . . 571474 | ybcM | b0546 | putative ARAC-type regulatory protein |
| MDS12 | CDS | 571689 . . . 572144 | ybcN | b0547 | orf, hypothetical protein |
| MDS12 | CDS | 572144 . . . 572314 | ninE | b0548 | similar to phage 82 and lambda proteins |
| MDS12 | CDS | 572307 . . . 572597 | ybcO | b0549 | orf, hypothetical protein |
| MDS12 | CDS | 572594 . . . 572956 | rus | b0550 | endodeoxyribonuclease RUS (Holliday junction resolvase) |
| MDS12 | CDS | 573179 . . . 573562 | ybcQ | b0551 | orf, hypothetical protein |
| MDS12 | CDS | complement(573960 . . . 574976) | trs5_2 | b0552 | IS5 transposase |
| MDS12 | CDS | complement(574981 . . . 576108) | nmpC | b0553 | outer membrane porin protein; locus of qsr prophage |
| MDS12 | CDS | 576621 . . . 576836 | ybcR | b0554 | orf, hypothetical protein |
| MDS12 | CDS | 576836 . . . 577333 | ybcS | b0555 | bacteriophage lambda lysozyme homolog |
| MDS12 | CDS | 577330 . . . 577791 | ybcT | b0556 | bacteriophage lambda endopeptidase homolog |
| MDS12 | CDS | complement(577823 . . . 578116) | ybcU | b0557 | bacteriophage lambda Bor protein homolog |
| MDS12 | CDS | complement(578407 . . . 578859) | ybcV | b0558 | putative an envelop protein |
| MDS12 | CDS | 579103 . . . 579309 | ybcW | b0559 | orf, hypothetical protein |
| MDS12 | CDS | 580057 . . . 580602 | nohB | b0560 | bacteriophage DNA packaging protein |
| MDS12 | CDS | 580577 . . . 581320 | ybcX | b0561 | orf, hypothetical protein |
| MDS12 | CDS | complement(581375 . . . 581959) | ybcY | b0562 | orf, hypothetical protein |
| MDS12 | CDS | 582098 . . . 582283 | ylcE | b0563 | orf, hypothetical protein |
| MDS12 | CDS | 582904 . . . 583653 | appY | b0564 | regulatory protein affecting appA and other genes |
| MDS12 | CDS | complement(583903 . . . 584856) | ompT | b0565 | outer membrane protein 3b (a), protease VII |
| MDS13 | CDS | 15445 . . . 16557 | yi81_ | b0016 | IS186 hypothetical protein 1 |
| MDS13 | CDS | complement(15869 . . . 16177) | yi82_1 | b0017 | |
| MDS13 | CDS | complement(16751 . . . 16960) | mokC | b0018 | regulatory peptide whose translation enables hokC (gef) expression |
| MDS13 | CDS | 17489 . . . 18655 | nhaA | b0019 | Na+/H antiporter, pH dependent |
| MDS13 | CDS | 18715 . . . 19620 | nhaR | b0020 | transcriptional activator of nhaA |
| MDS13 | CDS | complement(19811 . . . 20314) | insB_1 | b0021 | IS1 protein InsB |
| MDS13 | CDS | complement(20233 . . . 20508) | insA | b0022 | IS1 protein InsA_1 |
| MDS13 | CDS | complement(16751 . . . 16903) | hokC | b4412 | small toxic membrane polypeptide |
| MDS13 | misc_RNA | 16952 . . . 17006 | sokC | b4413 | antisense RNA blocking mokC (orf69) and hokC (gef) translation |
| MDS14 | CDS | complement(602639 . . . 603886) | ybdG | b0577 | putative transport |
| MDS14 | CDS | complement(603994 . . . 604647) | nfnB | b0578 | oxygen-insensitive NAD(P)H nitroreductase |
| MDS14 | CDS | complement(604741 . . . 605109) | ybdF | b0579 | orf, hypothetical protein |
| MDS14 | CDS | complement(605174 . . . 605422) | ybdJ | b0580 | orf, hypothetical protein |
| MDS14 | CDS | complement(605488 . . . 606606) | ybdK | b0581 | orf, hypothetical protein |
| MDS14 | CDS | 607288 . . . 608400 | yi81_2 | b0582 | IS186 hypothetical protein |
| MDS14 | CDS | 607059 . . . 607211 | hokE | b4415 | small toxic membrane polypeptide |
| MDS15 | CDS | 2507652 . . . 2508908 | | b2389 | orf, hypothetical protein |
| MDS15 | CDS | 2509023 . . . 2509349 | ypeC | b2390 | orf, hypothetical protein |
| MDS15 | CDS | complement(2509490 . . . 2510728) | | b2392 | |
| MDS15 | CDS | 2511064 . . . 2512266 | nupC | b2393 | permease of transport system for 3 nucleosides |
| MDS15 | CDS | 2512347 . . . 2513465 | yi81_3 | b2394 | |
| MDS15 | CDS | complement(2513665 . . . 2515971) | yfeA | b2395 | orf, hypothetical protein |
| MDS16 | CDS | complement(379293 . . . 380066) | yaiO | b0358 | orf, hypothetical protein |
| MDS16 | CDS | complement(380068 . . . 380511) | | b0359 | putative transferase |
| MDS16 | CDS | 380530 . . . 380940 | yi21_1 | b0360 | IS2 hypothetical protein |
| MDS16 | CDS | 380898 . . . 381803 | yi22_1 | b0361 | IS2 hypothetical protein |
| MDS16 | CDS | complement(381728 . . . 382114) | | b0362 | orf, hypothetical protein |
| MDS16 | CDS | complement(381963 . . . 383159) | yaiP | b0363 | polysaccharide metabolism |
| MDS16 | CDS | complement(383283 . . . 383693) | yaiS | b0364 | orf, hypothetical protein |
| MDS16 | CDS | 384399 . . . 385418 | tauA | b0365 | taurine transport system periplasmic protein |
| MDS16 | CDS | 385431 . . . 386198 | tauB | b0366 | taurine ATP-binding component of a transport system |
| MDS16 | CDS | 386195 . . . 387022 | tauC | b0367 | taurine transport system permease protein |
| MDS16 | CDS | 387019 . . . 387870 | tauD | b0368 | taurine dioxygenase, 2-oxoglutarate-dependent |
| MDS17 | CDS | complement(389121 . . . 389390) | | b0370 | orf, hypothetical protein |
| MDS17 | CDS | 389475 . . . 390935 | yaiT | b0371 | orf, hypothetical protein |
| MDS17 | CDS | complement(390963 . . . 391829) | tra5_1 | b0372 | |

TABLE 2-continued

| Strain | Type | Coordinates | Name | B | Function |
|---|---|---|---|---|---|
| MDS17 | CDS | complement(391826 . . . 392134) | | b0373 | putative flagellin structural protein |
| MDS17 | CDS | 392239 . . . 393642 | yaiU | b0374 | putative flagellin structural protein |
| MDS17 | CDS | 393685 . . . 394353 | yaiV | b0375 | orf, hypothetical protein |
| MDS17 | CDS | complement(394354 . . . 395511) | yaiH | b0376 | |
| MDS17 | CDS | 395863 . . . 397083 | sbmA | b0377 | sensitivity to microcin B17, possibly envelope protein |
| MDS17 | CDS | 397096 . . . 398190 | yaiW | b0378 | orf, hypothetical protein |
| MDS17 | CDS | complement(398249 . . . 398557) | yaiY | b0379 | orf, hypothetical protein |
| MDS17 | CDS | 398685 . . . 399029 | | b0380 | orf, hypothetical protein |
| MDS18 | CDS | complement(2992959 . . . 2993114) | | b2856 | orf, hypothetical protein |
| MDS18 | CDS | complement(2993336 . . . 2993767) | | b2857 | orf, hypothetical protein |
| MDS18 | CDS | complement(2993770 . . . 2993991) | | b2858 | orf, hypothetical protein |
| MDS18 | CDS | complement(2993984 . . . 2994409) | | b2859 | orf, hypothetical protein |
| MDS18 | CDS | complement(2994394 . . . 2995299) | yi22_4 | b2860 | IS2 hypothetical protein |
| MDS18 | CDS | complement(2995257 . . . 2995622) | yi21_4 | b2861 | IS2 hypothetical protein |
| MDS18 | CDS | complement(2995711 . . . 2996010) | | b2862 | orf, hypothetical protein |
| MDS18 | CDS | complement(2996056 . . . 2996892) | | b2863 | orf, hypothetical protein |
| MDS19 | CDS | 3182802 . . . 3183152 | | b3042 | orf, hypothetical protein |
| MDS19 | CDS | 3183436 . . . 3183987 | ygiL | b3043 | putative fimbrial-like protein |
| MDS19 | CDS | 3184209 . . . 3184574 | yi21_5 | b3044 | IS2 hypothetical protein |
| MDS19 | CDS | 3184532 . . . 3185437 | yi22_5 | b3045 | IS2 hypothetical protein |
| MDS19 | CDS | 3185422 . . . 3187887 | yqiG | b3046 | putative membrane protein |
| MDS19 | CDS | 3187894 . . . 3188652 | yqiH | b3047 | putative membrane protein |
| MDS19 | CDS | 3188654 . . . 3189718 | yqiI | b3048 | orf, hypothetical protein |
| MDS20 | CDS | complement(687220 . . . 688236) | trs5_3 | b0656 | IS5 transposase |
| MDS21 | CDS | 1386912 . . . 1387919 | ycjG | b1325 | putative muconate cycloisomerase I (EC 5.5 |
| MDS21 | CDS | complement(1387894 . . . 1388682) | ycjI | b1326 | putative carboxypeptidase |
| MDS21 | CDS | complement(1388957 . . . 1389889) | | b1327 | orf, hypothetical protein |
| MDS21 | CDS | 1390015 . . . 1390914 | ycjZ | b1328 | putative transcriptional regulator LYSR-type |
| MDS21 | CDS | 1391230 . . . 1392864 | | b1329 | |
| MDS21 | CDS | complement(1392915 . . . 1393946) | | b1330 | orf, hypothetical protein |
| MDS21 | CDS | 1394100 . . . 1395116 | trs5_4 | b1331 | IS5 transposase |
| MDS21 | CDS | 1395389 . . . 1395646 | ynaJ | b1332 | orf, hypothetical protein |
| MDS21 | CDS | complement(1395696 . . . 1396646) | ydaA | b1333 | orf, hypothetical protein |
| MDS22 | CDS | complement(2099919 . . . 2100935) | trs5_7 | b2030 | |
| MDS22 | CDS | complement(2100940 . . . 2101413) | yefJ | b2031 | |
| MDS22 | CDS | complement(2101415 . . . 2102533) | wbbK | b2032 | putative glucose transferase |
| MDS22 | CDS | complement(2102518 . . . 2103108) | wbbJ | b2033 | putative O-acetyl transferase |
| MDS22 | CDS | complement(2103089 . . . 2104081) | wbbI | b2034 | putative Galf transferase |
| MDS22 | CDS | complement(2104084 . . . 2105250) | wbbH | b2035 | O-antigen polymerase |
| MDS22 | CDS | complement(2105250 . . . 2106353) | glf | b2036 | UDP-galactopyranose mutase |
| MDS22 | CDS | complement(2106361 . . . 2107608) | rfbX | b2037 | putative O-antigen transporter |
| MDS22 | CDS | complement(2107605 . . . 2108162) | rfbC | b2038 | dTDP-6-deoxy-D-glucose-3,5 epimerase |
| MDS22 | CDS | complement(2108162 . . . 2109043) | rfbA | b2039 | glucose-1-phosphate thymidylyltransferase |
| MDS22 | CDS | complement(2109101 . . . 2110000) | rfbD | b2040 | dTDP-6-deoxy-L-mannose-dehydrogenase |
| MDS22 | CDS | complement(2110000 . . . 2111085) | rfbB | b2041 | dTDP-glucose 4,6 dehydratase |
| MDS22 | CDS | complement(2111458 . . . 2112351) | galF | b2042 | homolog of Salmonella UTP--glucose-1-P uridyltransferase, probably a UDP-gal transferase |
| MDS22 | CDS | complement(2112526 . . . 2113920) | wcaM | b2043 | orf, hypothetical protein |
| MDS22 | CDS | complement(2113931 . . . 2115151) | wcaL | b2044 | putative colanic acid biosynthesis glycosyl transferase |
| MDS22 | CDS | complement(2115148 . . . 2116428) | wcaK | b2045 | putative galactokinase (EC 2.7.1.6 |
| MDS22 | CDS | complement(2116704 . . . 2118182) | wzxC | b2046 | probable export protein |
| MDS22 | CDS | complement(2118184 . . . 2119578) | wcaJ | b2047 | putative colanic acid biosynthsis UDP-glucose lipid carrier transferase |
| MDS22 | CDS | complement(2119633 . . . 2121003) | cpsG | b2048 | phosphomannomutase |
| MDS22 | CDS | complement(2121108 . . . 2122544) | cpsB | b2049 | mannose-1-phosphate guanyltransferase |
| MDS22 | CDS | complement(2122547 . . . 2123770) | wcaI | b2050 | putative colanic biosynthesis glycosyl transferase |
| MDS22 | CDS | complement(2123767 . . . 2124249) | wcaH | b2051 | GDP-mannose mannosyl hydrolase |
| MDS22 | CDS | complement(2124249 . . . 2125214) | wcaG | b2052 | putative nucleotide di-P-sugar epimerase or dehydratase |
| MDS22 | CDS | complement(2125217 . . . 2126338) | gmd | b2053 | GDP-D-mannose dehydratase |
| MDS22 | CDS | complement(2126364 . . . 2126912) | wcaF | b2054 | putative transferase |
| MDS22 | CDS | complement(2126928 . . . 2127674) | wcaE | b2055 | putative colanic acid biosynthesis glycosyl transferase |
| MDS22 | CDS | complement(2127685 . . . 2128902) | wcaD | b2056 | putative colanic acid polymerase |
| MDS22 | CDS | complement(2128877 . . . 2130094) | wcaC | b2057 | putative glycosyl transferase |
| MDS22 | CDS | complement(2130091 . . . 2130579) | wcaB | b2058 | putative transferase |
| MDS22 | CDS | complement(2130582 . . . 2131421) | wcaA | b2059 | putative regulator |
| MDS22 | CDS | complement(2131514 . . . 2133712) | | b2060 | |

TABLE 2-continued

| Strain | Type | Coordinates | Name | B | Function |
|---|---|---|---|---|---|
| MDS22 | CDS | complement(2133679 ... 2134122) | wzb | b2061 | low molecular weight protein-tyrosine-phosphatase |
| MDS22 | CDS | complement(2134128 ... 2135267) | wza | b2062 | putative polysaccharide export protein |
| MDS23 | CDS | complement(2284412 ... 2286922) | yejO | b2190 | putative ATP-binding component of a transport system |
| MDS23 | CDS | 2286927 ... 2287049 | | b2191 | orf, hypothetical protein |
| MDS23 | CDS | complement(2287087 ... 2288103) | trs5_8 | b2192 | IS5 transposase |
| MDS24 | CDS | 3360134 ... 3360808 | yhcA | b3215 | putative chaperone |
| MDS24 | CDS | 3360829 ... 3363210 | yhcD | b3216 | putative outer membrane protein |
| MDS24 | CDS | 3363207 ... 3363686 | yhcE | b3217 | orf, hypothetical protein |
| MDS24 | CDS | complement(3363724 ... 3364740) | trs5_10 | b3218 | IS5 transposase |
| MDS24 | CDS | 3364948 ... 3365664 | yhcF | b3219 | putative transcriptional regulator |
| MDS25 | CDS | 3649314 ... 3650096 | yhiS | b3504 | orf, hypothetical protein |
| MDS25 | CDS | complement(3650205 ... 3651221) | trs5_11 | b3505 | IS5 transposase |
| MDS26 | CDS | complement(1128637 ... 1129053) | flgN | b1070 | protein of flagellar biosynthesis |
| MDS26 | CDS | complement(1129058 ... 1129351) | flgM | b1071 | anti-FliA (anti-sigma) factor; also known as RflB protein |
| MDS26 | CDS | complement(1129427 ... 1130086) | flgA | b1072 | flagellar biosynthesis; assembly of basal-body periplasmic P ring |
| MDS26 | CDS | 1130241 ... 1130657 | flgB | b1073 | flagellar biosynthesis, cell-proximal portion of basal-body rod |
| MDS26 | CDS | 1130661 ... 1131065 | flgC | b1074 | flagellar biosynthesis, cell-proximal portion of basal-body rod |
| MDS26 | CDS | 1131077 ... 1131772 | flgD | b1075 | flagellar biosynthesis, initiation of hook assembly |
| MDS26 | CDS | 1131797 ... 1133005 | flgE | b1076 | flagellar biosynthesis, hook protein |
| MDS26 | CDS | 1133025 ... 1133780 | flgF | b1077 | flagellar biosynthesis, cell-proximal portion of basal-body rod |
| MDS26 | CDS | 1133952 ... 1134734 | flgG | b1078 | flagellar biosynthesis, cell-distal portion of basal-body rod |
| MDS26 | CDS | 1134787 ... 1135485 | flgH | b1079 | flagellar biosynthesis, basal-body outer-membrane L (lipopolysaccharide layer) ring protein |
| MDS26 | CDS | 1135497 ... 1136594 | flgI | b1080 | homolog of *Salmonella* P-ring of flagella basal body |
| MDS26 | CDS | 1136594 ... 1137535 | flgJ | b1081 | flagellar biosynthesis |
| MDS26 | CDS | 1137601 ... 1139244 | flgK | b1082 | flagellar biosynthesis, hook-filament junction protein 1 |
| MDS26 | CDS | 1139256 ... 1140209 | flgL | b1083 | flagellar biosynthesis; hook-filament junction protein |
| MDS27 | CDS | complement(1960604 ... 1960996) | flhE | b1878 | flagellar protein |
| MDS27 | CDS | complement(1960996 ... 1963074) | flhA | b1879 | flagellar biosynthesis; possible export of flagellar proteins |
| MDS27 | CDS | complement(1963067 ... 1964215) | flhB | b1880 | putative part of export apparatus for flagellar proteins |
| MDS27 | CDS | complement(1964417 ... 1965061) | cheZ | b1881 | chemotactic response; CheY protein phophatase; antagonist of CheY as switch regulator |
| MDS27 | CDS | complement(1965072 ... 1965461) | cheY | b1882 | chemotaxis regulator transmits chemoreceptor signals to flagelllar motor components |
| MDS27 | CDS | complement(1965476 ... 1966525) | cheB | b1883 | response regulator for chemotaxis (cheA sensor); protein methylesterase |
| MDS27 | CDS | complement(1966528 ... 1967388) | cheR | b1884 | response regulator for chemotaxis protein glutamate methyltransferase |
| MDS27 | CDS | complement(1967407 ... 1969008) | tap | b1885 | methyl-accepting chemotaxis protein IV peptide sensor receptor |
| MDS27 | CDS | complement(1969054 ... 1970715) | tar | b1886 | methyl-accepting chemotaxis protein II aspartate sensor receptor |
| MDS27 | CDS | complement(1970860 ... 1971363) | cheW | b1887 | positive regulator of CheA protein activity |
| MDS27 | CDS | complement(1971384 ... 1973348) | cheA | b1888 | sensory transducer kinase between chemo-signal receptors and CheB and CheY |
| MDS27 | CDS | complement(1973353 ... 1974279) | motB | b1889 | enables flagellar motor rotation linking torque machinery to cell wall |
| MDS27 | CDS | complement(1974276 ... 1975163) | motA | b1890 | proton conductor component of motor; no effect on switching |
| MDS27 | CDS | complement(1975290 ... 1975868) | flhC | b1891 | regulator of flagellar biosynthesis acting on class 2 operons; transcription initiation factor |
| MDS27 | CDS | complement(1975871 ... 1976230) | flhD | b1892 | regulator of flagellar biosynthesis acting on class 2 operons; transcription initiation factor |
| MDS27 | CDS | complement(1976542 ... 1977045) | insB_5 | b1893 | IS1 protein InsB |
| MDS27 | CDS | complement(1976964 ... 1977239) | insA_5 | b1894 | IS1 protein InsA |
| MDS28 | CDS | complement(1995086 ... 1995838) | yecC | b1917 | putative ATP-binding component of a transport system |

TABLE 2-continued

| Strain | Type | Coordinates | Name | B | Function |
|---|---|---|---|---|---|
| MDS28 | CDS | complement(1995835 . . . 1996503) | yecS | b1918 | putative transport system permease protein (former yecC) |
| MDS28 | CDS | complement(1996518 . . . 1997600) | yedO | b1919 | putative 1-aminocyclopropane-1-carboxylate deaminase |
| MDS28 | CDS | complement(1997609 . . . 1998409) | fliY | b1920 | putative periplasmic binding transport protein |
| MDS28 | CDS | complement(1998497 . . . 1999084) | fliZ | b1921 | orf, hypothetical protein |
| MDS28 | CDS | complement(1999094 . . . 1999813) | fliA | b1922 | flagellar biosynthesis; alternative sigma factor 28; regulation of flagellar operons |
| MDS28 | CDS | complement(2000134 . . . 2001630) | fliC | b1923 | flagellar biosynthesis; flagellin filament structural protein |
| MDS28 | CDS | 2001896 . . . 2003302 | fliD | b1924 | flagellar biosynthesis; filament capping protein; enables filament assembly |
| MDS28 | CDS | 2003327 . . . 2003737 | fliS | b1925 | flagellar biosynthesis; repressor of class 3a and 3b operons (RflA activity) |
| MDS28 | CDS | 2003737 . . . 2004102 | fliT | b1926 | flagellar biosynthesis; repressor of class 3a and 3b operons (RflA activity) |
| MDS28 | CDS | 2004180 . . . 2005667 | amyA | b1927 | cytoplasmic alpha-amylase |
| MDS28 | CDS | complement(2005701 . . . 2006114) | yedD | b1928 | orf, hypothetical protein |
| MDS28 | CDS | 2006301 . . . 2007506 | yedE | b1929 | putative transport system permease protein |
| MDS28 | CDS | 2007503 . . . 2007736 | yedF | b1930 | orf, hypothetical protein |
| MDS28 | CDS | 2007845 . . . 2008513 | yedK | b1931 | orf, hypothetical protein |
| MDS28 | CDS | 2008624 . . . 2009103 | yedL | b1932 | orf, hypothetical protein |
| MDS28 | CDS | complement(2009372 . . . 2009563) | | b1933 | orf, hypothetical protein |
| MDS28 | CDS | complement(2009573 . . . 2009893) | yedN | b1934 | orf, hypothetical protein |
| MDS28 | CDS | complement(2010025 . . . 2010375) | yedM | b1935 | orf, hypothetical protein |
| MDS28 | CDS | 2010526 . . . 2010804 | | b1936 | orf, hypothetical protein |
| MDS28 | CDS | complement(2010724 . . . 2011038) | fliE | b1937 | flagellar biosynthesis; basal-body component, possibly at (MS-ring)-rod junction |
| MDS28 | CDS | 2011253 . . . 2012911 | fliF | b1938 | flagellar biosynthesis; basal-body MS(membrane and supramembrane)-ring and collar protein |
| MDS28 | CDS | 2012904 . . . 2013899 | fliG | b1939 | flagellar biosynthesis, component of motor switching and energizing, enabling rotation and determinin its direction |
| MDS28 | CDS | 2013871 . . . 2014578 | fliH | b1940 | flagellar biosynthesis; export of flagellar proteins |
| MDS28 | CDS | 2014578 . . . 2015951 | fliI | b1941 | flagellum-specific ATP synthase |
| MDS28 | CDS | 2015970 . . . 2016413 | fliJ | b1942 | flagellar fliJ protein |
| MDS28 | CDS | 2016410 . . . 2017537 | fliK | b1943 | flagellar hook-length control protein |
| MDS28 | CDS | 2017642 . . . 2018106 | fliL | b1944 | flagellar biosynthesis |
| MDS28 | CDS | 2018111 . . . 2019115 | fliM | b1945 | flagellar biosynthesis, component of motor switch and energizing, enabling rotation and determining its direction |
| MDS28 | CDS | 2019112 . . . 2019525 | fliN | b1946 | flagellar biosynthesis, component of motor switch and energizing, enabling rotation and determining its direction |
| MDS28 | CDS | 2019588 . . . 2019893 | fliO | b1947 | flagellar biosynthesis |
| MDS28 | CDS | 2019893 . . . 2020630 | fliP | b1948 | flagellar biosynthesis |
| MDS28 | CDS | 2020640 . . . 2020909 | fliQ | b1949 | flagellar biosynthesis |
| MDS28 | CDS | 2020917 . . . 2021702 | fliR | b1950 | flagellar biosynthesis |
| MDS29 | CDS | 4552599 . . . 4553372 | uxuR | b4324 | regulator for uxu operon |
| MDS29 | CDS | complement(4553513 . . . 4554343) | yjiC | b4325 | orf, hypothetical protein |
| MDS29 | CDS | 4555007 . . . 4555408 | yjiD | b4326 | orf, hypothetical protein |
| MDS29 | CDS | complement(4555401 . . . 4556312) | yjiE | b4327 | putative transcriptional regulator LYSR-type |
| MDS29 | CDS | complement(4556377 . . . 4557549) | iadA | b4328 | isoaspartyl dipeptidase |
| MDS29 | CDS | complement(4557562 . . . 4558023) | yjiG | b4329 | orf, hypothetical protein |
| MDS29 | CDS | complement(4558020 . . . 4558715) | yjiH | b4330 | orf, hypothetical protein |
| MDS29 | CDS | 4558851 . . . 4559507 | yjiI | b4331 | orf, hypothetical protein |
| MDS29 | CDS | complement(4559520 . . . 4560698) | yjiJ | b4332 | putative transport protein |
| MDS29 | CDS | complement(4560766 . . . 4561737) | yjiK | b4333 | orf, hypothetical protein |
| MDS29 | CDS | complement(4561945 . . . 4562718) | yjiL | b4334 | putative enzyme |
| MDS29 | CDS | complement(4562722 . . . 4563894) | yjiM | b4335 | orf, hypothetical protein |
| MDS29 | CDS | complement(4563989 . . . 4565269) | yjiN | b4336 | orf, hypothetical protein |
| MDS29 | CDS | complement(4565310 . . . 4566542) | yjiO | b4337 | putative transport protein |
| MDS29 | CDS | 4567021 . . . 4567332 | yjiP | b4338 | orf, hypothetical protein |
| MDS29 | CDS | 4567381 . . . 4567941 | yjiQ | b4339 | orf, hypothetical protein |
| MDS29 | CDS | complement(4568185 . . . 4569597) | yjiR | b4340 | putative regulator |
| MDS29 | CDS | 4569774 . . . 4569938 | yjiS | b4341 | orf, hypothetical protein |
| MDS29 | CDS | 4570389 . . . 4571954 | yjiT | b4342 | orf, hypothetical protein |
| MDS29 | CDS | complement(4574935 . . . 4575981) | mcrC | b4345 | component of McrBC 5-methylcytosine restriction system |

TABLE 2-continued

| Strain | Type | Coordinates | Name | B | Function |
|---|---|---|---|---|---|
| MDS29 | CDS | complement(4575981 . . . 4577378) | mcrB | b4346 | component of McrBC 5-methylcytosine restriction system |
| MDS29 | CDS | complement(4577522 . . . 4577920) | yjiW | b4347 | orf, hypothetical protein |
| MDS29 | CDS | complement(4578091 . . . 4579485) | hsdS | b4348 | specificity determinant for hsdM and hsdR |
| MDS29 | CDS | complement(4579482 . . . 4581071) | hsdM | b4349 | host modification; DNA methylase M |
| MDS29 | CDS | complement(4581272 . . . 4584838) | hsdR | b4350 | host restriction; endonuclease R |
| MDS29 | CDS | 4584972 . . . 4585886 | mrr | b4351 | restriction of methylated adenine |
| MDS29 | CDS | complement(4585932 . . . 4586786) | yjiA | b4352 | orf, hypothetical protein |
| MDS29 | CDS | complement(4586899 . . . 4587102) | yjiX | b4353 | orf, hypothetical protein |
| MDS29 | CDS | complement(4587152 . . . 4589317) | yjiY | b4354 | putative carbon starvation protein |
| MDS29 | CDS | 4589680 . . . 4591335 | tsr | b4355 | methyl-accepting chemotaxis protein I serine sensor receptor |
| MDS29 | CDS | complement(4591384 . . . 4592745) | yjiZ | b4356 | putative transport protein, cryptic orf, joins former yjiZ and yjjL |
| MDS29 | CDS | complement(4592960 . . . 4593874) | yjjM | b4357 | orf, hypothetical protein |
| MDS29 | CDS | 4593998 . . . 4595035 | yjjN | b4358 | putative oxidoreductase |
| MDS29 | CDS | 4572158 . . . 4574878 | yjiV | b4486 | conserved hypothetical protein |
| MDS30 | CDS | 522485 . . . 526765 | rhsD | b0497 | rhsD protein in rhs element |
| MDS30 | CDS | 526805 . . . 527173 |  | b0498 | orf, hypothetical protein |
| MDS30 | CDS | 527173 . . . 527883 |  | b0499 | orf, hypothetical protein |
| MDS30 | CDS | 527864 . . . 528124 | ybbD | b0500 | orf, hypothetical protein |
| MDS30 | CDS | 528163 . . . 528354 |  | b0501 | orf, hypothetical protein |
| MDS30 | CDS | complement(528869 . . . 529276) |  | b0502 | orf, hypothetical protein |
| MDS31 | CDS | 728806 . . . 732999 | rhsC | b0700 |  |
| MDS31 | CDS | 732593 . . . 732814 |  | b0701 |  |
| MDS31 | CDS | 732999 . . . 733325 | ybfB | b0702 | orf, hypothetical protein |
| MDS31 | CDS | 733443 . . . 734876 |  | b0703 | orf, hypothetical protein |
| MDS31 | CDS | 734873 . . . 735442 | ybfC | b0704 | orf, hypothetical protein |
| MDS31 | CDS | 736327 . . . 737184 | ybfL | b0705 | putative receptor protein |
| MDS31 | CDS | 737315 . . . 738076 | ybfD | b0706 | putative DNA ligase |
| MDS32 | CDS | 1525914 . . . 1527962 | rhsE | b1456 |  |
| MDS32 | CDS | 1527946 . . . 1528428 | ydcD | b1457 | orf, hypothetical protein |
| MDS32 | CDS | 1528610 . . . 1529356 |  | b1458 | orf, hypothetical protein |
| MDS32 | CDS | 1529400 . . . 1529600 |  | b1459 | orf, hypothetical protein |
| MDS32 | CDS | 1529840 . . . 1530976 | ydcC | b1460 | H repeat-associated protein (ORF-H) |
| MDS32 | CDS | 1531076 . . . 1531309 | ydcE | b1461 | orf, hypothetical protein |
| MDS32 | CDS | complement(1531306 . . . 1531923) |  | b1462 | orf, hypothetical protein |
| MDS33 | CDS | 3616611 . . . 3617012 | yhhG | b3481 |  |
| MDS33 | CDS | 3617215 . . . 3621450 | rhsB | b3482 | rhsB protein in rhs element |
| MDS33 | CDS | 3621437 . . . 3621805 | yhhH | b3483 | orf, hypothetical protein |
| MDS33 | CDS | 3622401 . . . 3623537 | yhhI | b3484 | putative receptor |
| MDS34 | CDS | complement(3759370 . . . 3759978) | yibF | b3592 | putative S-transferase |
| MDS34 | CDS | 3760206 . . . 3764339 | rhsA | b3593 | rhsA protein in rhs element |
| MDS34 | CDS | 3764360 . . . 3765202 | yibA | b3594 | orf, hypothetical protein |
| MDS34 | CDS | 3765244 . . . 3765945 | yibJ | b3595 | orf, hypothetical protein |
| MDS34 | CDS | 3766200 . . . 3766661 | yibG | b3596 | orf, hypothetical protein |
| MDS35 | CDS | complement(1041253 . . . 1043433) | yccC | b0981 | orf, hypothetical protein |
| MDS35 | CDS | complement(1043453 . . . 1043911) | yccY | b0982 | yccY putative phosphatase |
| MDS35 | CDS | complement(1043887 . . . 1045026) | yccZ | b0983 | putative function in exopolysaccharide production |
| MDS35 | CDS | complement(1045072 . . . 1047168) | ymcA | b0984 | orf, hypothetical protein |
| MDS35 | CDS | complement(1047168 . . . 1047914) | ymcB | b0985 | orf, hypothetical protein |
| MDS35 | CDS | complement(1047911 . . . 1048555) | ymcC | b0986 | putative regulator |
| MDS35 | CDS | complement(1048662 . . . 1048985) | ymcD | b0987 | orf, hypothetical protein |
| MDS35 | CDS | 1049250 . . . 1049753 | insB_4 | b0988 | IS1 protein InsB |
| MDS36 | CDS | complement(1085329 . . . 1085742) | ycdP | b1021 | orf, hypothetical protein |
| MDS36 | CDS | complement(1085744 . . . 1087069) | ycdQ | b1022 | orf, hypothetical protein |
| MDS36 | CDS | complement(1087062 . . . 1089080) | ycdR | b1023 | orf, hypothetical protein |
| MDS36 | CDS | complement(1089089 . . . 1091512) | ycdS | b1024 | putative outer membrane protein |
| MDS36 | CDS | 1092099 . . . 1093457 | ycdT | b1025 | orf, hypothetical protein |
| MDS36 | CDS | complement(1093498 . . . 1094364) | tra5_3 | b1026 |  |
| MDS36 | CDS | complement(1094361 . . . 1094669) |  | b1027 |  |
| MDS36 | CDS | 1094746 . . . 1095069 |  | b1028 | orf, hypothetical protein |
| MDS36 | CDS | 1095066 . . . 1096052 | ycdU | b1029 | orf, hypothetical protein |
| MDS37 | CDS | 2163174 . . . 2163545 |  | b2080 | orf, hypothetical protein |
| MDS37 | CDS | 2163692 . . . 2165053 | yegQ | b2081 | orf, hypothetical protein |
| MDS37 | CDS | complement(2165326 . . . 2165544) | ogrK | b2082 | prophage P2 ogr protein |
| MDS37 | CDS | complement(2165626 . . . 2165772) |  | b2083 | orf, hypothetical protein |
| MDS37 | CDS | complement(2165759 . . . 2166025) |  | b2084 | orf, hypothetical protein |
| MDS37 | CDS | complement(2166013 . . . 2166390) | yegR | b2085 | orf, hypothetical protein |
| MDS37 | CDS | 2166736 . . . 2167635 |  | b2086 | orf, hypothetical protein |
| MDS37 | CDS | complement(2167717 . . . 2168163) | gatR_1 | b2087 | split galactitol utilization operon repressor |
| MDS37 | CDS | 2168251 . . . 2168559 |  | b2088 |  |
| MDS37 | CDS | 2168556 . . . 2169422 | tra5_4 | b2089 |  |
| MDS37 | CDS | complement(2169419 . . . 2169757) | gatR_2 | b2090 |  |
| MDS37 | CDS | complement(2169857 . . . 2170897) | gatD | b2091 | galactitol-1-phosphate dehydrogenase |

TABLE 2-continued

| Strain | Type | Coordinates | Name | B | Function |
|---|---|---|---|---|---|
| MDS37 | CDS | complement(2170945 . . . 2172300) | gatC | b2092 | PTS system galactitol-specific enzyme IIC |
| MDS37 | CDS | complement(2172304 . . . 2172588) | gatB | b2093 | galactitol-specific enzyme IIB of phosphotransferase system |
| MDS37 | CDS | complement(2172619 . . . 2173071) | gatA | b2094 | galactitol-specific enzyme IIA of phosphotransferase system |
| MDS37 | CDS | complement(2173081 . . . 2174343) | gatZ | b2095 | putative tagatose 6-phosphate kinase 1 |
| MDS37 | CDS | complement(2174372 . . . 2175232) | gatY | b2096 | tagatose-bisphosphate aldolase 1 |
| MDS37 | misc_RNA | 2165136 . . . 2165221 | ryeE | b4438 | |
| MDS38 | CDS | complement(3577791 . . . 3578828) | yhhX | b3440 | putative regulator |
| MDS38 | CDS | 3579161 . . . 3579649 | yhhY | b3441 | orf, hypothetical protein |
| MDS38 | CDS | 3579886 . . . 3581064 | yhhZ | b3442 | orf, hypothetical protein |
| MDS38 | CDS | 3581061 . . . 3581477 | yrhA | b3443 | orf, hypothetical protein |
| MDS38 | CDS | 3581506 . . . 3581781 | insA_6 | b3444 | IS1 protein InsA |
| MDS38 | CDS | 3581700 . . . 3582203 | insB_6 | b3445 | IS1 protein InsB |
| MDS38 | misc_RNA | complement(3578946 . . . 3579039) | ryhB | b4451 | regulatory RNA mediating Fur regulon |
| MDS39 | CDS | 3718072 . . . 3718284 | cspA | b3556 | cold shock protein 7.4, transcriptional activator of hns |
| MDS39 | CDS | 3718703 . . . 3719224 | yi5A | b3557 | IS150 hypothetical protein |
| MDS39 | CDS | 3719221 . . . 3720072 | t150 | b3558 | IS150 putative transposase |
| MDS39 | CDS | complement(3718471 . . . 3718623) | hokA | b4455 | small toxic membrane polypeptide |
| MDS40 | CDS | 1869885 . . . 1871555 | yeaJ | b1786 | orf, hypothetical protein |
| MDS41 | CDS | 167484 . . . 169727 | fhuA | b0150 | outer membrane protein receptor for ferrichrome, colicin M, and phages T1, T5, and phi80 |
| MDS41 | CDS | 169778 . . . 170575 | fhuC | b0151 | ATP-binding component of hydroxymate-dependent iron transport |
| MDS41 | CDS | 170575 . . . 171465 | fhuD | b0152 | hydroxamate-dependent iron uptake cytoplasmic membrane component |
| MDS41 | CDS | 171462 . . . 173444 | fhuB | b0153 | hydroxamate-dependent iron uptake cytoplasmic membrane component |

TABLE 3

| Strain | Type | Coordinates | Name | B | Function |
|---|---|---|---|---|---|
| MDS43 | CDS | 331595 . . . 332683 | yahA | b0315 | orf, hypothetical protein |
| MDS43 | CDS | complement(332725 . . . 333657) | yahB | b0316 | putative transcriptional regulator LYSR-type |
| MDS43 | CDS | complement(333749 . . . 334246) | yahC | b0317 | orf, hypothetical protein |
| MDS43 | CDS | 334504 . . . 335109 | yahD | b0318 | putative transcription factor |
| MDS43 | CDS | 335149 . . . 336012 | yahE | b0319 | orf, hypothetical protein |
| MDS43 | CDS | 336002 . . . 337549 | yahF | b0320 | putative oxidoreductase subunit |
| MDS43 | CDS | 337549 . . . 338967 | yahG | b0321 | orf, hypothetical protein |
| MDS43 | CDS | 339389 . . . 340339 | yahI | b0323 | putative kinase (EC 2.7.2.2 |
| MDS43 | CDS | 340349 . . . 341731 | yahJ | b0324 | putative deaminase |
| MDS43 | CDS | 342108 . . . 343157 | yahK | b0325 | putative oxidoreductase |
| MDS43 | CDS | 343400 . . . 344215 | yahL | b0326 | orf, hypothetical protein |
| MDS43 | CDS | 344598 . . . 344873 | yahM | b0327 | orf, hypothetical protein |
| MDS43 | CDS | complement(344890 . . . 345561) | yahN | b0328 | putative cytochrome subunit of dehydrogenase |
| MDS43 | CDS | 345708 . . . 345983 | yahO | b0329 | orf, hypothetical protein |
| MDS43 | CDS | complement(346081 . . . 347667) | prpR | b0330 | regulator for prp operon |
| MDS43 | CDS | 347906 . . . 348796 | prpB | b0331 | putative phosphonomutase 2 |
| MDS43 | CDS | 349236 . . . 350405 | prpC | b0333 | putative citrate synthase; propionate metabolism |
| MDS43 | CDS | 350439 . . . 351890 | prpD | b0334 | orf, hypothetical protein |
| MDS43 | CDS | 351930 . . . 353816 | prpE | b0335 | putative propionyl-CoA synthetase |
| MDS43 | CDS | 354146 . . . 355405 | codB | b0336 | cytosine permease/transport |
| MDS43 | CDS | 355395 . . . 356678 | codA | b0337 | cytosine deaminase |
| MDS43 | CDS | complement(357015 . . . 357914) | cynR | b0338 | cyn operon positive regulator |
| MDS43 | CDS | 358023 . . . 358682 | cynT | b0339 | carbonic anhydrase |
| MDS43 | CDS | 358713 . . . 359183 | cynS | b0340 | cyanate aminohydrolase, cyanase |
| MDS43 | CDS | 359216 . . . 360370 | cynX | b0341 | cyanate transport |
| MDS43 | CDS | complement(360473 . . . 361084) | lacA | b0342 | thiogalactoside acetyltransferase |
| MDS43 | CDS | complement(361150 . . . 362403) | lacY | b0343 | galactoside permease (lactose permease M protein) (MFS family |
| MDS43 | CDS | complement(362455 . . . 365529) | lacZ | b0344 | beta-D-galactosidase |
| MDS43 | CDS | complement(365652 . . . 366734) | lacI | b0345 | transcriptional repressor of the lac operon |
| MDS43 | CDS | complement(366811 . . . 367758) | mhpR | b0346 | transcriptional regulator for mhp operon |
| MDS43 | CDS | 367835 . . . 369499 | mhpA | b0347 | 3-(3-hydroxyphenyl)propionate hydroxylase |

TABLE 3-continued

| Strain | Type | Coordinates | Name | B | Function |
|---|---|---|---|---|---|
| MDS43 | CDS | 369501 ... 370445 | mhpB | b0348 | 2,3-dihydroxyphenylpropionate 1,2-dioxygenase |
| MDS43 | CDS | 370400 ... 371329 | mhpC | b0349 | 2-hydroxy-6-ketonona-2,4-dienedioic acid hydrolase |
| MDS43 | CDS | 371333 ... 372148 | mhpD | b0350 | 2-keto-4-pentenoate hydratase |
| MDS43 | CDS | 372145 ... 373095 | mhpF | b0351 | acetaldehyde dehydrogenase |
| MDS43 | CDS | 373092 ... 374105 | mhpE | b0352 | 4-hydroxy-2-ketovalerate aldolase |
| MDS43 | CDS | 374638 ... 375894 | mhpT | b0353 | 2,3-dihydroxyphenylpropionate 1,2-dioxygenase |
| MDS43 | CDS | 375879 ... 376535 | yaiL | b0354 | nucleoprotein/polynucleotide-associated enzyme |

TABLE 4

| Strain | Type | Coordinates | Name | B | Function |
|---|---|---|---|---|---|
| MDS44 | CDS | 2599223 ... 2599840 | hyfA | b2481 | hydrogenase 4 Fe—S subunit |
| MDS44 | CDS | 2599840 ... 2601858 | hyfB | b2482 | hydrogenase 4 membrane subunit |
| MDS44 | CDS | 2601869 ... 2602816 | hyfC | b2483 | hydrogenase 4 membrane subunit |
| MDS44 | CDS | 2602833 ... 2604272 | hyfD | b2484 | hydrogenase 4 membrane subunit |
| MDS44 | CDS | 2604284 ... 2604934 | hyfE | b2485 | hydrogenase 4 membrane subunit |
| MDS44 | CDS | 2604939 ... 2606519 | hyfF | b2486 | hydrogenase 4 membrane subunit |
| MDS44 | CDS | 2606509 ... 2608176 | hyfG | b2487 | hydrogenase 4 subunit |
| MDS44 | CDS | 2608186 ... 2608731 | hyfH | b2488 | hydrogenase 4 Fe—S subunit |
| MDS44 | CDS | 2608728 ... 2609486 | hyfI | b2489 | hydrogenase 4 Fe—S subunit |
| MDS44 | CDS | 2609479 ... 2609892 | hyfJ | b2490 | hydrogenase 4 component J |
| MDS44 | CDS | 2609922 ... 2611934 | hyfR | b2491 | putative 2-component regulator interaction with sigma 54 |
| MDS44 | CDS | 2611956 ... 2612804 | focB | b2492 | probable formate transporter (formate channel 2) |

TABLE 5

| Strain | Type | Coordinates | Name | B | Function |
|---|---|---|---|---|---|
| MDS45 | CDS | 2318065 ... 2319891 | atoS | b2219 | sensor protein AtoS for response regulator AtoC |
| MDS45 | CDS | 2319888 ... 2321273 | atoC | b2220 | response regulator of ato, ornithine decarboxylase antizyme (sensor ATOS) |
| MDS45 | CDS | 2321469 ... 2322131 | atoD | b2221 | acetyl-CoA:acetoacetyl-CoA transferase alpha subunit |
| MDS45 | CDS | 2322131 ... 2322781 | atoA | b2222 | acetyl-CoA:acetoacetyl-CoA transferase beta subunit |
| MDS45 | CDS | 2322778 ... 2324100 | atoE | b2223 | short chain fatty acid transporter |
| MDS45 | CDS | 2324131 ... 2325315 | atoB | b2224 | acetyl-CoA acetyltransferase |
| MDS45 | CDS | complement(2325389 ... 2326165) | yfaP | b2225 | orf, hypothetical protein |
| MDS45 | CDS | complement(2326170 ... 2327819) | yfaQ | b2226 | orf, hypothetical protein |
| MDS45 | CDS | complement(2327820 ... 2328305) | yfaS_2 | b2227 | orf, hypothetical protein |
| MDS45 | pseudogene | complement(2327820 ... 2332424) | yfaS | b4500 | pseudogene |
| MDS45 | CDS | complement(2328321 ... 2332424) | yfaS_1 | b2228 | putative membrane protein |
| MDS45 | CDS | complement(2332358 ... 2332981) | yfaT | b2229 | orf, hypothetical protein |
| MDS45 | CDS | complement(2332978 ... 2334666) | yfaA | b2230 | orf, hypothetical protein |

TABLE 6

| Strain | Type | Coordinates | Name | B | Function |
|---|---|---|---|---|---|
| MDS46 | CDS | 3886458 ... 3886532 | tnaL | b3707 | tryptophanase leader peptide |
| MDS46 | CDS | 3886753 ... 3888168 | tnaA | b3708 | tryptophanase |
| MDS46 | CDS | 3888259 ... 3889506 | tnaB | b3709 | low affinity tryptophan permease |
| MDS46 | CDS | 3889638 ... 3890813 | yidY | b3710 | putative transport protein |
| MDS46 | CDS | 3890788 ... 3891747 | yidZ | b3711 | putative transcriptional regulator LYSR-type |
| MDS46 | CDS | 3891892 ... 3892653 | yieE | b3712 | orf, hypothetical protein |
| MDS46 | CDS | 3892675 ... 3893241 | yieF | b3713 | orf, hypothetical protein |

TABLE 6-continued

| Strain | Type | Coordinates | Name | B | Function |
|---|---|---|---|---|---|
| MDS46 | CDS | complement(3893295...3894632) | yieG | b3714 | putative membrane/transport protein |
| MDS46 | CDS | 3894797...3895462 | yieH | b3715 | putative phosphatase |
| MDS46 | CDS | 3895529...3895996 | yieI | b3716 | orf, hypothetical protein |
| MDS46 | CDS | 3896045...3896632 | yieJ | b3717 | orf, hypothetical protein |
| MDS46 | CDS | complement(3896694...3897416) | yieK | b3718 | pyrimidine-specific nucleoside hydrolase |
| MDS46 | CDS | complement(3897431...3898627) | yieL | b3719 | putative xylanase |
| MDS46 | CDS | complement(3898627...3900243) | yieC | b3720 | putative receptor protein |
| MDS46 | CDS | complement(3900312...3901724) | bglB | b3721 | phospho-beta-glucosidase B; cryptic |
| MDS46 | CDS | complement(3901743...3903620) | bglF | b3722 | PTS system beta-glucosides, enzyme II, cryptic |
| MDS46 | CDS | complement(3903754...3904590) | bglG | b3723 | positive regulation of bgl operon |

TABLE 7

| Strain | Type | Coordinates | Name | B | Function |
|---|---|---|---|---|---|
| MDS47 | CDS | complement(674793...675770) | ybeQ | b0644 | orf, hypothetical protein |
| MDS47 | CDS | 675934...676641 | ybeR | b0645 | orf, hypothetical protein |
| MDS47 | CDS | 676638...678065 | ybeS | b0646 | putative enzyme of polynucleotide modification |
| MDS47 | CDS | complement(678075...678629) | ybeT | b0647 | orf, hypothetical protein |
| MDS47 | CDS | 678731...679438 | ybeU | b0648 | putative tRNA ligase |
| MDS47 | CDS | 679435...680886 | ybeV | b0649 | orf, hypothetical protein |
| MDS47 | CDS | complement(680946...682616) | hscC | b0650 | putative heatshock protein (Hsp70 family) |

TABLE 8

| Strain | Type | Coordinates | Name | B | Function |
|---|---|---|---|---|---|
| MDS48 | CDS | complement(4295242...4297389) | fdhF | b4079 | selenopolypeptide subunit of formate dehydrogenase H |
| MDS48 | CDS | complement(4297587...4299053) | yjcP | b4080 | putative enzyme |
| MDS48 | CDS | complement(4299050...4301101) | yjcQ | b4081 | putative enzyme |
| MDS48 | CDS | complement(4301101...4302132) | yjcR | b4082 | putative membrane protein |
| MDS48 | CDS | complement(4302635...4304620) | yjcS | b4083 | orf, hypothetical protein |
| MDS48 | CDS | complement(4304893...4305822) | alsK | b4084 | putative D-allose kinase |
| MDS48 | CDS | complement(4305806...4306501) | alsE | b4085 | allulose-6-phosphate 3-epimerase |
| MDS48 | CDS | complement(4306512...4307492) | alsE | b4086 | D-allose ABC transporter |
| MDS48 | CDS | complement(4307471...4309003) | alsA | b4087 | D-allose ABC transporter |
| MDS48 | CDS | complement(4309130...4310065) | alsB | b4088 | D-allose ABC transporter |
| MDS48 | CDS | complement(4310124...4311014) | rpiR | b4089 | transcriptional repressor of rpiB expression |
| MDS48 | CDS | 4311373...4311822 | rpiB | b4090 | ribose 5-phosphate isomerase B |
| MDS48 | CDS | 4311891...4312220 | yjdP | b4487 | conserved hypothetical protein |
| MDS48 | CDS | complement(4312367...4313125) | phnP | b4092 | phosphonate metabolism |
| MDS48 | CDS | complement(4313127...4313561) | phnO | b4093 | putative regulator, phn operon |
| MDS48 | CDS | complement(4313548...4314105) | phnN | b4094 | ATP-binding component of phosphonate transport |
| MDS48 | CDS | complement(4314105...4315241) | phnM | b4095 | phosphonate metabolism |
| MDS48 | CDS | complement(4315238...4315918) | phnL | b4096 | ATP-binding component of phosphonate transport |
| MDS48 | CDS | complement(4316029...4316787) | phnK | b4097 | ATP-binding component of phosphonate transport |
| MDS48 | CDS | complement(4316784...4317629) | phnJ | b4098 | phosphonate metabolism |
| MDS48 | CDS | complement(4317622...4318686) | phnI | b4099 | phosphonate metabolism |
| MDS48 | CDS | complement(4318686...4319270) | phnH | b4100 | phosphonate metabolism |
| MDS48 | CDS | complement(4319267...4319719) | phnG | b4101 | phosphonate metabolism |
| MDS48 | CDS | complement(4319720...4320445) | phnF | b4102 | putative transcriptional regulator |
| MDS48 | CDS | complement(4320466...4320834) | phnE_2 | b4103 | orf, hypothetical protein |
| MDS48 | CDS | complement(4320684...4321304) | phnE | b4104 | membrane channel protein component of Pn transporter |
| MDS48 | CDS | complement(4321359...4322375) | phnD | b4105 | periplasmic binding protein component of Pn transporter |
| MDS48 | CDS | complement(4322400...4323188) | phnC | b4106 | ATP-binding component of phosphonate transport |

TABLE 9

| Strain | Type | Coordinates | Name | B | Function |
|---|---|---|---|---|---|
| MDS49 | CDS | complement(764376 . . . 765098) | farR | b0730 | transcriptional regulator of succinyl-CoA synthetase operon |
| MDS49 | CDS | 765207 . . . 767183 | hrsA | b0731 | protein modification enzyme, induction of ompC |
| MDS49 | CDS | 767201 . . . 769834 | ybgG | b0732 | putative sugar hydrolase |

TABLE 10

| Strain | Type | Coordinates | Name | B | Function |
|---|---|---|---|---|---|
| MDS50 | CDS | 3737728 . . . 3738981 | avtA | b3572 | alanine-alpha-ketoisovalerate (or valine-pyruvate) transaminase, transaminase C |
| MDS50 | CDS | complement(3739132 . . . 3739605) | yiaI | b3573 | orf, hypothetical protein |
| MDS50 | CDS | complement(3739707 . . . 3740555) | yiaJ | b3574 | transcriptional repressor of the yiaK-S operon. |
| MDS50 | CDS | 3740756 . . . 3741754 | yiaK | b3575 | putative dehydrogenase |
| MDS50 | CDS | 3741766 . . . 3742233 | yiaL | b3576 | putative lipase |
| MDS50 | CDS | 3742351 . . . 3742824 | yiaM | b3577 | orf, hypothetical protein |
| MDS50 | CDS | 3742827 . . . 3744104 | yiaN | b3578 | putative membrane protein |
| MDS50 | CDS | 3744117 . . . 3745103 | yiaO | b3579 | putative solute-binding transport protein |
| MDS50 | CDS | 3745107 . . . 3746603 | lyxK | b3580 | L-xylulose kinase, cryptic |
| MDS50 | CDS | 3746600 . . . 3747262 | sgbH | b3581 | probable 3-hexulose 6-phosphate synthase |
| MDS50 | CDS | 3747255 . . . 3748115 | sgbU | b3582 | putative 3-hexulose-6-phosphate isomerase |
| MDS50 | CDS | 3748109 . . . 3748804 | sgbE | b3583 | L-ribulose-5-phosphate 4-epimerase |
| MDS50 | CDS | complement(3749151 . . . 3749891) | yiaT | b3584 | putative outer membrane protein |
| MDS50 | CDS | 3750015 . . . 3750989 | yiaU | b3585 | putative transcriptional regulator LYSR-type |
| MDS50 | CDS | complement(3750986 . . . 3752122) | yiaV | b3586 | putative membrane protein |
| MDS50 | CDS | complement(3752128 . . . 3752451) | yiaW | b3587 | orf, hypothetical protein |

TABLE 11

| Strain | Type | Coordinates | Name | B | Function |
|---|---|---|---|---|---|
| MDS51 | CDS | 1727111 . . . 1731727 | lhr | b1653 | member of ATP-dependent helicase superfamily II |

TABLE 12

| Strain | Type | Coordinates | Name | B | Function |
|---|---|---|---|---|---|
| MD52 | CDS | complement(2858489 . . . 2859286) | ygbI | b2735 | putative DEOR-type transcriptional regulator |
| MD52 | CDS | 2859452 . . . 2860360 | ygbJ | b2736 | putative dehydrogenase |
| MD52 | CDS | 2860357 . . . 2861523 | ygbK | b2737 | orf, hypothetical protein |
| MD52 | CDS | 2861615 . . . 2862253 | ygbL | b2738 | putative epimerase/aldolase |
| MD52 | CDS | 2862258 . . . 2863034 | ygbM | b2739 | orf, hypothetical protein |
| MD52 | CDS | 2863123 . . . 2864487 | ygbN | b2740 | putative transport protein |

TABLE 13

| Strain | Type | Coordinates | Name | B | Function |
|---|---|---|---|---|---|
| MDS53 | CDS | complement(2519615 . . . 2520499) | xapR | b2405 | regulator for xapA |
| MDS53 | CDS | complement(2520751 . . . 2522007) | xapB | b2406 | xanthosine permease |
| MDS53 | CDS | complement(2522067 . . . 2522900) | xapA | b2407 | xanthosine phosphorylase |

TABLE 14

| Strain | Type | Coordinates | Name | B | Function |
|---|---|---|---|---|---|
| MDS54 | CDS | 4085025 . . . 4086080 | yiiG | b3896 | orf, hypothetical protein |
| MDS54 | CDS | complement(4086130 . . . 4087878) | frvR | b3897 | putative frv operon regulatory protein |

TABLE 14-continued

| Strain | Type | Coordinates | Name | B | Function |
|---|---|---|---|---|---|
| MDS54 | CDS | complement(4087878 . . . 4088948) | frvX | b3898 | frv operon protein |
| MDS54 | CDS | complement(4088938 . . . 4090389) | frvB | b3899 | PTS system, fructose-like enzyme IIBC component |
| MDS54 | CDS | complement(4090400 . . . 4090846) | frvA | b3900 | PTS system, fructose-specific IIA component |

TABLE 15

| Strain | Type | Coordinates | Name | B | Function |
|---|---|---|---|---|---|
| MDS55 | CDS | complement(1252308 . . . 1255175) | yogV | b1202 | putative adhesion and penetration protein |

TABLE 16

| Strain | Type | Coordinates | Name | B | Function |
|---|---|---|---|---|---|
| MDS56 | CDS | complement(4486584 . . . 4488086) | yjgR | b4263 | orf, hypothetical protein |
| MDS56 | CDS | complement(4488164 . . . 4489162) | idnR | b4264 | L-idonate transcriptional regulator |
| MDS56 | CDS | complement(4489229 . . . 4490548) | idnT | b4265 | L-idonate transporter |
| MDS56 | CDS | complement(4490610 . . . 4491374) | idnO | b4266 | 5-keto-D-gluconate 5-reductase |
| MDS56 | CDS | complement(4491398 . . . 4492429) | idnD | b4267 | L-idonate dehydrogenase |
| MDS56 | CDS | 4492646 . . . 4493209 | idnK | b4268 | gluconate kinase |

TABLE 17

| Strain | Type | Coordinates | Name | B | Function |
|---|---|---|---|---|---|
| MDS57 | CDS | complement(643420 . . . 644226) | rna | b0611 | RNase I, cleaves phosphodiester bond between any two nucleotides |

TABLE 18

| Strain | Type | Coordinates | Name | B | Function |
|---|---|---|---|---|---|
| MDS58 | CDS | complement(2474716 . . . 2475651) | dsdC | b2364 | D-serine dehydratase (deaminase) transcriptional activator |
| MDS58 | CDS | 2475869 . . . 2477206 | dsdX | b2365 | transport system permease (serine) |
| MDS58 | CDS | 2477224 . . . 2478552 | dsdA | b2366 | D-serine dehydratase (deaminase) |

TABLE 19

| Strain | Type | Coordinates | Name | B | Function |
|---|---|---|---|---|---|
| MDS59 | CDS | 879950 . . . 881152 | dacC | b0839 | D-alanyl-D-alanine carboxypeptidase penicillin-binding protein 6 |

TABLE 20

| Strain | Type | Coordinates | Name | B | Function |
|---|---|---|---|---|---|
| MDS60 | CDS | complement(513625 ... 514080) | ybbJ | b0488 | orf, hypothetical protein |
| MDS60 | CDS | complement(514080 ... 514997) | ybbK | b0489 | putative protease |
| MDS60 | CDS | 515143 ... 515820 | ybbL | b0490 | putative ATP-binding component of a transport system |
| MDS60 | CDS | 515807 ... 516586 | ybbM | b0491 | putative metal resistance protein |
| MDS60 | CDS | complement(516649 ... 517503) | ybbN | b0492 | putative thioredoxin-like protein |
| MDS60 | CDS | complement(517564 ... 518373) | ybbO | b0493 | putative oxidoreductase |
| MDS60 | CDS | complement(518363 ... 518989) | tesA | b0494 | acyl-CoA thioesterase I; also functions as protease I |
| MDS60 | CDS | 518957 ... 519643 | ybbA | b0495 | putative ATP-binding component of a transport system |
| MDS60 | CDS | 519640 ... 522054 | ybbP | b0496 | putative oxidoreductase |
| MDS60 | CDS | 522485 ... 526765 | rhsD | b0497 | rhsD protein in rhs element |
| MDS60 | CDS | 526805 ... 527173 | ybbC | b0498 | orf, hypothetical protein |
| MDS60 | CDS | 527173 ... 527883 | ylbH | b0499 | orf, hypothetical protein |
| MDS60 | CDS | 527864 ... 528124 | ybbD | b0500 | orf, hypothetical protein |
| MDS60 | CDS | complement(528869 ... 529240) | ylbJ | b0502 | orf, hypothetical protein |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09085765B2). An electronic copy of the "Sequence Listing" will also be available from the USPTO upon request and payment of the fee set forth in 37 CFR 1.19(b)(3).

What is claimed is:

1. A strain of *Escherichia coli* (*E. coli*) having a genome with the nucleic acid sequence set forth in SEQ ID NO: 1 and comprising deletions of the following genes: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b2699, b0315-b0321, b0323-b0331, b0333-b0354, b2481-b2492, b2219-b2227, b4500, b2228-b2230, b3707-b3723, b0644-b0650, b4079-b4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502.

2. A method of producing a polypeptide comprising: (a) providing the strain of claim 1; (b) transforming the strain with a heterologous nucleic acid encoding the polypeptide operatively linked to an expression control sequence; and (c) culturing the transformed strain under conditions suitable to express the polypeptide.

3. A method of introducing a heterologous nucleic acid into a microorganism comprising: (a) providing the strain of claim 1; and (b) transforming the strain with the heterologous nucleic acid.

4. The method of claim 3 wherein the heterologous nucleic acid is a vector.

5. A method of amplifying a heterologous nucleic acid comprising:
(a) providing the strain of claim 1; (b) transforming the strain of claim 1 with a vector comprising the heterologous nucleic acid; and (c) culturing the transformed strain under conditions suitable to amplify the heterologous nucleic acid.

* * * * *